United States Patent
Ortega Muñoz et al.

(10) Patent No.: US 10,214,477 B2
(45) Date of Patent: Feb. 26, 2019

(54) (HETERO)ARYL CYCLOPROPYLAMINE COMPOUNDS AS LSD1 INHIBITORS

(71) Applicant: Oryzon Genomics S.A., Cornella de Llobregat, Barcelona (ES)

(72) Inventors: Alberto Ortega Muñoz, Barcelona (ES); Matthew Colin Thor Fyfe, Chipping Norton (GB); Marc Martinell Pedemonte, Barcelona (ES); Maria de los Àngeles Estiarte Martinez, San Francisco, CA (US); Nuria Valls Vidal, Barcelona (ES); Guido Kurz, Barcelona (ES); Julio Cesar Castro Palomino Laria, Barcelona (ES)

(73) Assignee: Oryzon Genomics S.A., Madrid (ES)

( * ) Notice: Subject to any disclaimer, the term of this patent is extended or adjusted under 35 U.S.C. 154(b) by 0 days.

(21) Appl. No.: 15/497,556

(22) Filed: Apr. 26, 2017

(65) Prior Publication Data

US 2018/0079709 A1    Mar. 22, 2018

Related U.S. Application Data

(60) Continuation of application No. 15/254,020, filed on Sep. 1, 2016, now Pat. No. 9,670,136, which is a (Continued)

(30) Foreign Application Priority Data

Oct. 20, 2011  (EP) ..................... 11382324
Oct. 27, 2011  (EP) ..................... 11382329

(51) Int. Cl.
| | | |
|---|---|---|
| *C07C 211/36* | (2006.01) | |
| *C07D 213/74* | (2006.01) | |
| *C07C 271/24* | (2006.01) | |
| *C07C 275/26* | (2006.01) | |
| *C07D 231/12* | (2006.01) | |
| *C07D 207/14* | (2006.01) | |
| *C07D 277/28* | (2006.01) | |
| *C07D 295/096* | (2006.01) | |
| *C07D 295/135* | (2006.01) | |
| *C07D 295/26* | (2006.01) | |
| *C07D 213/30* | (2006.01) | |
| *C07D 213/38* | (2006.01) | |
| *C07D 307/52* | (2006.01) | |
| *C07C 311/08* | (2006.01) | |
| *C07C 311/21* | (2006.01) | |

(Continued)

(52) U.S. Cl.
CPC .......... *C07C 211/36* (2013.01); *C07C 209/28* (2013.01); *C07C 211/38* (2013.01); *C07C 211/40* (2013.01); *C07C 213/00* (2013.01); *C07C 215/46* (2013.01); *C07C 215/64* (2013.01); *C07C 217/54* (2013.01); *C07C 217/74* (2013.01); *C07C 269/00* (2013.01); *C07C 271/24* (2013.01); *C07C 273/00* (2013.01); *C07C 273/18* (2013.01); *C07C 275/26* (2013.01); *C07C 311/08* (2013.01); *C07C 311/21* (2013.01); *C07D 207/14* (2013.01); *C07D 213/30* (2013.01); *C07D 213/38* (2013.01); *C07D 213/57* (2013.01); *C07D 213/73* (2013.01); *C07D 213/74* (2013.01); *C07D 231/12* (2013.01); *C07D 231/56* (2013.01); *C07D 277/28* (2013.01); *C07D 295/096* (2013.01); *C07D 295/135* (2013.01); *C07D 295/26* (2013.01); *C07D 307/52* (2013.01); *C07D 333/20* (2013.01); *C07B 2200/07* (2013.01); *C07C 2601/02* (2017.05); *C07C 2601/04* (2017.05); *C07C 2601/14* (2017.05); *C07C 2602/08* (2017.05)

(58) Field of Classification Search
CPC ........................ C07C 211/36; C07D 213/74
See application file for complete search history.

(56) References Cited

U.S. PATENT DOCUMENTS

| | | |
|---|---|---|
| 3,106,578 A | 10/1963 | Kaiser et al. |
| 3,365,458 A | 1/1968 | Biel et al. |

(Continued)

FOREIGN PATENT DOCUMENTS

| | | |
|---|---|---|
| EP | 1193268 | 4/2002 |
| EP | 1704859 | 9/2006 |

(Continued)

OTHER PUBLICATIONS

Ahmed et al, "Ticagrelor: a new reversible oral antiplatelet agent" Int Research Journal of Pharmacy, 2010, 1(1), 62-69.
(Continued)

*Primary Examiner* — Golam M Shameem
(74) *Attorney, Agent, or Firm* — Finnegan, Henderson, Farabow, Garrett & Dunner, LLP

(57) ABSTRACT

The invention relates to (hetero)aryl cyclopropylamine compounds, including particularly the compounds of formula (I) as described and defined herein, and their use in therapy, including, e.g., in the treatment or prevention of cancer, a neurological disease or condition, or a viral infection.

(I)

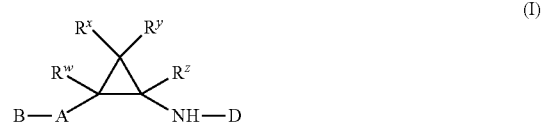

8 Claims, No Drawings

Related U.S. Application Data division of application No. 14/352,719, filed as application No. PCT/EP2012/070900 on Oct. 22, 2012, now Pat. No. 9,469,597.

(60) Provisional application No. 61/558,370, filed on Nov. 10, 2011, provisional application No. 61/558,369, filed on Nov. 10, 2011.

(51) Int. Cl.

| | | |
|---|---|---|
| C07C 215/46 | (2006.01) | |
| C07C 217/54 | (2006.01) | |
| C07C 209/28 | (2006.01) | |
| C07C 211/38 | (2006.01) | |
| C07C 269/00 | (2006.01) | |
| C07C 273/18 | (2006.01) | |
| C07C 211/40 | (2006.01) | |
| C07C 213/00 | (2006.01) | |
| C07C 215/64 | (2006.01) | |
| C07C 217/74 | (2006.01) | |
| C07C 273/00 | (2006.01) | |
| C07D 213/57 | (2006.01) | |
| C07D 213/73 | (2006.01) | |
| C07D 231/56 | (2006.01) | |
| C07D 333/20 | (2006.01) | |

(56) References Cited

U.S. PATENT DOCUMENTS

| | | | |
|---|---|---|---|
| 3,471,522 A | 10/1969 | Biel et al. | |
| 3,532,712 A | 10/1970 | Biel et al. | |
| 3,532,749 A | 10/1970 | Biel et al. | |
| 3,758,684 A | 9/1973 | Elion et al. | |
| 4,409,243 A | 10/1983 | Lieb | |
| 4,522,811 A | 6/1985 | Eppstein et al. | |
| 4,530,901 A | 7/1985 | Weissmann | |
| 6,043,393 A | 3/2000 | de Meijere et al. | |
| 6,211,244 B1 | 4/2001 | Van Wagenen et al. | |
| 6,337,074 B1 | 1/2002 | Marsden et al. | |
| 6,809,120 B1 | 10/2004 | Warrington et al. | |
| 7,399,825 B2 | 7/2008 | Lipps et al. | |
| 7,611,704 B2 | 11/2009 | Thorpe et al. | |
| 7,628,993 B2 | 12/2009 | Vilalta et al. | |
| 7,799,782 B2 | 9/2010 | Munson et al. | |
| 8,524,717 B2 | 9/2013 | Guibourt et al. | |
| 8,722,743 B2 | 5/2014 | Ortega-Munoz et al. | |
| 8,859,555 B2 | 10/2014 | Ortega Munoz et al. | |
| 8,946,296 B2 | 2/2015 | Ortega Munoz et al. | |
| 8,993,808 B2 | 3/2015 | Guibourt | |
| 9,006,449 B2 | 4/2015 | Fyfe et al. | |
| 9,061,966 B2 | 6/2015 | Laria et al. | |
| 9,149,447 B2 | 10/2015 | Munoz et al. | |
| 9,181,198 B2 | 11/2015 | Ortega Munoz et al. | |
| 9,186,337 B2 | 11/2015 | Baker et al. | |
| 9,469,597 B2 * | 10/2016 | Ortega Munoz | C07C 271/24 |
| 9,487,512 B2 | 11/2016 | Ortega Munoz et al. | |
| 9,616,058 B2 | 4/2017 | Cesar Castro Palomino Laria et al. | |
| 9,670,136 B2 * | 6/2017 | Ortega Munoz | C07C 271/24 |
| 9,676,701 B2 | 6/2017 | Fyfe et al. | |
| 9,708,309 B2 | 7/2017 | Ortega Munoz et al. | |
| 9,790,196 B2 | 10/2017 | Baker et al. | |
| 2003/0008844 A1 | 1/2003 | Spero et al. | |
| 2003/0236225 A1 | 12/2003 | Protopopova et al. | |
| 2004/0019117 A1 | 1/2004 | Protopopova et al. | |
| 2004/0033986 A1 | 2/2004 | Protopopova et al. | |
| 2004/0048802 A1 | 3/2004 | Ripka et al. | |
| 2004/0132820 A1 | 7/2004 | Gosselin et al. | |
| 2004/0147741 A1 | 7/2004 | Sundermann et al. | |
| 2004/0162287 A1 | 8/2004 | Sundermann et al. | |
| 2004/0176469 A1 | 9/2004 | Nadackal | |
| 2004/0229872 A1 | 11/2004 | Friderichs et al. | |
| 2004/0254158 A1 | 12/2004 | Qiao et al. | |
| 2005/0009832 A1 | 1/2005 | Sun et al. | |
| 2005/0154056 A1 | 7/2005 | Yang et al. | |
| 2006/0116370 A1 | 6/2006 | Dollinger et al. | |
| 2006/0148904 A1 | 7/2006 | Protopopova et al. | |
| 2006/0211709 A1 | 9/2006 | Buhr et al. | |
| 2006/0270673 A1 | 11/2006 | Duggan et al. | |
| 2006/0275366 A1 | 12/2006 | Malcom et al. | |
| 2006/0287287 A1 | 12/2006 | Gerritz et al. | |
| 2007/0213338 A1 | 9/2007 | Lebsack et al. | |
| 2008/0139666 A1 | 6/2008 | Schuele et al. | |
| 2008/0242698 A1 | 10/2008 | Flor et al. | |
| 2008/0269228 A1 | 10/2008 | Moore et al. | |
| 2009/0203750 A1 | 8/2009 | Kozikowski et al. | |
| 2009/0247530 A1 | 10/2009 | Nolte et al. | |
| 2010/0016262 A1 | 1/2010 | Mehal et al. | |
| 2010/0240649 A1 | 9/2010 | Zhang | |
| 2010/0292225 A1 | 11/2010 | Chamoin et al. | |
| 2010/0324147 A1 | 12/2010 | McCafferty et al. | |
| 2012/0202810 A1 | 8/2012 | Nolte et al. | |
| 2013/0197095 A1 | 8/2013 | Nolte et al. | |
| 2013/0303545 A1 | 11/2013 | Maes et al. | |
| 2014/0163041 A1 | 6/2014 | Fyfe et al. | |
| 2014/0256742 A1 | 9/2014 | Baker et al. | |
| 2014/0296255 A1 | 10/2014 | Maes et al. | |
| 2014/0329833 A1 | 11/2014 | Maes et al. | |
| 2015/0232436 A1 | 8/2015 | Baker et al. | |
| 2015/0368186 A1 | 12/2015 | Muñoz et al. | |
| 2016/0000768 A1 | 1/2016 | Castro-Palomino Laria et al. | |
| 2017/0008844 A1 | 1/2017 | Ortega Muñoz et al. | |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO2001/092264 | 12/2001 |
| WO | WO2002/079152 | 10/2002 |
| WO | WO2003/087064 | 10/2003 |
| WO | WO2003/093297 | 11/2003 |
| WO | WO2003/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |

(56) References Cited

FOREIGN PATENT DOCUMENTS

| WO | WO2009/052078 | 4/2009 |
|---|---|---|
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022486 | 2/2011 |
| WO | WO2011/031934 | 3/2011 |
| WO | WO 2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO 2011/131697 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |

OTHER PUBLICATIONS

Arya et al., "Synthesis of 5H-dibenzo[a,d]cycloheptene derivatives with diverse biological activities", Indian J Chemistry B, 1978, 16B,220-225.
Bar-Am et al, "Regulation of Bcl-2 family proteins, neurtrophic factors, and APP processing in the neurorescue activity of propargylamine", FASEB J, 2005, 19(13), 1899-1901.
Barlesi et al, "Global histone modifications predict prognosis of resected non small-cell lung cancer",J Clin Oncol,2007,25, 4358-4364.
Benelkebir et al, "Enantioselective synthesis of tranylcypromine analogues as lysine demethylase (LSD1) inhibitors", Bioorg Med Chem, 2011, 19(12),3709-3716.
Biljak et al,"Platelet count, mean platelet volume and smoking status in stable chronic obstructive pulmonary disease", Platelets, 2011,22(6), 466-70.
Binda et al, "Biochemical, structural, and biological evaluation of tranylcypromine derivatives as inhibitors of histone demethylases LSD1 and LSD2", J Am Chem Soc,2010,132(19),6827-6833.
Bisi et al, "Multidrug resistance reverting activity and antitumor profile of new phenothiazine derivatives", Biorg Med Chem, 2008, 16(13), 6474-6482.
Boilard et al. "Platelets amplify inflammation in arthritis via collagen-dependent microparticle production", Science, 2010,327(5965), 580-583.
Bolesov et al. "Cyclopropanes and cyclobutanes LXIX", Zhurnal Organicheskoi Khimii (English Translation), 1974, 10(10), 2122-2128.
Bolesov et al, "Cyclopropanes and cyclobutanes LXVII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.
Brydon et al, "Platelets, coronary heart disease and stress", Brain, Behavior and Immunity,2006,20(2), 113-119.
Burakova et al, "N- and O-alkylation of 3-indolylcyclopropylacetic acid derivatives", Russian Chemical Bulletin, 2002, 51(10) 1829-1840.
Burk et al, "Cognitive deficits in spinocerebellar ataxia 2", Brain, 1999, 122(4), 769-777.
Cakmak et al, "Platelets: indicator of inflammation in COPD", Int J Med Med Sci, 2009, 1(5), 227-229.
Calogero et al, "Inhibition of cell growth by EGR-1 in human primary cultures from malignant glioma", Cancer Cell International,2004,4 1.
Casero et al, "Recent advances in the development of polyamine analogues as antitumor agents", J Med Chem, 2009, 52(15),4551-4573.
Chen et al, "Association of insulin resistance and hematologic parameters: study of a middle-aged and elderly chinese population in Taiwan", J Chin Med Assoc,2006, 69(6), 248-253.
Chimenti et al "Synthesis, Sterochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.
Choi et al "Histone demethylase LSD1 is required to induce skeletal muscle differentiation by regulating myogenic factors" (2010) Biochemical and Biophysical Research Communications 401(3), 327-332.
Choo et al. "Genetic organization and diveristy of the hepatitis C virus", Proc Natl Acad Sci, 1991, 88,2451-2455.
Culhane et al, A mechanism-based inactivator for histone demethylase LSD1, J Am Chem Soc, 2006, 128(14), 4536-4537.
Culhane et al, "Comparative anaylsis of small molecules and histone substrate analgues as LSD1 lysine demethylase inhibitors", J Am Chem Soc, 2010, 132(9),3164-3176.
Danese et al, "Platelets in inflammatory bowel disease: clinical, pathogenic and therapeutic implications", Am J Gastroenterol, 2004,99(5), 938-45.
Di Stefano et al, Mutation of *Drosophila* Lsd1 distrupts H3-K4 methylation, resulting in tissue-specific defects during development, Curr Biol,2007, 17(9), 808-12.
East et al, "An orally bioavailable positive allosteric modulator of the mGlu4 receptor with efficacy in an animal model of motor dysfunction", Bioorg Med Chem Lett, 2010, 20(16), 4901-5.
Ellis et al, "Expression of *Drosophila* glass protein and evidence for negative regulation of its activity in non-neuronal cells by another DNA-binding protein",Development, 1993, 119, 855-865.
Elsheikh et al "Global histone modification in breast cancer correlate with tumor phenotypes prognostic factors and patient outcome", Canc Res, 2009,69, 3802-3809.
Erazo et al, "Varicella-zoster virus open reading frame 66 protein kinase is required for efficient viral growth in primary human corneal stromal fibroblast cells", J Virol, 2008,82, 7653-7665.
Faler et al, "The Kulinkovich reaction in the synthesis of contrained N,N-dialkyl nerotransmitter analogues", Organic Letters 2007,9(10),1987-1990.
Ferlay et al, "Estimates of the cancer incidence and mortality in Europe in 2006", Annals of Oncology 2007, 18(3), 581-92.
Ferraro et al, "EGR1 predicts PTEN and survival in patients with non-small-cell lung cancer", J Clin Oncol, 2005, 23(9), 1921-26.
Fischer et al, "Recovery of learning and memory is associated with chromatin remolding", Nature, 2007,447, 178-182.
Forneris et al "LSD1: oxidative chemistry for multifaceted functions in chromatin Regulation." Trends in Biochemical Sciences 2008,33(4), 181-189.
Gawaz et al, "Platelets in inflammation and atherogenesis", J Clin Invest, 2005,115(12), 3378-3384.
Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.

(56) References Cited

OTHER PUBLICATIONS

Han et al "Modulation of breast cancer resistance protein (BCRP/ABCG2) by non-basic chalcone analgues" Eur. J. Pharma. 2008, 35(1-2) 30-41.
Han et al, "Antidepressants reveal differential effect against 1-methyl-4-phenylpyridinium toxicity in differentiated PC12 cells", Eur J Pharmacol, 2009, 604 (1-3),36-44.
Hayami et al, "Overexpression of LSD1 contributes to human carcinogenesis through chromatin regulation in various cancers", Int J Cancer, 2011, 128(3), 574-86.
Hruschka et al, "Fluorinated phenylcyclopropylamines. Part 5:Effect of electron-withdrawing or-donating aryl substituents on the inhibition of monoamine oxidases A and B by 2-aryl-2-fluoro-cyclopropylamines", Bioorg Med Chem,2008, 16(15), 7148-7166.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reexpression of aberranlty silenced genes", PNAS,2007, 104(19), 8023-8028.
Jackson et al, "Polyglutamine-expanded human Huntingtin transgenes induce degeneration of *Drosophila* photoreceptor neurons", Neuron, 1998, 21, 633-642.
Kahl et al,"Androgen receptor coactivators lysine-specific histone demethylase 1 and four and a half LIM domain protein 2 predict risk of prostate cancer recurrence". Cancer Res,2006,66 (23), 11341-11347.
Kaiser et al, "2-substituted cyclopropylamines. I. Derivatives and analogs of 2-phenylcyclopropylamine", J Med Pharm Chem (ACS), 1962, 5, 1243-1265.
Kiefmann et al, "Red blood cells induce hypoxic lung inflammation", Blood, 2008,111(10),5205-14.
Kim et al, "Flavin chemical models for monoamine oxidase inactivation by cyclopropylamines, α-silylamines, and hydrazines", J Am Chem Soc 1995, 117, 100-105.
Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Bioorg Med Chem Lett 2011, 21(15), 4429-4435.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75, 4614-4624.
Lan et al "Mechanisms involved in the regulation of histone lysine demethylases", Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications",Chem Biol, 2006,13(6), 563-567.
Li et al, "Associatian between inflammatory mediators and angiographic morphologic features indication thrombus formation in patients with acute myocardial infarction", Chin Med J, 2009, 122(15), 1738-42.
Liang et al, "Inhibition of the histone demethylase LSD1 blocks alpha-herpesvirus lytic replication and reactivation from latency",Nat Med, 2009,15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Lucerna et al, "Sustained expression of early growth response protein-1 blocks angiogenesis and tumor growth",Cancer Research,2006, 66,6708-6713.
Lupu Roxana, "Up-to-date in the hematological malignancies treatment", Maedica, 2006.1(1), 63-65.

Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection", Cardiovascular & Haematological Disorders—Drug Targets, 2008,8, 99-117.
Meanwell, "Synopsis of some recent tactical application of bioisosteres in drug design", J Med Chem, 2011, 54(8),2529-91.
Metzger et al, "LSD1 demethylates repressive histone marks to promote androgen-receptor-dependent transcription",Nature,2005, 437(7057),436-9.
Mimasu et al "Crystal structure of histone demethylase LSD1 and tranylcypromine at 2.25 Å" Biochemical and Biophysical Research Communications ,2008,366, 15-22.
Mimasu et al, "Structurally designed trans-2-phenylcyclopropylamine derivatives potently inhibit histone demethylae LSD1/KDM1", Biochemistry,2010,49(30), 6494-6503.
Moritani et al, "Activation of platelets in bronchial asthma". Chest, 1998,113. 452-458.
Nabil Aboul-Enein et al, "Synthesis of some 4-substituted amino-1-methylpiperidines structurally related to antihistaminics", Pharmaceutica Acta Helvetiae, 1973, 48(3): 151-156.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure—activity relationship of 4-(2-aryl-cyclopropylamino)-quinoline-3-carbonitriles as EGFR tyrosine kinase inhibitors". Bioorg & Med Chem Lett , 2007,17(21), 5978-5082.
Pitchford et al, "Platelet P-selectin is required for pulmonary eosiniphil and lymphocyte recruitment in a murine model of allergic inflammation", Blood, 2005, 105, 2074-2081.
Pollock et al, Lysine-specific histone demethylase 1 inhibitors control breast cancer proliferation in ERalpha-dependent and -independent manners, ACS Chem Biol 2012,7,1221-1231.
Ravina et al, "The relationship between CAG repeat length and clinical progression in Huntington's disease", Movement Disorders,2008,23(9), 1223-7.
Reddy et al, "Role of lysine-specific demethylase 1 in the proinflammatory phenotype of vascular smooth muscle cells of diabetic mice",Circ Res,2008,103, 615-23.
Riley et al, "Absolute configuration of (+)- and (−)-trans-2-phenylcyclopropylamine hydrochloride",J Med Chem, 1972,15(11), 1187-1188.
Rinder et al, "Correlation of thrombosis with increased platelet turnover in thrombocytosis", Blood, 1998,91(4), 1288-1294.
Schmidt et al,"trans-2-phenycyclopropylamine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation", Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.
Seligson et al,"Global levels of histone modifications predict prognosis in different cancers",Am J Path, 2009, 174,1619-28.
Sharma et al, "(Bis)urea and (bis)thiourea inhibitors of lysine-specific demethylase 1 as epigenetic modulators", J Med Chem, 2010,53(14), 5197-5212.
Shi et al, "Histone demethylation mediated by the nuclear amine oxidase homolog LSD1", Cell, 2004,119,941-953.

(56) References Cited

OTHER PUBLICATIONS

Shi, "Histone lysine demethylases: emerging roles in development, physiology and disease", Nature Reviews Genetics 2007, 8:829-833.
Silverman, R. B. "The Organic Chemistry of Drug Design and Drug Action" (Second Edition), Elsevier Academic Press, 2004, pp. 29-34.
Stephens et al, "The determination of the absolute configurations of chiral molecules using vibrational circular dichroism (VCD) spectroscopy",Chirality, 2008,20(5), 643-663.
Stoffel et al, "Leukocyte count and risk of thrombosis in patients undergoing haematopoietic stem cell transplantation or intensive chemotherapy",Thromb Haemost, 2010,103(6), 1228-32.
Stratmann et al, "Pathobiology and cell interactions of platelets in diabetes", Diabetes & Vascular Disease Research,2005, 2(1), 16-23.
Szewczuk et al, "Mechanistic analysis of a suicide inactivator of histone demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin an dplatelet factor 4", Allergology International,2008, 57, 391-396.
Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identifiation of cell-active lysine specific demethylase 1-selective inhibitors",J Am Chem Soc, 2009,131(48), 17536-17537.
Vagner et al, "Peptidomimetics, a synthetic tool of drug discovery", Current Opinion on Chemical Biology, 2008, 12:292-296.
Wagner et al, "Platelets in inflammation and thrombosis", Arteriosclerosis, Thrombosis and Vascular Biology, 2003,23, 2131-2137.
Wang et al, Novel histone demethylase LSD1 inhibitors selectively target cancer cells with pluripotent stem cell properties, Cancer Research, 2011, 71(23):7238-49.
Wang et al "LSD1 is a Subunit of the NuRD Complex and Targets the Metastasis Programs in Breast Cancer" Cell 2009, 138, 660-672.
Wang et al. "The lysince demethylase LSD1 (KDM1) is required for maintenance of global DNA methylation", Nature Genetics, 2009,41(1), 125-129.
Weinreb et al, "Novel neuroprotective mechanism of action of rasagiline is associated with its propargyl moiety: interaction of Bcl-2 family members with PKC pathway", Ann NY Acad Sci, 2005, 1053, 348-55.
Wermuth, "Molecular variations based on isisteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promoters during intiiation of reactivation from latency of herpes simplex virus type 1", J Virol. 2009,83(18):9591-5.
Willoughby et al, "Platelets and cardivascular disease",Eur J Cardiovasc Nursing,2002,1, 273-288.
XP002568777 Database chemcats, database accession No. 2088922753, order No. kbsb-0063197. Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenycyclopropylamines. Part 3: inhibition monoamine oxidase A and B",Bioorg Med Chem,2004, 12(10),2645-2652.
Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dörwald "Side reactions in Organic Synthesis: a guide to successful synthesis design", Wiley-VCH Verlag GmbH & Co, KGaA, Wilenheim, Chapter 1, 2005.
Zirkle et al, "2-substituted oyclopropylamines. II. Effect of structure upon monoamine oxidase-inhibitory activity as measured in vivo by potentiation of tryptamine convulsions", J Med Pharm Chem (ACS), 1962. 5, 1265-84.
"Definition of Cancer" —MedicineNetcom Medical references for patients, http://www.medterms.com, 2005.
Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guandinomethylcyclohexanes useful in pain management", 1999.
CAS Registry No. RN220351-30-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN124811-33-7, entered STN Oct. 29, 2010.
CAS Registry No. RN1248913-30-5 entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 30, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3, 2011.
CAS Registry No. RN1274681-54-7, entered STN Apr. 4, 2011.
CAS Registry No. RN1280568-04-8, entered STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281356-83-4, entered STN Apr. 18, 2011.
CAS Registry No. RN1281886-96-1, entered STN Apr. 18, 2011.
CAS Registry No. RN1282014-65-6, entered STN Apr. 18, 2011.
CAS Registry No. RN1282165-83-6, entered STN Apr. 19, 2011.
CAS Registry No. RN1282245-50-4, entered STN Apr. 19, 2011.
CAS Registry No. RN1282292-27-6, entered STN Apr. 19, 2011.
CAS Registry No. RN1282425-35-7, entered STN Apr. 19, 2011.
CAS Registry No. RN1282679-60-0, entered STN Apr. 20, 2011.
CAS Registry No. RN1282773-23-2, entered STN Apr. 20, 2011.
CAS Registry No. RN1282804-36-7, entered STN Apr. 20, 2011.
CAS Registry No. RN1282928-27-1, entered STN Apr. 20, 2011.
CAS Registry No. RN1283337-81-4, entered STN Apr. 21, 2011.
CAS Registry No. RN128356-05-7, entered STN Apr. 21, 2011.
CAS Registry No. RN1283449-65-9 entered STN Apr. 21, 2011.
CAS Registry No. RN1283533-13-0, entered STN Apr. 21, 2011.
CAS Registry No. RN1283662-53-2, entered STN Apr. 21, 2011.
CAS Registry No. RN1283728-98-2, entered STN Apr. 21, 2011.
CAS Registry No. RN1283887-44-4, entered STN Apr. 22, 2011.
CAS Registry No. RN1284036-80-1, entered STN Apr. 22, 2011.
CAS Registry No. RN1284049-14-4, entered STN Apr. 22, 2011.
CAS Registry No. RN1284310-21-9, entered STN Apr. 22, 2011.
CAS Registry No. RN1285070-57-6, entered STN Apr. 24, 2011.
CAS Registry No. RN1285129-34-1, entered STN Apr. 24, 2011.

(56) References Cited

OTHER PUBLICATIONS

CAS Registry No. RN1285144-86-6, entered STN Apr. 24, 2011.
CAS Registry No. RN1285176-99-9, entered STN Apr. 24, 2011.
CAS Registry No. RN1285178-46-2, entered STN Apr. 24, 2011.
CAS Registry No. RN1285235-05-3 entered STN Apr. 24, 2011.
CAS Registry No. RN1285348-65-3, entered STN Apr. 25, 2011.
CAS Registry No. RN1285612-69-2, entered STN Apr. 25, 2011.
CAS Registry No. RN1290805-79-6, entered STN May 6, 2011.
CAS Registry No. RN1290906-73-8, entered STN May 6, 2011.
CAS Registry No. RN1290912-35-4, entered STN May 6, 2011.
CAS Registry No. RN1290912-36-5, entered STN May 6, 2011.
CAS Registry No. RN1290949-23-3, entered STN May 6, 2011.
CAS Registry No. RN1290949-24-4, entered STN May 6, 2011.
CAS Registry No. RN1290949-25-5, entered STN May 6, 2011.
CAS Registry No. RN1290971-74-2, entered STN May 6, 2011.
CAS Registry No. RN1290972-32-5, entered STN May 6, 2011.
CAS Registry No. RN1291186-57-6, entered STN May 8, 2011.
CAS Registry No. RN1291186-59-8, entered STN May 8, 2011.
CAS Registry No. RN1291186-62-3, entered STN May 8, 2011.
CAS Registry No. RN1291186-64-5, entered STN May 8, 2011.
CAS Registry No. RN1291230-78-8, entered STN May 8, 2011.
CAS Registry No. RN1291273-81-8, entered STN May 8, 2011.
CAS Registry No. RN1291273-82-9, entered STN May 8, 2011.
CAS Registry No. RN1291273-84-1, entered STN May 8, 2011.
CAS Registry No. RN1291273-86-3, entered STN May 8, 2011.
CAS Registry No. RN1291273-87-4 entered STN May 8, 2011.
CAS Registry No. RN1292446-11-7, entered STN May 10, 2011.
CAS Registry No. RN1304214-87-6, entered STN Jun. 2, 2011.
CAS Registry No. RN1304214-96-7, entered STN Jun. 2, 2011.
CAS Registry No. RN1304214-97-8, entered STN Jun. 2, 2011.
CAS Registry No. RN1304215-06-2, entered STN Jun. 2, 2011.
CAS Registry No. RN1304827-17-5, entered STN Jun. 3, 2011.
CAS Registry No. RN1304845-37-1, entered STN Jun. 3, 2011.
CAS Registry No. RN1304845-55-3, entered STN Jun. 3, 2011.
CAS Registry No. RN1304845-63-3, entered STN Jun. 3, 2011.
CAS Registry No. RN1304845-67-7, entered STN Jun. 3, 2011.
CAS Registry No. RN1304845-70-2, entered STN Jun. 3, 2011.
CAS Registry No. RN1304845-72-4, entered STN Jun. 3, 2011.
CAS Registry No. RN1304845-83-7, entered STN Jun. 3, 2011.
CAS Registry No. RN1305397-75-4, entered STN Jun. 5, 2011.
CAS Registry No. RN1305397-86-7, entered STN Jun. 5, 2011.
CAS Registry No. RN1305398-16-6 entered STN Jun. 5, 2011.
CAS Registry No. RN1306275-88-6, entered STN Jun. 5, 2011.
CAS Registry No. RN1306275-95-5, entered STN Jun. 5, 2011.
CAS Registry No. RN1306276-35-6, entered STN Jun. 5, 2011.
CAS Registry No. RN1306322-57-5, entered STN Jun. 6, 2011.
CAS Registry No. RN1306373-68-1 entered STN Jun. 6, 2011.
CAS Registry No. RN1306589-39-8 entered STN Jun. 6, 2011.
CAS Registry No. RN1307573-60-9, entered STN Jun. 8, 2011.
CAS Registry No. RN1307574-08-8, entered STN Jun. 8, 2011.
Co-pending U.S. Appl. No. 14/184,74 filed Feb. 20, 2014.
Co-pending U.S. Appl. No. 14/118,330, filed Jun. 6, 2014.
Co-pending U.S. Appl. No. 14/843,095, filed Sep. 2, 2015.
Co-pending U.S. Appl. No. 15/271,772, filed Sep. 21, 2016.
Co-pending U.S. Appl. No. 15/369,003, filed Dec. 5, 2016.
Co-pending U.S. Appl. No. 15/623,866, filed Jun. 15, 2017.
Co-pending U.S. Appl. No. 15/710,912, filed Sep. 21, 2017.
Written Opinion of the International Searhcing Authority for PCT/EP2012/070900, dated Apr. 20, 2014.
International Search Report of International Application No. PCT/EP2012/070900, dated Jan. 17, 2013.

* cited by examiner

(HETERO)ARYL CYCLOPROPYLAMINE COMPOUNDS AS LSD1 INHIBITORS

The invention relates to (hetero)aryl cyclopropylamine compounds, particularly compounds of formula I, Ia, Ia-1, Ib and Ic, more particularly compounds of formula I and Ia, as described and defined herein, and their use in therapy, including e.g., in the treatment or prevention of cancer, a neurological disease, or a viral infection.

Aberrant gene expression in affected tissue as compared to normal tissue is a common characteristic of many human diseases. This is true for cancer and many neurological diseases which are characterized by changes in gene expression patterns. Gene expression patterns are controlled at multiple levels in the cell. Control of gene expression can occur through modifications of DNA: DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modifications have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multi-protein complexes containing other proteins involved in reading and modifying histone marks. The components of these protein complexes are typically cell-type specific and typically comprise transcriptional regulators, repressors, co-repressors, receptors associated with gene expression modulation (e.g., estrogen or androgen receptor). Histone deacetylase inhibitors alter the histone acetylation profile of chromatin. Accordingly, histone deacetylase inhibitors like Vorinostat (SAHA), Trichostatin A (TSA), and many others have been shown to alter gene expression in various in vitro and in vivo animal models. Clinically, histone deacetylase inhibitors have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved in histone lysine modifications. One particular human histone lysine demethylase enzyme called Lysine Specific Demethylase-1 (LSD1) was recently discovered (Shi et al. (2004) Cell 119:941) to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds. LSD1 has been recognized as an interesting target for the development of new drugs to treat cancer, neurological diseases and other conditions.

Cyclopropylamine containing compounds are known to inhibit a number of medically important targets including amine oxidases like Monoamine Oxidase A (MAO-A; or MAOA), Monoamine Oxidase B (MAO-B; or MAOB), and Lysine Specific Demethylase-1 (LSD1). Tranylcypromine (also known as 2-phenylcyclopropylamine), which is the active ingredient of Parnate® and one of the best known examples of a cyclopropylamine, is known to inhibit all of these enzymes. Since MAO-A inhibition may cause undesired side effects, it would be desirable to identify cyclopropylamine derivatives that exhibit potent LSD1 inhibitory activity while being devoid of or having substantially reduced MAO-A inhibitory activity.

In view of the lack of adequate treatments for conditions such as cancer and neurodegeneration, there is a desperate need for disease modifying drugs and drugs that work by inhibiting novel targets. There is thus a need for the development of LSD1 inhibitors, particularly those which selectively inhibit LSD1.

SUMMARY OF THE INVENTION

The present invention relates to the identification of compounds and their use in treating or preventing diseases. The invention provides (hetero)aryl cyclopropylamine compounds, including the compounds of Formula I, Ia, Ia-1, Ib and Ic, and particularly the compounds I, Ia and Ia-1, as described and defined herein. The present invention particularly provides a compound of Formula I, Ia, Ia-1, Ib and Ic, and particularly a compound of Formula I, Ia and Ia-1, pharmaceutical compositions comprising a compound of Formula I, Ia, Ia-1, Ib or Ic, and particularly a compound of Formula I, Ia or Ia-1, and a pharmaceutically acceptable carrier, and their uses for treating diseases. One use of the compound of Formula I, Ia, Ia-1, Ib and Ic is for treating or preventing cancer. Another use for the compound of Formula I, Ia, Ia-1, Ib and Ic is to inhibit LSD1. The invention thus relates to a compound of Formula I, Ia, Ia-1, Ib or Ic, and particularly a compound of Formula I, Ia or Ia-1, for use in treating or preventing human disease. The present invention further relates to a compound of Formula I, Ia, Ia-1, Ib or Ic, and particularly a compound of Formula I, Ia and Ia-1, for use in treating or preventing cancer. The present invention further relates to a compound of Formula I, Ia, Ia-1, Ib or Ic, and particularly a compound of Formula I, Ia and Ia-1, for use in treating or preventing a neurological disease. The present invention further relates to a compound of Formula I, Ia, Ia-1, Ib or Ic, and particularly a compound of Formula I, Ia and Ia-1, for use in treating or preventing a viral infection.

Accordingly, the present invention provides a compound of Formula I:

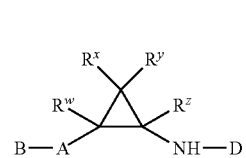

I wherein:

A is aryl or heteroaryl, wherein said aryl or said heteroaryl is optionally substituted with one or more $R^1$;

B is hydrogen, $R^1$ or -L-E;

E is aryl or heteroaryl, wherein said aryl or said heteroaryl is optionally substituted with one or more $R^2$;

L is a bond, —O—, —NH—, —N($C_{1-4}$ alkyl)-, $C_{1-4}$ alkylene or heteroC$_{1-4}$ alkylene;

D is a cycloalkyl group having from 4 to 7 C atoms, wherein said cycloalkyl group has one or two substituents $R^3$ and is further optionally substituted with one or more $R^4$, and wherein the cycloalkyl group optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

each $R^1$ is independently selected from $C_{1-8}$ alkyl, $C_{2-8}$ alkenyl, $C_{2-8}$ alkynyl, cyclyl, amino, amido, hydroxyl, nitro, halo, haloC$_{1-8}$ alkyl, haloC$_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^2$ is independently selected from $C_{1-8}$ alkyl, $C_{2-8}$ alkenyl, $C_{2-8}$ alkynyl, cyclyl, amino, amido, hydroxyl, nitro, halo, haloC$_{1-8}$ alkyl, haloC$_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^3$ is independently selected from —NR$^7$R$^8$, —NHOH, —NR$^9$COR$^{10}$, —NR$^9$SO$_2$R$^{10}$, —NR$^9$COOR$^{10}$, —NR$^9$CONR$^7$R$^8$, —NR$^9$SO$_2$NR$^7$R$^8$, —OH, —CONR$^7$R$^8$, oxo, —$C_{1-4}$ alkylene-NR$^7$R$^8$, —$C_{1-4}$ alkylene-NHOH, —$C_{1-4}$ alkyene-NR$^9$COR$^{10}$, —$C_{1-4}$ alkylene-NR$^9$SO$_2$R$^{10}$, —$C_{1-4}$ alkylene-NR$^9$COOR$^{10}$, —$C_{1-4}$ alkylene-NR$^9$CONR$^7$R$^8$, —$C_{1-4}$ alkylene-NR$^9$SO$_2$NR$^7$R$^8$, —$C_{1-4}$ alkylene-OH and —$C_{1-4}$ alkylene-CONR$^7$R$^8$;

each $R^4$ and each $R^6$ is independently selected from $C_{1-8}$ alkyl, halo, haloC$_{1-8}$ alkyl, haloC$_{1-8}$ alkoxy and $C_{1-8}$ alkoxy;

each $R^5$ is independently selected from $C_{1-8}$ alkyl, $C_{2-8}$ alkenyl, $C_{2-8}$ alkynyl, cyclyl, amino, amido, hydroxyl, nitro, halo, haloC$_{1-8}$ alkyl, haloC$_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^7$ and each $R^8$ is independently selected from hydrogen, $C_{1-8}$ alkyl, $R^{12}R^{13}$N—$C_{1-8}$ alkyl and hydroxyC$_{1-8}$ alkyl, or $R^7$ and $R^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more $R^{11}$;

each $R^9$ is independently selected from hydrogen and $C_{1-4}$ alkyl;

each $R^{10}$ is independently selected from $C_{1-8}$ alkyl, haloC$_{1-8}$ alkyl, cyclyl and cyclylC$_{1-8}$ alkyl, wherein said cyclyl or the cyclyl moiety comprised in said cyclylC$_{1-8}$ alkyl is optionally substituted with one or more $R^{14}$;

each $R^{11}$ is independently selected from $C_{1-8}$ alkyl, halo, $C_{1-8}$ alkoxy, hydroxyl and —NR$^{12}$R$^{13}$;

each $R^{12}$ and each $R^{13}$ is independently selected from hydrogen and $C_{1-8}$ alkyl;

each $R^{14}$ is independently selected from $C_{1-8}$ alkyl, $C_{2-8}$ alkenyl, $C_{2-8}$ alkynyl, amino, amido, hydroxyl, nitro, halo, haloC$_{1-8}$ alkyl, haloC$_{1-8}$ alkoxy, cyano, sulfinyl, sulfonyl, sulfonamide, $C_{1-8}$ alkoxy, acyl, carboxyl, O-carboxy, C-carboxy, carbamate and urea; and each $R^w$, $R^x$, $R^y$ and $R^z$ is independently selected from hydrogen, halo and $C_{1-4}$ alkyl;

with the proviso that the following compounds are excluded: 2-((2-phenylcyclopropyl)amino)cycloheptanol, and 2-((2-phenylcyclopropyl)amino)cyclopentanol.

It is furthermore preferred that the compound 2-((2-phenylcyclopropyl)amino)cyclohexanol is excluded.

In another embodiment, the present invention provides a compound of Formula I wherein $R^w$, $R^x$, $R^y$ and $R^z$ are each hydrogen, i.e. a compound of formula Ia:

Ia wherein:

A is aryl or heteroaryl, wherein said aryl or said heteroaryl is optionally substituted with one or more $R^1$;

B is hydrogen, $R^1$ or -L-E;

E is aryl or heteroaryl, wherein said aryl or said heteroaryl is optionally substituted with one or more $R^2$;

L is a bond, —O—, —NH—, —N($C_{1-4}$ alkyl)-, $C_{1-4}$ alkylene or heteroC$_{1-4}$ alkylene;

D is a cycloalkyl group having from 4 to 7 C atoms, wherein said cycloalkyl group has one or two substituents $R^3$ and is further optionally substituted with one or more $R^4$, and wherein the cycloalkyl group optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

each $R^1$ is independently selected from $C_{1-8}$ alkyl, $C_{2-8}$ alkenyl, $C_{2-8}$ alkynyl, cyclyl, amino, amido, hydroxyl, nitro, halo, haloC$_{1-8}$ alkyl, haloC$_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^2$ is independently selected from $C_{1-8}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-4}$ alkoxy, acyl, carboxyl, O-carboxy, C-carboxy, carbamate and urea;

each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$;

each $R^4$ and each $R^6$ is independently selected from $C_{1-8}$ alkyl, halo, halo$C_{1-8}$ alkyl, halo$C_{1-8}$ alkoxy and $C_{1-8}$ alkoxy;

each $R^5$ is independently selected from $C_{1-8}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl, or $R^7$ and $R^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or $SO_2$ groups, and wherein said heterocyclic ring is optionally substituted with one or more $R^{11}$;

each $R^9$ is independently selected from hydrogen and $C_{1-4}$ alkyl;

each $R^{10}$ is independently selected from $C_{1-8}$ alkyl, halo$C_{1-8}$ alkyl, cyclyl and cyclyl$C_{1-8}$ alkyl, wherein said cyclyl or the cyclyl moiety comprised in said cyclyl$C_{1-8}$ alkyl is optionally substituted with one or more $R^{14}$;

each $R^{11}$ is independently selected from $C_{1-8}$ alkyl, halo, $C_{1-8}$ alkoxy, hydroxyl and —$NR^{12}R^{13}$;

each $R^{12}$ and each $R^{13}$ is independently selected from hydrogen and $C_{1-8}$ alkyl; and each $R^{14}$ is independently selected from $C_{1-8}$ alkyl, $C_{2-8}$ alkenyl, $C_{2-8}$ alkynyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea;

with the proviso that the following compounds are excluded:
2-((2-phenylcyclopropyl)amino)cycloheptanol, and
2-((2-phenylcyclopropyl)amino)cyclopentanol.

It is furthermore preferred that the compound 2-((2-phenylcyclopropyl)amino)cyclohexanol is excluded.

In another embodiment, the invention provides a compound of formula Ia as defined above wherein the substituents of the cyclopropyl moiety -A-B and —NH-D are in the trans-configuration, i.e. a compound of formula Ia-1:

Ia-1 wherein the groups and variables of formula Ia-1, including A, B, D, E, L, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$, are as defined above in relation to a compound of formula Ia, with the proviso that the following compounds are excluded:
2-((2-phenylcyclopropyl)amino)cycloheptanol, and
2-((2-phenylcyclopropyl)amino)cyclopentanol.

It is furthermore preferred that the compound 2-((2-phenylcyclopropyl)amino)cyclohexanol is excluded.

The above chemical representation for a compound of formula Ia-1 does not intend to indicate absolute stereochemistry of the two chiral centers on the cyclopropyl ring, but only their relative stereochemistry (which is trans). Thus a compound of formula Ia-1 could likewise be represented as

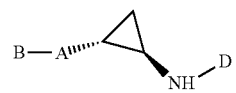

A compound of formula Ia-1 therefore relates to the individual optically active trans isomers as well as any mixtures thereof.

In another embodiment, the invention provides a compound of formula I as defined above wherein each $R^w$, $R^x$, $R^y$ and $R^z$ is independently selected from hydrogen, halo and $C_{1-4}$ alkyl, with the proviso that at least one of $R^w$, $R^x$, $R^y$ and $R^z$ is not hydrogen; that compound is referred to as a compound of formula Ib in the following. In a more preferred embodiment, $R^w$ is selected from halo and $C_{1-4}$ alkyl, preferably from fluoro and methyl, and each $R^x$, $R^y$ and $R^z$ is hydrogen. A compound of formula I wherein $R^w$ is selected from halo and $C_{1-4}$ alkyl, preferably from fluoro and methyl, and each $R^x$, $R^y$ and $R^z$ is hydrogen is referred to as a compound of formula Ic in the following.

Also included within the scope of the invention are all isomers, including all stereoisomers and mixtures thereof, of the compounds of formula I, Ia, Ia-1, Ib and Ic (as defined herein). All salts and all solvates, preferably pharmaceutically acceptable salts and solvates, of the compounds of formula I, Ia, Ia-1, Ib and Ic are also encompassed within the scope of the invention. Furthermore, all physical forms (including amorphous and crystalline forms) of any such compounds are also encompassed within the scope of the invention. Any reference to a compound of formula I, Ia, Ia-1, Ib or Ic, respectively, should be construed, unless otherwise indicated, as a reference to a compound of formula I, Ia, Ia-1, Ib or Ic (respectively), any isomer thereof (including any stereoisomer thereof or any mixtures thereof), any salt thereof (including any pharmaceutically acceptable salt thereof), any solvate thereof (including any pharmaceutically acceptable solvate thereof), and any physical form thereof.

The compounds of formula Ia, including also the compounds of formula Ia-1, are particularly preferred compounds according to the present invention. The most preferred compounds of the invention are the compounds of formula Ia-1.

Any chemical drawing or formula given herein is intended to represent unlabeled forms as well as isotopically labeled forms of the compounds of the invention. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Particularly preferred are the deuterated forms of the compounds of the invention, i.e. a compound of formula I, Ia, Ia-1, Ib and Ic above wherein one or more hydrogen atoms has been replaced with deuterium. Isotopically labeled compounds of the invention can generally be prepared by carrying out the procedures disclosed in the schemes or in the examples and preparations described below by substituting a readily available isotopically labeled reagent for a non-isotopically labeled reagent. In addition to the unlabeled form, all isotopically labeled forms of the compounds of formula I, Ia, Ia-1, Ib and Ic are included within the scope of the invention.

In a compound of formula I, Ia, Ib or Ic the substituents -A-B and —NH-D on the cyclopropyl moiety are preferably in the trans-configuration.

The compounds of formula I, Ia, Ia-1, Ib and Ic are potent inhibitors of LSD1 and therefore can be useful for the treatment or prevention of any disease associated with LSD1.

The invention thus provides a pharmaceutical composition comprising a compound of Formula I, Ia, Ia-1, Ib or Ic and a pharmaceutically acceptable carrier.

In one embodiment, the invention provides a pharmaceutical composition comprising a compound of formula I

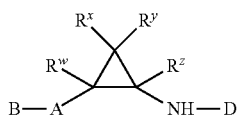

wherein the groups and variables in formula I, including A, B, D, $R^w$, $R^x$, $R^y$ and $R^z$, are as defined above, with the proviso that the following compounds are excluded:
2-((2-phenylcyclopropyl)amino)cycloheptanol, and
2-((2-phenylcyclopropyl)amino)cyclopentanol;
and a pharmaceutically acceptable carrier.

In another embodiment, the invention provides a pharmaceutical composition comprising a compound of formula Ia

wherein the groups and variables in formula Ia, including A, B, and D, are as defined above, with the proviso that the following compounds are excluded:
2-((2-phenylcyclopropyl)amino)cycloheptanol, and
2-((2-phenylcyclopropyl)amino)cyclopentanol;
and a pharmaceutically acceptable carrier.

In another embodiment, the invention provides a pharmaceutical composition comprising a compound of formula Ia-1

wherein the groups and variables in formula Ia-1, including A, B, and D, are as defined above, with the proviso that the following compounds are excluded:
2-((2-phenylcyclopropyl)amino)cycloheptanol, and
2-((2-phenylcyclopropyl)amino)cyclopentanol;
and a pharmaceutically acceptable carrier.

Preferred embodiments of the compounds of Formula I, Ia, Ia-1, Ib and Ic, e. g. for use in the compositions of the invention, are defined and described herein below in more detail.

In another aspect, the invention provides a method of treating or preventing a disease comprising administering, to a patient (preferably a human) in need of such treatment or prevention, an amount of a compound of Formula I, Ia, Ia-1, Ib or Ic (as described above or as defined in the embodiments thereof described below) effective to treat or prevent said disease. In one embodiment, such disease is a disease associated with LSD1.

In a related aspect, the invention provides a compound of Formula I, Ia, Ia-1, Ib or Ic (as described above or as defined in the embodiments thereof as described below) for use as a medicament. In a more specific embodiment, the invention provides a compound of Formula I, Ia, Ia-1, Ib or Ic for use in the treatment or prevention of a disease associated with LSD1.

Thus, in one embodiment, the invention provides a compound of formula I

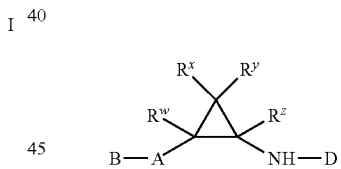

wherein the groups and variables in formula I, including A, B, D, $R^w$, $R^x$, $R^y$ and $R^z$, are as defined above, with the proviso that the following compounds are excluded:
2-((2-phenylcyclopropyl)amino)cycloheptanol, and
2-((2-phenylcyclopropyl)amino)cyclopentanol;
for use as a medicament.

In another embodiment, the invention provides a compound of formula Ia

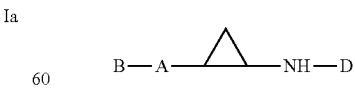

wherein the groups and variables in formula Ia, including A, B, and D, are as defined above, with the proviso that the following compounds are excluded:
2-((2-phenylcyclopropyl)amino)cycloheptanol, and
2-((2-phenylcyclopropyl)amino)cyclopentanol;
for use as a medicament.

In another embodiment, the invention provides a compound of formula Ia-1

Ia-1 wherein the groups and variables in formula Ia-1, including A, B, and D, are as defined above, with the proviso that the following compounds are excluded:
2-((2-phenylcyclopropyl)amino)cycloheptanol, and
2-((2-phenylcyclopropyl)amino)cyclopentanol;
for use as a medicament.

In yet another aspect, the invention provides a method of inhibiting LSD1 activity comprising administering, to a patient in need of treatment, an amount of a compound of Formula I, Ia, Ia-1, Ib or Ic sufficient to inhibit LSD1 activity. Preferably the patient is a human. In a related aspect, the invention provides a compound of Formula I, Ia, Ia-1, Ib or Ic as herein defined for use as a LSD1 inhibitor. Preferred embodiments of the compounds of Formula I, Ia, Ia-1, Ib or Ic for use herein are as described in more detail below.

In another aspect, the invention provides a method of treating or preventing cancer comprising administering, to a patient (preferably a human) in need of such treatment or prevention, an amount of a compound of Formula I, Ia, Ia-1, Ib or Ic (as defined above or as defined in the embodiments described in more detail herein) sufficient to treat or prevent such cancer. In a related aspect, the invention provides a method of treating or preventing a cancer wherein said cancer is chosen from breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma and myeloma, comprising administering to a patient (preferably a human) in need of such treatment or prevention, an amount of a compound of Formula I, Ia, Ia-1, Ib or Ic (as defined above or as defined in the embodiments described in more detail herein) sufficient to treat or prevent such cancer. In an even more specific aspect, said cancer is chosen from prostate, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia). In one specific aspect, the cancer is breast cancer. In one specific aspect, the cancer is colorectal cancer. In one specific aspect, the cancer is lymphoma. In one specific aspect, the cancer is myeloma. In a preferred embodiment, the method comprises administering a therapeutically effective amount of a compound of Formula I, Ia, Ia-1, Ib or Ic sufficient for treating or preventing said cancer. In a preferred aspect, the therapeutically effective amount of a compound of Formula I, Ia, Ia-1, Ib or Ic is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels. While the present invention relates to both the treatment and the prevention of cancer, the treatment of cancer is particularly preferred.

Thus, in one embodiment, the invention provides a method of treating or preventing cancer comprising administering, to a patient (preferably a human) in need of such treatment or prevention, an amount of a compound of Formula I

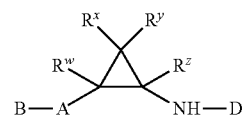

I wherein the groups and variables in formula I, including A, B, D, $R^w$, $R^x$, $R^y$ and $R^z$, are as defined above, with the proviso that the following compounds are excluded:
2-((2-phenylcyclopropyl)amino)cycloheptanol, and
2-((2-phenylcyclopropyl)amino)cyclopentanol.

In another embodiment, the invention provides a method of treating or preventing cancer comprising administering, to a patient (preferably a human) in need of such treatment or prevention, an amount of a compound of Formula Ia

Ia wherein the groups and variables in formula Ia, including A, B, and D, are as defined above, with the proviso that the following compounds are excluded:
2-((2-phenylcyclopropyl)amino)cycloheptanol, and
2-((2-phenylcyclopropyl)amino)cyclopentanol.

In another embodiment, the invention provides a method of treating or preventing cancer comprising administering, to a patient (preferably a human) in need of such treatment or prevention, an amount of a compound of Formula Ia-1

Ia-1 wherein the groups and variables in formula Ia-1, including A, B, and D, are as defined above, with the proviso that the following compounds are excluded:
2-((2-phenylcyclopropyl)amino)cycloheptanol, and
2-((2-phenylcyclopropyl)amino)cyclopentanol.

In a related aspect, the invention provides a compound of Formula I, Ia, Ia-1, Ib or Ic (as defined above or as defined in the embodiments described in more detail herein), for use in the treatment or prevention of cancer. In another related aspect, the invention provides a compound of Formula I, Ia, Ia-1, Ib or Ic for use in the treatment or prevention of a cancer wherein said cancer is chosen from breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma and myeloma. In a more specific aspect, said cancer is chosen from prostate, brain, colorectal, lung, breast, skin, and blood cancer. In one specific aspect, the cancer is prostate cancer. In one specific aspect, the cancer is lung cancer. In one specific aspect, the cancer is brain cancer. In one specific aspect, the cancer is blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia). In one specific aspect, the cancer is breast cancer. In one specific aspect, the cancer is colorectal cancer. In one specific aspect, the cancer is lymphoma. In one specific aspect, the cancer is myeloma. In preferred embodiment, a therapeutically effective amount of a compound of Formula I, Ia, Ia-1, Ib or Ic sufficient for treating or preventing said cancer is administered. In a preferred aspect, the therapeutically effective amount of a compound of Formula I, Ia, Ia-1, Ib or Ic is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels.

Thus, in one embodiment, the invention provides a compound of formula I

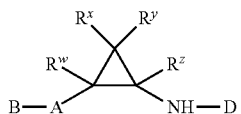

wherein the groups and variables in formula I, including A, B, D, R$^w$, R$^x$, R$^y$ and R$^z$, are as defined above, with the proviso that the following compounds are excluded:
2-((2-phenylcyclopropyl)amino)cycloheptanol, and
2-((2-phenylcyclopropyl)amino)cyclopentanol;
for use in the treatment or prevention of cancer.

In another embodiment, the invention provides a compound of formula Ia

wherein the groups and variables in formula Ia, including A, B, and D, are as defined above, with the proviso that the following compounds are excluded:
2-((2-phenylcyclopropyl)amino)cycloheptanol, and
2-((2-phenylcyclopropyl)amino)cyclopentanol;
for use in the treatment or prevention of cancer.

In another embodiment, the invention provides a compound of formula Ia-1

wherein the groups and variables in formula Ia-1, including A, B, and D, are as defined above, with the proviso that the following compounds are excluded:
2-((2-phenylcyclopropyl)amino)cycloheptanol, and
2-((2-phenylcyclopropyl)amino)cyclopentanol;
for use in the treatment or prevention of cancer.

In another aspect, the invention provides a method of treating or preventing a neurological disease (e.g., a neurodegenerative disease) comprising administering, to a patient in need of such treatment or prevention, an amount of a compound of Formula I, Ia, Ia-1, Ib or Ic (as defined above or in the embodiments described in more detail herein) sufficient to treat or prevent said neurological disease. In a related aspect, the invention provides a method of treating or preventing a neurological disease wherein said neurological disease is selected from depression, Alzheimer's disease, Huntington disease, Parkinson's disease, Amyotrophic Lateral Sclerosis, Dementia with Lewy Bodies, or Frontotemporal Dementia, particularly from depression, Alzheimer's disease, Huntington disease, Parkinson's disease, or Dementia with Lewy Bodies, comprising administering to a patient (preferably a human) in need of such treatment or prevention, an amount of a compound of Formula I, Ia, Ia-1, Ib or Ic (as defined above or as defined in the embodiments described in more detail herein) sufficient to treat or prevent such neurological disease. In a preferred embodiment, the method comprises administering a therapeutically effective amount of a compound of Formula I, Ia, Ia-1, Ib or Ic sufficient for treating or preventing said neurological disease. In a preferred aspect, the therapeutically effective amount of a compound of Formula I, Ia, Ia-1, Ib or Ic is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels.

In another related aspect, the invention provides a compound of Formula I, Ia, Ia-1, Ib or Ic (as defined above or in the embodiments described in more detail herein) for use in the treatment or prevention of a neurological disease (e.g., a neurodegenerative disease). In one embodiment, said neurological disease is selected from depression, Alzheimer's disease, Huntington disease, Parkinson's disease, Amyotrophic Lateral Sclerosis, Dementia with Lewy Bodies and Frontotemporal Dementia, particularly from depression, Alzheimer's disease, Huntington disease, Parkinson's disease and Dementia with Lewy Bodies. In a preferred embodiment, a therapeutically effective amount of a compound of Formula I, Ia, Ia-1, Ib or Ic sufficient for treating or preventing said neurological disease is administered. In a preferred aspect, the therapeutically effective amount of a compound of Formula I, Ia, Ia-1, Ib or Ic is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels.

In another preferred aspect, the therapeutically effective amount is an amount sufficient to modulate histone-3 lysine-9 methylation levels.

In another aspect, the invention provides a method of treating or preventing a viral infection comprising administering to a patient in need thereof (preferably a human) an amount of a compound of Formula I, Ia, Ia-1, Ib or Ic (as defined above or in the embodiments described in more detail herein) sufficient to treat or prevent said viral infection. In a related aspect, the invention also provides a compound of Formula I, Ia, Ia-1, Ib or Ic (as defined above or in the embodiments described in more detail herein) for use in treating or preventing a viral infection. In one specific embodiment, the viral infection is a herpesvirus infection. In a more specific embodiment, the herpesvirus infection is caused by and/or associated with a herpesvirus chosen from HSV-1, HSV-2, and Epstein-Barr virus. In another embodiment, the viral infection is caused by and/or associated with HIV. In another embodiment, the viral infection is caused by and/or associated with a Hepadnavirus (i.e. a virus of the Hepadnaviridae family), particularly Hepatitis B virus (HBV). In another embodiment, the viral infection is caused by and/or associated with a Flavivirus (i.e. a virus of the Flaviviridae family), particularly Hepatitis C virus (HCV), yellow fever virus, West Nile virus, Dengue virus or Japanese encephalitis virus, and more preferably HCV. In an even more specific embodiment, the invention provides a method for treating or preventing viral reactivation after latency, the method comprising administering to an individual (preferably a human) a compound of Formula I, Ia, Ia-1, Ib or Ic (as defined above or in the embodiments described in more detail herein). Accordingly, the invention also provides a compound of Formula I, Ia, Ia-1, Ib or Ic (as defined above or in the embodiments described in more detail herein) for use in treating or preventing viral reactivation after latency. In a specific embodiment, the virus that is reactivating is a herpesvirus. In a more specific embodiment, the herpesvirus that is reactivating is chosen from HSV-1, HSV-2, and Epstein-Barr virus. In an even more specific embodiment, the virus that is reactivating is HSV. In a further specific embodiment, the virus that is reactivating is HIV.

In still another aspect, the invention provides the use of a compound of Formula I, Ia, Ia-1, Ib or Ic (as defined above or in the embodiments described in more detail herein) for the manufacture of a medicament for the treatment or prevention of cancer. In a preferred embodiment, said cancer is chosen from breast cancer, lung cancer, prostate cancer, colorectal cancer, brain cancer, skin cancer, blood cancer (e.g., leukemia, including, for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphoma and myeloma.

In still another aspect, the invention provides the use of a compound of Formula I, Ia, Ia-1, Ib or Ic (as defined above or in the embodiments described in more detail herein) for the manufacture of a medicament for the treatment or prevention of a neurological disease (e.g., a neurodegenerative disease). In a preferred embodiment said neurological disease is selected from depression, Alzheimer's disease, Huntington disease, Parkinson's disease, Amyotrophic Lateral Sclerosis, Dementia with Lewy Bodies, or Frontotemporal Dementia, particularly from depression, Alzheimer's disease, Huntington disease, Parkinson's disease, and Dementia with Lewy Bodies.

In still another aspect, the invention provides the use of a compound of Formula I, Ia, Ia-1, Ib or Ic (as defined above or in the embodiments described in more detail herein) for the manufacture of a medicament for the treatment or prevention of a viral infection. In a preferred embodiment, said viral infection is a herpesvirus infection (e.g., a herpesvirus infection caused by and/or associated with a herpesvirus chosen from HSV-1, HSV-2, and Epstein-Barr virus) or a viral infection caused by and/or associated with HIV. In another preferred embodiment, said viral infection is caused by and/or associated with a Hepadnavirus, particularly Hepatitis B virus (HBV). In another embodiment, said viral infection is caused by and/or associated with a Flavivirus, particularly Hepatitis C virus (HCV), yellow fever virus, West Nile virus, Dengue virus or Japanese encephalitis virus, and more preferably HCV.

In still another aspect, the invention provides the use of a compound of Formula I, Ia, Ia-1, Ib or Ic (as defined above or in the embodiments described in more detail herein) for the manufacture of a medicament for the treatment or prevention of viral reactivation after latency. In a preferred embodiment, the virus that is reactivating is a herpesvirus (e.g., HSV-1, HSV-2, or Epstein-Barr virus), HSV, or HIV.

In still another aspect, the invention provides a method for identifying a compound which is a selective inhibitor of LSD1, the method comprising selecting or providing a compound of Formula I, Ia, Ia-1, Ib or Ic as defined herein, and determining the ability of the compound to inhibit LSD1 and MAO-A and/or MAO-B, wherein a compound that inhibits LSD1 to a greater extent than MAO-A and/or MAO-B is identified as a LSD1 selective inhibitor. The compound of this aspect that is an LSD1 inhibitor can be used to treat disease, particularly human disease.

In another aspect, the invention provides a process for the preparation of a compound of formula I, or a salt thereof, which comprises reacting a compound of formula II

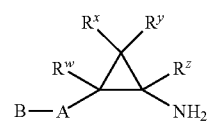

wherein A, B, $R^w$, $R^x$, $R^y$, $R^z$ have the meaning disclosed above in relation to a compound of formula I, with a compound of formula III

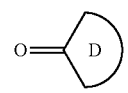

wherein D has the meaning disclosed above in relation to a compound of formula I and wherein the group(s) $R^3$ on ring D are optionally protected with a protecting group,
in the presence of a reducing agent, followed by the removal of any protecting group that may be present. The reducing agent may be, e.g., a borohydride, such as sodium borohydride or sodium triacetoxyborohydride.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

The present invention relates to the identification of compounds and their use in treating and preventing diseases. The present invention provides compounds of Formula I, Ia, Ia-1, Ib and Ic, pharmaceutical compositions comprising a compound of Formula I, Ia, Ia-1, Ib or Ic and a pharmaceutically acceptable carrier, and their use for treating diseases. One use of the compounds of Formula I, Ia, Ia-1, Ib and Ic is for treating cancer.

The present invention provides a compound of Formula I

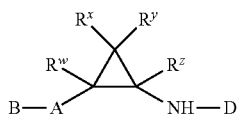

I

In a compound of formula I, each $R^w$, $R^x$, $R^y$ and $R^z$ is independently selected from hydrogen, halo and $C_{1-4}$ alkyl. In one embodiment, each $R^w$, $R^x$, $R^y$ and $R^z$ is independently selected from hydrogen, fluoro and $C_{1-4}$ alkyl, preferably from hydrogen, fluoro and methyl. In another embodiment, each $R^w$, $R^x$, $R^y$ and $R^z$ is independently selected from hydrogen and fluoro. In another embodiment, $R^w$ is fluoro and each $R^x$, $R^y$ and $R^z$ is independently selected from hydrogen, halo and $C_{1-4}$ alkyl; preferably, $R^w$ is fluoro and each $R^x$, $R^y$ and $R^z$ is hydrogen. In another embodiment, $R^z$ is fluoro and each $R^w$, $R^x$ and $R^y$ is independently selected from hydrogen, halo and $C_{1-4}$ alkyl; preferably, $R^z$ is fluoro and each $R^w$, $R^x$ and $R^y$ is hydrogen. In another embodiment, $R^w$ and $R^z$ are fluoro and each $R^x$ and $R^y$ is independently selected from hydrogen, halo and $C_{1-4}$ alkyl; preferably, $R^w$ and $R^z$ are fluoro and each $R^x$ and $R^y$ is hydrogen. In a preferred embodiment, $R^w$ is selected from hydrogen, halo and $C_{1-4}$ alkyl, preferably from hydrogen, fluoro and methyl, and each $R^x$, $R^y$ and $R^z$ is hydrogen. In a more preferred embodiment, each $R^w$, $R^x$, $R^y$ and $R^z$ is hydrogen. A compound of formula I wherein each $R^w$, $R^x$, $R^y$ and $R^z$ is hydrogen is a compound of formula Ia, which can be depicted as follows:

Ia

In another embodiment, in a compound of formula I each $R^w$, $R^x$, $R^y$ and $R^z$ is independently selected from hydrogen, halo and $C_{1-4}$ alkyl with the proviso that at least one is not hydrogen, this is a compound of formula Ib. In a more preferred embodiment, $R^w$ is selected from halo and $C_{1-4}$ alkyl, preferably fluoro and methyl, and each $R^x$, $R^y$ and $R^z$ is hydrogen. A compound of formula I wherein $R^w$ is selected from halo and $C_{1-4}$ alkyl, preferably fluoro and methyl, and each $R^x$, $R^y$ and $R^z$ is hydrogen is a compound of formula Ic. Preferably, in a compound of formula Ic $R^w$ is methyl.

In a compound of formula I, Ia, Ia-1, Ib or Ic, the group A is aryl or heteroaryl, wherein said aryl or said heteroaryl is optionally substituted with one or more $R^1$. In one embodiment, A is aryl (preferably phenyl or naphthyl) optionally substituted with one or more $R^1$. In a specific embodiment, A is phenyl optionally substituted with one or more $R^1$. In another specific embodiment, A is naphthyl optionally substituted with one or more $R^1$. In another embodiment, A is heteroaryl (preferably monocyclic heteroaryl), optionally substituted with one or more $R^1$. In a preferred embodiment, A is phenyl, naphthyl or monocyclic heteroaryl, wherein said phenyl, naphthyl or monocyclic heteroaryl is optionally substituted with one or more $R^1$. Preferably, A is monocyclic aryl (i.e. phenyl) or monocyclic heteroaryl, wherein said monocyclic aryl or said monocyclic heteroaryl is optionally substituted with one or more $R^1$. More preferably, A is phenyl, pyridyl, thiophenyl, pyrrolyl, furanyl, or thiazolyl, wherein A (i.e. said phenyl, said pyridyl, said thiophenyl, said pyrrolyl, said furanyl, or said thiazolyl) is optionally substituted with one or more $R^1$. More preferably, A is phenyl, pyridyl, thiazolyl or thiophenyl, wherein A (i.e. said phenyl, said pyridyl, said thiazolyl or said thiophenyl) is optionally substituted with one or more $R^1$. Still more preferably, A is phenyl, pyridyl or thiazolyl, wherein A is optionally substituted with one or more $R^1$. Even more preferably, A is phenyl, 3-pyridyl or 5-thiazolyl, as shown below:

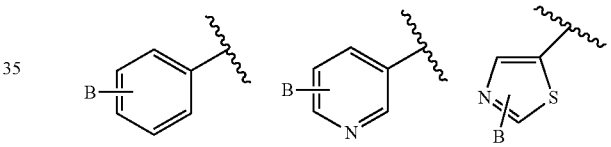

wherein A is optionally substituted with one or more $R^1$. In one embodiment, A is phenyl or pyridyl, preferably phenyl or 3-pyridyl. In another embodiment, A is phenyl. In another embodiment, A is pyridyl, preferably 3-pyridyl. In another embodiment, A is thiazolyl, preferably 5-thiazolyl. In one embodiment, A has 0, 1 or 2 substituents $R^1$. In a further embodiment, A has 0 or 1 substituent $R^1$. In a further embodiment, A has 0 substituent $R^1$. In a further embodiment, A has 1 or 2 substituents $R^1$. In a further embodiment, A has 1 substituent $R^1$. In the aforementioned embodiments, in which A has 0, 1 or 2 substituents $R^1$, the total number of substituents $R^1$ is defined, including the possibility that B may be $R^1$. Accordingly, if A has 0 substituents $R^1$, then B is not $R^1$.

In a compound of formula I, Ia, Ia-1, Ib or Ic, B is hydrogen, $R^1$ or -L-E. In one embodiment, B is -L-E. In a preferred embodiment, B is hydrogen or $R^1$. In a further preferred embodiment, B is hydrogen. In another embodiment, B is $R^1$.

In a compound of formula I, Ia, Ia-1, Ib or Ic, E is aryl or heteroaryl, wherein said aryl or said heteroaryl is optionally substituted with one or more $R^2$. In one embodiment, E is an aryl group (e.g., phenyl, naphthyl or anthracenyl) optionally substituted with one or more $R^2$. In another embodiment, E is a heteroaryl group (e.g., pyridinyl, thiophenyl, pyrrolyl, furanyl, thiazolyl, oxazolyl, isoxazolyl, oxadiazolyl, thiadiazolyl, triazinyl, pyridazinyl, pyrazinyl, pyrimidinyl, quinolyl, indolyl, pyrazolyl, indazolyl, imidazolyl or benzimidazolyl) optionally substituted with one or more $R^2$. Preferably, E is monocyclic aryl (i.e. phenyl) or monocyclic heteroaryl, wherein said monocyclic aryl or said monocyclic heteroaryl is optionally substituted with one or more $R^2$. In one embodiment, E has 0, 1, 2 or 3 substituents $R^2$. In another embodiment, E has 0, 1 or 2 substituents $R^2$. In another embodiment, E has 0 or 1 substituents $R^2$. In another embodiment, E has 0 substituents $R^2$. In another embodiment, E has 1 substituent $R^2$. Preferably, E is phenyl optionally substituted with one or more $R^2$. In one embodiment, E is phenyl optionally substituted with one, two or three $R^2$. In another embodiment, E is phenyl optionally substituted with one or two $R^2$. In a further embodiment, E is phenyl optionally substituted with one $R^2$. In another embodiment, E is phenyl. In another embodiment, E is phenyl substituted with one, two or three, preferably one or two, $R^2$. In another preferred embodiment, E is heteroaryl, preferably monocyclic heteroaryl, optionally substituted with one or more (preferably one, two or three) $R^2$. In one embodiment, E is heteroaryl, preferably monocyclic heteroaryl. In another embodiment, E is heteroaryl (preferably monocyclic heteroaryl) substituted with one, two or three, preferably one or two, $R^2$.

In a compound of formula I, Ia, Ia-1, Ib or Ic, L is a bond, —O—, —NH—, —N($C_{1-4}$ alkyl)-, $C_{1-4}$ alkylene or hetero$C_{1-4}$ alkylene. Preferably said hetero$C_{1-4}$ alkylene is —$(CH_2)_x$—NH— or —$(CH_2)_x$—O—, wherein x is 1, 2, 3 or 4; still more preferably, said —$(CH_2)_x$—NH— or —$(CH_2)_x$—O— groups are linked to ring A through the N or O atom, respectively, and are linked to ring E through the —$(CH_2)_x$— group. More preferably, said hetero$C_{1-4}$ alkylene is —$CH_2$—NH— or —$CH_2$—O—, wherein said —$CH_2$—NH— and —$CH_2$—O— groups are linked to ring A through the N or O atom, respectively, and are linked to ring E through the —$CH_2$— group.

In one embodiment, L is a bond, —O—, —NH—, —N($C_{1-4}$ alkyl)-, —$CH_2$—, $CH_2$—$CH_2$—, —$CH_2$—NH— or —$CH_2$—O—. In a preferred embodiment, L is a bond, —O—, —NH—, —N($C_{1-4}$ alkyl)-, —$CH_2$—NH— or —$CH_2$—O—. In a more preferred embodiment, L is a bond, —O—, —NH—, —$CH_2$—NH—, or —$CH_2$—O—. In a still more preferred embodiment, L is a bond or —$CH_2$—O—. In a further preferred embodiment, L is a bond. In another embodiment, L is —O—, —NH—, —N($C_{1-4}$ alkyl)-, $C_{1-4}$ alkylene or hetero$C_{1-4}$ alkylene; preferably, L is —O—, —NH—, —N($C_{1-4}$ alkyl)-, —$CH_2$—, $CH_2$—$CH_2$—, —$CH_2$—NH— or —$CH_2$—O—; more preferably L is —O—, —NH—, —N($C_{1-4}$ alkyl)-, —$CH_2$—NH— or —$CH_2$—O—; even more preferably L is —O—, —NH—, —$CH_2$—NH—, or —$CH_2$—O—; still more preferably L is —NH—, —$CH_2$—NH—, or —$CH_2$—O—; and particularly preferably L is —$CH_2$—O—. Preferably, in all these embodiments, said —$CH_2$—NH— or —$CH_2$—O— groups are linked to ring A through the N or O atom, respectively, and are linked to ring E through the —$CH_2$— group.

In one embodiment, B is -L-E; E is aryl or heteroaryl, wherein said aryl or said heteroaryl is optionally substituted with one or more $R^2$; and L is a bond, —O—, —NH—, —$CH_2$—NH—, or —$CH_2$—O—, wherein the groups —$CH_2$—NH— and —$CH_2$—O— are linked to ring A through the N or O atom, respectively, and are linked to ring E through the —$CH_2$— group. In another embodiment, B is -L-E; E is phenyl optionally substituted with one or more $R^2$; and L is a bond, —O—, —NH—, —$CH_2$—NH—, or —$CH_2$—O—, wherein the groups —$CH_2$—NH— and —$CH_2$—O— are linked to ring A through the N or O atom, respectively, and are linked to ring E through the —$CH_2$— group. In another embodiment, B is -L-E; E is aryl or heteroaryl, wherein said aryl or said heteroaryl is optionally substituted with one or more $R^2$; and L is a bond or —$CH_2$—O—, wherein the group —$CH_2$—O— is linked to ring A through the O atom and to ring E through the —$CH_2$— group. In another embodiment, B is -L-E; E is phenyl optionally substituted with one or more $R^2$; and L is a bond or —$CH_2$—O—, wherein the group —$CH_2$—O— is linked to ring A through the O atom and to ring E through the —$CH_2$— group. In another embodiment, B is -L-E; E is aryl or heteroaryl, wherein said aryl or said heteroaryl is optionally substituted with one or more $R^2$; and L is a bond. In another embodiment, B is -L-E; E is phenyl optionally substituted with one or more $R^2$; and L is a bond. In another embodiment, B is -L-E; E is heteroaryl optionally substituted with one or more $R^2$; and L is a bond. In another embodiment, B is -L-E; E is aryl or heteroaryl; and L is a bond. In another embodiment, B is -L-E; E is aryl or heteroaryl, wherein said aryl or said heteroaryl is optionally substituted with one or more $R^2$; and L is —$CH_2$—O—, wherein the group —$CH_2$—O— is linked to ring A through the O atom and to ring E through the —$CH_2$— group. In another embodiment, B is -L-E; E is phenyl optionally substituted with one or more $R^2$; and L is —$CH_2$—O—, wherein the group —$CH_2$—O— is linked to ring A through the O atom and to ring E through the —$CH_2$— group. In another embodiment, B is -L-E; E is heteroaryl (preferably monocyclic heteroaryl, more preferably pyridinyl), wherein said heteroaryl is optionally substituted with one or more $R^2$; and L is —$CH_2$—O—, wherein the group —$CH_2$—O— is linked to ring A through the O atom and to ring E through the —$CH_2$— group. In another embodiment, B is -L-E; E is aryl or heteroaryl, wherein said aryl or said heteroaryl is optionally substituted with one or more $R^2$; and L is —O—, —NH—, —N($C_1$ alkyl)-, $C_{1-4}$ alkylene, or —$CH_2$—NH—, and more preferably L is —O—, —NH— or —$CH_2$—NH— wherein the group —$CH_2$—NH— is linked to ring A through the N atom and to ring E through the —$CH_2$— group. In another embodiment, B is -L-E; E is aryl or heteroaryl, wherein said aryl or said heteroaryl is optionally substituted with one or more $R^2$; and L is —NH— or —$CH_2$—NH—, wherein the group —$CH_2$—NH— is linked to ring A through the N atom and to ring E through the —$CH_2$— group.

In a compound of formula I, Ia, Ia-1, Ib or Ic, each $R^1$ is independently selected from $C_{1-8}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea. When there is more than one $R^1$ as a substituent on ring A, they can be the same or different. In one embodiment, each $R^1$ is independently selected from $C_{1-8}$ alkyl, cyclyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another embodiment, each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another embodiment, each $R^1$ is independently selected from $C_{1-8}$ alkyl, amino, amido, halo, halo$C_{1-8}$ alkyl, halo$C_{1-8}$ alkoxy, cyano, sulfonamide, $C_{1-8}$ alkoxy, acyl, carboxyl, carbamate, and urea. In another embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl), preferably each $R^1$ is independently selected from halo, $C_{1-4}$ alkyl (e.g. methyl) and $C_{1-4}$ alkoxy (e.g. methoxy). In another embodiment, each $R^1$ is independently selected from halo, $C_{1-4}$ alkyl and $C_{3-6}$ cycloalkyl.

In a compound of formula I, Ia, Ia-1, Ib or Ic, each $R^2$ is independently selected from $C_{1-8}$ alkyl, $C_{2-8}$ alkenyl, $C_{2-8}$ alkynyl, cyclyl, amino, amido, hydroxyl, nitro, halo, $haloC_{1-8}$ alkyl, $haloC_{1-8}$ alkoxy, cyano, sulfinyl, sulfonyl, sulfonamide, $C_{1-8}$ alkoxy, acyl, carboxyl, O-carboxy, C-carboxy, carbamate and urea. When there is more than one $R^2$ as a substituent on ring E, they can be the same or different. In one embodiment, each $R^2$ is independently selected from $C_{1-8}$ alkyl, cyclyl, hydroxyl, halo, $haloC_{1-8}$a alkyl, $haloC_{1-8}$ alkoxy, cyano, sulfonamide and $C_{1-8}$ alkoxy. Preferably, each $R^2$ is independently selected from $C_{1-8}$ alkyl, cyclyl, hydroxyl, halo, $haloC_{1-8}$ alkyl, $haloC_{1-8}$ alkoxy, cyano, N-sulfonamido and $C_{1-8}$ alkoxy; more preferably each $R^2$ is independently selected from $C_{1-8}$ alkyl, hydroxyl, halo, $haloC_{1-8}$ alkyl, $haloC_{1-8}$ alkoxy, cyano, N-sulfonamido and $C_{1-8}$ alkoxy. In another embodiment, each $R^2$ is independently selected from hydroxyl, halo (for example fluoro or chloro), $haloC_{1-8}$ alkyl (for example trifluoromethyl) and sulfonamide (preferably N-sulfonamido). In another embodiment, each $R^2$ is independently selected from hydroxyl, halo, $haloC_{1-8}$ alkyl and N-sulfonamido. In another embodiment, each $R^2$ is independently selected from hydroxyl, halo, $haloC_{1-8}$ alkyl and —$NR'SO_2R$ (wherein R and R' are as defined herein below; preferably R' is H and R is $C_{1-8}$ alkyl (for example, methyl, ethyl or isopropyl) or R' is H and R is optionally substituted phenyl). In another embodiment, each $R^2$ is independently selected from hydroxyl, halo, $haloC_{1-8}$ alkyl and —$NHSO_2R$ (wherein R is $C_{1-8}$ alkyl (for example, methyl, ethyl or isopropyl), optionally substituted phenyl (for example phenyl, 2-cyanophenyl, 3-cyanophenyl, 4-cyanophenyl, 2-aminophenyl, 3-aminophenyl or 4-aminophenyl), optionally substituted heterocycloalkyl (for example piperazin-1-yl), or optionally substituted heteroaryl (for example 3-pyridyl or 6-amino-3-pyridyl)). In another embodiment, each $R^2$ is independently selected from hydroxyl, halo and $haloC_{1-8}$ alkyl. In another embodiment, each $R^2$ is independently selected from hydroxyl, halo and $haloC_{1-4}$ alkyl. In another embodiment, each $R^2$ is independently selected from hydroxyl, chloro, fluoro or trifluoromethyl. In a further embodiment, ring E is substituted with one $R^2$ and said $R^2$ is —$NHSO_2R$, wherein R is $C_{1-8}$ alkyl (for example, methyl, ethyl or isopropyl), optionally substituted phenyl (for example phenyl or 2-cyanophenyl), optionally substituted heterocycloalkyl (for example piperazin-1-yl), or optionally substituted heteroaryl (for example 3-pyridyl or 6-amino-3-pyridyl).

In a compound of formula I, Ia, Ia-1, Ib or Ic, D is a cycloalkyl group having from 4 to 7 C atoms, wherein said cycloalkyl group has one or two substituents $R^3$ and is further optionally substituted with one or more $R^4$, and wherein the cycloalkyl group optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group —$(C(R^a)_2)_p$— linking together any two non-adjacent ring carbon atoms of the cycloalkyl group (i.e. forming a bridged structure), wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings (i.e. forming a spiro cycle), and wherein said second ring is optionally substituted with one or more $R^6$.

The cycloalkyl group in D is thus always substituted with either one or two groups $R^3$, which can be the same or different and can be placed on any available position of the cycloalkyl group, preferably on different ring C atoms, but preferably not on the ring C atom linking said cycloalkyl group to the rest of the molecule. Preferably, the $R^3$ group (or one of the two $R^3$ groups, if two $R^3$ groups are present) is placed at the most opposed C atom to the C atom linking the cycloalkyl group to the remainder of the compound of formula I, this meaning a "1,4"-like or "para"-like disposition for cyclobutyl and cyclohexyl rings and a "1,3"-like or "meta"-like disposition for cyclopentyl and cycloheptyl rings. In a preferred embodiment, there is only one $R^3$ group on the cycloalkyl group. Said cycloalkyl group may have one or more further additional substituents $R^4$, which can be the same or different and may be placed at any available position of the cycloalkyl group. Additionally, the cycloalkyl group can be fused to a second ring, or form bridged or spiro structures, as defined in more detail above.

In one embodiment, D is a cycloalkyl group having from 4 to 7 C atoms, preferably a cyclohexyl group, wherein said cycloalkyl group (preferably cyclohexyl) has one or two substituents $R^3$ and is further optionally substituted with one or more $R^4$, and wherein the cycloalkyl group (preferably, cyclohexyl) is optionally fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$.

In a preferred embodiment, D is a cycloalkyl group having from 4 to 7 C atoms, preferably a cyclohexyl group, wherein said cycloalkyl group (preferably, cyclohexyl) has one or two substituents $R^3$ and is further optionally substituted with one or more $R^4$.

In a more preferred embodiment, D is a cycloalkyl group having from 4 to 7 C atoms, preferably a cyclohexyl group, wherein said cycloalkyl group (preferably cyclohexyl) has one substituent $R^3$ and is further optionally substituted with one or more $R^4$.

In a still more preferred embodiment, D is a cycloalkyl group having from 4 to 7 C atoms, preferably a cyclohexyl group, wherein said cycloalkyl group (preferably cyclohexyl) has one substituent $R^3$.

In another embodiment, D is a cycloalkyl group having from 4 to 7 C atoms, preferably a cyclohexyl group, wherein said cycloalkyl group (preferably cyclohexyl) has one or two substituents $R^3$ and is further optionally substituted with one or more $R^4$, and wherein the cycloalkyl group (preferably cyclohexyl) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$.

In another embodiment, D is a cycloalkyl group having from 4 to 7 C atoms, preferably a cyclohexyl group, wherein said cycloalkyl group has one or two substituents $R^3$ and is further optionally substituted with one or more $R^4$, and wherein the cycloalkyl group is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl.

In another embodiment, D is a cycloalkyl group having from 4 to 7 C atoms, preferably a cyclohexyl group, wherein said cycloalkyl group has one or two substituents $R^3$ and is further optionally substituted with one or more $R^4$, and wherein the cycloalkyl group is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$.

In a preferred embodiment, D is selected from D1, D2, D3 and D4:

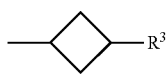

D1

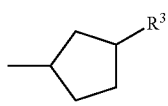

D2

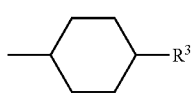

D3

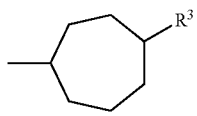

D4 wherein the cyclobutyl ring comprised in D1, the cyclopentyl ring comprised in D2, the cyclohexyl ring comprised in D3 and the cycloheptyl ring comprised in D4 is optionally substituted with one further $R^3$ and is optionally substituted with one or more $R^4$, wherein the cyclobutyl ring comprised in D1 optionally:
(a) is bonded to a linker group $—(C(R^a)_2)_p—$ linking together any two non-adjacent ring carbon atoms of the cyclobutyl ring comprised in D1, wherein p is 1 or 2 and each $R^a$ independently is hydrogen or $C_{1-4}$ alkyl; or
(b) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cyclobutyl ring comprised in D1 via a single carbon atom common to both rings, and wherein said second ring is optionally substituted with one or more $R^6$;

and wherein the cyclopentyl ring comprised in D2, the cyclohexyl ring comprised in D3 and the cycloheptyl ring comprised in D4 optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group $—(C(R^a)_2)_p—$ linking together any two non-adjacent ring carbon atoms of the cycloalkyl group (i.e., of the cyclopentyl ring comprised in D2, the cyclohexyl ring comprised in D3 or the cycloheptyl ring comprised in D4), wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., with the cyclopentyl ring comprised in D2, the cyclohexyl ring comprised in D3 or the cycloheptyl ring comprised in D4) via a single carbon atom common to both rings, and wherein said second ring is optionally substituted with one or more $R^6$.

It is to be understood that the bond to the opposite of $R^3$ shown in the above formulae D1, D2, D3 and D4 denotes the point of attachment of the respective group D1, D2, D3 or D4 to the remainder of the compound of Formula I, Ia, Ia-1, Ib or Ic.

In another preferred embodiment, D is selected from D1, D2, D3 and D4:

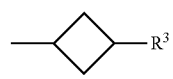

D1

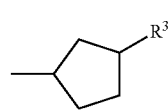

D2

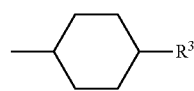

D3

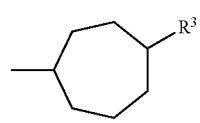

D4 wherein the cyclobutyl ring comprised in D1, the cyclopentyl ring comprised in D2, the cyclohexyl ring comprised in D3 and the cycloheptyl ring comprised in D4 is optionally substituted with one further $R^3$ and is optionally substituted with one or more $R^4$.

In another preferred embodiment, D is selected from D1, D2, D3 and D4:

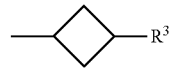

D1

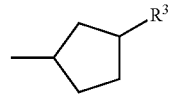

D2

D3

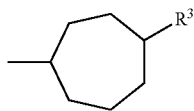

wherein the cyclobutyl ring comprised in D1, the cyclopentyl ring comprised in D2, the cyclohexyl ring comprised in D3 and the cycloheptyl ring comprised in D4 is optionally substituted with one or more $R^4$.

In a more preferred embodiment, D is

wherein the cyclohexyl ring comprised in D is optionally substituted with one further $R^3$ and is optionally substituted with one or more $R^4$, and wherein the cyclohexyl ring comprised in D optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$.

In a still more preferred embodiment, D is

wherein the cyclohexyl ring is optionally substituted with one or more $R^4$, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$.

In an even more preferred embodiment, D is

wherein the cyclohexyl ring is optionally substituted with one or more $R^4$.

In a particularly preferred embodiment, D is

In another embodiment, D is a group of formula

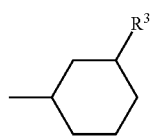

wherein the cyclohexyl ring is optionally substituted with one or more $R^4$.

In another embodiment, D is a group of formula

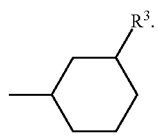

In a compound of formula I, Ia, Ia-1, Ib or Ic, each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$. When $R^3$ is oxo (i.e. a group of formula =O), then there can be no further substituent (either $R^3$, if a second $R^3$ is present, or $R^4$) in that position, i.e. on the C atom on which the oxo group is placed. It is further to be understood that, if $R^3$ in any of the above formulae D1, D2, D3 or D4 is oxo (i.e., =O), then this oxo group is bound to the respective cycloalkyl ring through a carbon-to-carbon double bond. In a preferred embodiment, there is only one $R^3$ on a compound of formula I, Ia, Ia-1, Ib or Ic.

In one embodiment, each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —C$_{1-4}$ alkylene-OH and —C$_{1-4}$ alkylene-CONR$^7$R$^8$. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^0$, —NR$^9$COOR$^{10}$, —NR$^9$CONR$^7$R$^8$, —NR$^9$SO$_2$NR$^7$R$^8$, —OH, oxo, —C$_{1-4}$ alkylene-NR$^7$R$^8$, —C$_{1-4}$ alkylene-NHOH, —C$_{1-4}$ alkyene-NR$^9$COR$^{10}$, —C$_{1-4}$ alkylene-NR$^9$SO$_2$R$^{10}$, —C$_{1-4}$ alkylene-NR$^9$COOR$^{10}$, —C$_{1-4}$ alkylene-NR$^9$CONR$^7$R$^8$, —C$_{1-4}$ alkylene-NR$^9$SO$_2$NR$^7$R$^8$, and —C$_{1-4}$ alkylene-OH. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^{10}$, —NR$^9$COOR$^{10}$, —NR$^9$CONR$^7$R$^8$, —NR$^9$SO$_2$NR$^7$R$^8$, oxo, —C$_{1-4}$ alkylene-NR$^7$R$^8$, —C$_{1-4}$ alkylene-NHOH, —C$_{1-4}$ alkyene-NR$^9$COR$^{10}$, —C$_{1-4}$ alkylene-NR$^9$SO$_2$R$^{10}$, —C$_{1-4}$ alkylene-NR$^9$COOR$^{10}$, —C$_{1-4}$ alkylene-NR$^9$CONR$^7$R$^8$, —C$_{1-4}$ alkylene-NR$^9$SO$_2$NR$^7$R$^8$, and —C$_{1-4}$ alkylene-OH. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^{10}$, —NR$^9$COOR$^{10}$, —NR$^9$CONR$^7$R$^8$, —NR$^9$SO$_2$NR$^7$R$^8$, —OH, —CONR$^7$R$^8$, and oxo. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^{10}$, —NR$^9$COOR$^{10}$, —NR$^9$CONR$^7$R$^8$, —NR$^9$SO$_2$NR$^7$R$^8$, —CONR$^7$R$^8$, and oxo. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^{10}$, —NR$^9$COOR$^{10}$, —NR$^9$CONR$^7$R$^8$, —NR$^9$SO$_2$NR$^7$R$^8$, —OH, and oxo. In a preferred embodiment, there is only one R$^3$.

In another embodiment, each R$^3$ is independently selected from —NR$^7$R$^8$, —NHOH, —NR$^9$COR$^{10}$, —NR$^9$SO$_2$R$^0$, —NR$^9$COOR$^{10}$, —NR$^9$CONR$^7$R$^8$, —NR$^9$SO$_2$NR$^7$R$^8$, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^{10}$, —NR$^9$COOR$^{10}$, —NR$^9$CONR$^7$R$^8$, —OH, —CONR$^7$R$^8$, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^{10}$, —NR$^9$COOR$^{10}$, —NR$^9$CONR$^7$R$^8$, —CONR$^7$R$^8$, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^{10}$, —NR$^9$COOR$^0$O, —NR$^9$CONR$^7$R$^8$, —OH, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^{10}$, —NR$^9$COOR$^{10}$, —NR$^9$CONR$^7$R$^8$, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^0$, —OH, and oxo. In a preferred embodiment, there is only one R$^3$.

In another embodiment, each R$^3$ is independently selected from —NR$^7$R$^8$, —NR$^9$COR$^{10}$, —NR$^9$SO$_2$R$^{10}$, and oxo. In a preferred embodiment, there is only one R$^3$.

In another embodiment, each R$^3$ is independently selected from —NR$^7$R$^8$, —OH, oxo, —C$_{1-4}$ alkylene-NR$^7$R$^8$, and —C$_{1-4}$ alkylene-OH. In a preferred embodiment, there is only one R$^3$.

In another embodiment, each R$^3$ is independently selected from —NR$^7$R$^8$, oxo, —C$_{1-4}$ alkylene-NR$^7$R$^8$, and —C$_{1-4}$ alkylene-OH. In a preferred embodiment, there is only one R$^3$.

In another embodiment, each R$^3$ is independently selected from —NR$^7$R$^8$, —OH and oxo. In a preferred embodiment, there is only one R$^3$.

In another embodiment, each R$^3$ is independently selected from —NR$^7$R$^8$, and —OH. In a preferred embodiment, there is only one R$^3$.

In a preferred embodiment, each R$^3$ is independently selected from —NR$^7$R$^8$ and —C$_{1-4}$ alkylene-NR$^7$R$^8$. Preferably, said —C$_{1-4}$ alkylene-NR$^7$R$^8$ is —C$_{1-2}$ alkylene-NR$^7$R$^8$. In a preferred embodiment, there is only one R$^3$.

In a more preferred embodiment, each R$^3$ is independently selected from —NR$^7$R$^8$. In a preferred embodiment, there is only one R$^3$.

In a compound of formula I, Ia, Ia-1, Ib or Ic, each R$^4$ and each R$^6$ is independently selected from C$_{1-8}$ alkyl, halo, haloC$_{1-8}$ alkyl, haloC$_{1-8}$ alkoxy and C$_{1-8}$ alkoxy. Preferably, each R$^4$ and each R$^6$ is independently selected from C$_{1-8}$ alkyl, halo and Cl-s alkoxy. More preferably, each R$^4$ and each R$^6$ is independently selected from C$_{1-4}$ alkyl, halo and C$_{1-4}$ alkoxy.

In a compound of formula I, Ia, Ia-1, Ib or Ic, each R$^7$ and each R$^8$ is independently selected from hydrogen, C$_{1-8}$ alkyl, R$^{12}$R$^{13}$N—C$_{1-8}$ alkyl and hydroxyC$_{1-8}$ alkyl, or R$^7$ and R$^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more R$^{11}$. Preferably, the alkyl groups indicated above, either as a group or part of a group (e.g. in an R$^{12}$R$^{13}$N—C$_{1-8}$ alkyl or hydroxyC$_{1-8}$ alkyl group), are C$_{1-4}$ alkyl, more preferably C$_{1-2}$ alkyl. In one embodiment, each R$^7$ and each R$^8$ is independently selected from hydrogen, C$_{1-8}$ alkyl, R$^{12}$R$^{13}$N—C$_{1-8}$ alkyl (preferably H$_2$N—C$_{1-8}$ alkyl) and hydroxyC$_{1-4}$ alkyl; preferably, each R$^7$ and each R$^8$ is independently selected from hydrogen, C$_{1-4}$ alkyl, R$^{12}$R$^{13}$N—C$_{1-4}$ alkyl (preferably H$_2$N—C$_{1-4}$ alkyl) and hydroxyC$_{1-4}$ alkyl, and more preferably each R$^7$ and each R$^8$ is independently selected from hydrogen, C$_{1-2}$ alkyl, R$^{12}$R$^{13}$N—C$_{1-2}$ alkyl (preferably H$_2$N—C$_{1-2}$ alkyl) and hydroxyC$_{1-2}$ alkyl. In a preferred embodiment, R$^7$ and R$^8$ are each hydrogen.

In another embodiment, R$^7$ and R$^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more R$^{11}$. In one specific embodiment, —NR$^7$R$^8$ is a group of formula:

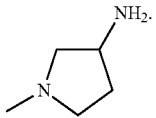

In a compound of formula I, Ia, Ia-1, Ib or Ic, each $R^9$ is independently selected from hydrogen and $C_{1-4}$ alkyl. In a preferred embodiment, each $R^9$ is hydrogen.

In a compound of formula I, Ia, Ia-1, Ib or Ic, each $R^{10}$ is independently selected from $C_{1-8}$ alkyl, halo$C_{1-8}$ alkyl, cyclyl and cyclyl$C_{1-8}$ alkyl, wherein said cyclyl or the cyclyl moiety comprised in said cyclyl$C_{1-8}$ alkyl (i.e., any of the aforementioned cyclyl groups, including also the cyclyl group forming part of the cyclyl$C_{1-8}$ alkyl group) is optionally substituted with one or more $R^{14}$. In one embodiment, each $R^{10}$ is selected from $C_{1-8}$ alkyl and cyclyl optionally substituted with one or more $R^{14}$, preferably each $R^{10}$ is selected from $C_{1-4}$ alkyl (e.g. methyl) and aryl (preferably phenyl) optionally substituted with one or more $R^{14}$. In another embodiment, each $R^{10}$ is $C_{1-8}$ alkyl, for example $C_{1-4}$ alkyl. In another embodiment, each $R^{10}$ is cyclyl optionally substituted with one or more $R^{14}$, for example aryl optionally substituted with one or more $R^{14}$, preferably phenyl optionally substituted with one or more $R^{14}$. The aforementioned groups optionally substituted with one or more $R^{14}$ may, e.g., be substituted with one, two or three $R^{14}$.

In another embodiment there is one $R^3$ and said $R^3$ is selected from —$NR^7R^8$ and —$C_{1-4}$ alkylene-$NR^7R^8$, wherein the moiety —$NR^7R^8$ in —$NR^7R^8$ and in —$C_{1-4}$ alkylene-$NR^7R^8$ is —$NH_2$ or a group of formula:

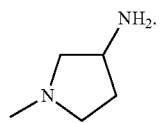

In a specific aspect of the above embodiment, there is one $R^3$ and said $R^3$ is selected from —$NH_2$ and —$C_{1-4}$ alkylene-$NH_2$, preferably from —$NH_2$ and —$C_{1-2}$ alkylene-$NH_2$ (e.g. —$CH_2$—$NH_2$, —$CH_2$—$CH_2$—$NH_2$ or —$CH(CH_3)$—$NH_2$).

In another embodiment there is one $R^3$ and said $R^3$ is —$NR^7R^8$, wherein —$NR^7R^8$ is —$NH_2$ or a group of formula:

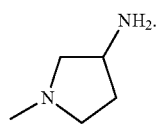

In another embodiment there is one $R^3$ and said $R^3$ is —$NH_2$.

In another embodiment there is one $R^3$ and said $R^3$ is a group of formula:

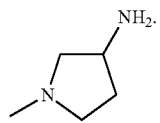

In the above embodiments as well as in all the embodiments of the compounds of the invention described below, the following compounds are excluded:
2-((2-phenylcyclopropyl)amino)cycloheptanol, and
2-((2-phenylcyclopropyl)amino)cyclopentanol.

Preferably, in the above embodiments as well as in all the embodiments of the compounds of the invention described below also the compound 2-((2-phenylcyclopropyl)amino) cyclohexanol is excluded.

The substituents of the cyclopropyl moiety -A-B and —NH-D in a compound of formula I, Ia, Ib or Ic are preferably in the trans-configuration. Thus, in one embodiment, the invention provides a compound of formula I (including a compound Ia, Ib or Ic) wherein the groups -A-B and —NH-D are in trans configuration. In a preferred embodiment, the invention provides a compound of formula Ia wherein the groups -A-B and —NH-D are in trans configuration, which is a compound of formula Ia-1:

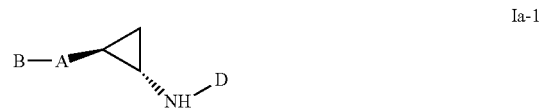

wherein the groups and variables of formula Ia-1, including A, B, D, E, L, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$, are as defined above in relation to a compound of formula I and Ia and in the various preferred embodiments for a compound of formula I and Ia described above. The above chemical representation for a compound of formula Ia-1 does not intend to indicate absolute stereochemistry of the two chiral centers on the cyclopropyl ring, but only their relative stereochemistry (which is trans). Thus a compound of formula Ia-1 therefore relates to individual optically active trans isomers as well as mixtures of trans-isomers.

In one embodiment, the invention provides a compound of formula I wherein each $R^w$, $R^x$, $R^y$ and $R^z$ is independently selected from hydrogen, fluoro and $C_{1-4}$ alkyl, preferably from hydrogen, fluoro and methyl.

In another embodiment, the invention provides a compound of formula I wherein each $R^w$, $R^x$, $R^y$ and $R^z$ is independently selected from hydrogen and fluoro.

In another embodiment, the invention provides a compound of formula I wherein $R^w$ is fluoro and each $R^x$, $R^y$ and $R^z$ is independently selected from hydrogen, halo and $C_{1-4}$ alkyl; preferably, $R^w$ is fluoro and each $R^x$, $R^y$ and $R^z$ is hydrogen.

In another embodiment, the invention provides a compound of formula I wherein $R^z$ is fluoro and each $R^w$, $R^x$ and $R^y$ is independently selected from hydrogen, halo and $C_{1-4}$ alkyl; preferably, $R^z$ is fluoro and each $R^w$, $R^x$ and $R^y$ is hydrogen.

In another embodiment, the invention provides a compound of formula I wherein $R^w$ and $R^z$ are fluoro and each $R^x$ and $R^y$ is independently selected from hydrogen, halo and $C_{1-4}$ alkyl; preferably, $R^w$ and $R^z$ are fluoro and each $R^x$ and $R^y$ is hydrogen.

In a preferred embodiment, the invention provides a compound of formula I wherein $R^w$ is selected from hydrogen, halo and $C_{1-4}$ alkyl, preferably from hydrogen, fluoro and methyl, and each $R^x$, $R^y$ and $R^z$ is hydrogen.

In a more preferred embodiment, the invention provides a compound of formula I wherein each $R^w$, $R^x$, $R^y$ and $R^z$ is hydrogen, i.e. a compound of formula Ia:

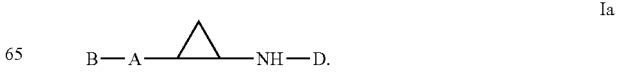

In another embodiment, the invention provides a compound of formula I wherein each $R^w$, $R^x$, $R^y$ and $R^z$ is independently selected from hydrogen, halo and $C_{1-4}$ alkyl with the proviso that at least one is not hydrogen, i.e. a compound of formula Ib.

In another embodiment, the invention provides a compound of formula I wherein $R^w$ is selected from halo and $C_{1-4}$ alkyl, preferably from fluoro and methyl, and each $R^x$, $R^y$ and $R^z$ is hydrogen, i.e. a compound of formula Ic. Preferably, in a compound of formula Ic $R^w$ is methyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is selected from D1, D2, D3 and D4:

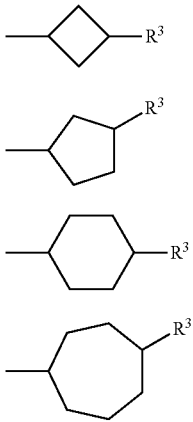

wherein the cyclobutyl ring comprised in D1, the cyclopentyl ring comprised in D2, the cyclohexyl ring comprised in D3 and the cycloheptyl ring comprised in D4 is optionally substituted with one further $R^3$ and is optionally substituted with one or more $R^4$, and wherein the cyclobutyl ring comprised in D1, the cyclopentyl ring comprised in D2, the cyclohexyl ring comprised in D3 and the cycloheptyl ring comprised in D4 optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$ (option (a) applies only to D2, D3 and D4 but not to D1); or
  (b) is bonded to a linker group —$(C(R^a)_2)_p$— linking together any two non-adjacent ring carbon atoms of the cycloalkyl group (i.e., the cyclobutyl ring comprised in D1, the cyclopentyl ring comprised in D2, the cyclohexyl ring comprised in D3 or the cycloheptyl ring comprised in D4), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclobutyl ring comprised in D1, the cyclopentyl ring comprised in D2, the cyclohexyl ring comprised in D3 or the cycloheptyl ring comprised in D4) via a single carbon atom common to both rings, and wherein said second ring is optionally substituted with one or more $R^6$.

In a preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

wherein the cyclohexyl ring comprised in D is optionally substituted with one further $R^3$ and is optionally substituted with one or more $R^4$, and wherein the cyclohexyl ring comprised in D optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

wherein the cyclohexyl ring is optionally substituted with one or more $R^4$, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$.

In a more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

wherein the cyclohexyl ring is optionally substituted with one or more $R^4$.

In a still more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

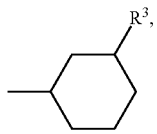

wherein the cyclohexyl ring is optionally substituted with one or more $R^4$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein D is

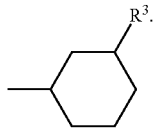

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene- $NR^9SO_2NR^7R^8$, and —$C_{1-4}$ alkylene-OH.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, and oxo.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, and oxo.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$, —$NR^9COR^{10}$, —$NR^9SO_2R^{10}$, —$NR^9COOR^{10}$, —$NR^9CONR^7R^8$, —OH, and oxo. In a more specific embodiment, each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl; preferably, each $R^7$ and each $R^8$ is independently selected from hydrogen, $C_{1-4}$ alkyl, $R^{12}R^{13}N$—$C_{1-4}$ alkyl and hydroxy$C_{1-4}$ alkyl, more preferably each $R^7$ and each $R^8$ is independently selected from hydrogen, $C_{1-2}$ alkyl, $R^{12}R^{13}N$—$C_{1-2}$ alkyl and hydroxy$C_{1-2}$ alkyl, and even more preferably $R^7$ and $R^8$ are each hydrogen; and each $R^{10}$ is selected from $C_{1-8}$ alkyl and cyclyl optionally substituted with one or more $R^{14}$, preferably each $R^{10}$ is selected from $C_{1-4}$ alkyl (e.g. methyl) and aryl (preferably phenyl) optionally substituted with one or more $R^{14}$. The aforementioned groups optionally substituted with one or more $R^{14}$ may, e.g., be substituted with one, two or three $R^{14}$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$, —$NR^9COR^{10}$, —$NR^9SO_2R^{10}$, —$NR^9COOR^{10}$, —$NR^9CONR^7R^8$, and oxo. In a more specific embodiment, each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl; preferably, each $R^7$ and each $R^8$ is independently selected from hydrogen, $C_{1-4}$ alkyl, $R^{12}R^{13}N$—$C_{1-4}$ alkyl and hydroxy$C_{1-4}$ alkyl, more preferably each $R^7$ and each $R^8$ is independently selected from hydrogen, $C_{1-2}$ alkyl, $R^{12}R^{13}N$—$C_{1-2}$ alkyl and hydroxy$C_{1-2}$ alkyl, and even more preferably $R^7$ and $R^8$ are each hydrogen; and each $R^{10}$ is selected from $C_{1-8}$ alkyl and cyclyl optionally substituted with one or more $R^{14}$, preferably each $R^{10}$ is selected from $C_{1-4}$ alkyl (e.g. methyl) and aryl (preferably phenyl) optionally substituted with one or more $R^{14}$. The aforementioned groups optionally substituted with one or more $R^{14}$ may, e.g., be substituted with one, two or three $R^{14}$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —NR$^7$R$^8$, —NR$^9$COR$^{10}$, —NR$^9$SO$_2$R$^{10}$, —OH, and oxo. In a more specific embodiment, each R$^7$ and each R$^8$ is independently selected from hydrogen, C$_{1-8}$ alkyl, R$^{12}$R$^{13}$N—C$_{1-8}$ alkyl and hydroxyC$_{1-8}$ alkyl; preferably, each R$^7$ and each R$^8$ is independently selected from hydrogen, C$_{1-4}$ alkyl, R$^{12}$R$^{13}$N—C$_{1-4}$ alkyl and hydroxyC$_{1-4}$ alkyl, more preferably each R$^7$ and each R$^8$ is independently selected from hydrogen, C$_{1-2}$ alkyl, R$^{12}$R$^{13}$N—C$_{1-2}$ alkyl and hydroxyC$_{1-2}$ alkyl, and even more preferably R$^7$ and R$^8$ are each hydrogen; and each R$^{10}$ is selected from C$_{1-8}$ alkyl and cyclyl optionally substituted with one or more R$^{14}$, preferably each R$^{10}$ is selected from C$_{1-4}$ alkyl (e.g. methyl) and aryl (preferably phenyl) optionally substituted with one or more R$^{14}$. The aforementioned groups optionally substituted with one or more R$^{14}$ may, e.g., be substituted with one, two or three R$^{14}$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each R$^3$ is independently selected from —NR$^7$R$^8$, —NR$^9$COR$^{10}$, —NR$^9$SO$_2$R$^{10}$, and oxo. In a more specific embodiment, each R$^7$ and each R$^8$ is independently selected from hydrogen, C$_{1-8}$ alkyl, R$^{12}$R$^{13}$N—C$_{1-8}$ alkyl and hydroxyC$_{1-8}$ alkyl; preferably, each R$^7$ and each R$^8$ is independently selected from hydrogen, C$_{1-4}$ alkyl, R$^{12}$R$^{13}$N—C$_{1-4}$ alkyl and hydroxyC$_{1-4}$ alkyl, more preferably each R$^7$ and each R$^8$ is independently selected from hydrogen, C$_{1-2}$ alkyl, R$^{12}$R$^{13}$N—C$_{1-2}$ alkyl and hydroxyC$_{1-2}$ alkyl, and even more preferably R$^7$ and R$^8$ are each hydrogen; and each R$^{10}$ is selected from C$_{1-8}$ alkyl and cyclyl optionally substituted with one or more R$^{14}$, preferably each R$^{10}$ is selected from C$_{1-4}$ alkyl (e.g. methyl) and aryl (preferably phenyl) optionally substituted with one or more R$^{14}$. The aforementioned groups optionally substituted with one or more R$^{14}$ may, e.g., be substituted with one, two or three R$^{14}$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each R$^3$ is independently selected from —NR$^7$R$^8$, —OH, oxo, —C$_{1-4}$ alkylene-NR$^7$R$^8$, and —C$_{1-4}$ alkylene-OH. In a more specific embodiment each R$^7$ and each R$^8$ is independently selected from hydrogen, C$_{1-8}$ alkyl, R$^{12}$R$^{13}$N—C$_{1-8}$ alkyl and hydroxyC$_{1-8}$ alkyl; preferably, each R$^7$ and each R$^8$ is independently selected from hydrogen, C$_{1-4}$ alkyl, R$^{12}$R$^{13}$N—C$_{1-4}$ alkyl and hydroxyC$_{1-4}$ alkyl, more preferably each R$^7$ and each R$^8$ is independently selected from hydrogen, C$_{1-2}$ alkyl, R$^{12}$R$^{13}$N—C$_{1-2}$ alkyl and hydroxyC$_{1-2}$ alkyl, and even more preferably R$^7$ and R$^8$ are each hydrogen. In another specific embodiment, R$^7$ and R$^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more (e.g., one, two or three) R$^1$, and preferably —NR$^7$R$^8$ is a group of formula:

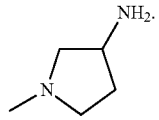

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each R$^3$ is independently selected from —NR$^7$R$^8$, oxo, —C$_{1-4}$ alkylene-NR$^7$R$^8$, and —C$_{1-4}$ alkylene-OH. In a more specific embodiment each R$^7$ and each R$^8$ is independently selected from hydrogen, C$_{1-8}$ alkyl, R$^{12}$R$^{13}$N—C$_{1-8}$ alkyl and hydroxyC$_{1-8}$ alkyl; preferably, each R$^7$ and each R$^8$ is independently selected from hydrogen, C$_{1-4}$ alkyl, R$^{12}$R$^{13}$N—C$_{1-4}$ alkyl and hydroxyC$_{1-4}$ alkyl, more preferably each R$^7$ and each R$^8$ is independently selected from hydrogen, C$_{1-2}$ alkyl, R$^{12}$R$^{13}$N—C$_{1-2}$ alkyl and hydroxyC$_{1-2}$ alkyl, and even more preferably R$^7$ and R$^8$ are each hydrogen. In another specific embodiment, R$^7$ and R$^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more (e.g., one, two or three) R$^{11}$, and preferably —NR$^7$R$^8$ is a group of formula:

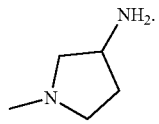

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each R$^3$ is independently selected from —NR$^7$R$^8$ and —OH. In a more specific embodiment each R$^7$ and each R$^8$ is independently selected from hydrogen, C$_{1-8}$ alkyl, R$^{12}$R$^{13}$N—C$_{1-8}$ alkyl and hydroxyC$_8$a alkyl; preferably, each R$^7$ and each R$^8$ is independently selected from hydrogen, C$_{1-4}$ alkyl, R$^{12}$R$^{13}$N—C$_{1-4}$ alkyl and hydroxyC$_{1-4}$ alkyl, more preferably each R$^7$ and each R$^8$ is independently selected from hydrogen, C$_{1-2}$ alkyl, R$^{12}$R$^{13}$N—C$_{1-2}$ alkyl and hydroxyC$_{1-2}$ alkyl, and even more preferably R$^7$ and R$^8$ are each hydrogen. In another specific embodiment, R$^7$ and R$^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or SO$_2$ groups, and wherein said heterocyclic ring is optionally substituted with one or more (e.g., one, two or three) R$^{11}$, and preferably —NR$^7$R$^8$ is a group of formula:

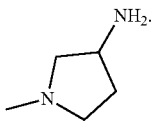

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$ and —$C_{1-4}$ alkylene-$NR^7R^8$, preferably from —$NR^7R^8$ and —$C_{1-2}$ alkylene-$NR^7R^8$. In a more specific embodiment each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl; preferably, each $R^7$ and each $R^8$ is independently selected from hydrogen, $C_{1-4}$ alkyl, $R^{12}R^{13}N$—$C_{1-4}$ alkyl and hydroxy$C_{1-4}$ alkyl, more preferably each $R^7$ and each $R^8$ is independently selected from hydrogen, $C_{1-2}$ alkyl, $R^{12}R^{13}N$—$C_{1-2}$ alkyl and hydroxy$C_{1-2}$ alkyl, and even more preferably $R^7$ and $R^8$ are each hydrogen. In another specific embodiment, $R^7$ and $R^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or $SO_2$ groups, and wherein said heterocyclic ring is optionally substituted with one or more (e.g., one, two or three) $R^{11}$, and preferably —$NR^7R^8$ is a group of formula:

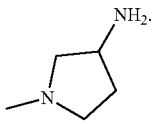

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein each $R^3$ is independently selected from —$NR^7R^8$. In a more specific embodiment each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl; preferably, each $R^7$ and each $R^8$ is independently selected from hydrogen, $C_{1-4}$ alkyl, $R^{12}R^{13}N$—$C_{1-4}$ alkyl and hydroxy$C_{1-4}$ alkyl, more preferably each $R^7$ and each $R^8$ is independently selected from hydrogen, $C_{1-2}$ alkyl, $R^{12}R^{13}N$—$C_{1-2}$ alkyl and hydroxy$C_{1-2}$ alkyl, and even more preferably $R^7$ and $R^8$ are each hydrogen. In another specific embodiment, $R^7$ and $R^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or $SO_2$ groups, and wherein said heterocyclic ring is optionally substituted with one or more (e.g., one, two or three) $R^{11}$, and preferably —$NR^7R^8$ is a group of formula:

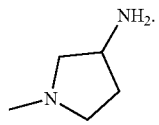

In a preferred embodiment, the invention provides a compound of formula I, Ia, Ia-1, Ib or Ic, including a compound I, Ia, Ia-1, Ib or Ic as defined in the specific embodiments disclosed herein, wherein there is only one substituent $R^3$ on ring D.

In one embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is selected from D1, D2, D3 and D4:

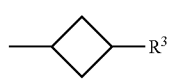

D1

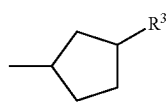

D2

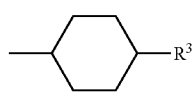

D3

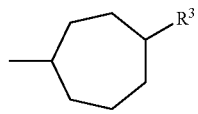

D4 wherein the cyclobutyl ring comprised in D1, the cyclopentyl ring comprised in D2, the cyclohexyl ring comprised in D3 and the cycloheptyl ring comprised in D4 is optionally substituted with one further $R^3$ and is optionally substituted with one or more $R^4$, and wherein the cyclobutyl ring comprised in D1, the cyclopentyl ring comprised in D2, the cyclohexyl ring comprised in D3 and the cycloheptyl ring comprised in D4 optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$ (option (a) applies only to D2, D3 and D4 but not to D1); or
  (b) is bonded to a linker group —$(C(R^a)_2)_p$— linking together any two non-adjacent ring carbon atoms of the cycloalkyl group (i.e., the cyclobutyl ring comprised in D1, the cyclopentyl ring comprised in D2, the cyclohexyl ring comprised in D3 or the cycloheptyl ring comprised in D4), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclobutyl ring comprised in D1, the cyclopentyl ring comprised in D2, the cyclohexyl ring comprised in D3 or the cycloheptyl ring comprised in D4) via a single carbon atom common to both rings, and wherein said second ring is optionally substituted with one or more $R^6$; and each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2RO$, —$C_{1-4}$ alkylene-$NR^9COOR^{10}$, —$C_{1-4}$ alkylene-$NR^9CONR^7R^8$, —$C_{1-8}$ alkylene-$NR^9SO_2NR^7R^8$, —$C_{1-4}$ alkylene-OH and —$C_{1-4}$ alkylene-$CONR^7R^8$. More preferably, there is only one group $R^3$.

In one embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is selected from D1, D2, D3 and D4:

D1

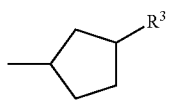
D2

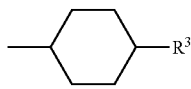
D3

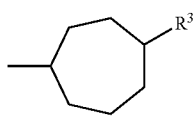
D4 wherein the cyclobutyl ring comprised in D1, the cyclopentyl ring comprised in D2, the cyclohexyl ring comprised in D3 and the cycloheptyl ring comprised in D4 is optionally substituted with one further $R^3$ and is optionally substituted with one or more $R^4$, and wherein the cyclobutyl ring comprised in D1, the cyclopentyl ring comprised in D2, the cyclohexyl ring comprised in D3 and the cycloheptyl ring comprised in D4 optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$ (option (a) applies only to D2, D3 and D4 but not to D1); or
  (b) is bonded to a linker group —$(C(R^a)_2)_p$— linking together any two non-adjacent ring carbon atoms of the cycloalkyl group (i.e., the cyclobutyl ring comprised in D1, the cyclopentyl ring comprised in D2, the cyclohexyl ring comprised in D3 or the cycloheptyl ring comprised in D4), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclobutyl ring comprised in D1, the cyclopentyl ring comprised in D2, the cyclohexyl ring comprised in D3 or the cycloheptyl ring comprised in D4) via a single carbon atom common to both rings, and wherein said second ring is optionally substituted with one or more $R^6$; and each $R^3$ is independently selected from —$NR^7R^8$ and —$C_{1-4}$ alkylene-$NR^7R^8$. More preferably, there is only one group $R^3$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring comprised in D is optionally substituted with one further $R^3$ and is optionally substituted with one or more $R^4$, and wherein the cyclohexyl ring comprised in D optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$. More preferably, there is only one group $R^3$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring comprised in D is optionally substituted with one further $R^3$ and is optionally substituted with one or more $R^4$, and wherein the cyclohexyl ring comprised in D optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, and oxo. More preferably, there is only one group $R^3$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring comprised in D is optionally substituted with one further $R^3$ and is optionally substituted with one or more $R^4$, and wherein the cyclohexyl ring comprised in D optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and
each $R^3$ is independently selected from —$NR^7R^8$ and —$C_{1-4}$ alkylene-$NR^7R^8$. More preferably, there is only one group $R^3$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

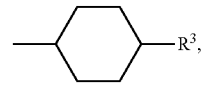

wherein the cyclohexyl ring is optionally substituted with one or more $R^4$, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and
$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
  (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and $R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, and oxo.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

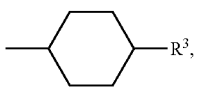

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and $R^3$ is selected from —$NR^7R^8$ and —$C_{1-4}$alkylene-$NR^7R^8$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

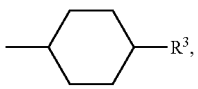

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group (i.e., the cyclohexyl ring), wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group (i.e., the cyclohexyl ring) via a single carbon atom common to both rings, and wherein said second ring is optionally substituted with one or more $R^6$; and $R^3$ is —$NR^7R^8$.

In the above embodiment, $R^3$ is preferably —$NH_2$. In another preferred embodiment, $R^3$ is

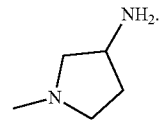

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$; and
$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$; and
$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, and oxo.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$; and
$R^3$ is selected from —$NR^7R^8$ and —$C_{1-4}$alkylene-$NR^7R^8$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$; and
$R^3$ is —$NR^7R^8$.

In the above embodiment, $R^3$ is preferably —$NH_2$. In another preferred embodiment, $R^3$ is

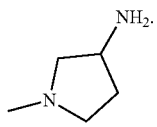

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

and
$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^1$, —$C_{1-4}$ alkylene-$NR^9CONR^7R^8$, —$C_{1-4}$ alkylene-$NR^9SO_2NR^7R^8$, —$C_{1-4}$ alkylene-OH and —$C_{1-4}$ alkylene-$CONR^7R^8$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

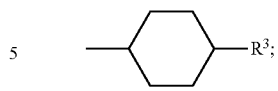

and
$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, and oxo.

In a preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

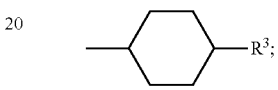

and
$R^3$ is selected from —$NR^7R^8$ and —$C_{1-4}$alkylene-$NR^7R^8$. In a preferred embodiment, $R^7$ and $R^8$ are each hydrogen.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

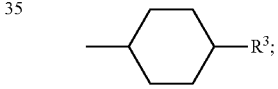

and
$R^3$ is —$NR^7R^8$.

In the above embodiment, $R^3$ is preferably —$NH_2$. In another preferred embodiment, $R^3$ is

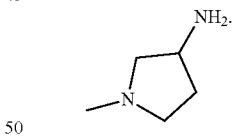

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

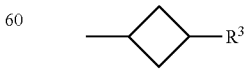

wherein the cyclobutyl ring is optionally substituted with one or more $R^4$; and
$R^3$ is selected from —$NR^7R^8$ and —$C_{1-4}$alkylene-$NR^7R^8$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

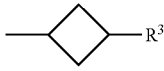

wherein the cyclobutyl ring is optionally substituted with one or more $R^4$; and $R^3$ is —$NR^7R^8$. In this embodiment, $R^3$ is preferably —$NH_2$. In another preferred embodiment, $R^3$ is

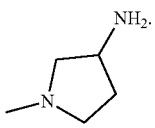

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

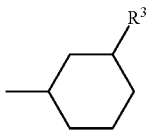

wherein the cyclohexyl ring is optionally substituted with one or more $R^4$; and $R^3$ is selected from —$NR^7R^8$ and —$C_{1-4}$alkylene-$NR^7R^8$. In a preferred embodiment, $R^7$ and $R^8$ are each hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

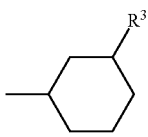

wherein the cyclohexyl ring is optionally substituted with one or more $R^4$; and $R^3$ is —$NR^7R^8$. In this embodiment, $R^3$ is preferably —$NH_2$. In another preferred embodiment, $R^3$ is

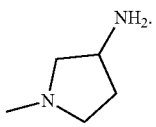

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein A is phenyl, naphthyl or monocyclic heteroaryl, wherein said phenyl, naphthyl or monocyclic heteroaryl is optionally substituted with one or more (e.g., one or two) $R^1$. In a more preferred embodiment, A is phenyl, naphthyl, pyridyl, thiophenyl, pyrrolyl, furanyl, or thiazolyl, wherein A is optionally substituted with one or more $R^1$. More preferably, A is phenyl, naphthyl, pyridyl or thiazolyl, wherein A is optionally substituted with one or more $R^1$. Still more preferably, A is phenyl, 2-naphthyl, 3-pyridyl or 5-thiazolyl, wherein A is optionally substituted with one or more $R^1$. In one embodiment, A is phenyl optionally substituted with one or more $R^1$. In another embodiment, A is naphthyl, preferably 2-naphthyl, optionally substituted with one or more $R^1$. In another embodiment, A is pyridyl, preferably 3-pyridyl, optionally substituted with one or more $R^1$. In another embodiment, A is thiazolyl, preferably 5-thiazolyl, optionally substituted with one or more $R^1$.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein A is phenyl or monocyclic heteroaryl, wherein said phenyl or said monocyclic heteroaryl is optionally substituted with one or more (e.g., one or two) $R^1$. In a more preferred embodiment, A is phenyl, pyridyl, thiophenyl, pyrrolyl, furanyl, or thiazolyl, wherein A is optionally substituted with one or more $R^1$. More preferably, A is phenyl, pyridyl or thiazolyl, wherein A is optionally substituted with one or more $R^1$. In one embodiment, A is phenyl. In another embodiment, A is 3-pyridyl. In another embodiment, A is 5-thiazolyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein A is phenyl optionally substituted with one or more $R^1$.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein A is naphthyl (e.g. 2-naphthyl) optionally substituted with one or more $R^1$.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein A is heteroaryl optionally substituted with one or more $R^1$. Preferably, A is monocyclic heteroaryl optionally substituted with one or more $R^1$.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl or monocyclic heteroaryl (preferably phenyl, pyridyl or thiazolyl, more preferably phenyl, 3-pyridyl or 5-thiazolyl), wherein A is optionally substituted with one or more $R^1$;

B is hydrogen, $R^1$ or -L-E;

E is phenyl optionally substituted with one or more $R^2$; and

L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. In a more specific embodiment, L is a bond or —$CH_2$—O—, wherein said —$CH_2$—O— group is linked to ring A through the O atom and to ring E through the —$CH_2$— group.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is aryl or heteroaryl, wherein said aryl or said heteroaryl is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl, naphthyl or monocyclic heteroaryl, wherein said phenyl, said naphthyl or said monocyclic heteroaryl is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl or monocyclic heteroaryl, wherein said phenyl or said monocyclic heteroaryl is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and Cm cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl, pyridyl or thiazolyl (preferably phenyl, 3-pyridyl or 5-thiazolyl), wherein A is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is naphthyl optionally substituted with one or more $R^1$; and

B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and Cm cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl, naphthyl or monocyclic heteroaryl; and

B is hydrogen.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl, pyridyl or thiazolyl (preferably phenyl, 3-pyridyl or 5-thiazolyl); and B is hydrogen.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is phenyl; and

B is hydrogen.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:

A is naphthyl; and
B is hydrogen.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
A is heteroaryl, preferably monocyclic heteroaryl; and
B is hydrogen.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
A is phenyl or monocyclic heteroaryl (preferably phenyl, pyridyl or thiazolyl, and more preferably phenyl, 3-pyridyl or 5-thiazolyl), wherein said phenyl or said monocyclic heteroaryl is optionally substituted with one or more $R^1$; and
B is -L-E. In the above embodiment preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more $R^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$—O—, wherein said —CH$_2$—O— group is linked to ring A through the O atom and to ring E through the —CH$_2$— group.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
A is phenyl or pyridyl (preferably phenyl or 3-pyridyl), wherein A is optionally substituted with one or more $R^1$; and
B is -L-E. In the above embodiment preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more $R^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$—O—, wherein said —CH$_2$—O— group is linked to ring A through the O atom and to ring E through the —CH$_2$— group.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
A is phenyl; and
B is -L-E. In the above embodiment preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more $R^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$—O—, wherein said —CH$_2$—O— group is linked to ring A through the O atom and to ring E through the —CH$_2$— group.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
A is 3-pyridyl; and
B is -L-E. In the above embodiment preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more $R^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$—O—, wherein said —CH$_2$—O— group is linked to ring A through the O atom and to ring E through the —CH$_2$— group.

In another embodiment, the invention provides a compound of Formula I, Ia, Ia-1, Ib or Ic (preferably a compound of formula I, Ia, or Ia-1, more preferably a compound of formula Ia or Ia-1, and most preferably a compound of formula Ia-1) wherein:
B is -L-E;
L is a bond, —O—, —NH—, —CH$_2$—NH—, or —CH$_2$—O—, wherein the groups —CH$_2$—NH— and —CH$_2$—O— are linked to ring A through the N or O atom, respectively, and are linked to ring E through the —CH$_2$— group; and
E is aryl or heteroaryl, wherein said aryl or said heteroaryl is optionally substituted with one or more $R^2$. In a specific embodiment, each $R^2$ is independently selected from hydroxyl, halo, halo$C_{1-8}$ alkyl and N-sulfonamido.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$, and wherein the cyclohexyl ring optionally:
 (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
 (b) is bonded to a linker group —(C($R^a$)$_2$)$_p$— linking together any two non-adjacent ring carbon atoms of the cycloalkyl group, wherein p is 1 or 2 and each $R^a$ independently is hydrogen or $C_{1-4}$ alkyl; or
 (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is phenyl, pyridyl or thiazolyl (preferably phenyl, 3-pyridyl or 5-thiazolyl), wherein A is optionally substituted with one or more $R^1$;

B is hydrogen, $R^1$ or -L-E;

E is phenyl optionally substituted with one or more $R^2$;

L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring s optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is aryl or heteroaryl, wherein A is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and Cm cycloalkyl (e.g. cyclopropyl). In another preferred embodiment, each $R^1$ is independently selected from halo, $C_{1-4}$ alkyl and $C_M$ cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

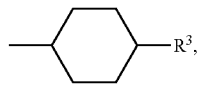

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is phenyl, pyridyl or thiazolyl (preferably phenyl, 3-pyridyl or 5-thiazolyl), wherein A is optionally substituted with one or more $R^1$; and B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and Cm cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is phenyl optionally substituted with one or more $R^1$; and

B is hydrogen or $R^1$.

In the above embodiment, preferably each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$-cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

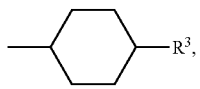

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is aryl or heteroaryl (preferably phenyl, naphthyl, pyridyl or thiazolyl); and B is hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

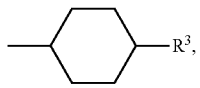

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is phenyl; and

B is hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

A is phenyl or pyridyl (preferably phenyl or 3-pyridyl), wherein A is optionally substituted with one or more $R^1$; and B is -L-E. Preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more $R^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$O—, wherein said —CH$_2$—O— group is linked to ring A through the O atom and to ring E through the —CH$_2$— group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

$R^3$ is selected from —$NR^7R^8$ and —$C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a preferred embodiment of the above embodiment, $R^3$ is —$NR^7R^8$. More preferably $R^3$ is —$NH_2$. In another preferred embodiment, $R^3$ is

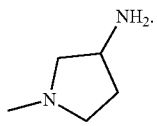

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

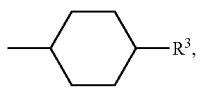

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

$R^3$ is selected from —$NR^7R^8$ and —$C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a preferred embodiment of the above embodiment, $R^3$ is —$NR^7R^8$. More preferably $R^3$ is —$NH_2$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

$R^3$ is selected from —$NR^7R^8$ and —$C_{1-4}$alkylene-$NR^7R^8$;

A is aryl or heteroaryl, wherein A is optionally substituted with one or more $R^1$; and
B is hydrogen or $R^1$.

In a preferred embodiment of the above embodiment, $R^3$ is $-NR^7R^8$. More preferably $R^3$ is $-NH_2$.

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

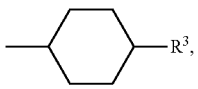

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group $-(C(R^a)_2)_p-$ linking together any two non-adjacent ring carbon atoms of the cycloalkyl group, wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;
$R^3$ is selected from $-NR^7R^8$ and $-C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.

In a preferred embodiment of the above embodiment, $R^3$ is $-NR^7R^8$. More preferably $R^3$ is $-NH_2$. In another preferred embodiment, $R^3$ is

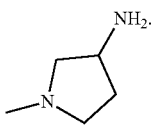

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

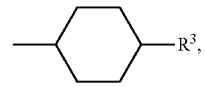

wherein the cyclohexyl ring is optionally substituted with one or more $R^4$, and wherein the cyclohexyl ring optionally:
(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or
(b) is bonded to a linker group $-(C(R^a)_2)_p-$ linking together any two non-adjacent ring carbon atoms of the cycloalkyl group, wherein p is 1 or 2 and each $R^a$ independently is hydrogen or $C_{1-4}$ alkyl; or
(c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;
$R^3$ is selected from $-NR^7R^8$ and $-C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.

In a preferred embodiment of the above embodiment, $R^3$ is $-NR^7R^8$. More preferably $R^3$ is $-NH_2$.

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-8}$ cycloalkyl (e.g. cyclopropyl). In another preferred embodiment, each $R^1$ is independently selected from halo, $C_{1-4}$ alkyl and $C_{3-6}$ cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R⁴, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more R⁵; or
  (b) is bonded to a linker group —(C(R$^a$)₂)$_p$— linking together any two non-adjacent ring carbon atoms of the cycloalkyl group, wherein p is 1 or 2 and each R$^a$ independently is hydrogen or C$_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more R⁶;
R³ is selected from —NR⁷R⁸ and —C$_{1-4}$alkylene-NR⁷R⁸;
A is phenyl optionally substituted with one or more R¹; and
B is hydrogen or R¹.

In a preferred embodiment of the above embodiment, R³ is —NR⁷R⁸. More preferably R³ is —NH₂.

Preferably in the above embodiment each R¹ is independently selected from C$_{1-8}$ alkyl, amino, amido, hydroxyl, halo, haloC$_{1-8}$ alkyl, haloC$_{1-8}$ alkoxy, cyano, sulfonamide, C$_{1-4}$ alkoxy, acyl, carboxyl, carbamate, and urea. In another preferred embodiment, each R¹ is independently selected from halo, C$_{1-4}$ alkyl (e.g. methyl), haloC$_{1-4}$ alkyl (e.g. trifluoromethyl), C$_{1-4}$ alkoxy (e.g. methoxy) and C$_6$ cycloalkyl (e.g. cyclopropyl). In another preferred embodiment, each R¹ is independently selected from halo, C$_{1-4}$ alkyl and C$_{3-6}$cycloalkyl.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R⁴, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more R⁵; or
  (b) is bonded to a linker group —(C(R$^a$)₂)$_p$— linking together any two non-adjacent ring carbon atoms of the cycloalkyl group, wherein p is 1 or 2 and each R$^a$ independently is hydrogen or C$_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more R⁶;
R³ is selected from —NR⁷R⁸ and —C$_{1-4}$alkylene-NR⁷R⁸;
A is phenyl; and
B is hydrogen.

In a preferred embodiment of the above embodiment, R³ is —NR⁷R⁸. More preferably R³ is —NH₂. In another preferred embodiment, R³ is

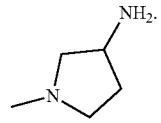

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R⁴, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more R⁵; or
  (b) is bonded to a linker group —(C(R$^a$)₂)$_p$— linking together any two non-adjacent ring carbon atoms of the cycloalkyl group, wherein p is 1 or 2 and each R$^a$ independently is hydrogen or C$_{1-4}$ alkyl; or
  (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more R⁶;
R³ is selected from —NR⁷R⁸ and —C$_{1-4}$alkylene-NR⁷R⁸;
A is phenyl; and
B is hydrogen.

In a preferred embodiment of the above embodiment, R³ is —NR⁷R⁸. More preferably R³ is —NH₂.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R⁴, and wherein the cyclohexyl ring optionally:
  (a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

$R^3$ is selected from —$NR^7R^8$ and —$C_{1-4}$alkylene-$NR^7R^8$;

A is phenyl or pyridyl (preferably phenyl or 3-pyridyl), wherein A is optionally substituted with one or more $R^1$; and B is -L-E. Preferably L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. In a more specific embodiment, E is phenyl optionally substituted with one or more $R^2$ and L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a preferred embodiment of the above embodiment, $R^3$ is —$NR^7R^8$. More preferably $R^3$ is —$NH_2$. In another preferred embodiment, $R^3$ is

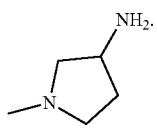

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

wherein the cyclohexyl ring is optionally substituted with one or more $R^4$, and wherein the cyclohexyl ring optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

$R^3$ is selected from —$NR^7R^8$ and —$C_{1-4}$alkylene-$NR^7R^8$;

A is phenyl or pyridyl (preferably phenyl or 3-pyridyl), wherein A is optionally substituted with one or more $R^1$; and B is -L-E. Preferably L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. In a more specific embodiment, E is phenyl optionally substituted with one or more $R^2$ and L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a preferred embodiment of the above embodiment, $R^3$ is —$NR^7R^8$. More preferably $R^3$ is —$NH_2$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

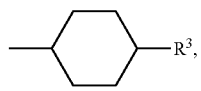

wherein the cyclohexyl ring is optionally substituted with one or more $R^4$;

$R^3$ is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$ alkylene-$NR^7R^8$, —$C_{1-4}$ alkylene-NHOH, —$C_{1-4}$ alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9NR^7R^8$, —$C_{1-4}$ alkylene-$NR^9SO_2NR^7R^8$, —$C_{1-4}$ alkylene-OH and —$C_{1-4}$ alkylene-$CONR^7R^8$;

A is phenyl, pyridyl or thiazolyl (preferably phenyl, 3-pyridyl or 5-thiazolyl), wherein A is optionally substituted with one or more $R^1$;

B is hydrogen, $R^1$ or -L-E;

E is phenyl optionally substituted with one or more $R^2$;

L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is

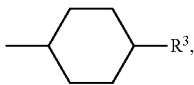

wherein the cyclohexyl ring is optionally substituted with one or more $R^4$;
$R^3$ is selected from $-NR^7R^8$, $-NHOH$, $-NR^9COR^{10}$, $-NR^9SO_2R^{10}$, $-NR^9COOR^{10}$, $-NR^9CONR^7R^8$, $-NR^9SO_2NR^7R^8$, $-OH$, $-CONR^7R^8$, oxo, $-C_{1-4}$ alkylene-$NR^7R^8$, $-C_{1-4}$ alkylene-NHOH, $-C_{1-4}$ alkyene-$NR^9COR^{10}$, $-C_{1-4}$ alkylene-$NR^9SO_2R^{10}$, $-C_{1-4}$ alkylene-$NR^9COOR^{10}$, $-C_{1-4}$ alkylene-$NR^9CONR^7R^8$, $-C_{1-4}$ alkylene-$NR^9SO_2NR^7R^8$, $-C_{1-4}$ alkylene-OH and $-C_{1-4}$ alkylene-$CONR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

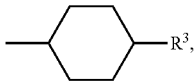

wherein the cyclohexyl ring is optionally substituted with one or more $R^4$;
$R^3$ is selected from $-NR^7R^8$, $-NHOH$, $-NR^9COR^{10}$, $-NR^9SO_2R^{10}$, $-NR^9COOR^{10}$, $-NR^9CONR^7R^8$, $-NR^9SO_2NR^7R^8$, $-OH$, $-CONR^7R^8$, oxo, $-C_{1-4}$ alkylene-$NR^7R^8$, $-C_{1-4}$ alkylene-NHOH, $-C_{1-4}$ alkyene-$NR^9COR^{10}$, $-C_{1-4}$ alkylene-$NR^9SO_2R^{10}$, $-C_{1-4}$ alkylene-$NR^9COOR^{10}$, $-C_{1-4}$ alkylene-$NR^9CONR^7R^8$, $-C_{1-4}$ alkylene-$NR^9SO_2NR^7R^8$, $-C_{1-4}$ alkylene-OH and $-C_{1-4}$ alkylene-$CONR^7R^8$;
A is phenyl; and
B is hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is selected from $-NR^7R^8$, $-NHOH$, $-NR^9COR^{10}$, $-NR^9SO_2R^1$, $-NR^9COOR^{10}$, $-NR^9CONR^7R^8$, $-NR^9SO_2NR^7R^8$, $-OH$, $-CONR^7R^8$, oxo, $-C_{1-4}$ alkylene-$NR^7R^8$, $-C_{1-4}$ alkylene-NHOH, $-C_{1-4}$ alkyene-$NR^9COR^{10}$, $-C_{1-4}$ alkylene-$NR^9SO_2R^1$, $-C_{1-4}$ alkylene-$NR^9COOR^{1'}$, $-C_{1-4}$ alkylene-$NR^9CONR^7R^8$, $-C_{1-4}$ alkylene-$NR^9SO_2NR^7R^8$, $-C_{1-4}$ alkylene-OH and $-C_{1-4}$ alkylene-$CONR^7R^8$;

A is phenyl or pyridyl (preferably phenyl or 3-pyridyl), wherein A is optionally substituted with one or more $R^1$; and
B is -L-E. Preferably L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. In a more specific embodiment, E is phenyl optionally substituted with one or more $R^2$ and L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. Preferably, L is a bond or $-CH_2-O-$, wherein said $-CH_2-O-$ group is linked to ring A through the O atom and to ring E through the $-CH_2-$ group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

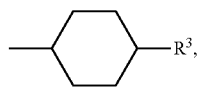

wherein the cyclohexyl ring is optionally substituted with one or more $R^4$;
$R^3$ is selected from $-NR^7R^8$, $-NHOH$, $-NR^9COR^{10}$, $-NR^9SO_2R^{10}$, $-NR^9COOR^{10}$, $-NR^9CONR^7R^8$, $-NR^9SO_2NR^7R^8$, $-OH$, and oxo;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. Preferably, L is a bond or $-CH_2-O-$, wherein said $-CH_2-O-$ group is linked to ring A through the O atom and to ring E through the $-CH_2-$ group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is selected from $-NR^7R^8$, $-NHOH$, $-NR^9COR^{10}$, $-NR^9SO_2R^0$, $-NR^9COOR^{10}$, $-NR^9CONR^7R^8$, $-NR^9SO_2NR^7R^8$, $-OH$, and oxo;
A is phenyl, pyridyl or thiazolyl (preferably phenyl, 3-pyridyl or 5-thiazolyl), wherein A is optionally substituted with one or more $R^1$; and
B is hydrogen or $R^1$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

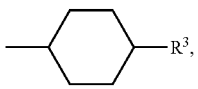

wherein the cyclohexyl ring is optionally substituted with one or more $R^4$;
$R^3$ is selected from $-NR^7R^8$, $-NHOH$, $-NR^9COR^{10}$, $-NR^9SO_2R^{10}$, $-NR^9COOR^{10}$, $-NR^9CONR^7R^8$, $-NR^9SO_2NR^7R^8$, $-OH$, and oxo;
A is phenyl; and
B is hydrogen.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

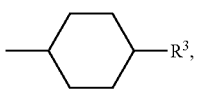

wherein the cyclohexyl ring is optionally substituted with one or more $R^4$;
$R^3$ is selected from $-NR^7R^8$, $-NHOH$, $-NR^9COR^{10}$, $-NR^9SO_2R^{10}$, $-NR^9COOR^{10}$, $-NR^9CONR^7R^8$, $-NR^9SO_2NR^7R^8$, $-OH$, and oxo;
A is phenyl or pyridyl (preferably phenyl or 3-pyridyl), wherein A is optionally substituted with one or more $R^1$; and
B is -L-E. Preferably L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. In a more specific embodiment, E is phenyl optionally substituted with one or more $R^2$ and L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. Preferably, L is a bond or $-CH_2-O-$, wherein said $-CH_2-O-$ group is linked to ring A through the O atom and to ring E through the $-CH_2-$ group.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

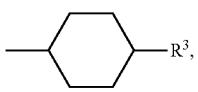

wherein the cyclohexyl ring is optionally substituted with one or more $R^4$;

$R^3$ is selected from $-NR^7R^8$ and $-C_{1-4}alkylene-NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. Preferably, L is a bond or $-CH_2-O-$, wherein said $-CH_2-O-$ group is linked to ring A through the O atom and to ring E through the $-CH_2-$ group.

In a more specific embodiment of the above embodiment, $R^3$ is $-NH_2$. In another specific embodiment, $R^3$ is

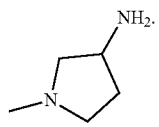

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

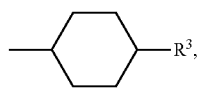

wherein the cyclohexyl ring is optionally substituted with one or more $R^4$;
$R^3$ is selected from $-NR^7R^8$ and $-C_{1-4}alkylene-NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, $-O-$, $-NH-$, $-CH_2-NH-$, or $-CH_2-O-$, wherein said $-CH_2-NH-$ or $-CH_2-O-$ groups are linked to ring A through the N or O atom, respectively, and are linked to ring E through the $-CH_2-$ group. Preferably, L is a bond or $-CH_2-O-$, wherein said $-CH_2-O-$ group is linked to ring A through the O atom and to ring E through the $-CH_2-$ group.

In a more specific embodiment of the above embodiment, $R^3$ is $-NH_2$.

In a preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

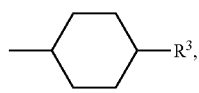

$R^3$ wherein the cyclohexyl ring is optionally substituted with one or more $R^4$;

$R^3$ is selected from —$NR^7R^8$ and —$C_{1-4}$alkylene-$NR^7R^8$;
A is aryl or heteroaryl, wherein said aryl or said heteroaryl is optionally substituted with one or more $R^1$; and
B is hydrogen or $R^1$.

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-8}$ cycloalkyl (e.g. cyclopropyl). In another preferred embodiment, each $R^1$ is independently selected from halo, $C_{1-4}$ alkyl and $C_M$ cycloalkyl.

In a more specific embodiment of the above embodiment, $R^3$ is —$NH_2$.

In a more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is selected from —$NR^7R^8$ and —$C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-5}$ cycloalkyl (e.g. cyclopropyl). In another preferred embodiment, each $R^1$ is independently selected from halo, $C_{1-4}$ alkyl and $C_M$ cycloalkyl.

In a more specific embodiment of the above embodiment, $R^3$ is —$NH_2$. In another specific embodiment, $R^3$ is

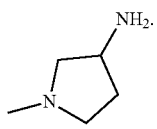

In a more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is selected from —$NR^7R^8$ and —$C_{1-4}$alkylene-$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.

Preferably in the above embodiment each $R^1$ is independently selected from $C_{1-8}$ alkyl, amino, amido, hydroxyl, halo, halo$C_{1-8}$ alkyl, halo$C_1$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In a more specific embodiment of the above embodiment, $R^3$ is —$NH_2$.

In a still more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

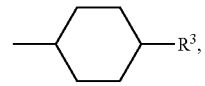

wherein the cyclohexyl ring is optionally substituted with one or more $R^4$;
$R^3$ is selected from —$NR^7R^8$ and —$C_{1-4}$alkylene-$NR^7R^8$;
A is phenyl optionally substituted with one or more $R^1$; and
B is hydrogen or $R^1$.

Preferably in the above embodiment each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In a more specific embodiment of the above embodiment, $R^3$ is —$NH_2$.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:

D is wherein the cyclohexyl ring is optionally substituted with one or more $R^4$;
$R^3$ is selected from —$NR^7R^8$ and —$C_{1-4}$alkylene-$NR^7R^8$;
A is napthyl optionally substituted with one or more $R^1$; and
B is hydrogen or $R^1$.

Preferably in the above embodiment each $R^1$ is independently selected from $C_{1-8}$ alkyl, amino, amido, hydroxyl, halo, haloC$_{1-8}$ alkyl, haloC$_{1-8}$ alkoxy, cyano, sulfonamide, C$_{1-8}$ alkoxy, acyl, carboxyl, carbamate, and urea. In another preferred embodiment, each R$^1$ is independently selected from halo, C$_{1-4}$ alkyl (e.g. methyl), haloC$_{1-4}$ alkyl (e.g. trifluoromethyl), C$_{1-4}$ alkoxy (e.g. methoxy) and C$_{3-6}$ cycloalkyl (e.g. cyclopropyl). In another preferred embodiment, each R$^1$ is independently selected from halo, C$_{1-4}$ alkyl and C$_{3-6}$ cycloalkyl.

In a more specific embodiment of the above embodiment, R$^3$ is —NH$_2$.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

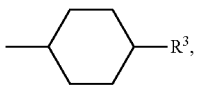

wherein the cyclohexyl ring is optionally substituted with one or more R$^4$;
R$^3$ is selected from —NR$^7$R$^8$ and —C$_{1-4}$alkylene-NR$^7$R$^8$;
A is heteroaryl, preferably monocyclic heteroaryl, optionally substituted with one or more R$^1$; and
B is hydrogen or R$^1$.

Preferably in the above embodiment each R$^1$ is independently selected from C$_{1-8}$ alkyl, amino, amido, hydroxyl, halo, haloC$_{1-8}$ alkyl, haloC$_{1-8}$ alkoxy, cyano, sulfonamide, C$_s$ alkoxy, acyl, carboxyl, carbamate, and urea. In another preferred embodiment, each R$^1$ is independently selected from halo, C$_{1-4}$ alkyl (e.g. methyl), haloC$_{1-4}$ alkyl (e.g. trifluoromethyl), C$_{1-4}$ alkoxy (e.g. methoxy) and C$_{3-6}$ cycloalkyl (e.g. cyclopropyl). In another preferred embodiment, each R$^1$ is independently selected from halo, C$_{1-4}$ alkyl and C$_{3-6}$ cycloalkyl.

In a more specific embodiment of the above embodiment, R$^3$ is —NH$_2$.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

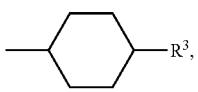

wherein the cyclohexyl ring is optionally substituted with one or more R$^4$;
R$^3$ is selected from —NR$^7$R$^8$ and —C$_{1-4}$alkylene-NR$^7$R$^8$;
A is phenyl; and
B is hydrogen.

In a more specific embodiment of the above embodiment, R$^3$ is —NH$_2$. In another specific embodiment, R$^3$ is

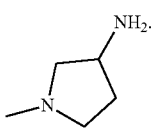

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R$^4$;
R$^3$ is selected from —NR$^7$R$^8$ and —C$_{1-4}$alkylene-NR$^7$R$^8$;
A is phenyl; and
B is hydrogen.

In a more specific embodiment of the above embodiment, R$^3$ is —NH$_2$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R$^4$;
R$^3$ is selected from —NR$^7$R$^8$ and —C$_{1-4}$alkylene-NR$^7$R$^8$;
A is phenyl or pyridyl (preferably phenyl or 3-pyridyl), wherein A is optionally substituted with one or more R$^1$; and
B is -L-E. Preferably L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. In a more specific embodiment, E is phenyl optionally substituted with one or more R$^2$ and L is a bond, —O—, —NH—, —CH$_2$—NH—, or —CH$_2$—O—, wherein said —CH$_2$—NH— or —CH$_2$—O— groups are linked to ring A through the N or O atom, respectively, and are linked to ring E through the —CH$_2$— group. Preferably, L is a bond or —CH$_2$—O—, wherein said —CH$_2$—O— group is linked to ring A through the O atom and to ring E through the —CH$_2$— group.

In a more specific embodiment of the above embodiment, R$^3$ is —NH$_2$.

In a preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more R$^4$;

$R^3$ is —$NR^7R^8$;
A is aryl or heteroaryl (e.g., phenyl, naphthyl or monocyclic heteroaryl), wherein said aryl or said heteroaryl is optionally substituted with one or more $R^1$; and
B is hydrogen, $R^1$ or -L-E.

In a more specific embodiment of the above embodiment, $R^3$ is —$NH_2$.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl), wherein A is optionally substituted with one or more $R^1$; and
B is hydrogen, $R^1$ or -L-E.

In a more specific embodiment of the above embodiment, $R^3$ is —$NH_2$.

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a more specific embodiment of the above embodiment, $R^3$ is —$NH_2$. In another specific embodiment, $R^3$ is

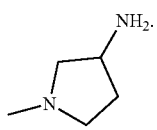

In another embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl), wherein A is optionally substituted with one or more $R^1$;
B is hydrogen, $R^1$ or -L-E;
E is phenyl optionally substituted with one or more $R^2$;
L is a bond, —O—, —NH—, —$CH_2$—NH—, or —$CH_2$—O—, wherein said —$CH_2$—NH— or —$CH_2$—O— groups are linked to ring A through the N or O atom, respectively, and are linked to ring E through the —$CH_2$— group. Preferably, L is a bond or —$CH_2$—O—, wherein said —$CH_2$—O— group is linked to ring A through the O atom and to ring E through the —$CH_2$— group.

In a more specific embodiment of the above embodiment, $R^3$ is —$NH_2$.

In a preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is —$NR^7R^8$;
A is aryl or heteroaryl (e.g., phenyl, naphthyl or monocyclic heteroaryl), wherein said aryl or said heteroaryl is optionally substituted with one or more $R^1$; and
B is hydrogen or $R^1$.

In a more specific embodiment of the above embodiment, $R^3$ is —$NH_2$.

Preferably in the above embodiments each $R^1$ is independently selected from $C_1$a alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$cycloalkyl.

In a more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

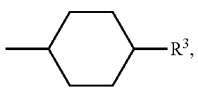

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.
In a more specific embodiment of the above embodiment, $R^3$ is —$NH_2$. In another specific embodiment, $R^3$ is

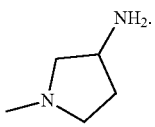

Preferably in the above embodiments each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$ cycloalkyl.

In a more preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

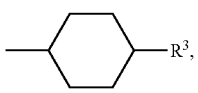

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl), wherein A is optionally substituted with one or more $R^1$; and
B is hydrogen or $R^1$.
In a more specific embodiment of the above embodiment, $R^3$ is —$NH_2$.
Preferably in the above embodiments each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$cycloalkyl.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

wherein the cyclohexyl ring is optionally substituted with one or more $R^4$;
$R^3$ is —$NR^7R^8$;
A is phenyl optionally substituted with one or more $R^1$; and
B is hydrogen or $R^1$.
In a more specific embodiment of the above embodiment, $R^3$ is —$NH_2$.
Preferably in the above embodiments each $R^1$ is independently selected from $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea. In another preferred embodiment, each $R^1$ is independently selected from halo, $C_{1-4}$ alkyl (e.g. methyl), halo$C_{1-4}$ alkyl (e.g. trifluoromethyl), $C_{1-4}$ alkoxy (e.g. methoxy) and $C_{3-6}$ cycloalkyl (e.g. cyclopropyl). In another preferred embodiment, each $R^1$ is independently selected from halo, $C_{1-4}$ alkyl and $C_{3-6}$cycloalkyl.

In a very preferred embodiment, the invention provides a compound of formula I, Ia, Ia-1, Ib or Ic wherein:
D is

wherein the cyclohexyl ring is optionally substituted with one or more $R^4$;
$R^3$ is —$NR^7R^8$;
A is phenyl, naphthyl or monocyclic heteroaryl; and
B is hydrogen.
In a more specific embodiment of the above embodiment, $R^3$ is —$NH_2$. In another very preferred embodiment, the invention provides a compound of formula I, Ia, Ia-1, Ib or Ic wherein:
D is

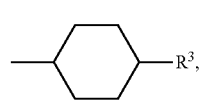

wherein the cyclohexyl ring is optionally substituted with one or more $R^4$;
$R^3$ is —$NR^7R^8$;
A is phenyl, pyridyl or thiazolyl (preferably phenyl, 3-pyridyl or 5-thiazolyl); and
B is hydrogen.

In a more specific embodiment of the above embodiment, R³ is —NH₂. In another very preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

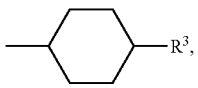

wherein the cyclohexyl ring is optionally substituted with one or more R⁴;
R³ is —NR⁷R⁸;
A is phenyl; and
B is hydrogen.

In a more specific embodiment of the above embodiment, R³ is —NH₂. In another specific embodiment, R³ is

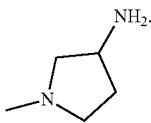

In another very preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

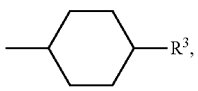

wherein the cyclohexyl ring is optionally substituted with one or more R⁴;
R³ is —NR⁷R⁸;
A is phenyl; and
B is hydrogen.

In a more specific embodiment of the above embodiment, R³ is —NH₂.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

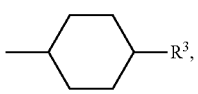

wherein the cyclohexyl ring is optionally substituted with one or more R⁴;
R³ is —NR⁷R⁸;
A is phenyl or pyridyl (preferably phenyl or 3-pyridyl), wherein A is optionally substituted with one or more R¹; and
B is -L-E.

Preferably, L is a bond, —O—, —NH—, —CH₂—NH—, or —CH₂—O—, wherein said —CH₂—NH— or —CH₂—O— groups are linked to ring A through the N or O atom, respectively, and are linked to ring E through the —CH₂— group; more preferably, L is a bond or —CH₂—O—, wherein said —CH₂—O— group is linked to ring A through the O atom and to ring E through the —CH₂— group.

In a more specific embodiment of the above embodiment, R³ is —NH₂. In another specific embodiment, R³ is

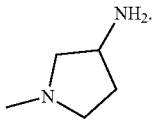

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

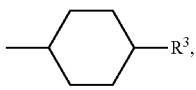

wherein the cyclohexyl ring is optionally substituted with one or more R⁴;
R³ is —NR⁷R⁸;
A is phenyl or pyridyl (preferably phenyl or 3-pyridyl), wherein A is optionally substituted with one or more R¹; and
B is -L-E.

Preferably, L is a bond, —O—, —NH—, —CH₂—NH—, or —CH₂—O—, wherein said —CH₂—NH— or —CH₂—O— groups are linked to ring A through the N or O atom, respectively, and are linked to ring E through the —CH₂— group; more preferably, L is a bond or —CH₂—O—, wherein said —CH₂—O— group is linked to ring A through the O atom and to ring E through the —CH₂— group.

In a more specific embodiment of the above embodiment, R³ is —NH₂.

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

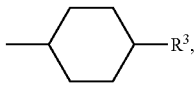

wherein the cyclohexyl ring is optionally substituted with one or more R⁴;
R³ is —NR⁷R⁸;
A is phenyl or pyridyl (preferably phenyl or 3-pyridyl), wherein A is optionally substituted with one or more R¹;
B is -L-E;
E is phenyl optionally substituted with one or more R²; and
L is a bond, —O—, —NH—, —CH₂—NH—, or —CH₂—O—, wherein said —CH₂—NH— or —CH₂—O— groups are linked to ring A through the N or O atom, respectively, and are linked to ring E through the —CH₂— group, and preferably, L is a bond or —CH₂—O—, wherein said —CH₂—O— group is linked to ring A through the O atom and to ring E through the —CH₂— group.

In a more specific embodiment of the above embodiment, R³ is —NH₂. In another specific embodiment, R³ is

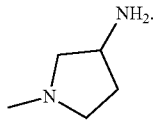

In another preferred embodiment, the invention provides a compound of formula I, Ia, Ia-1, Ib or Ic (preferably a compound of formula I, Ia, or Ia-1, more preferably a compound of formula Ia or Ia-1, and most preferably a compound of formula Ia-1) wherein:
D is

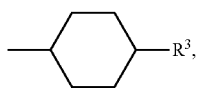

wherein the cyclohexyl ring is optionally substituted with one or more R⁴;
R³ is —NR⁷R⁸;
A is phenyl or pyridyl (preferably phenyl or 3-pyridyl), wherein A is optionally substituted with one or more R¹;
B is -L-E;
E is phenyl optionally substituted with one or more R²; and L is a bond, —O—, —NH—, —CH₂—NH—, or —CH₂—O—, wherein said —CH₂—NH— or —CH₂—O— groups are linked to ring A through the N or O atom, respectively, and are linked to ring E through the —CH₂— group, and preferably, L is a bond or —CH₂—O—, wherein said —CH₂—O— group is linked to ring A through the O atom and to ring E through the —CH₂— group.

In a more specific embodiment of the above embodiment, R³ is —NH₂.

In a further embodiment, the invention provides a compound of formula I, Ia or Ia-1 selected from:
N1-((trans)-2-phenylcyclopropyl)cyclohexane-1,4-diamine;
(cis)-N1-((1S,2R)-2-phenylcyclopropyl)cyclohexane-1,4-diamine;
(trans)-N1-((1S,2R)-2-phenylcyclopropyl)cyclohexane-1,4-diamine;
(cis)-N1-((1R,2S)-2-phenylcyclopropyl)cyclohexane-1,4-diamine;
(trans)-N1-((1R,2S)-2-phenylcyclopropyl)cyclohexane-1,4-diamine;
N1-((trans)-2-(thiazol-5-yl)cyclopropyl)cyclohexane-1,4-diamine;
N1-((trans)-2-(pyridin-3-yl)cyclopropyl)cyclohexane-1,4-diamine;
N1-((trans)-2-(6-(3-(trifluoromethyl)phenyl)pyridin-3-yl)cyclopropyl)cyclohexane-1,4-diamine;
N1-((trans)-2-(3'-(trifluoromethyl)-[1,1'-biphenyl]-4-yl)cyclopropyl)cyclohexane-1,4-diamine;
N1-((trans)-2-(4-(benzyloxy)phenyl)cyclopropyl)cyclohexane-1,4-diamine;
4-(((trans)-2-(6-(3-(trifluoromethyl)phenyl)pyridin-3-yl)cyclopropyl)amino)cyclohexanol;
4-(((trans)-2-(6-(3-(trifluoromethyl)phenyl)pyridin-3-yl)cyclopropyl)amino)cyclohexanecarboxamide;
N-(4-(((trans)-2-(6-(3-(trifluoromethyl)phenyl)pyridin-3-yl)cyclopropyl)amino)cyclohexyl)acetamide;
(R)-1-(4-(((trans)-2-phenylcyclopropyl)amino)cyclohexyl)pyrrolidin-3-amine;
N1-((trans)-2-(4'-chloro-[1,1'-biphenyl]-4-yl)cyclopropyl)cyclohexane-1,4-diamine;
N1-((trans)-2-(3'-chloro-[1,1'-biphenyl]-4-yl)cyclopropyl)cyclohexane-1,4-diamine;
4'-((trans)-2-((4-aminocyclohexyl)amino)cyclopropyl)-[1,1'-biphenyl]-3-ol;
N-(4'-((trans)-2-((4-aminocyclohexyl)amino)cyclopropyl)-[1,1'-biphenyl]-3-yl)methanesulfonamide;
N1-((trans)-2-(4-((2-fluorobenzyl)oxy)phenyl)cyclopropyl)cyclohexane-1,4-diamine;
N1-((trans)-2-(4-((3-fluorobenzyl)oxy)phenyl)cyclopropyl)cyclohexane-1,4-diamine;
N1-((trans)-2-(4-((4-fluorobenzyl)oxy)phenyl)cyclopropyl)cyclohexane-1,4-diamine;
N1-methyl-N4-((trans)-2-phenylcyclopropyl)cyclohexane-1,4-diamine;
N1-methyl-N4-((trans)-2-(3'-(trifluoromethyl)-[1,1'-biphenyl]-4-yl)cyclopropyl)cyclohexane-1,4-diamine;
N1-((trans)-2-(4-(benzyloxy)phenyl)cyclopropyl)-N4-methylcyclohexane-1,4-diamine;
N1-((trans)-2-phenylcyclopropyl)cyclobutane-1,3-diamine;
N1-((trans)-2-(3'-(trifluoromethyl)-[1,1'-biphenyl]-4-yl)cyclopropyl)cyclobutane-1,3-diamine;
N1-((trans)-2-(4-(benzyloxy)phenyl)cyclopropyl)cyclobutane-1,3-diamine;
N1-((trans)-2-phenylcyclopropyl)-2,3-dihydro-1H-indene-1,3-diamine;
N1-((trans)-2-(3'-(trifluoromethyl)-[1,1'-biphenyl]-4-yl)cyclopropyl)-2,3-dihydro-1H-indene-1,3-diamine;
N1-((trans)-2-(4-(benzyloxy)phenyl)cyclopropyl)-2,3-dihydro-1H-indene-1,3-diamine;
N1-((trans)-2-fluoro-2-phenylcyclopropyl)cyclohexane-1,4-diamine;
N1-((1S,2S)-2-fluoro-2-phenylcyclopropyl)cyclohexane-1,4-diamine;
N1-((1R,2R)-2-fluoro-2-phenylcyclopropyl)cyclohexane-1,4-diamine;
1-methyl-N4-((trans)-2-phenylcyclopropyl)cyclohexane-1,4-diamine;
4-(aminomethyl)-N-((trans)-2-phenylcyclopropyl)cyclohexanamine;
N1-((trans)-2-phenylcyclopropyl)cyclohexane-1,3-diamine;
N1-((cis)-2-phenylcyclopropyl)cyclohexane-1,4-diamine;
Tert-butyl (4-(((trans)-2-phenylcyclopropyl)amino)cyclohexyl)carbamate;
1-ethyl-3-(4-(((trans)-2-phenylcyclopropyl)amino)cyclohexyl)urea;
4-morpholino-N-((trans)-2-phenylcyclopropyl)cyclohexanamine;
N1-((trans)-2-(4-bromophenyl)cyclopropyl)cyclohexane-1,4-diamine;
N1-(2-(o-tolyl)cyclopropyl)cyclohexane-1,4-diamine;
N1-(2-(4-(trifluoromethyl)phenyl)cyclopropyl)cyclohexane-1,4-diamine
N1-(2-(4-methoxyphenyl)cyclopropyl)cyclohexane-1,4-diamine;
4-(2-((4-aminocyclohexyl)amino)cyclopropyl)phenol;
N1-(2-(2-fluorophenyl)cyclopropyl)cyclohexane-1,4-diamine;
N1-(2-(3,4-difluorophenyl)cyclopropyl)cyclohexane-1,4-diamine;

N1-(2-(naphthalen-2-yl)cyclopropyl)cyclohexane-1,4-diamine;
N1-(2-methyl-2-phenylcyclopropyl)cyclohexane-1,4-diamine;
(R)-1-(4-(((trans)-2-(3'-(trifluoromethyl)-[1,1'-biphenyl]-4-yl)cyclopropyl) amino)cyclohexyl)pyrrolidin-3-amine;
(Cis)-N1-((1S,2R)-2-(3'-(trifluoromethyl)-[1,1'-biphenyl]-4-yl)cyclopropyl)cyclohexane-1,4-diamine;
(Trans)-N1-((1S,2R)-2-(3'-(trifluoromethyl)-[1,1'-biphenyl]-4-yl)cyclo-propyl)cyclohexane-1,4-diamine;
(Cis)-N1-((1R,2S)-2-(3'-(trifluoromethyl)-[1,1'-biphenyl]-4-yl)cyclo-propyl)cyclohexane-1,4-diamine;
(Trans)-N1-((1R,2S)-2-(3'-(trifluoromethyl)-[1,1'-biphenyl]-4-yl)cyclo-propyl)cyclohexane-1,4-diamine;
N1-((trans)-2-(4-cyclopropylphenyl)cyclopropyl)cyclohexane-1,4-diamine;
N1-((trans)-2-(4-(pyridin-3-yl)phenyl)cyclopropyl)cyclohexane-1,4-diamine;
N1-((trans)-2-(4-(1H-indazol-6-yl)phenyl)cyclopropyl)cyclohexane-1,4-diamine;
N1-((trans)-2-(4-(1H-pyrazol-5-yl)phenyl)cyclopropyl)cyclohexane-1,4-diamine;
3-(5-((trans)-2-((4-aminocyclohexyl)amino)cyclopropyl)thiophen-2-yl)phenol;
3-(5-((trans)-2-((4-aminocyclohexyl)amino)cyclopropyl)thiazol-2-yl)phenol;
3-(5-((trans)-2-((4-aminocyclohexyl)amino)cyclopropyl)pyridin-2-yl)-5-methoxybenzonitrile;
5-(5-((trans)-2-((4-aminocyclohexyl)amino)cyclopropyl)pyridin-2-yl)-2-methylphenol;
N-(4'-((trans)-2-((4-aminocyclohexyl)amino)cyclopropyl)-6-methoxy-[1,1'-biphenyl]-3-yl)methanesulfonamide;
N-(3-(5-((trans)-2-((4-aminocyclohexyl)amino)cyclopropyl)thiazol-2-yl)phenyl)-2-cyanobenzenesulfonamide
N-(4'-((trans)-2-((4-aminocyclohexyl)amino)cyclopropyl)-[1,1'-biphenyl]-3-yl)-2-cyanobenzenesulfonamide;
6-amino-N-(4'-((trans)-2-((4-aminocyclohexyl)amino)cyclopropyl)-[1,1'-biphenyl]-3-yl)pyridine-3-sulfonamide;
N-4'-((trans)-2-((4-aminocyclohexyl)amino)cyclopropyl)-[1,1'-biphenyl]-3-yl)piperazine-1-sulfonamide;
N1-((cis)-2-fluoro-2-phenylcyclopropyl)cyclohexane-1,4-diamine;
N1-((trans)-2-(4-((3-(piperazin-1-yl)benzyl)oxy)phenyl)cyclopropyl)cyclohexane-1,4-diamine;
N1-((trans)-2-(4-(pyridin-3-ylmethoxy)phenyl)cyclopropyl)cyclohexane-1,4-diamine;
N1-((trans)-2-(6-((3-methyl benzyl)amino)pyridin-3-yl)cyclopropyl)cyclohexane-1,4-diamine;
3-((5-((trans)-2-((4-aminocyclohexyl)amino)cyclopropyl)pyridin-2-yl) amino)benzonitrile;
N1-((trans)-2-(naphthalen-2-yl)cyclopropyl)cyclohexane-1,4-diamine;
N1-((trans)-2-(o-tolyl)cyclopropyl)cyclohexane-1,4-diamine;
N1-((trans)-2-(4-(trifluoromethyl)phenyl)cyclopropyl)cyclohexane-1,4-diamine;
N1-((trans)-2-(4-methoxyphenyl)cyclopropyl)cyclohexane-1,4-diamine;
N1-((trans)-2-(2-fluorophenyl)cyclopropyl)cyclohexane-1,4-diamine;
N1-((trans)-2-(3,4-difluorophenyl)cyclopropyl)cyclohexane-1,4-diamine;
N1-((trans)-2-methyl-2-phenylcyclopropyl)cyclohexane-1,4-diamine;
(cis)-N1-((1S,2R)-2-(pyridin-3-yl)cyclopropyl)cyclohexane-1,4-diamine;
(trans)-N1-((1R,2S)-2-(pyridin-3-yl)cyclopropyl)cyclohexane-1,4-diamine;
(cis)-N1-((1R,2S)-2-(pyridin-3-yl)cyclopropyl)cyclohexane-1,4-diamine;
(trans)-N1-((1S,2R)-2-(pyridin-3-yl)cyclopropyl)cyclohexane-1,4-diamine;
(cis)-N1-((1S,2R)-2-phenylcyclopropyl)cyclobutane-1,3-diamine;
(trans)-N1-((1R,2S)-2-phenylcyclopropyl)cyclobutane-1,3-diamine;
(cis)-N1-((1R,2S)-2-phenylcyclopropyl)cyclobutane-1,3-diamine;
(trans)-N1-((1S,2R)-2-phenylcyclopropyl)cyclobutane-1,3-diamine;
(cis)-N1-((1S,2R)-2-(3,4-difluorophenyl)cyclopropyl)cyclohexane-1,4-diamine;
(trans)-N1-((1R,2S)-2-(3,4-difluorophenyl)cyclopropyl)cyclohexane-1,4-diamine;
(cis)-N1-((1R,2S)-2-(3,4-difluorophenyl)cyclopropyl)cyclohexane-1,4-diamine;
(trans)-N1-((1S,2R)-2-(3,4-difluorophenyl)cyclopropyl)cyclohexane-1,4-diamine;
(cis)-N1-((1S,2R)-2-(naphthalen-2-yl)cyclopropyl)cyclohexane-1,4-diamine;
(trans)-N1-((1R,2S)-2-(naphthalen-2-yl)cyclopropyl)cyclohexane-1,4-diamine;
(cis)-N1-((1R,2S)-2-(naphthalen-2-yl)cyclopropyl)cyclohexane-1,4-diamine;
(trans)-N1-((1S,2R)-2-(naphthalen-2-yl)cyclopropyl)cyclohexane-1,4-diamine;
(cis)-N1-((1S,2R)-2-(4-(1H-pyrazol-5-yl)phenyl)cyclopropyl)cyclohexane-1,4-diamine;
(trans)-N1-((1R,2S)-2-(4-(1H-pyrazol-5-yl)phenyl)cyclopropyl)cyclohexane-1,4-diamine;
(cis)-N1-((1R,2S)-2-(4-(1H-pyrazol-5-yl)phenyl)cyclopropyl)cyclohexane-1,4-diamine;
(trans)-N1-((1S,2R)-2-(4-(1H-pyrazol-5-yl)phenyl)cyclopropyl)cyclohexane-1,4-diamine;
N-(4'-((1R,2S)-2-(((cis)-4-aminocyclohexyl)amino)cyclopropyl)-[1,1'-biphenyl]-3-yl)piperazine-1-sulfonamide;
N-(4'-((1S,2R)-2-(((trans)-4-aminocyclohexyl)amino)cyclopropyl)-[1,1'-biphenyl]-3-yl)piperazine-1-sulfonamide;
N-(4'-((1S,2R)-2-(((cis)-4-aminocyclohexyl)amino)cyclopropyl)-[1,1'-biphenyl]-3-yl)piperazine-1-sulfonamide;
N-(4'-((1R,2S)-2-(((trans)-4-aminocyclohexyl)amino)cyclopropyl)-[1,1'-biphenyl]-3-yl)piperazine-1-sulfonamide;
(cis)-N1-((1S,2R)-2-(4-((2-fluorobenzyl)oxy)phenyl)cyclopropyl)cyclohexane-1,4-diamine;
(trans)-N1-((1R,2S)-2-(4-((2-fluorobenzyl)oxy)phenyl)cyclopropyl)cyclohexane-1,4-diamine;
(cis)-N1-((R,2S)-2-(4-((2-fluorobenzyl)oxy)phenyl)cyclopropyl)cyclohexane-1,4-diamine;
(trans)-N1-((1S,2R)-2-(4-((2-fluorobenzyl)oxy)phenyl)cyclopropyl)cyclohexane-1,4-diamine;
as well as salts and solvates thereof (including pharmaceutically acceptable salts and solvates thereof).

The invention also relates to any one or any subgroup of the compounds listed above. The invention likewise relates to a pharmaceutically acceptable salt, preferably a hydrochloride salt (such as, e.g., a monohydrochloride salt, a dihydrochloride salt or, where applicable, a trihydrochloride salt), of any of the compounds listed above.

Preferred embodiments of the compounds of Formula I, Ia, Ia-1, Ib and Ic for use in the compositions and methods of the invention are as defined herein above.

In a further aspect, the invention provides a method for identifying a compound which is a selective inhibitor of LSD1, the method comprising selecting or providing a compound of Formula I, Ia, Ia-1, Ib or Ic and determining the ability of the said compound to inhibit LSD1 and MAO-A and/or MAO-B using assays such as the ones disclosed in more detail later on, wherein a compound that inhibits LSD1 to a greater extent than MAO-A and/or MAO-B is identified as a LSD1 selective inhibitor. LSD1 selective inhibitors have IC50 values for LSD1 which are lower than the IC50 value for MAO-A and/or MAO-B. Preferably, the IC50 values for LSD1 are two-fold lower than for MAO-A and/or MAO-B. In one aspect of this embodiment, the LSD1 IC50 value is at least 5-fold lower than the IC50 value for MAO-A and/or MAO-B. In one aspect of this embodiment, the LSD1 IC50 value is at least 10-fold lower than the IC50 value for MAO-A and/or MAO-B. Preferably, a selective LSD1 inhibitor exhibits an IC50 value for LSD1 that is >50-fold, preferably >100-fold lower than the IC50 value for MAO-A and/or MAO-B.

Asymmetric centers exist in the compounds of formula I, Ia, Ia-1, Ib and Ic disclosed herein. It should be understood that the invention encompasses all individual stereochemical isomeric forms of a compound of formula I, Ia, Ia-1, Ib and Ic, including diastereomeric, enantiomeric, and epimeric forms, as well as d-isomers and l-isomers ((+)-isomers and (−)-isomers), and any mixtures thereof, including wholly or partially equilibrated mixtures. Individual stereoisomers of compounds of the invention can be prepared synthetically from commercially available chiral starting materials or by separation from mixtures of stereoisomers, as also shown in the Examples. Methods of separation of enantiomeric and diastereomeric mixtures are well known to one skilled in the art. For example, mixtures of diastereomers can be separated by conventional separation techniques such as recrystallization or chromatography. Mixtures of enantiomeric products can be separated by conversion to a mixture of diastereomers followed by separation using recrystallization or chromatographic techniques, direct separation of enantiomers on chiral chromatographic columns, or any other appropriate method of chiral resolution known in the art. Starting compounds of particular stereochemistry are either commercially available or can be made and resolved by techniques known in the art.

Additionally, the compounds disclosed herein may exist as geometric isomers. The present invention includes all cis, trans, syn, anti, entgegen (E), and zusammen (Z) isomers as well as the mixtures thereof.

Additionally, compounds may exist as tautomers; all tautomeric isomers are provided by this invention.

The compounds of the invention contain one or more basic nitrogen atoms and may therefore form salts with organic or inorganic acids. The compounds of the invention may also contain one or more acidic protons and therefore they may also form salts with bases. There is no limitation on the type of salt that can be used provided that these are pharmaceutically acceptable when used for therapeutic purposes. The salts of a compound of the invention can be obtained during the final isolation and purification of the compounds of the invention or can be obtained by treating a compound of formula I, Ia, Ia-1, Ib or Ic with a sufficient amount of the desired acid or base to give the corresponding salt in a conventional manner. All salts of the compounds of formula I, Ia, Ia-1, Ib and Ic, including pharmaceutically acceptable salts, are included within the scope of the invention. In one embodiment, a compound of formula I, Ia, Ia-1, Ib or Ic is provided in the form of a salt. In a more preferred embodiment, a compound of formula I, Ia and Ia-1 is provided in the form of a pharmaceutically acceptable salt. In one embodiment, such pharmaceutically acceptable salt is a hydrochloride, for example a monohydrochloride, a dihydrochloride or a trihydrochloride.

Additionally, the compounds disclosed herein can exist in unsolvated as well as solvated forms with pharmaceutically acceptable solvents such as water, ethanol, and the like. Solvated forms with water are known as hydrates. In general, the solvated forms are considered equivalent to the unsolvated forms. The invention thus relates to the unsolvated and solvated forms of the compounds of formula I, Ia, Ia-1, Ib or Ic (or of any salt thereof).

The compounds of formula I, Ia, Ia-1, Ib and Ic may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of the invention, including all polymorphic forms (also known as polymorphs) thereof, are included within the scope of the invention.

The present invention further covers all unlabeled and isotopically labeled forms of the compounds of formula I, Ia, Ia-1, Ib and Ic. In one embodiment, the invention relates to deuterated forms of the compounds of formula I, Ia, Ia-1, Ib and Ic.

The invention also relates to a compound of Formula I, Ia, Ia-1, Ib or Ic (preferably a compound of formula I, Ia, or Ia-1, more preferably a compound of formula Ia or Ia-1, and most preferably a compound of formula Ia-1) as described and defined herein, wherein the substituents -A-B and —NH-D on the cyclopropyl moiety are in trans-configuration and further wherein the compound is optically active. As used herein, the term "optically active" refers to the ability of a compound to rotate plane polarized light.

The invention, in another aspect, relates to a substantially pure, optically active stereoisomer of a compound of Formula I, Ia, Ia-1, Ib or Ic as described and defined herein, wherein the substituents -A-B and —NH-D on the cyclopropyl moiety are in trans-configuration, or a pharmaceutically acceptable salt or solvate thereof, as well as its use as a medicament. As used herein, "substantially pure" means that there is 90 mole-% or greater of the desired stereoisomer and 10 mole-% or less of any other stereoisomer, preferably that there is 95 mole-% or greater of the desired stereoisomer and 5 mole-% or less of any other stereoisomer, more preferably, that there is 98 mole-% or greater of the desired stereoisomer and 2 mole-% or less of any other stereoisomer, still more preferably, that there is 99 mole-% or greater of the desired stereoisomer and 1 mole-% or less of any other stereoisomer, and even more preferably that there is 99.5 mole-% or greater of the desired stereoisomer and 0.5 mole-% or less of any other stereoisomer. The substantially pure, optically active stereoisomer of a compound of Formula I, Ia, Ia-1, Ib or Ic as described and defined herein, wherein the substituents -A-B and —NH-D on the cyclopropyl moiety are in trans-configuration, is useful in treating or preventing a disease or disorder, particularly cancer, a neurological disease, or a viral infection.

Definitions

Any definition herein may be used in combination with any other definition to describe a composite structural group.

By convention, the trailing element of any such definition is that which attaches to the parent moiety. For example, the composite group cyclylC$_{1-8}$ alkyl would represent a cyclyl group attached to the parent molecule through a C$_{1-8}$ alkyl group.

As used herein, the term "acyl" refers to a carbonyl attached to an alkenyl, alkyl, aryl, cycloalkyl, heteroaryl, heterocyclyl, or any other moiety where the atom attached to the carbonyl is carbon. Preferably, the term "acyl" refers to a group of formula —C(=O)R", wherein R" represents alkenyl, alkyl, aryl, cycloalkyl, heteroaryl or heterocyclyl. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "alkenyl" refers to a straight-chain or branched-chain hydrocarbon group having one or more double bonds and containing from 2 to 20 carbon atoms. A C$_{2-8}$ alkenyl is an alkenyl group having from 2 to 8 carbon atoms.

As used herein, the term "alkoxy" refers to an alkyl ether group (ie a group of formula alkyl-O—), wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy. The term C$_{1-z}$ alkoxy refers to an alkoxy group wherein the alkyl moiety has from 1 to z carbon atoms; for example a C$_{1-8}$ alkoxy is an alkoxy group wherein the alkyl moiety is C$_{1-8}$ alkyl, i.e. a group of formula C$_{1-8}$ alkyl-O—.

As used herein, the term "alkyl" refers to a straight-chain or branched-chain alkyl group containing from 1 to 20 carbon atoms. A C$_{1-z}$ alkyl is an alkyl from 1 to z carbon atoms; thus, a C$_{1-8}$ alkyl has from 1 to 8 carbon atoms, a C$_{1-4}$ alkyl has from 1 to 4 carbon atoms and a C$_{1-2}$ alkyl has from 1 to 2 carbon atoms. Examples of alkyl groups include, but are not limited to, methyl, ethyl, n-propyl, isopropyl, n-butyl, isobutyl, sec-butyl, tert-butyl, pentyl, isopentyl, neopentyl, iso-amyl, hexyl, heptyl, octyl, or nonyl.

As used herein, the term "C$_{1-4}$ alkylene" refers to an C$_{1-4}$ alkyl group attached at two positions, i.e. an alkanediyl group. Examples include, but are not limited to, methylene (i.e. a group of formula —CH$_2$—), ethylene (including ethane-1,2-diyl and ethane-1,1-diyl), propylene (e.g. propane-1,3-diyl, propane-1,2-diyl and propane-1,1-diyl) and butylene (e.g. butane-1,4-diyl, butane-1,3-diyl or butane-1,1-diyl). Accordingly, the term "C$_{1-4}$ alkylene" may refer to a straight-chain or branched-chain alkylene group having from 1 to 4 carbon atoms.

As used herein, the term "alkynyl" refers to a straight-chain or branched-chain hydrocarbon group having one or more triple bonds and containing from 2 to 20 carbon atoms. A C$_{2-8}$ alkynyl has from 2 to 8 carbon atoms. Examples of alkynyl groups include, but are not limited to, ethynyl, propynyl, hydroxypropynyl, butyn-1-yl, butyn-2-yl, pentyn-1-yl, 3-methylbutyn-1-yl, or hexyn-2-yl.

As used herein, the term "amido" refers to an amino group as described below attached to the parent molecular moiety through a carbonyl group (e.g., —C(=O)NRR'), or vice versa (—N(R)C(=O)R'). "Amido" encompasses "C-amido" and "N-amido" as defined herein. R and R' are as defined herein.

As used herein, the term "C-amido" refers to a —C(=O)NRR' group with R and R' as defined herein.

As used herein, the term "N-amido" refers to a —N(R)C(=O)' group with R and R' as defined herein.

As used herein, the term "amino" refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl. Exemplary "amino" groups include, without being limited thereto, —NH$_2$, —NH(C$_{1-4}$ alkyl) and —N(C$_{1-4}$ alkyl)(C$_{1-4}$ alkyl).

As used herein, the term "aryl" refers to a carbocyclic aromatic system containing one ring, or two or three rings fused together where in the ring atoms are all carbon. The term "aryl" groups includes, but is not limited to groups such as phenyl, naphthyl, or anthracenyl. The term "monocyclic aryl" refers to phenyl.

As used herein, the term "aryloxy" refers to an aryl group attached to the parent molecular moiety through an oxy (—O—).

As used herein, the term "carbamate" refers to an O-carbamyl or N-carbamyl group as defined herein. An N-carbamyl group refers to —NR—COOR', wherein R and R' are as defined herein. An O-carbamyl group refers to —OCO—NRR', wherein R and R' are as defined herein.

As used herein, the term "carbonyl" when alone includes formyl —C(=O)H and in combination is a —C(=O)— group.

As used herein, the term "carboxyl" or "carboxy" refers to —C(=O)OH or the corresponding "carboxylate" anion, such as is in a carboxylic acid salt.

An "O-carboxy" group refers to a RC(=O)O— group, where R is as defined herein.

A "C-carboxy" group refers to a —C(=O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, cycloheptyl, tetrahydronaphthyl, indanyl, octahydronaphthyl, 2,3-dihydro-1H-indenyl, or adamantyl.

As used herein, the term "cycloalkyl", unless otherwise specified (as for example in the definition of ring D), refers to a saturated monocyclic, bicyclic or tricyclic group wherein the ring atoms of the cyclic system are all carbon and wherein each cyclic moiety contains from 3 to 12 carbon atom ring members. A C$_{3-6}$ cycloalkyl is a cycloalkyl that has from 3 to 6 carbon atoms, i.e. cyclopropyl, cyclobutyl, cyclopentyl and cyclohexyl. A cycloalkyl containing from 4 to 7 C atoms includes cyclobutyl, cyclopentyl, cyclohexyl and cycloheptyl. Examples of cycloalkyl groups include, but are not limited to, cyclopropyl, cyclobutyl, cyclopentyl, cyclohexyl, cycloheptyl, or adamantyl.

As used herein, the term "cyclyl" refers to an aryl, heterocyclyl, or carbocyclyl group as defined herein.

As used herein, the term "cyclylC$_{1-8}$ alkyl" refers to a C$_{1-8}$ alkyl as defined above wherein one hydrogen atom in the C$_{1-8}$ alkyl group has been replaced with one cyclyl group as defined above.

As used herein, the term "halo" or "halogen" refers to fluorine, chlorine, bromine, or iodine.

As used herein, the term "haloalkoxy" refers to a haloalkyl group (as defined below) attached to the parent molecular moiety through an oxygen atom. A haloC$_{1-8}$ alkoxy group refers to a haloalkoxy group wherein the haloalkyl moiety has from 1 to 8 C atoms. Examples of haloalkoxy groups include, but are not limited to, trifluoromethoxy, 2-fluoroethoxy, pentafluoroethoxy, or 3-chloropropoxy.

As used herein, the term "haloalkyl" refers to an alkyl group having the meaning as defined above wherein one or more hydrogens are replaced with a halogen. A haloC$_{1-8}$ alkyl group refers to a haloalkyl group wherein the alkyl moiety has from 1 to 8 C atoms. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, the term "heteroalkyl" refers to a straight or branched alkyl chain, wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at the end(s) or at an interior position of the heteroalkyl group, i.e., the heteroalkyl may be bound to the remainder of the molecule via a heteroatom or a carbon atom. Up to two heteroatoms may be consecutive, such as, for example, —CH$_2$—NH—OCH$_3$. Accordingly, a further example for a "heteroalkyl" group is a straight or branched alkyl group, in which two consecutive carbon atoms are replaced by the heteroatoms S and N, respectively, and the sulfur heteroatom is furthermore oxidized, resulting in moieties such as, e.g., —S(=O)$_2$—NH$_2$, —S(=O)$_2$—NH(alkyl) or —S(=O)$_2$—N(alkyl)(alkyl).

As used herein, the term "heteroC$_{1-4}$ alkylene" refers to a straight or branched C$_{1-4}$ alkylene group (i.e., a straight or branched C$_{1-4}$ alkanediyl group) linked to one heteroatom selected from O, N and S and also refers to a straight or branched C$_{1-4}$ alkylene group wherein one or more (e.g., 1, 2 (if present) or 3 (if present)) of the carbon atoms of said alkylene group are each replaced by a heteroatom independently selected from O, N or S. The nitrogen and/or sulfur heteroatom(s) (if present) may optionally be oxidized and the nitrogen heteroatom(s) (if present) may optionally be quaternized. The heteroatom(s) O, N and S may be placed at the end(s) and/or at an interior position of the heteroC$_{1-4}$ alkylene group. It is to be understood that the presence of hydrogen atoms will depend on the valence of the heteroatom replacing the respective carbon atom. If, for example, the carbon atom in a —CH$_2$— group is replaced by O or S, the resulting group will be —O— or —S—, respectively, while it will be —N(H)— when the carbon atom is replaced by N. Likewise, if the central carbon atom in a group —CH$_2$—CH(—CH$_3$)—CH$_2$— is replaced by N, the resulting group will be —CH$_2$—N(—CH$_3$)—CH$_2$—. An example for a "heteroC$_{1-4}$ alkylene" group is a straight or branched C$_{1-4}$ alkylene group, in which two consecutive carbon atoms are replaced by the heteroatoms S and N, respectively, and the sulfur heteroatom is furthermore oxidized, resulting in moieties such as, e.g., —S(=O)$_2$—N(H)— or —S(=O)$_2$—N(CH$_3$)—.

As used herein, the term "heteroaryl" refers to a 5 to 6 membered unsaturated monocyclic ring, or a fused bicyclic or tricyclic ring system in which the rings are aromatic and in which at least one ring contains at least one heteroatom selected from the group consisting of O, S, and N. Preferred heteroaryl groups are 5- to 6-membered monocyclic or 9- to 10-membered bicyclic heteroaryl groups. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "heterocycle" each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitrogen or sulfur atoms may be oxidized (e.g., —N=O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl" refers to a heterocyclyl group that is not fully unsaturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl" or "hydroxy" refers to —OH.

As used herein, the term "hydroxy$C_{1-8}$ alkyl" refers to an $C_{1-8}$ alkyl group, wherein one or more hydrogen atoms (preferably one or two) have been replaced by hydroxy groups.

As used herein, the term "$R^{12}R^{13}N$—$C_{1-8}$ alkyl" refers to an $C_{1-8}$ alkyl group, wherein one or more hydrogen atoms (preferably one or two, more preferably one) have been replaced by —$NR^{12}R^{13}$.

As used herein, the term "lower" where not otherwise specifically defined, means containing from 1 to and including 6 carbon atoms.

As used herein, the term "nitro" refers to —$NO_2$.

As used herein, the terms "sulfonate" "sulfonic acid" and "sulfonic" refer to the —$SO_3H$ group and its anion as the sulfonic acid is used in salt formation.

As used herein, the term "sulfinyl" refers to —S(=O)(R), with R as defined herein.

As used herein, the term "sulfonyl" refers to —S(=O)$_2$R, with R as defined herein.

As used herein, the term "sulfonamide" refers to an N-sulfonamido or S-sulfonamido group as defined herein.

As used herein, the term "N-sulfonamido" refers to a RS(=O)$_2$N(R')— group with R and R' as defined herein. Preferred N-sulfonamido groups are —NHSO$_2$R, wherein R is as defined herein, preferably R is alkyl, cycloalkyl, heteroalkyl, aryl, heteroaryl or heterocycloalkyl, more preferably R is alkyl, aryl, heteroaryl or heterocycloalkyl, wherein said alkyl, said cycloalkyl, said heteroalkyl, said aryl, said heteroaryl and said heterocycloalkyl are each optionally substituted. The optional substituents on said alkyl, said cycloalkyl, said heteroalkyl, said aryl, said heteroaryl and said heterocycloalkyl may be selected independently from lower alkyl, lower alkenyl, lower alkynyl, lower alkanoyl, lower heteroalkyl, lower heterocycloalkyl, lower haloalkyl, lower cycloalkyl, phenyl, aryl, heteroaryl, pyridyl, aryloxy, lower alkoxy, lower haloalkoxy, oxo, lower acyloxy, carbonyl, carboxyl, lower alkylcarbonyl, lower carboxyester, lower carboxamido, cyano, halogen, hydroxyl, amino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, carbamate, and urea. Preferably, the optional substituents are independently selected from hydroxyl, halo, alkyl, alkoxy, haloalkyl, haloalkoxy, —N($C_{1-3}$ alkyl)$_2$, —NH($C_{1-3}$ alkyl), —NHC(=O)($C_{1-3}$ alkyl), —C(=O)OH, —C(=O)O($C_{1-3}$ alkyl), —C(=O)($C_{1-3}$ alkyl), —C(=O)NH$_2$, —C(=O)NH($C_{1-3}$ alkyl), —C(=O)NH(cycloalkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, or tetrazolyl. Particularly preferred N-sulfonamido groups are —NHSO$_2$R, wherein R is alkyl, cycloalkyl, heteroalkyl, aryl, heteroaryl or heterocycloalkyl, and preferably R is alkyl, aryl, heteroaryl or heterocycloalkyl, and —NHSO$_2$ (optionally substituted aryl). Still more preferred N-sulfonamido groups are —NHSO$_2$alkyl and —NHSO$_2$ (optionally substituted aryl). Exemplary, non-limiting N-sulfonamido groups are —NHSO$_2$alkyl such as —NHSO$_2$CH$_3$, —NHSO$_2$CH$_2$CH$_3$ or —NHSO$_2$ (isopropyl), and —NHSO$_2$ (optionally substituted aryl) such as —NHSO$_2$-phenyl, —NHSO$_2$-(2-cyanophenyl), —NHSO$_2$-(3-cyanophenyl), —NHSO$_2$-(4-cyanophenyl), —NHSO$_2$-(2-aminophenyl), —NHSO$_2$-(3-aminophenyl) or —NHSO$_2$-(4-aminophenyl). Other exemplary N-sulfonamido groups are —NHSO$_2$ (optionally substituted heterocycloalkyl) such as —NHSO$_2$-(piperazin-1-yl) and —NHSO$_2$ (optionally substituted heteroaryl) such as —NHSO$_2$-(optionally substituted pyridyl) like —NHSO$_2$-(3-pyridyl) or —NHSO$_2$-(6-amino-3-pyridyl).

As used herein, the term "S-sulfonamido" refers to a —S(=O)$_2$NRR', group, with R and R' as defined herein.

As used herein, the term "urea" refers to a —N(R)C(=O)N(R)(R') group wherein R and R' are as defined herein.

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl. Both unsubstituted and substituted forms of the above groups are encompassed. Preferably, said groups are unsubstituted.

Whether an R group has a number designation or not, every R group, including R, R' and $R^z$ where z=(1, 2, 3, . . . z), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(=O)N(R)— may be attached to the parent moiety at either the carbon or the nitrogen.

As used herein, the term "optionally substituted" means the preceding or anteceding group may be substituted or unsubstituted. When substituted and unless otherwise specified, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower cycloalkyl, phenyl, aryl, heteroaryl, pyridyl, aryloxy, lower alkoxy, lower haloalkoxy, oxo, lower acyloxy, carbonyl, carboxyl, lower alkylcarbonyl, lower carboxyester, lower carboxamido, cyano, halogen, hydroxyl, amino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —N($C_{1-3}$ alkyl)$_2$, —NH($C_{1-3}$ alkyl), —NHC(=O)($C_{1-3}$ alkyl), —C(=O)OH, —C(=O)O($C_{1-3}$ alkyl), —C(=O)($C_{1-3}$ alkyl), —C(=O)NH$_2$, —C(=O)NH($C_{1-3}$ alkyl), —C(=O)NH(cycloalkyl), —C(=O)N($C_{1-3}$ alkyl)$_2$, —S(=O)$_2$($C_{1-3}$ alkyl), —S(=O)$_2$NH$_2$, —S(=O)$_2$N($C_{1-3}$ alkyl)$_2$, —S(=O)$_2$NH($C_{1-3}$ alkyl), —CHF$_2$, —OCF$_3$, —OCHF$_2$, —SCF$_3$, —CF$_3$, —CN, —NH$_2$, —NO$_2$, or tetrazolyl.

As used herein, the term "optional substituent" denotes that the corresponding substituent may be present or may be absent. Accordingly, a compound having 1, 2 or 3 optional substituents may be unsubstituted or may be substituted with 1, 2 or 3 substituents.

As used herein, the term "treating a disease" refers to a slowing of or a reversal of the progress of the disease. Treating a disease includes treating a symptom and/or reducing the symptoms of the disease.

As used herein, the term "preventing a disease" refers to a slowing of the disease or of the onset of the disease or the symptoms thereof. Preventing a disease or disorder can include stopping the onset of the disease or symptoms thereof.

As used herein, the term "dosage unit" refers to a physically discrete unit, such as a capsule or tablet suitable as a unitary dosage for a human patient. Each unit contains a predetermined quantity of a compound of Formula I which was discovered or believed to produce the desired pharmacokinetic profile which yields the desired therapeutic effect. The dosage unit is composed of a compound of Formula I in association with at least one pharmaceutically acceptable carrier, salt, excipient, or combination thereof.

As used herein, the term "subject" or "patient" or "individual", such as the subject in need of treatment or prevention, may be a eukaryote, an animal, a vertebrate animal, a mammal, a rodent (e.g., a guinea pig, a hamster, a rat, a mouse), a murine (e.g., a mouse), a canine (e.g., a dog), a feline (e.g., a cat), an equine (e.g. a horse), a primate, a simian (e.g., a monkey or ape), a monkey (e.g., a marmoset, a baboon), an ape (e.g., gorilla, chimpanzee, orangutan, gibbon), or a human. The meaning of the terms "eukaryote", "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pig, while, for example, cats and dogs may be considered as economically important animals. Preferably, the subject/patient/individual is a mammal; more preferably, the subject/patient/individual is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig); even more preferably, the subject/patient/individual is a human.

As used herein, the term "dose" or "dosage" refers to the amount of active ingredient that an individual takes or is administered at one time. For example, a 40 mg dose of a compound of Formula I refers to, in the case of a twice-daily dosage regimen, a situation where the individual takes 40 mg of a compound of Formula I twice a day, e.g., 40 mg in the morning and 40 mg in the evening. The 40 mg of a compound of Formula I dose can be divided into two or more dosage units, e.g., two 20 mg dosage units of a compound of Formula I in tablet form or two 20 mg dosage units of a compound of Formula I in capsule form.

As used herein, the term "therapeutically effective amount", such as the therapeutically effective amount of a compound of the present invention, refers to the amount sufficient to produce a desired biological effect (e.g., a therapeutic effect) in a subject. Accordingly, a therapeutically effective amount of a compound may be an amount which is sufficient to treat or prevent a disease or disorder, and/or delay the onset or progression of a disease or disorder, and/or alleviate one or more symptoms of the disease or disorder, when administered to a subject suffering from or susceptible to that disease or disorder.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, ethane-sulfonates, propanesulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. Pharmaceutically acceptable salts are well known in the art.

As used herein, a "pharmaceutically acceptable carrier" or "pharmaceutically acceptable excipient" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency. Pharmaceutically acceptable carriers or excipients are well known to those skilled in the art.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

The compounds of the invention are unexpectedly potent and selective inhibitors of LSD1. Avoiding inhibition of "off-targets" can avoid unwanted or undesirable side-effects like the cheese effect associated with MAO-A. The compounds of the invention are thus useful for the treatment or prevention of any disease or disorder associated with LSD1. This includes cancer, neurological diseases and viral infections, among others.

Preferably, the compounds of formula I, including compounds of formula Ia, Ia-1, Ib and Ic, as well as any salts and solvates thereof, are used for the treatment or prevention of cancer, and most preferably for the treatment of cancer. Cancers that may be treated (or prevented) with the compounds of the invention include, but are not limited to cancers such as:

Hematologic cancers (also designated herein as blood cancers), including cancers of the blood, bone marrow and lymph nodes such as leukemias (e.g. acute myelogenous leukemia (AML), acute promyelocytic leukemia (APL), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), myeloproliferative diseases, multiple myeloma, myelodysplastic syndrome, and lymphomas (e.g. Hodgkin's disease, non-Hodgkin's lymphoma (malignant lymphoma));

Breast cancer, including invasive ductal carcinoma, in situ ductal carcinoma, lobular carcinoma, and mixed ductal and lobular carcinoma;

Lung cancer such as bronchogenic carcinoma (e.g. squamous cell, undifferentiated small cell, undifferentiated large cell, adenocarcinoma), alveolar (bronchiolar) carcinoma, bronchial adenoma, sarcoma, lymphoma, chondromatous hamartoma, and mesothelioma;

Gastrointestinal cancers such as esophagus (e.g. squamous cell carcinoma, adenocarcinoma, leiomyosarcoma, lymphoma), stomach (e.g. carcinoma, lymphoma, leiomyosarcoma), pancreas (e.g. ductal adenocarcinoma, insulinoma, glucagonoma, gastrinoma, carcinoid tumors, vipoma), small bowel (e.g. adenocarcinoma, lymphoma, carcinoid tumors, Kaposi's sarcoma, leiomyoma, hemangioma, lipoma, neurofibroma, fibroma), and large bowel (e.g. adenocarcinoma, tubular adenoma, villous adenoma, hamartoma, leiomyoma);

Genitourinary tract cancers such as kidney (e.g. adenocarcinoma, Wilm's tumor (nephroblastoma), lymphoma, leukemia), bladder and urethra (e.g. squamous cell carcinoma, transitional cell carcinoma, adenocarcinoma), prostate (e.g. adenocarcinoma, sarcoma), and testis (e.g. seminoma, teratoma, embryonal carcinoma, teratocarcinoma, choriocarcinoma, sarcoma, interstitial cell carcinoma, fibroma, fibroadenoma, adenomatoid tumors, lipoma);

Liver cancer such as hepatoma (hepatocellular carcinoma), cholangiocarcinoma, hepatoblastoma, angiosarcoma, hepatocellular adenoma, and hemangioma;

Bone cancer such as osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system cancers such as skull (e.g. osteoma, hemangioma, granuloma, xanthoma, osteitis deformans), meninges (e.g. meningioma, meningiosarcoma, gliomatosis), brain (e.g. astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, and sarcoma;

Gynecological cancers such as uterus (e.g. endometrial carcinoma), cervix (e.g. cervical carcinoma, pre-tumor cervical dysplasia), ovaries (e.g. ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (e.g. squamous cell carcinoma, intraepithelial carcinoma, adenocarcinoma, fibrosarcoma, melanoma), vagina (e.g. clear cell carcinoma, squamous cell carcinoma, botryoid sarcoma (embryonal rhabdomyosarcoma)), and fallopian tubes (carcinoma);

Cardiac cancer such as sarcoma (e.g. angiosarcoma, fibrosarcoma, rhabdomyosarcoma, liposarcoma), myxoma, rhabdomyoma, fibroma, lipoma and teratoma;

Skin cancer such as malignant melanoma, basal cell carcinoma, squamous cell carcinoma, and Kaposi's sarcoma; and Adrenal glands cancer such as neuroblastoma.

Accordingly, in one embodiment, the compounds of the invention are used for the treatment or prevention of cancer, particularly for the treatment of cancer, wherein said cancer is chosen from blood cancer, leukemia, lymphoma, breast cancer, lung cancer, prostate cancer, colorectal cancer, brain cancer, neuroblastoma, bladder cancer, liver cancer, sarcoma, myeloma and skin cancer. In another embodiment, the compounds of the invention are used for the treatment or prevention (particularly for the treatment) of blood cancers (also known as hematological cancers), including leukemias (for example, acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), or hairy cell leukemia), lymphomas and myelomas, prostate cancer, breast cancer, lung cancer, colorectal cancer, brain cancer or skin cancer. In a preferred embodiment, the compounds of formula I, including compounds of formula Ia, Ia-1, Ib and Ic, are used for the treatment of a blood cancer. More preferably, the compounds of formula I, including compounds of formula Ia, Ia-1, Ib and Ic, are used for the treatment of leukemia, including acute myelogenous leukemia (AML), chronic myelogenous leukemia (CML), chronic neutrophilic leukemia, chronic eosinophilic leukemia, chronic lymphocytic leukemia (CLL), acute lymphoblastic leukemia (ALL), and hairy cell leukemia.

Typically, compounds according to Formula I, Ia, Ia-1, Ib or Ic can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg. Even more preferably, the amount of active ingredient administered is from about 5 µg to about 100 mg per day. These doses will depend on the pharmacokinetic parameters of the particular compound and other ADME properties as well as the efficacy of the compound in a particular disease setting.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

While it is possible that a compound of the invention may be administered for use in therapy directly as such, it is typically administered in the form of a pharmaceutical composition, which comprises said compound as active pharmaceutical ingredient together with one or more pharmaceutically acceptable excipients or carriers.

The compounds of the invention may be administered by any means that accomplish their intended purpose. Examples include administration by the oral, parenteral, intravenous, subcutaneous or topical routes.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.*, 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammatory agents, antiviral agents, antibiotics, antifungal agents, antithrombotic agents, cardiovascular drugs, cholesterol lowering agents, anti-cancer drugs, hypertension drugs, and the like.

Combination therapy includes administration of a single pharmaceutical dosage formulation which contains a compound of the invention and one or more additional active agents, as well as administration of the compound of the invention and each additional active agent in its own separate pharmaceutical dosage formulation. If administered separately, the administration can be simultaneous, sequential or separate, and the compound of the invention and the additional therapeutic agent(s) can be administered via the same administration route or using different administration routes, for example one compound can be administered orally and the other intravenously.

In particular, when a compound of formula I, Ia, Ia-1, Ib or Ic is used for the treatment or prevention of cancer, said compound can be administered in combination with one or more further agents known to be useful in the treatment or prevention of cancer, including chemotherapy or radiotherapy.

Typically, for combination therapy with a compound of the invention any antineoplastic agent that has activity versus a cancer being treated or prevented with a compound of the invention may be used. Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic agents include the anthracyclines, vinca drugs, mitomycins, bleomycins, cytotoxic nucleosides, epothilones, discodermolides, pteridines, diynenes and podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

Thus, a compound of formula I, Ia, Ia-1, Ib or Ic according to the present invention can be used for the treatment or prevention of cancer, wherein said compound is to be administered in combination with one or more antineoplastic agents. The antineoplastic agents to be administered for combination therapy may be selected, as appropriate, from: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analog antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analog); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); aminopeptidase inhibitors; proteasome inhibitors; cyclooxygenase inhibitors (for example, cyclooxygenase-1 or cyclooxygenase-2 inhibitors); topoisomerase inhibitors (for example, topoisomerase I inhibitors or topoisomerase II inhibitors); or retinoid agents.

An alkylating agent which can be used as an antineoplastic agent in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an antineoplastic agent in combination with a compound of the present invention may be, for example, cisplatin, carboplatin, nedaplatin, oxaliplatin, satraplatin, or triplatin tetranitrate.

A cytotoxic drug which can be used as an antineoplastic agent in combination with a compound of the present invention may be, for example, an antimetabolite, including folic acid analog antimetabolites (such as aminopterin, methotrexate, pemetrexed, or raltitrexed), purine analog antimetabolites (such as cladribine, clofarabine, fludarabine, 6-mercaptopurine (including its prodrug form azathioprine), pentostatin, or 6-thioguanine), and pyrimidine analog antimetabolites (such as cytarabine, decitabine, azacytidine, 5-fluorouracil (including its prodrug forms capecitabine and tegafur), floxuridine, gemcitabine, enocitabine, or sapacitabine).

An antimitotic agent which can be used as an antineoplastic agent in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, vinzolidine, or vinorelbine), an epothilone (such as epothilone A, epothilone B, epothilone C, epothilone D, epothilone E, or epothilone F) or an epothilone B analog (such as ixabepilone/azaepothilone B).

An anti-tumor antibiotic which can be used as an antineoplastic agent in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an antineoplastic agent in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an antineoplastic agent in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further antineoplastic agents may be used in combination with a compound of the present invention. The antineoplastic agents may include biological or chemical molecules, such as TNF-related apoptosis-inducing ligand (TRAIL), tamoxifen, toremifene, fluoxymesterol, raloxifene, diethylstibestrol, bicalutamide, nilutamide, flutamide, aminoglutethimide, anastrozole, tetrazole, luteinizing hormone release hormone (LHRH) analogues, ketoconazole, goserelin acetate, leuprolide, megestrol acetate, prednisone, mifepristone, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Examples of retinoid agents include all natural, recombinant, and synthetic derivatives or mimetics of vitamin A, for example, retinyl palmitate, retinoyl-beta-glucuronide (vitamin A1 beta-glucuronide), retinyl phosphate (vitamin A1 phosphate), retinyl esters, 4-oxoretinol, 4-oxoretinaldehyde, 3-dehydroretinol (vitamin A2), 11-cis-retinal (11-cis-retinaldehyde, 11-cis or neo b vitamin A1 aldehyde), 5,6-epoxyretinol (5,6-epoxy vitamin A1 alcohol), anhydroretinol (anhydro vitamin A1) and 4-ketoretinol (4-keto-vitamin A1 alcohol), all-trans retinoic acid (ATRA; Tretinoin; vitamin A acid; 3,7-dimethyl-9-(2,6,6,-trimethyl-1-cyclohenen-1-yl)-2,4,6,8-nonatetraenoic acid [CAS No. 302-79-4]), lipid formulations of all-trans retinoic acid (e.g., ATRA-IV), 9-cis retinoic acid (9-cis-RA; Alitretinoin; Panretin™; LGD1057), 13-cis retinoic acid (Isotretinoin), (E)-4-[2-(5, 5,8,8-tetramethyl-5,6,7,8-tetrahydro-2-naphthalenyl)-1-propenyl]-benzoic acid, 3-methyl-(E)-4-[2-(5,5,8,8-tetramethyl-5,6,7,8-tetrahydro-2-naphthalenyl)-1-propenyl]-benzoic acid, Fenretinide (N-(4-hydroxyphenyl)retinamide; 4-HPR), Etretinate ((all-E)-9-(4-methoxy-2,3,6-trimethypheny)-3,7-dimethyl-2,4,6,8-nnatetraenic acid ethyl ester; Tegison), Acitretin ((all-E)-9-(4-methoxy-2,3,6-trimethylphenyl)-3,7-dimethyl-2,4,6,8-nonatetraenic acid; Ro 10-1670; Soriatane; Neotigason), Tazarotene (ethyl 6-[2-(4, 4-dimethylthiochroman-6-yl)-ethynyl] nicotinate; Tazorac; Avage; Zorac), Tocoretinate (9-cis-tretinoin; Tocoferil), Adapalene (6-[3-(1-adamantyl)-4-methoxyphenyl]-2-naphthoic acid; Differin), Motretinide (trimethylmethoxyphenyl-N-ethyl retinamide; Trasmaderm), retinaldehyde (Retinal), CD437 (6-[3-(1-adamantyl)-4-hydroxyphenyl)-2-naphthalene carboxylic acid; AHPN), CD2325, ST1926 ([E-3-(4'-hydroxy-3'-adamantylbiphenyl-4-yl)acrylic acid), ST1878 (methyl 2-[3-[2-[3-(2-methoxy-1,1-dimethyl-2-oxoethoxy) phenoxy]ethoxy]phenoxy]isobutyrate), ST2307, ST1898, ST2306, ST2474, MM11453, MM002 (3-CI-AHPC), MX2870-1, MX3350-1, MX84, and MX90-1, docosahexaenoic acid (DHA), phytanic acid (3,7,11,15-tetramethyl hexadecanoic acid), MS6682 (methoprene acid), LG100268 (LG268), LG100324, SR11203 ([2-(4-carboxyphenyl)-2-(5, 6,7,8-tetrahydro-5,5,8,8-tetramethyl-2-naphthalenyl)-1,3-dithiane), SR11217 (4-(2-methyl-1-(5,6,7,8-tetrahydro-5,5, 8,8-tetramethyl-2-naphthalenyl)propenyl)benzoic acid), SR11234, SR11236 (2-(4-carboxyphenyl)-2-(5,6,7,8-tetrahydro-5,5,8,8-tetramethyl-2-naphthalenyl)-1,3-dioxane), SR11246, AGN194204, derivatives of 9-cis-RA such as LGD1069 (3-methyl TTNEB; Bexarotene; Targretin®; 4-[1-(5,6,7,8-tetrahydro-3,5,5,8,8-pentamethyl-2-naphthalenyl) ethenyl]benzoic acid).

Examples of histone deacetylase inhibitors include, without limitation, MS-275 (SNDX-275; Entinostat), FK228 (FR901228; depsipeptide; Romidepsin), CI-994 (Acetyldinaline; Tacedinaline), Apicidin (cyclo[(2S)-2-amino-8-oxodecanoyl-1-methoxy-L-tryptophyl-L-isoleucyl-(2R)-2-piperidinexcarbonyl]), A-161906 (7-[4-(4-cyanophenyl) phenoxy]-heptanohydroxamic acid), Scriptaid (6-(1,3-Dioxo-1H,3H-benzo[de]isoquinolin-2-yl)-hexanoic acid hydroxyamide), PXD-101 (Belinostat), CHAP (cyclic hydroxamic acid-containing peptide), LAQ-824 (Dacinostat), BML-E1319 (Depudecin), 03139 (Oxamflatin), NSC 696085 (Pyroxamide), MW2796; MW2996, T2580 (Trapoxin A), AN-9 (Pivanex), W222305 (Tributyrin) Trichostatin A, Trichostatin C, Butyric acid, Valproic acid (VPA), Suberoylanilide hydroxamic acid (SAHA; Vorinostat), m-Carboxycinnamic acid bishydroxamide (CBHA), Salicylbishydroxamic acid (S607; SHA; SHAM); Suberoyl bishydroxamic acid (SBHA); Azelaic bishydroxamic acid (ABHA); Azelaic-1-hydroxamate-9-anilide (AAHA); 3Cl-UCHA (6-(3-chlorophenylureido) caproic hydroxamic acid); and sodium butyrate, 4-phenylbutyrate, phenylacetate, valerate, isovalerate, butyramide, isobutyramide, 3-bromopropionate, and valproate.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in cancer can be employed in cotherapeutic approaches with the compounds of the invention. Examples of such biological molecules are alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rituximab, rovelizumab, rolizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Other biologic agents include, but are not limited to, immunomodulating proteins such as cytokines (such as interleukin-2 (IL-2, Aldesleukin), Epoietin-alpha; EPO), granulocyte-CSF (G-CSF; Filgrastin), and granulocyte-macrophage-CSF (GM-CSF; Sargramostim) and interferons, (e.g., interferon-alpha, interferon-beta and interferon-gamma), *bacillus* Calmette-Guerin, levamisole, and octreotide, endostatin, tumor suppressor genes (e.g., DPC4, NF-1, NF-2, RB, p53, WT1, BRCA1, and BRCA2), and cancer vaccines (e.g., tumor associated antigens such as gangliosides (GM2), prostate specific antigen (PSA), alpha-fetoprotein (AFP), carcinoembryonic antigen (CEA) (produced by colon cancers and other adenocarcinomas, e.g., breast, lung, gastric, and pancreatic cancers), melanoma-associated antigens (MART-I, gap100, MAGE 1,3 tyrosinase), papillomavirus E6 and E7 fragments, whole cells or portions/lysates of autologous tumor cells and allogeneic tumor cells.

General Synthetic Route Description

Compounds of Formula I can be synthesized in accordance with or in analogy to the general routes described below. Unless otherwise stated, in the methods described below the meanings of the different substituents in each synthetic intermediate and in each compound of formula I are the meanings described above with regard to a compound of formula I. Other routes known by the ordinary skilled artisan, as well as other reactants and intermediates, can also be used to arrive at the compounds of Formula I. The reaction schemes described below are only meant to represent examples of the invention and are in no way meant to be a limit of the invention. In some of the processes described below it may be necessary or advisable to protect reactive or labile groups with conventional protecting groups. Both the nature of these protecting groups and the procedures for their introduction and removal are well known in the art (see for example Greene T W and Wuts P G M "Greene's Protecting Groups in Organic Synthesis", 4$^{th}$ edition, Wiley, 2006). Whenever a protecting group is present, a subsequent deprotection step will be required, which can be performed under standard conditions well known in the art, such as those described in the above reference.

In general, the compounds of formula I can be prepared by reductive alkylation of a cyclopropylamino derivative of formula II with a ketone of formula Ill, as shown below in Scheme 1:

SCHEME 1

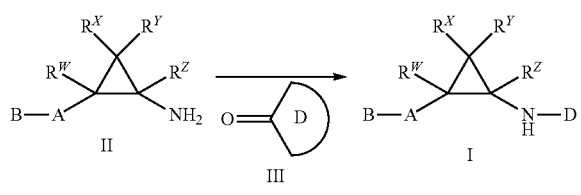

Wherein A, B, D, $R^w$, $R^x$, $R^y$, $R^z$ have the meaning disclosed above in relation to a compound of formula I.

Said reductive alkylation can be performed under standard conditions for reductive alkylations, well known in the art. For example, a suitable set of conditions is reacting II with III using a reducing agent such as a borohydride (e.g., sodium triacetoxyborohydride or sodium borohydride) in a suitable solvent such as dichloroethane or methanol, optionally in the presence of an acid such as acetic acid. In order to conduct the reaction, it is necessary that any other amino group that may be present either in II or in III be protected using conventional amino-protecting groups to avoid any side reactions; a subsequent deprotection step will be required then if such amino protecting group is present, in order to obtain a compound of formula I. Any suitable amino-protecting group may be used, such as for example a tert-butoxycarbonyl (Boc) group. If Boc is used, deprotection can be carried out under standard conditions, for example under acidic conditions using HCl in an organic solvent such as diethyl ether or 1,4-dioxane, or trifluoroacetic acid (TFA) in dichloromethane. When HCl is used in the last step of the synthesis, compounds of formula I are obtained as a hydrochloride salt. Likewise, if TFA is used, the compounds will be obtained as a trifluoroacetate.

The cyclopropylamino derivatives of formula II and the ketones of formula III are commercially available or can be prepared following methods disclosed in the literature.

More detailed methods to obtain compounds of formula I are described below.

The compounds of Formula I wherein $R^w$, $R^x$, $R^y$, $R^z$=H can be synthesized, for example, by the general route described in Scheme 2. This route is particularly suitable for compounds wherein B=H or $R^1$ since the corresponding aldehyde (1) is either commercially available or can be readily obtained. In Scheme 2 below, for schematic purposes "B" has been omitted.

SCHEME 2: DCE (Dichloroethane), DMSO (Dimethyl sulfoxide), THF (Tetrahydrofuran). aq = aqueous.

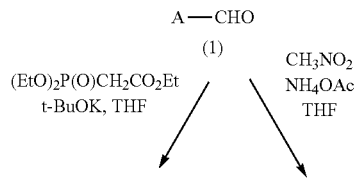

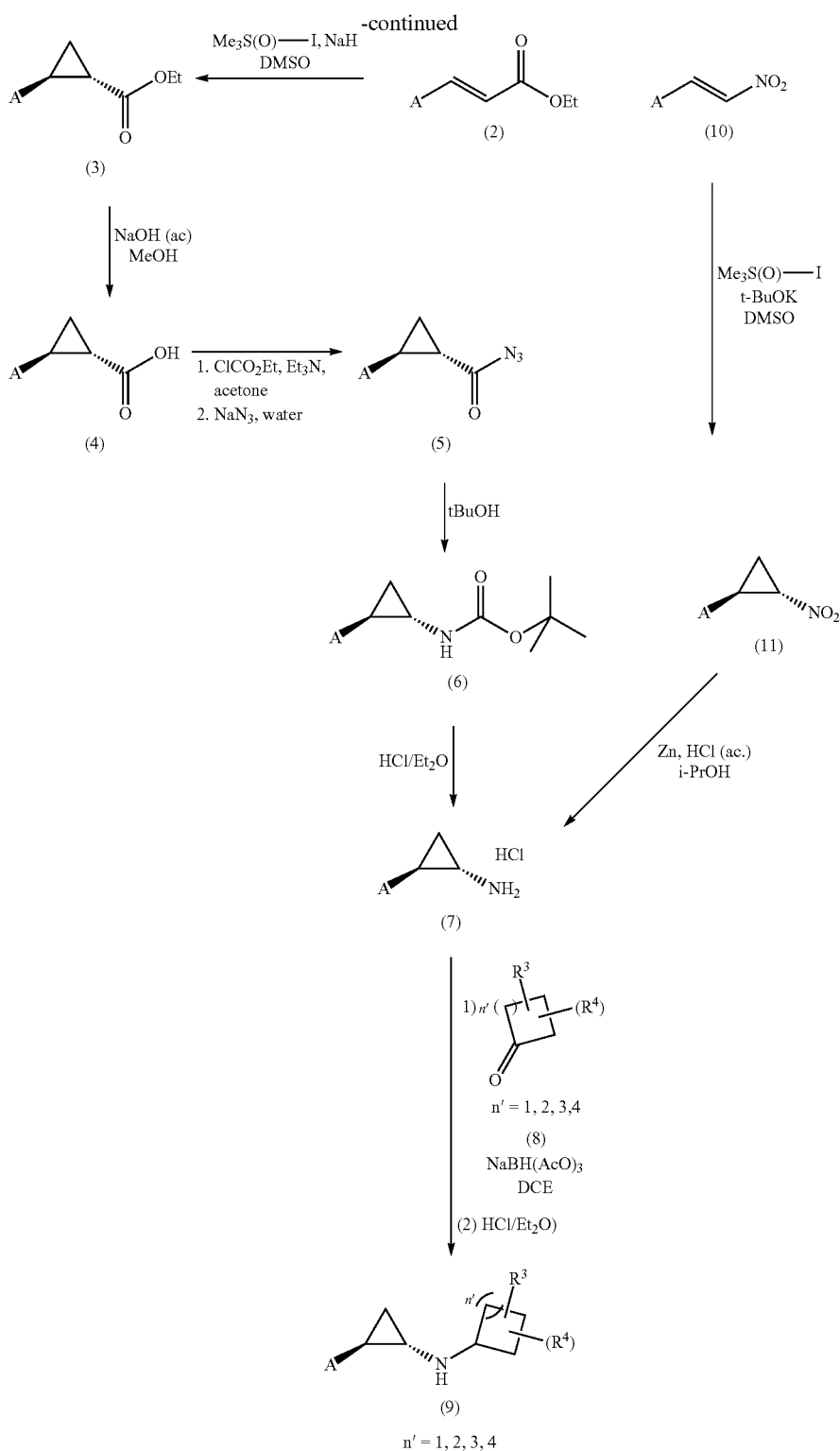

Aldehydes of Formula (1) are subjected to a Horner-Wadsworth-Emmons reaction using triethyl phosphono acetate and a base preferably potassium tert-butoxide in a suitable solvent such as tetrahydrofuran to get the ethyl acrylate derivatives of formula (2) which are then subjected to cyclopropanation reaction using trimethylsulfoxonium iodide and sodium hydride in dimethyl sulfoxide as a solvent leading to (trans)-ethyl cyclopropanecarboxylate derivatives of formula (3) (obtained as a trans ((1S,2R) and (1R,2S)) racemic mixture). Hydrolysis to the corresponding (trans)-cyclopropanecarboxylic acid derivatives of formula (4) can be performed under basic conditions using for example NaOH in a suitable solvent such as MeOH. The subsequent reaction of compound (4), first with ethyl chloroformate and triethylamine in acetone and later with sodium azide in water leads to the formation of (trans)-cyclopropanecarbonyl azide derivatives of formula (5). Reaction with tert-butanol results in the formation of tert-butyl (trans)-cyclopropylcarbamate derivatives of formula (6). Deprotection of the Boc-group in acidic conditions, for example using HCl 2M in diethyl ether in a suitable solvent such as diethyl ether or using HCl in 1,4-dioxane, leads to the formation of the (trans)-cyclopropanamine derivatives of formula (7).

Alternatively, the (trans)-cyclopropanamine derivatives of formula (7) can be synthesized by reaction of aldehydes of formula (1) with nitromethane and ammonium acetate using tetrahydrofuran as a solvent, leading to the formation of nitrostyrene of formula (10). Later cyclopropanation reaction using trimetilsulfoxonium iodide and potassium tert-butoxide results in the formation of trans nitrocyclopropyl derivatives of formula (11) (obtained as a trans ((1S,2R), (1R,2S)) racemic mixture) and final reduction using zinc in hydrochloric acid affords the (trans)-cyclopropanamine derivatives of formula (7).

Reductive alkylation of the derivatives of formula (7) with ketones of formula (8) under standard conditions, for example using sodium triacetoxyborohydride or sodium borohydride as reducing agent in a suitable solvent such as dichloroethane or methanol leads to the formation of (trans)-cyclopropylamino derivatives of formula (9), which corresponds to a compound of formula I, and particularly Ia, wherein $R^w$, $R^x$, $R^y$, $R^z$=H. In case the ketones of formula (8) contain a protected amino group, for example a Boc-protected amine (Boc:tert-butoxycarbonyl), an additional deprotection reaction step will be required to render a compound (9), which can be performed in acidic conditions, for example using HCl 2M in diethyl ether in a suitable solvent such as diethyl ether, or using HCl in 1,4-dioxane.

Aldehydes of formula (1) and ketones of formula (8) are commercially available or can be prepared using well known synthetic procedures starting from readily available starting materials.

The compounds of Formula I wherein B=-L-E and $R^w$, $R^x$, $R^y$, $R^z$=H and L=—$(CH_2)$—O— (wherein x is as defined previously) can be synthesized, for example, by the general route described in Scheme 3:

SCHEME 3: DCE (Dichloroethane), DMF (N,N-dimethylformamide), DMSO (Dimethyl sulfoxide), THF (Tetrahydrofuran)

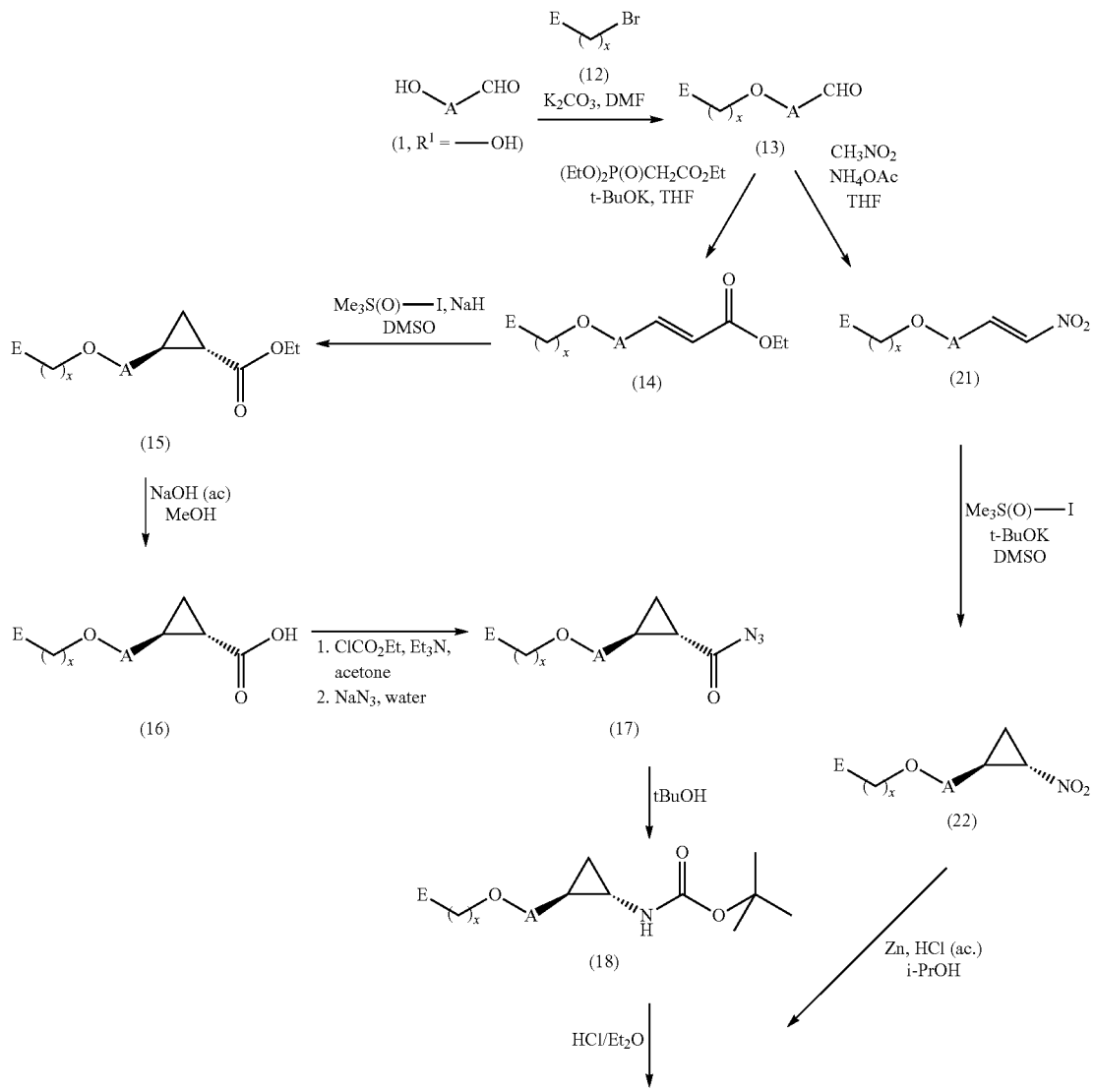

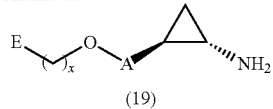

(19)

1) n' 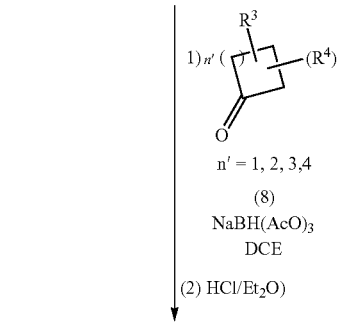

(8)

NaBH(AcO)₃
DCE (2) HCl/Et₂O

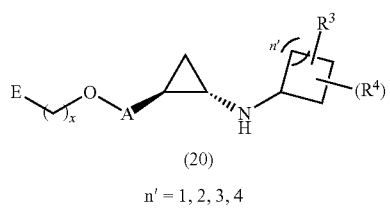

(20)

n' = 1, 2, 3, 4

The alkylation of aldehydes of formula 1 (where $R^1$=—OH) using bromo derivatives of formula (12) (other halo derivatives could also be used) and a base, preferably potassium carbonate in a suitable solvent such as N,N-dimethylformamide leads to the formation of the aldehyde derivatives of formula (13). These are subjected to a Horner-Wadsworth-Emmons reaction under the same conditions disclosed in Scheme 2 to get the ethyl acrylate derivatives of formula (14) which are then subjected to cyclopropanation reaction under the same conditions disclosed in Scheme 2 to give the (trans)-ethyl cyclopropanecarboxylate derivatives of formula (15). Following the same conditions disclosed for the conversion of a compound (3) to a compound (7) in scheme 2, a compound (15) is converted into the (trans)-cyclopropanamine derivative of formula (19).

Alternatively, the (trans)-cyclopropanamine derivatives of formula (19) can be synthesized from aldehydes of formula (13) by conversion into a nitrostyrene (21), subsequent cyclopropanation to give a compound (22) and reduction of the nitro group under the same conditions disclosed in scheme 2 for the conversion of a compound (1) into a compound (7) via compounds (10) and (11).

Reductive alkylation of the derivatives of formula (19) with ketones of formula (8) under the conditions disclosed in scheme 1 or 2 yields a compound (20), which corresponds to a compound of formula I wherein B=-L-E and $R^w$, $R^x$, $R^y$, $R^z$=H and L=—(CH₂)ₓ—O—. In case the ketone of formula (8) contains a protected amino group, for example a Boc-protected amine (Boc: tert-butoxycarbonyl), an additional deprotection reaction step will be required to render a compound (20), which can be performed in acidic conditions, for example using HCl 2M in diethyl ether in a suitable solvent such as diethyl ether, or using HCl in 1,4-dioxane.

Aldehydes of formula (1, where $R^1$=—OH), bromo derivatives of formula (12) and ketones of formula (8) are commercially available or can be prepared using well known synthetic procedures starting from readily available starting materials.

The compounds of Formula I where B=-L-E and $R^w$, $R^x$, $R^y$, $R^z$=H and L=—O— can be synthesized, for example, by the general route described in Scheme 4:

SCHEME 4:

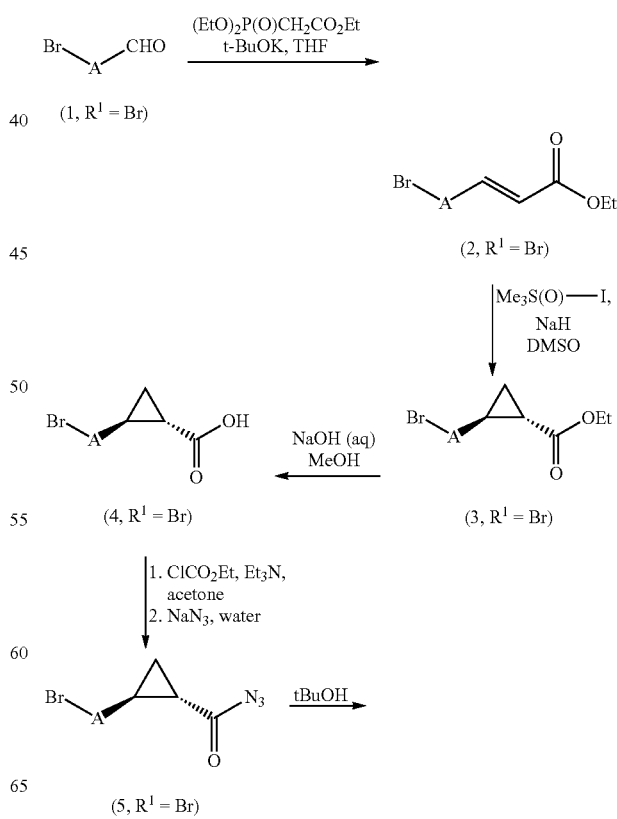

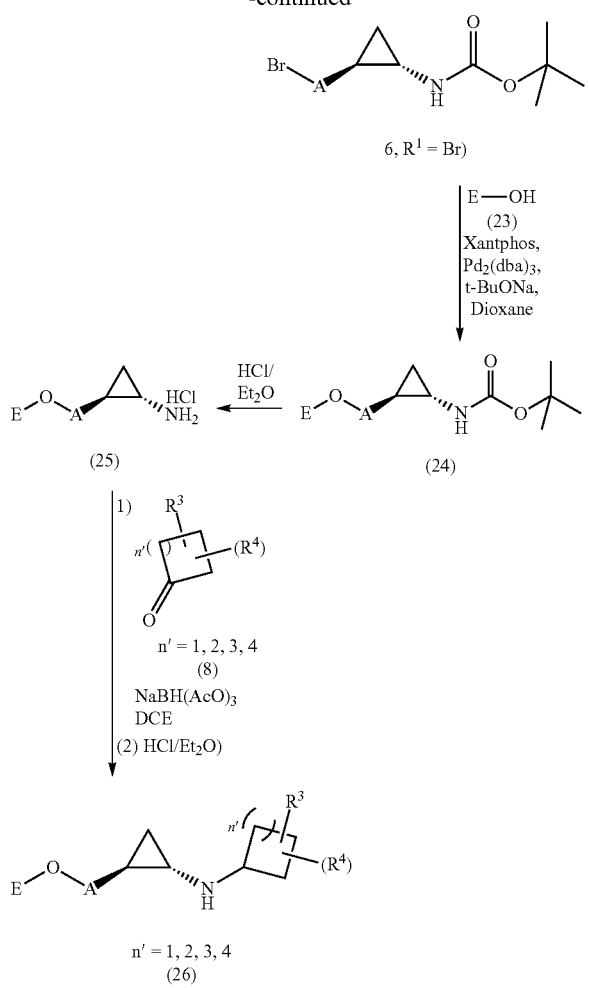

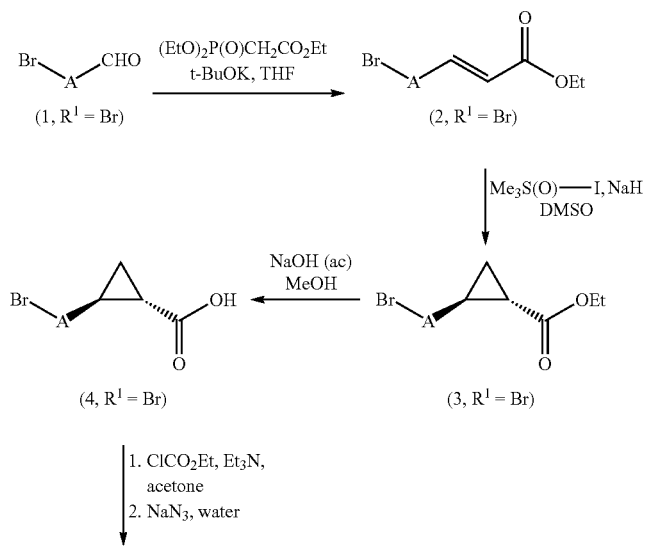

Aldehydes of Formula (1, where $R^1$=Br) are subjected to a Horner-Wadsworth-Emmons reaction under the conditions disclosed in Scheme 2 to get the ethyl acrylate derivatives of formula (2, where $R^1$=Br) which are then subjected to cyclopropanation reaction under the same conditions disclosed in Scheme 2 for converting a compound (2) into (3), leading to the (trans)-ethyl cyclopropanecarboxylate derivatives of formula (3, where $R^1$=Br). Compounds of formula (3) (where $R^1$=Br) are converted into the corresponding (trans)-cyclopropanecarboxylic acid derivatives of formula (4, where $R^1$=Br), which are then converted into the (trans)-cyclopropanecarbonyl azide derivatives of formula (5, where $R^1$=Br) and then into the tert-butyl (trans)-cyclopropylcarbamate derivatives of formula (6, where $R^1$=Br) following the same conditions disclosed in Scheme 2. The reaction of the compounds (6, where $R^1$=Br) with hydroxy-derivatives of formula (23) using a palladium catalyst such as Tris(dibenzylideneacetone)dipalladium(0), Xantphos and a base such as sodium tert-butoxide in a suitable solvent such as dioxane leads to the formation of tert-butyl (trans)-cyclopropylcarbamate derivatives of formula (24). Deprotection of the Boc-group in acidic conditions, for example using HCl 2M in diethyl ether in a suitable solvent such as diethyl ether leads to the formation of the (trans)-cyclopropanamine derivatives of formula (25). Reductive alkylation with ketones of formula (8) under the same conditions disclosed in Scheme 1 or 2 leads to the formation of (trans)-cyclopropylamino derivatives of formula (26), which correspond to a compound of formula I wherein B=-L-E and $R^w$, $R^x$, $R^y$, $R^z$=H and L is O. In case the ketones of formula (8) contain a protected amino group, for example a Boc-protected amine (Boc: tert-butoxycarbonyl), an additional deprotection reaction step will be required to render a compound (26), which can be performed in acidic conditions, for example using HCl 2M in diethyl ether in a suitable solvent such as diethyl ether, or using HCl in 1,4-dioxane.

Aldehydes of formula (1, where $R^1$=Br), hydroxy-derivatives of formula (25) and ketones of formula (8) are commercially available or can be prepared using well known synthetic procedures starting from readily available starting materials.

The compounds of Formula I wherein B=-L-E and $R^w$, $R^x$, $R^y$, $R^z$=H and L=—NH— or —$(CH_2)_x$—NH— can be synthesized, for example, by the general route described in Scheme 5.

DCE (Dichloroethane), DMSO (Dimethyl sulfoxide), $Pd_2(dba)_3$ (Tris(dibenzylideneacetone)dipalladium(0)), THF (Tetrahydrofuran), Xantphos (4,5-Bis(diphenylphosphino)-9,9-dimethylxanthene).

SCHEME 5: $Boc_2O$ (Di-tert-butyl dicarbonate), DCE (Dichloroethane), DMSO (Dimethyl sulfoxide), $Pd_2(dba)_3$ (Tris(dibenzylideneacetone)dipalladium(0)), THF (Tetrahydrofuran), Xantphos (4,5-Bis(diphenylphosphino)-9,9-dimethylxanthene).

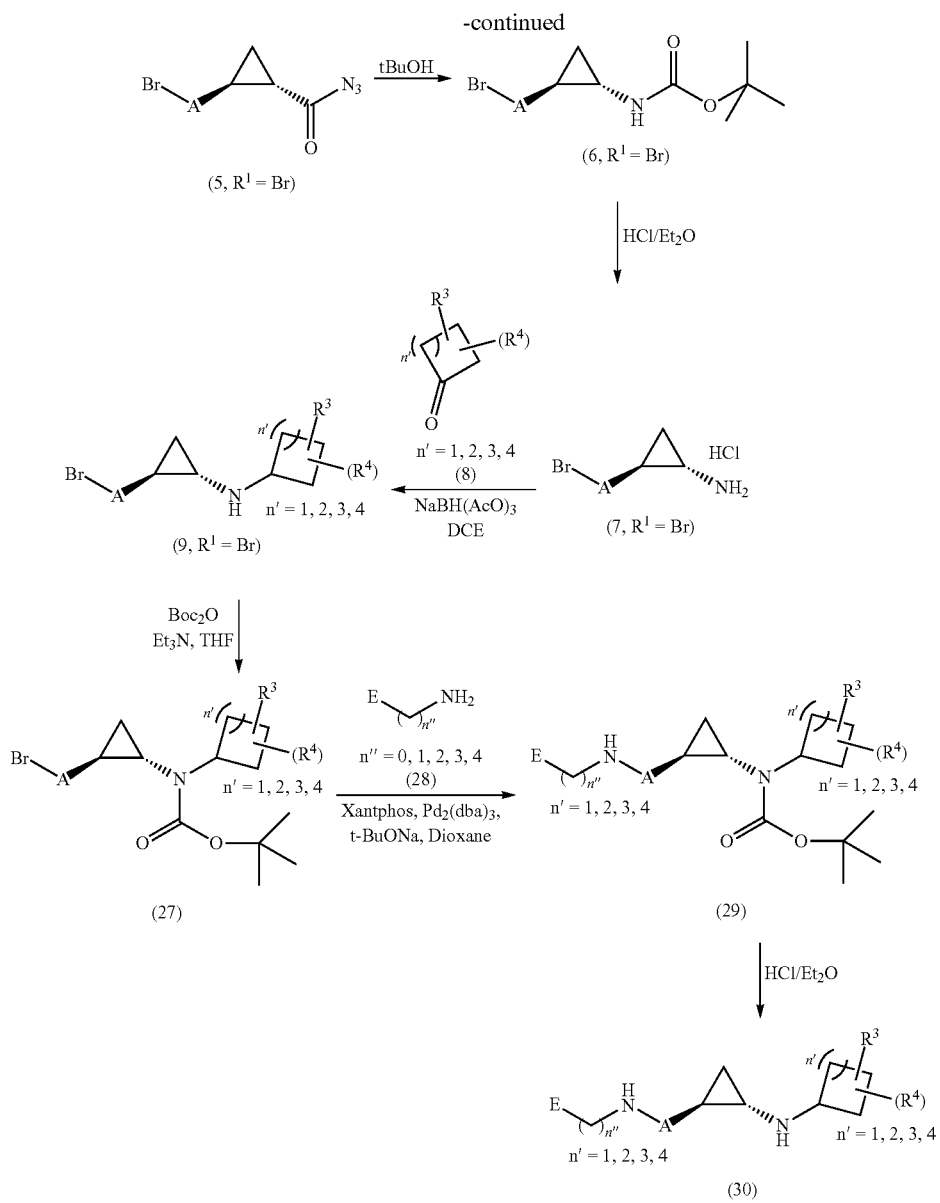

Tert-butyl (trans)-cyclopropylcarbamate derivatives of formula (6, where $R^1$=Br), obtained following the same procedure disclosed in Scheme 4, are converted into the (trans)-cyclopropanamine derivatives of formula (7, where $R^1$=Br) by deprotection of the Boc-group in acidic conditions, for example using HCl 2M in diethyl ether in a suitable solvent such as diethyl ether or using HCl in 1,4-dioxane. Reductive alkylation of compounds (7, $R^1$=Br) with ketones of formula (8) under the same conditions disclosed above, for example using sodium triacetoxyborohydride or sodium borohydride as reducing agent in a suitable solvent such as dichloroethane or methanol, leads to the formation of (trans)-cyclopropylamino derivatives of formula (9, where $R^1$=Br). Reaction of (9, $R^1$=Br) with di-t-butyl dicarbonate under basic conditions using for example triethylamine in a suitable solvent such as tetrahydrofuran leads to the Boc-protected derivatives of formula (27), which are then reacted with amino-derivatives of formula (28) using a palladium catalyst such as Tris(dibenzylideneacetone)dipalladium(0), Xantphos and a base such as sodium tert-butoxide in a suitable solvent such as dioxane to give the tert-butyl (trans)-cyclopropylcarbamate derivatives of formula (29). Deprotection of the Boc-group of a compound (29) in acidic conditions, for example using HCl 2M in diethyl ether in a suitable solvent such as diethyl ether leads to the formation of the (trans)-cyclopropanamine derivatives of formula (30), which correspond to compound of formula I wherein B=-L-E and $R^w$, $R^x$, $R^y$, $R^z$=H and L=—NH— or —$(CH_2)_x$—NH—.

Aldehydes of formula (1, where $R^1$=Br), amines of formula (28) and ketones of formula (8) are commercially available or can be prepared using well known synthetic procedures starting from readily available starting materials.

The compounds of Formula I wherein $R^w$=F can be synthesized, for example, by the general route described in Scheme 6. This method is useful to obtain compounds having either a trans- or cis-configuration at the cyclopropyl ring (i.e. wherein the B-A- and —NH-D groups are in trans or cis configuration), or mixtures thereof, since the cyclopropanation reaction used yields a mixture of cis/trans isomers, as represented by the wavy line in Scheme 6, which can be used as such to obtain compounds of the invention as cis/trans mixtures, or can be separated if desired to yield at the end of the synthesis the desired cis or trans products.

using HCl 2M in diethyl ether in a suitable solvent such as diethyl ether or HCl in 1,4-dioxane, leads to the formation of the cyclopropanamine derivatives of formula (37). Reductive alkylation with ketones of formula (8) under the same conditions disclosed in Scheme 1 or 2 leads to the formation of cyclopropylamino derivatives of formula (38), SCHEME 6: Boc₂O (Di-tert-butyl dicarbonate), DCE (Dichloroethane), DPPA (Diphenylphosphoryl azide), Cu(acac)₂ (Copper(II) acetylacetonate), NBS (N-Bromosuccinimide).

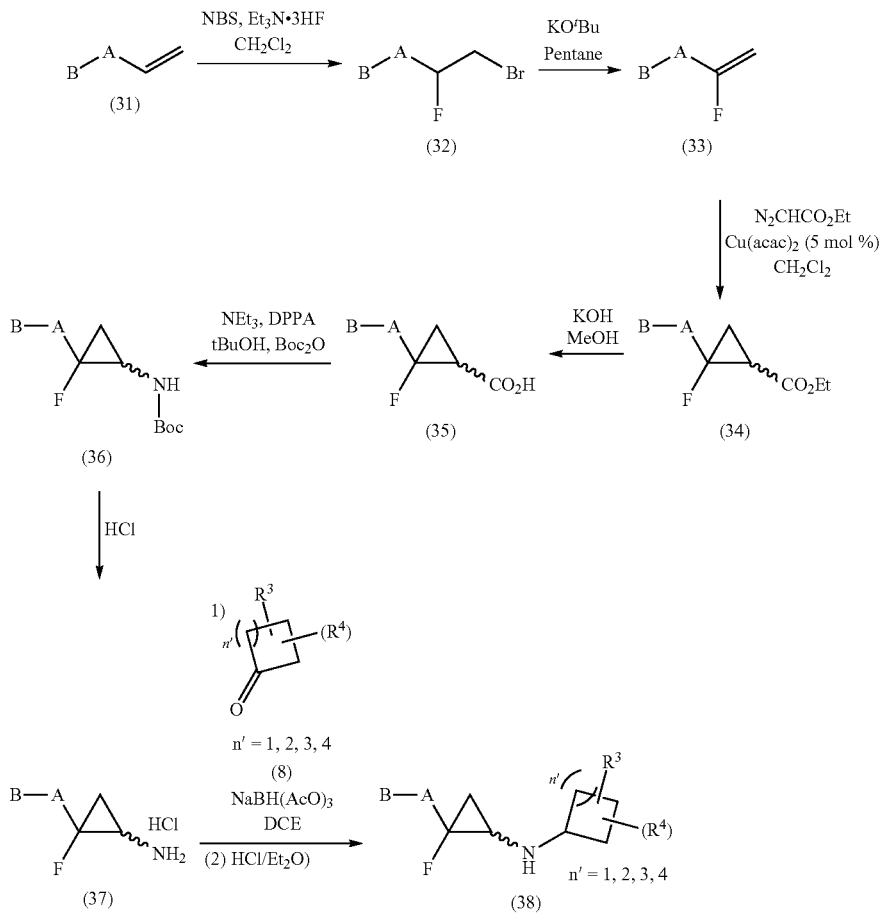

Bromofluorination of derivatives of formula (31) using N-Bromosuccinimide and triethylamine trihydrofluoride in a suitable solvent such as dichloromethane leads to the formation of fluoro-derivatives of formula (32). Elimination reaction using a base, as for example potassium tert-butoxide in a suitable solvent, as for example pentane leads to fluoro-derivatives of formula (33). Cyclopropanation using ethyl diazoacetate and copper (II) acetylacetonate, as catalyst, in a suitable solvent such as dichloromethane leads to a 1:1 mixtures of cis- and trans-derivatives of formula (34). The diastereomers can be separated at this point either chromatographically or, after saponification (performed under basic conditions using for example NaOH in a suitable solvent such as MeOH), by recrystallisation of the corresponding carboxylic acids of formula (35). Curtius degradation to Boc-protected cyclopropylamines of formula (36) can be performed by using a base, as for example, triethylamine, diphenylphosphoryl azide and di-tert-butyl dicarbonate in a suitable solvent, as for example, tert-butanol. Deprotection of the Boc-group in acidic conditions, for example which correspond to a compound of formula I wherein $R^w$=F. In case the ketones of formula (8) contain a protected amino group, for example a Boc-protected amine (Boc: tert-butoxycarbonyl), an additional deprotection reaction step will be required to render a compound (38), which can be performed in acidic conditions, for example using HCl 2M in a suitable solvent such as diethyl ether or using HCl in 1,4-dioxane.

Compounds of formula (31) and ketones of formula (8) are commercially available or can be prepared using well known synthetic procedures starting from readily available starting materials.

Compounds of Formula I wherein $R^w$ is H, fluoro or $C_{1-4}$ alkyl and $R^x$, $R^y$, $R^z$=H can be synthesized, for example, by the general route described in Scheme 7 below. This method is useful to obtain compounds wherein $R^w$ is different from hydrogen having either a trans- or cis-configuration at the cyclopropyl ring (i.e. wherein the B-A- and —NH-D groups are in trans or cis configuration), as well as compounds of formula I wherein $R^w$, $R^x$, $R^y$, $R^z$=H (i.e. a compound of formula Ia) having a cis configuration, since the cyclopropanation reaction used yields a mixture of cis/trans isomers, as represented by the wavy line in Scheme 7, which can be separated to yield the desired cis or trans compounds of the invention.

as 1,4-dioxane or HCl in Et$_2$O using Et$_2$O as solvent leads to the formation of the cyclopropanamine derivatives of formula (44). Reductive alkylation with ketones of formula (8) under the same conditions disclosed in Scheme 1 leads to the formation of cyclopropylamino derivatives of the

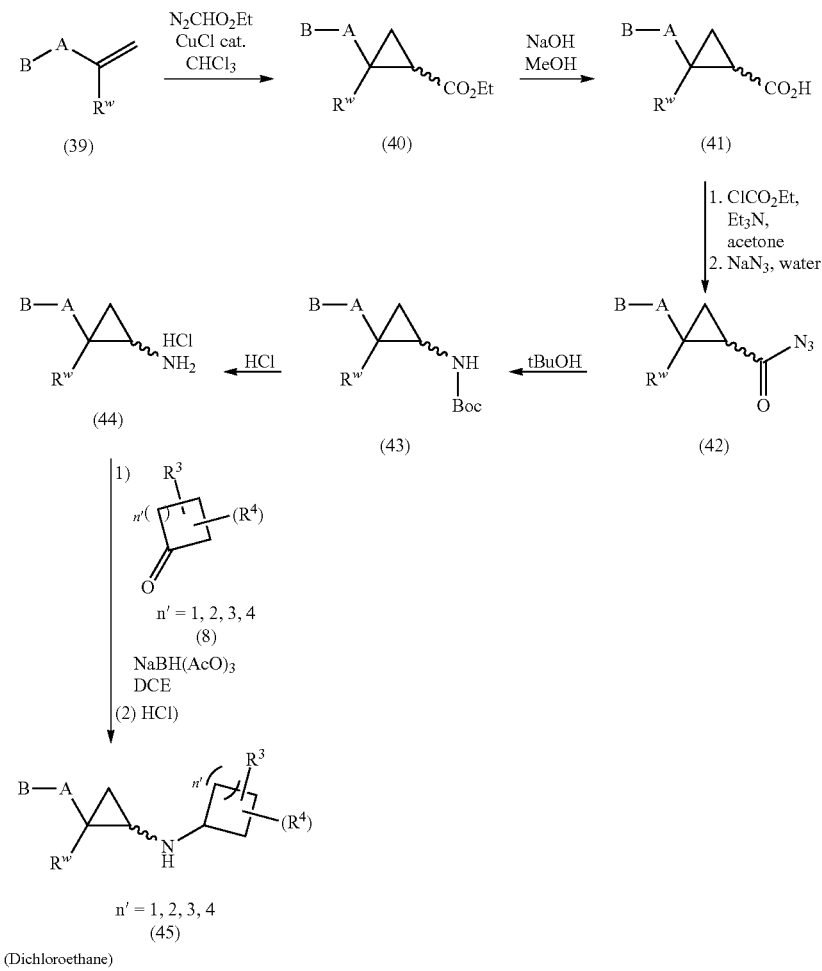

SCHEME 7:

DCE (Dichloroethane)

Derivatives of formula (39) are subjected to cyclopropanation using ethyl diazoacetate and copper (I) chloride, as catalyst, in a suitable solvent such as chloroform, affording a 1:1 mixture of cis- and trans-derivatives of formula (40). Alternatively, the copper catalyst disclosed in Scheme 6 can be used. The diastereomers can be separated at this point either chromatographically or, after saponification (performed under basic conditions using for example NaOH in a suitable solvent such as MeOH), by recrystallisation of the corresponding carboxylic acids of formula (41). Curtius degradation to Boc-protected cyclopropylamines of formula (43) can be performed, first by using ethyl chloro formate and a base, as for example, triethylamine in a suitable solvent, as for example, acetone, and subsequent reaction with sodium azide in water leading to cyclopropanecarbonyl azide derivatives of formula (42). Reaction with tert-butanol results in the formation of Boc-protected cyclopropylamines of formula (43).

Deprotection of the Boc-group in acidic conditions, for example using HCl in 1,4-dioxane in a suitable solvent such invention, designated as compounds of formula (45) in the above scheme. In case the ketone of formula (8) contains a protected amino group, for example a Boc-protected amine (Boc: tert-butoxycarbonyl), an additional deprotection reaction step will be required to render a compound (45), which can be performed in acidic conditions, for example using HCl in 1,4-dioxane in a suitable solvent such as 1,4-dioxane or HCl in Et$_2$O using Et$_2$O as solvent.

Compounds of formula (39) and ketones of formula (8) are commercially available or can be prepared using well known synthetic procedures starting from readily available starting materials.

The compounds of Formula I wherein B=-L-E and R$^w$, R$^x$, R$^y$, R$^z$=H and L=bond can be synthesized, for example, by the general route described in Scheme 8.

SCHEME 8: ACN (Acetonitrile), DCE (Dichloroethane), DMSO (Dimethyl sulfoxide), THF (Tetrahydrofuran)

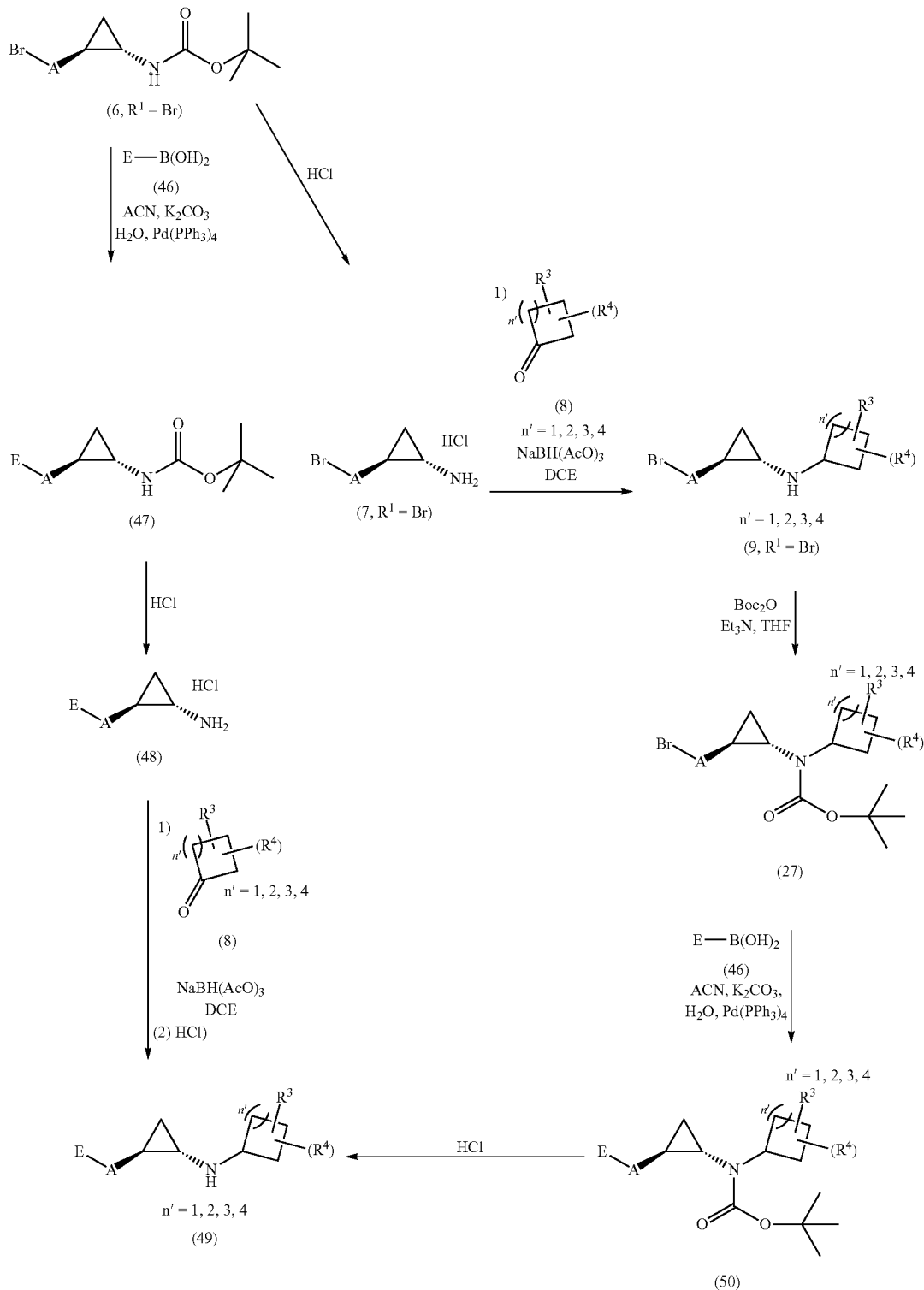

Tert-butyl (trans)-cyclopropylcarbamate derivatives of formula (6), obtained by following the same procedure as disclosed in Scheme 4, are converted into the (trans)-cyclopropanamine derivatives of formula (47) by reaction with boronic acid or ester derivatives of formula (46) using a suitable solvent such as acetonitrile and water, a base, such as for example potassium carbonate, and a palladium catalyst such as tetrakis(triphenylphospine)palladium (0). Deprotection of the Boc-group in acidic conditions, for example using HCl in 1,4-dioxane in a suitable solvent such as 1,4-dioxane leads to the formation of the (trans)-cyclopropanamine derivatives of formula (48). Reductive alkylation with ketones of formula (8) under the same conditions disclosed in Scheme 1 leads to the formation of (trans)-cyclopropylamino derivatives of formula (49), which correspond to compounds of formula I wherein B=-L-E and $R^w$, $R^x$, $R^y$, $R^z$=H and L=bond. When the ketones of formula (8) contain a protected amino group, for example a Boc-protected amine (Boc: tert-butoxycarbonyl), an additional deprotection reaction step will be required to render a compound (49). The deprotection can be performed in acidic conditions, for example using HCl 1,4-dioxane in a suitable solvent such as 1,4-dioxane or HCl in $Et_2O$ using $Et_2O$ as solvent.

Alternatively, (trans)-cyclopropylamino derivatives of formula (49) can be synthesized by removal of the Boc-group of tert-butyl (trans)-cyclopropylcarbamate derivatives of formula (6) in acidic conditions, for example using HCl in a suitable solvent such as 1,4-dioxane, resulting in the (trans)-cyclopropanamine derivatives of formula (7). Reductive alkylation of compounds (7) with ketones of formula (8) under the same conditions as disclosed in Scheme 1 or 2, for example using sodium triacetoxyborohydride or sodium borohydride as reducing agent in a suitable solvent such as dichloroethane or methanol, leads to the formation of (trans)-cyclopropylamino derivatives of formula (9). Reaction of (9) with di-t-butyl dicarbonate under basic conditions using for example triethylamine in a suitable solvent such tetrahydrofuran leads to the Boc-protected derivatives of formula (27). These are converted into the (trans)-cyclopropanamine derivatives of formula (50) by reaction with commercially available boronic acid or ester derivatives of formula (46) using a suitable solvent such as acetonitrile and water, a base, such as for example potassium carbonate and a palladium catalyst such as Tetrakis(triphenylphospine) Palladium (0). Removal of the Boc-group in acidic conditions, for example using HCl in 1,4-dioxane in a suitable solvent such as 1,4-dioxane or HCl in $Et_2O$ using $Et_2O$ as solvent, leads to the formation of the (trans)-cyclopropanamine derivatives of formula (49).

Aldehydes of formula (1), boronic acid or ester derivatives of formula (46) and ketones of formula (8) are commercially available or can be prepared using well known synthetic procedures starting from readily available starting materials.

Furthermore, some compounds of the invention can be obtained from other compounds of formula I by appropriate interconversion reactions of functional groups present in a compound of formula I in one or several steps, using well known reactions in organic synthesis under standard experimental conditions. Said transformations can be carried out upon $R^1$, $R^2$ or $R^3$ and include, for example, the substitution of a primary or secondary amine or of an alcohol by treatment with an alkylating agent, the reduction of a nitro group to an amine, the conversion of an amine into an amide, sulfonamide, sulfamide, carbamate or urea, the palladium-catalyzed cross-coupling of amines with aryl halides, etc. Such interconversion reactions can be performed upon a compound of formula I as well as upon any suitable synthetic intermediate described in the above Schemes.

The salts of a compound of formula I can be obtained during the final isolation and purification of the compounds of the invention or can be prepared by treating a compound of formula I with a sufficient amount of the desired acid (or base) to give the salt in a conventional manner.

In the above schemes 2 to 5 and 8 the cyclopropanation reaction under the conditions disclosed always leads to a racemic mixture of the trans-isomers of compounds (3), (11), (15) and (22). If the synthetic procedures are continued using the trans racemic mixture thus obtained, the corresponding compounds of formula I are obtained as mixtures of trans-isomers. Likewise, in schemes 6 and 7 the cyclopropanation reaction under the conditions disclosed leads to a mixture of cis/trans isomers of compounds (34) and (40). If the synthetic procedure is continued using said isomer mixture, the corresponding compounds of formula I are obtained as mixtures of cis/trans isomers. As used herein, cis and trans refers to the disposition of groups -A-B versus —NH-D on the cyclopropyl ring.

Where the processes for the preparation of the compounds of the invention give rise to mixtures of stereoisomers, individual stereoisomers of a compound of formula I can be obtained by separation from a compound of formula I obtained as a mixture of stereoisomers, using well known methods such as formation of diastereomeric pairs by salt formation with an optically active acid followed by fractional crystallization and regeneration of the free base, or by chiral preparative chromatography. Alternatively, it is possible to obtain optically pure or enantiomerically enriched synthetic intermediates, which can then be used as such in subsequent steps, at various stages of the synthetic procedures described above, using any known method for chiral resolution. Preferably, the chiral separation is performed upon trans-cyclopropylamines of formula (7), (19), (25), (37) or (48). Separation can also be performed at other stages of the procedure, for example upon a compound of formula (34) or (40). A suitable method to obtain the enantiomers of the trans cyclopropylamines (7), (19), (25), (37) and (48) comprises contacting a trans-substituted cyclopropylamine with a chiral recrystallization agent in a solvent (particularly under conditions that are sufficient for the crystallization of the salt of the chiral recrystallization agent and the trans substituted cyclopropylamine); and isolating the crystallized salt of the chiral recrystallization agent and the trans substituted cyclopropylamine, thereby preparing an enantiomer of a trans N-substituted cyclopropylamine. A suitable chiral recrystallization agent is S (+) mandelic acid, D (−) tartaric acid, L (+) tartaric acid, L (−) di-p-toluoyl tartaric acid, or R (−) mandelic acid. Suitable solvents are tetrahydrofuran, ethanol or mixtures thereof with $H_2O$.

Alternatively, it is possible for a person skilled in the art to obtain optically pure or enantiomerically enriched final compounds (or synthetic intermediates) by using chiral chromatography.

EXAMPLES

Unless stated otherwise, in the compounds of all Examples of the present specification the stereochemical configuration is defined by the chemical name indicated for the respective compound, even though the drawn structure may represent a more specific configuration. Nevertheless, the invention relates to all stereoisomers of the compounds described and defined herein. Accordingly, the invention encompasses the compounds described in the Examples as defined by their chemical names and, in addition thereto, also the corresponding compounds having the absolute configuration shown in the respective drawn structures.

The following abbreviations have been used:
ACN: acetonitrile, AcOH: acetic acid, aq: aqueous, Boc: tert-butyloxycarbonyl, $(Boc)_2O$: di-tert-butyl dicarbonate, brm: broad multiplet, brs: broad singlet, $Cu(acac)_2$: copper (II) acetylacetonate, d: doublet, DCE: 1,2-dichloroethane, DCM: dichloromethane, DMF: N,N-dimethylformamide, DMSO: dimethylsulfoxide, DPPA: diphenylphosphoryl azide, Et₂O: diethyl ether, EtOAc: ethyl acetate, HPLC: high performance liquid chromatography, m: multiplet, MEM: methoxy methyl ether, MeOH: methanol, NBS: N-bromosuccinimide, NMR: nuclear magnetic resonance, Pd₂(dba)₃: tris(dibenzylideneacetone)dipalladium(0), Pet ether: petroleum ether, q: quadruplet, Rf: retention factor, RT: room temperature, s: singlet, sat.: saturated, t: triplet, TEA: triethylamine, THF: tetrahydrofuran, TLC: thin layer chromatography, Xantphos: 4,5-Bis(diphenylphosphino)-9,9-dimethylxanthene.

Intermediate A: 1-(benzyloxy)-4-[(trans)-2-nitrocyclopropyl]benzene

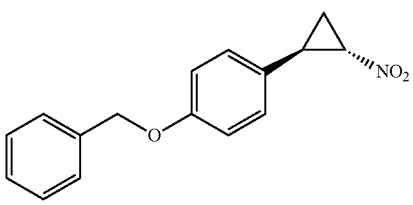 [SMILES: O=[N+]([O-])[C@H]1C[C@@H]1c1ccc(OCc2ccccc2)cc1]

Trimethylsulfoxonium iodide (0.62 g, 2.82 mmol) was added in portions to a solution of t-BuOK (0.32 g, 2.82 mmol) in dry DMSO (5 mL). After 10 min a solution of 1-(benzyloxy)-4-[(E)-2-nitrovinyl]benzene (0.60 g, 2.35 mmol) in DMSO (5 mL) was transferred via canula and the mixture was stirred at room temperature for 6 h. The reaction was poured over water (10 mL) and extracted with Et₂O (3×10 mL); the organic layers were washed with brine (2×15 mL), dried over anhydrous Na₂SO₄ and filtered. After removal of the solvent, the residual orange oil was purified by column chromatography on silica gel (5% EtOAc/hexanes) affording 0.16 g of 1-(benzyloxy)-4-[(trans)-2-nitrocyclopropyl]benzene [Rf=0.5 (20% EtOAc/hexanes), white solid, 26% yield].

Intermediate B: Trans-2-[4-(benzyloxy)phenyl]cyclopropanamine

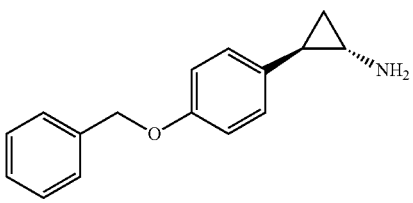

Zn dust (1.97 g, 30 mmol) was added in small portions, over a period of 30 min, to a vigorously stirred solution of 1-(benzyloxy)-4-[(trans)-2-nitrocyclopropyl]benzene (Intermediate A, 0.81 g, 3.0 mmol) in i-PrOH (25 mL) and HCl (11 mL of aqueous solution 2.7 N, 30 mmol). After 17 h the mixture was filtered through a pad of celite, that was washed with 10 mL of methanol. The filtrate was concentrated and 10 mL of water were added, washing with CH₂Cl₂ (3×15 mL). The organic layers were dried over anhydrous Na₂SO₄ and filtered. After removal of the solvent, the crude product was purified by column chromatography on silica gel (10% MeOH/CH₂Cl₂) affording 0.50 g of (trans)-2-[4-(benzyloxy)phenyl]cyclopropanamine [Rf=0.2 (10% MeOH/CH₂Cl₂), white solid, 70% yield].

¹H-NMR (MeOH, 250 MHz, δ): 7.45-7.27 (m, 5H, ArH); 6.96 (d, J=8.5 Hz, 2H, ArH); 6.86 (d, J=8.5 Hz, 2H, ArH); 5.03 (s, 2H, CH2); 2.41-2.34 (m, 1H, CH); 1.86-1.76 (m, 1H, CH); 0.98-0.85 (m, 2H, CH2).

Intermediate C: 4-(benzyloxy)benzaldehyde

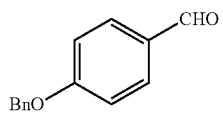

Potassium Carbonate (678 g, 4.91 mol) was added to a solution of 4-hydroxybenzaldehyde (200 g, 1.63 mol) in DMF (2 L) followed to the addition of benzyl bromide (214 mL, 1.80 mol) at 0° C. and stirred for 18 h at RT. After completion, the reaction mixture was poured into ice water (3 L), filtered the solid and dried to get 4-(benzyloxy)benzaldehyde (230 g, 66%).

Intermediate D: (E)-ethyl 3-(4-(benzyloxy)phenyl)acrylate

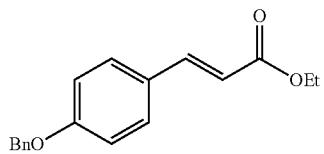 [SMILES: CCOC(=O)/C=C/c1ccc(OCc2ccccc2)cc1]

Triethyl phosphonoacetate (259 mL, 1.3 mol) was added slowly dropwise to a solution of Potassium-tert-butoxide (145 g, 1.29 mol) in dry THF (2 L) at −5° C. and stirred for 30-45 mins. Then a solution of 4-(benzyloxy)benzaldehyde (Intermediate C, 230 g, 1.08 mol) in dry THF (1.5 L) was added slowly dropwise at −10° C. over a period of 15 mins and stirred for 30 mins. After completion, the reaction mixture was poured into ice water (1 L) and extracted with EtOAc (2×1.5 L). The combined organic extracts were washed with sat NaHCO₃ solution (1 L), water (1 L), brine (1 L), dried over anhydrous Na₂SO₄, filtered and evaporated to get crude (E)-ethyl 3-(4-(benzyloxy)phenyl)acrylate (290 g, 95%). The crude was carried to next step without further purification.

Intermediate E: (Trans)-ethyl 2-(4-(benzyloxy)phenyl)cyclopropanecarboxylate

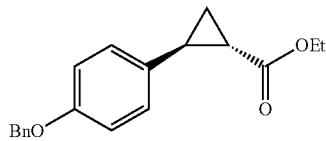 [SMILES: CCOC(=O)[C@H]1C[C@@H]1c1ccc(OCc2ccccc2)cc1]

Trimethyl sulfoxonium iodide (224 g, 1.02 mol) was added portion wise to a suspension of NaH (40.8 g, 1.02 mol) in dry DMSO (2 L) at RT over a period of 20 min and stirred for 1 h till the formation of a clear solution. A solution of (E)-ethyl 3-(4-(benzyloxy) phenyl) acrylate (Intermediate D, 240 g, 0.85 mol) in dry DMSO (2 L) was added dropwise and stirred at RT for 30 mins. After completion, the reaction mixture was poured into ice water (2 L), extracted with EtOAc (2×1 L). Combined organic extracts were washed with ice water (1 L), brine (1 L), dried over anhydrous Na₂SO₄, filtered and evaporated to afford (Trans)-ethyl 2-(4-(benzyloxy)phenyl)cyclopropanecarboxylate (142 g, 58.6%) as an off white solid. The crude was carried to next step without further purification.

Intermediate F: (Trans)-2-(4-(benzyloxy)phenyl) cyclopropanecarboxylic Acid

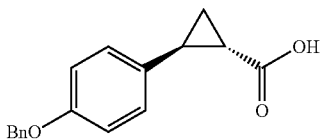 [SMILES: O=C(O)[C@H]1C[C@@H]1c1ccc(OCc2ccccc2)cc1]

4N NaOH solution (4 L) was added to a solution of (trans)-ethyl 2-(4-(benzyloxy)phenyl)cyclopropanecarboxylate (Intermediate E, 250 g, 0.844 mol) in Methanol (1.2 L) at 0° C. and stirred at RT for 4 h. After completion, the solvent was evaporated, the residue was diluted with water (1 L), acidified with 4 N HCl solution, extracted with EtOAc (2×2 L). Combined organic extracts were washed with water (1 L), brine (1 L), dried over anhydrous Na₂SO₄, filtered and evaporated to afford (trans)-2-(4-(benzyloxy)phenyl)cyclopropanecarboxylic acid (190 g, 84%) as off white solid. The crude was carried to next step without further purification.

Intermediate G: (Trans)-2-(4-(benzyloxy)phenyl) cyclopropanecarbonyl azide

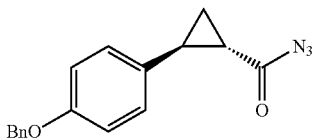 [SMILES: [N-]=[N+]=NC(=O)[C@H]1C[C@@H]1c1ccc(OCc2ccccc2)cc1]

Ethyl chloroformate (143 mL, 1.48 mol) was added to a solution of (trans)-2-(4-(benzyloxy) phenyl) cyclopropanecarboxylic acid (Intermediate F, 190 g, 0.70 mol), Triethyl amine (229 mL, 1.63 mol) in acetone (2.8 L) at −20° C. and stirred for 1 h, then a solution of NaN₃ (138 g, 2.1 mol) in water (200 mL) was added and stirred at RT for 30 mins. After completion, the solvent was evaporated, residue was dissolved in EtOAc (2 L), washed with water (2 L), brine (1 L), dried over anhydrous Na₂SO₄, filtered and evaporated to afford (trans)-2-(4-(benzyloxy)phenyl)cyclopropanecarbonyl azide (178 g, 85.9%).

Intermediate H: Tert-butyl ((trans)-2-(4-(benzyloxy) phenyl)cyclopropyl)carbamate

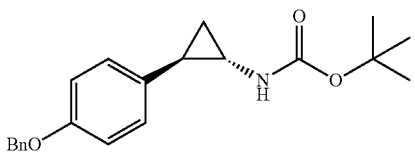 [SMILES: CC(C)(C)OC(=O)N[C@H]1C[C@@H]1c1ccc(OCc2ccccc2)cc1]

A solution of (trans)-2-(4-(benzyloxy)phenyl)cyclopropanecarbonyl azide (Intermediate G, 178 g, 0.64 mol) in tert-butanol (2.6 L) was heated at 90° C. for 16 h. After completion, the solvent was evaporated and the crude residue was purified by column chromatography by using (SiO₂) EtOAc:Pet ether (4:96) to get tert-butyl ((trans)-2-(4-(benzyloxy)phenyl)cyclopropyl)carbamate (78 g, 37.8%) as off-white solid.

Intermediate I: (E)-ethyl 3-(6-bromopyridin-3-yl)acrylate

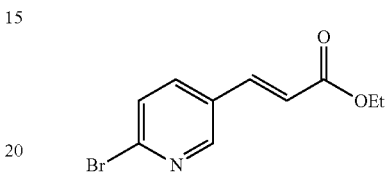

Triethyl phosphonoacetate (26.6 g, 118.8 mmol) was added slowly dropwise to a mixture of Potassium-tert-butoxide (14.5 g, 129.6 mmol) in dry THF (200 mL) at −5° C., stirred for 20 min and then a solution of 6-bromopyridine-3-carboxaldehyde (20 g, 108 mmol) in dry THF (100 mL) was added slowly dropwise at −5° C. and stirred for 30 min. After completion, the reaction mixture was poured into ice water (350 mL) and extracted with EtOAc (2×300 mL). The combined organic extracts were washed with saturated NaHCO₃ solution (250 mL), water (250 mL) and brine (250 mL) and dried over anhydrous Na₂SO₄, filtered and evaporated to get (E)-ethyl 3-(6-bromopyridin-3-yl) acrylate (20 g, 72.9%) as brown color liquid. This is carried to next step without further purification.

Intermediate J: (Trans)-ethyl-2-(6-bromopyridin-3-yl)cyclopropanecarboxylate

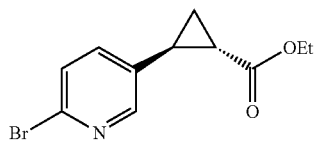 [SMILES: CCOC(=O)[C@H]1C[C@@H]1c1ccc(Br)nc1]

Trimethyl sulfoxonium iodide (20.8 g, 94.7 mmol) was added in small portions to a suspension of sodium hydride (4 g, 170.6 mmol) in dry DMSO (400 mL) at rt., stirred for 1 h until clear solution was obtained. A solution of (E)-ethyl 3-(6-bromopyridin-3-yl) acrylate (Intermediate I, 20 g, 78.7 mmol) in dry DMSO (20 mL) was added and stirred for 4 h. After completion, the reaction mixture was poured into ice water (700 mL), extracted with EtOAc (2×350 mL). The combined organic extracts were washed with water (250 mL), brine (250 mL) and dried over anhydrous Na₂SO₄, filtered and evaporated to give (trans)-ethyl-2-(6-bromopyridin-3-yl)cyclopropanecarboxylate (10 g, 47%) as brown liquid.

Intermediate K: (Trans)-2-(6-bromopyridin-3-yl) cyclopropanecarboxylic acid hydrochloride

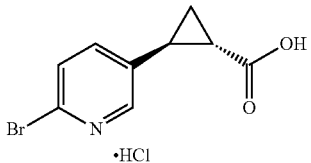 [SMILES: O=C(O)[C@H]1C[C@@H]1c1ccc(Br)nc1 ; Cl]

NaOH 4N solution (60 mL) was added to a solution of (trans)-ethyl-2-(6-bromopyridin-3-yl)cyclopropanecarboxylate (Intermediate J, 10 g, 37.1 mmol) in methanol (100 mL) and the reaction mixture was stirred at RT for 4 h. After completion, the solvent was evaporated and the residue was diluted with ice water (250 mL) and acidified with 4 N HCl solution, the aqueous layer was extracted with EtOAc (2×350 mL). The combined organic extracts were washed with water (250 mL), brine (250 mL) and dried over anhydrous $Na_2SO_4$, filtered and evaporated to give (trans)-2-(6-bromopyridin-3-yl)cyclopropanecarboxylic acid hydrochloride (5 g, 55.8%) as a light brown color solid.

Intermediate L: (Trans)-2-(6-bromopyridin-3-yl) cyclopropanecarbonyl azide

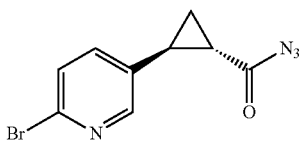 [SMILES: [N-]=[N+]=NC(=O)[C@H]1C[C@@H]1c1ccc(Br)nc1]

Ethyl chloroformate (5.8 mL, 62 mmol) was added to a solution of (trans)-2-(6-bromopyridin-3-yl)cyclopropanecarboxylic acid hydrochloride (Intermediate K, 5 g, 20.7 mmol) and $Et_3N$ (14.2 mL, 103.7 mmol) in Acetone (100 mL) at −5° C., then reaction mixture was stirred at −5° C. for 1 h, then a solution of $NaN_3$ (2.7 g, 41.4 mmol) in water (10 mL) was added and stirred for 30 mins at RT. After completion the solvent was evaporated under vacuum. The crude residue was dissolved in ethyl acetate (200 mL), washed with water (80 mL), brine (80 mL), dried over anhydrous $Na_2SO_4$, filtered and evaporated to get (trans)-2-(6-bromopyridin-3-yl)cyclopropanecarbonyl azide (2.5 g, 45.5%) as a brown color gummy liquid.

Intermediate M: tert-butyl (trans)-2-(6-bromopyridin-3-yl)cyclopropylcarbamate

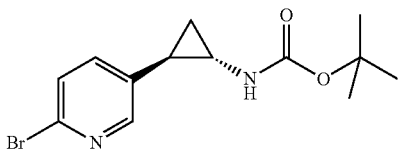 [SMILES: CC(C)(C)OC(=O)N[C@H]1C[C@@H]1c1ccc(Br)nc1]

A solution of (trans)-2-(6-bromopyridin-3-yl)cyclopropanecarbonyl azide (Intermediate L, 2.5 g, 9.36 mmol) in tert-butanol (80 mL) was heated at 90° C. for 16 h. After completion, the solvent was evaporated under vacuum and the residue was taken in water (100 mL) and extracted with EtOAc (2×100 mL). The combined organic extracts were washed with water (100 mL), brine (100 mL) and dried over anhydrous $Na_2SO_4$, filtered and evaporated. The crude residue was purified by flash column chromatography ($SiO_2$) by eluting with EtOAc:Hexane (2:8) to get tert-butyl (trans)-2-(6-bromopyridin-3-yl)cyclopropylcarbamate (1.1 g, 37.5%) as a light yellow solid.

$^1$H-NMR ($CDCl_3$) δ (ppm): 1.16 (q, 1H), 1.23 (quin, 1H), 1.45 (s, 9H), 2.01 (m, 1H), 2.69 (m, 1H), 4.88 (br, 1H), 7.36 (s, 2H), 8.20 (s, 1H).

Intermediate N: (E)-ethyl 3-(4-bromophenyl)acrylate

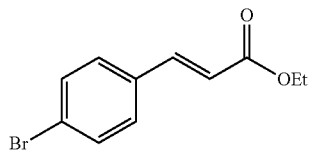 [SMILES: CCOC(=O)/C=C/c1ccc(Br)cc1]

A solution of triethyl phosphonoacetate (13.1 g, 0.0589 mol) was added slowly (dropwise) to a solution of Potassium-tert-butoxide (6.59 g, 0.0589 mol), in dry THF (150 mL) at −5° C., stirred for 30-45 mins at the same temperature, then a solution of 4-Bromo benzaldehyde (10 g, 0.054 mol), in dry THF (50 mL) was slowly added dropwise at −5° C. over a period of 15 mins, stirred the reaction mixture for 30 mins at the same temperature. After completion of reaction by TLC, the reaction mixture was poured into ice water (300 mL), extracted with EtOAc (2×200 mL). The combined organic extracts were washed with sat $NaHCO_3$ solution (200 mL), water (200 mL), brine (200 mL) and dried over anhydrous $Na_2SO_4$, filtered and evaporated to get crude (E)-ethyl 3-(4-bromophenyl) acrylate (10 g, 72%) as pale green liquid. This is carried to next step without further purification.

Intermediate O: (Trans)-ethyl 2-(4-bromophenyl)cyclopropanecarboxylate

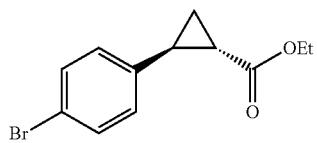 [SMILES: CCOC(=O)[C@H]1C[C@@H]1c1ccc(Br)cc1]

Trimethyl sulfoxonium iodide (5.19 g, 0.0236 mol) was added slowly in small portions over a period of 20 min. to a suspension of sodium hydride (0.44 g, 0.0236 mol) in dry DMSO (80 mL) at rt, stirred for 1 h, till the formation of clear solution. Then a solution of (E)-ethyl 3-(4-bromophenyl) acrylate (Intermediate N, 5 g, 0.01968), in dry DMSO (20 mL) was added slowly dropwise, stirred at rt for 30 mins. After completion of reaction, checked by TLC, the reaction mixture was poured into ice water (200 mL), extracted with EtOAc (2×150 mL). Combined organic extracts were washed with ice water (2×150 mL), brine (150 mL), dried over anhydrous $Na_2SO_4$, filtered and evaporated to get (trans)-ethyl 2-(4-bromophenyl)cyclopropanecarboxylate (4 g, 75.9%) as a green liquid. The crude is carried to next step without further purification.

Intermediate P: (Trans)-2-(4-bromophenyl)cyclopropanecarboxylic Acid

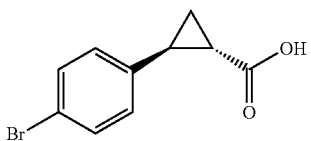 [SMILES: O=C(O)[C@H]1C[C@@H]1c1ccc(Br)cc1]

NaOH 4N (20 mL) was added to a solution of (trans)-ethyl 2-(4-bromophenyl)cyclopropanecarboxylate (Intermediate O, 4 g, 0.0149 mol), in Methanol (40 mL) and stirred at rt for 2 h. After completion of reaction, checked by TLC, the solvent was evaporated and the residue was diluted with water (50 mL), acidified with HCl 4 N solution, the solid formed was filtered and dried to get (trans)-2-(4-bromophenyl)cyclopropanecarboxylic acid (2.59 g, 72%), as a white solid.

Intermediate Q: (Trans)-2-(4-bromophenyl)cyclopropanecarbonyl azide

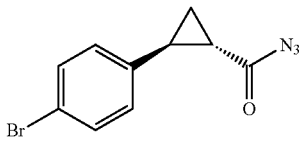 [SMILES: [N-]=[N+]=NC(=O)[C@H]1C[C@@H]1c1ccc(Br)cc1]

Ethyl chloroformate (1.9 mL) was added to a solution of (trans)-2-(4-bromophenyl) cyclopropanecarboxylic acid (Intermediate P, 4 g, 0.0165 mol) and Et$_3$N (2.51 mL, 0.0199 mol) in acetone (60 mL) at −20° C., stirred at same temperature for 1 h, then a solution of NaN$_3$ (1.3 g, 0.0199 mol) in water (5 mL), was added and stirred for 30 mins at rt. After completion of reaction, checked by TLC, the solvent was evaporated and crude residue was dissolved in ethyl acetate (100 mL), washed with water (40 mL), dried over anhydrous Na$_2$SO$_4$, filtered and evaporated to get (trans)-2-(4-bromophenyl)cyclopropanecarbonyl azide (4 g). The crude residue is carried to next step without further purification.

Intermediate R: tert-butyl (trans)-2-(4-bromophenyl)cyclopropylcarbamate

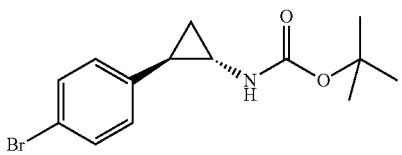 [SMILES: CC(C)(C)OC(=O)N[C@H]1C[C@@H]1c1ccc(Br)cc1]

A solution of (trans)-2-(4-bromophenyl) cyclopropanecarbonyl azide (Intermediate Q, 4 g) in tert-Butanol (40 mL) was heated at 90° C. for 16 h. After completion of reaction, checked by TLC, the solvent was evaporated residue was poured into water (50 mL), extracted with EtOAc (2×50 mL). The combined organic extracts were washed with water (50 mL), brine (50 mL), dried over anhydrous Na$_2$SO$_4$, filtered and evaporated. The crude residue was purified by column chromatography (SiO$_2$) by eluting with EtOAc:Petroleum ether (2:98), to get tert-butyl (trans)-2-(4-bromophenyl)cyclopropylcarbamate (2.5 g, 48% overall 2 steps) as a white solid.

$^1$H-NMR (CDCl$_3$, 250 MHz) δ: 1.07-1.19 (m, 2H), 1.44 (s, 9H); 2.05-1.94 (m, 1H); 2.72-2.62 (m, 1H); 4.85 (br, 1H,); 7.09-6.96 (m, 2H); 7.44-7.33 (m, 2H).

Intermediate S: (E)-ethyl 3-(pyridin-3-yl)acrylate

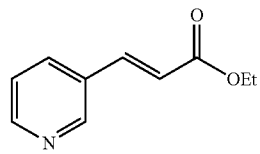 [SMILES: CCOC(=O)/C=C/c1cccnc1]

A solution of triethyl phosphonoacetate (66.75 mL, 336.44 mmol) was added dropwise to a solution of Potassium-tert-butoxide (37.7 g, 280.37 mmol) in dry THF (300 mL) at −5° C. over a period of 10 mins and stirred at 0° C. for 30 mins. Then a solution of nicotinaldehyde (30 g, 280.37 mmol) in dry THF (50 mL) was added dropwise at 0° C. over a period of 15 mins and stirred at RT for 2 h. After completion, the reaction mixture was poured into ice water (150 ml) and extracted with EtOAc (2×300 mL). The combined extracts were washed with sat NaHCO$_3$ solution (200 mL), water (200 mL), brine (200 mL), dried over anhydrous Na$_2$SO$_4$, filtered and evaporated to afford crude liquid (E)-ethyl 3-(pyridin-3-yl) acrylate (42 g, 84.67%). The crude was carried to next step without further purification.

Intermediate T: (Trans)-ethyl 2-(pyridin-3-yl)cyclopropanecarboxylate

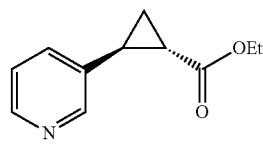 [SMILES: CCOC(=O)[C@H]1C[C@@H]1c1cccnc1]

Trimethyl sulfoxonium iodide (14.90 g, 67.76 mmol) was added portion wise to a suspension of NaH (2.71 g, 67.76 mmol) in dry DMSO (100 mL) at RT over a period of 20 min. and stirred for 1 h till the formation of a clear solution. A solution of (E)-ethyl 3-(pyridin-3-yl) acrylate (Intermediate S, 10 g, 56.47 mmol) in dry DMSO (50 mL) was added dropwise and stirred at RT for 20 min. After completion, the reaction mixture was poured into ice water (200 mL), extracted with EtOAc (2×200 mL). Combined organic extracts were washed with ice water (150 mL), brine (150 mL), dried over anhydrous Na$_2$SO$_4$, filtered and evaporated to afford (trans)-ethyl 2-(pyridin-3-yl)cyclopropanecarboxylate (4 g, 37.07%) as pale brown liquid. The crude was carried to next step without further purification.

Intermediate U: (Trans)-2-(pyridin-3-yl)cyclopropanecarboxylic Acid

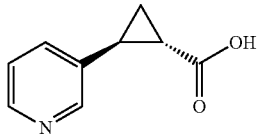 [SMILES: O=C(O)[C@H]1C[C@@H]1c1cccnc1]

A solution of NaOH (7.116 g in 45 mL of H₂O, 177.92 mmol) was added to a solution of (trans)-ethyl 2-(pyridin-3-yl) cyclopropanecarboxylate (Intermediate T, 17 g, 88.96 mmol) in Methanol (170 mL) at 0° C. and stirred at RT for 16 h. After completion, the solvent was evaporated, the residue was diluted with water (50 mL), neutralized with Acetic acid and extracted with EtOAc (4×100 mL). The combined extracts were washed with water (100 mL), brine (100 mL), dried over anhydrous Na₂SO₄, filtered and evaporated to afford (trans)-2-(pyridin-3-yl)cyclopropanecarboxylic acid (9 g, 62.06%) as off white solid. The crude was carried to next step without further purification.

Intermediate V: (Trans)-2-(pyridin-3-yl)cyclopropanecarbonyl azide

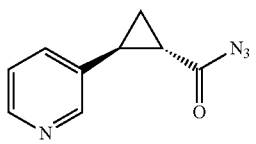 [SMILES: [N-]=[N+]=NC(=O)[C@H]1C[C@@H]1c1cccnc1]

Ethyl chloroformate (6.89 mL, 71.15 mmol) was added to a solution of (trans)-2-(pyridin-3-yl)cyclopropanecarboxylic acid (Intermediate U, 9 g, 55.194 mmol) and triethyl amine (11.03 mL, 82.79 mmol) in acetone (90 mL) at −20° C. and stirred for 1 h, then a solution of NaN₃ (5.38 g, 82.79 mmol) in water (25 mL) was added and stirred at RT for 30 mins. After completion, the solvent was evaporated, residue was dissolved in EtOAc (100 mL), washed with water (2×50 mL), brine (50 mL), dried over anhydrous Na₂SO₄, filtered and evaporated to afford (trans)-2-(pyridin-3-yl)cyclopropanecarbonyl azide (8.4 g, 81%). The crude was carried to next step without further purification.

Intermediate W: tert-butyl ((trans)-2-(pyridin-3-yl)cyclopropyl)carbamate

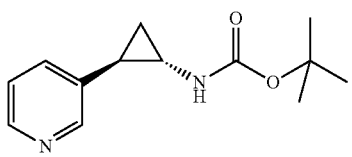 [SMILES: CC(C)(C)OC(=O)N[C@H]1C[C@@H]1c1cccnc1]

A solution of (trans)-2-(pyridin-3-yl)cyclopropanecarbonyl azide (Intermediate V, 8.4 g, 44.66 mmol) in tert-butanol (85 mL) was heated at 90° C. for 16 h. After completion, the solvent was evaporated and crude residue was purified by column chromatography (SiO₂) using EtOAc:Petroleum ether (25:75) to afford tert-butyl (trans)-2-(pyridin-3-yl) cyclopropylcarbamate (3.9 g, 37.32%) as colourless liquid.

Intermediate X: (Trans)-2-(pyridin-3-yl)cyclopropanamine hydrochloride

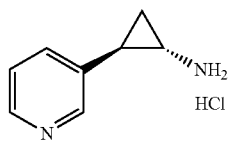

HCl in Dioxane (10 mL) was added to a solution of tert-butyl (trans)-2-(pyridin-3-yl)cyclopropylcarbamate (Intermediate W, 2 g, 8.541 mmol) in 1,4-dioxane (10 mL) at 0° C. and stirred at RT for 12 h. After completion, the solvent was evaporated and the residue was triturated with diethyl ether (20 mL) followed by hexane (20 mL) to get (trans)-2-(pyridin-3-yl)cyclopropanamine hydrochloride (1.2 g, 82.7%).

Intermediate Y: (E)-ethyl 3-(thiazol-5-yl)acrylate

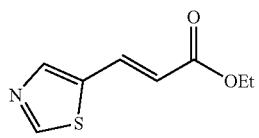 [SMILES: CCOC(=O)/C=C/c1cncs1]

A solution of triethyl phosphonoacetate (11.88 g, 53.03 mmol) was added dropwise to a solution of Potassium-tert-butoxide (5.94 g, 53.03 mmol) in dry THF (100 mL) at −5° C. and stirred for 30 mins. A solution of thiazole-5-carbaldehyde (5 g, 44.19 mmol) in dry THF (25 mL) was then added dropwise at −5° C. over a period of 15 mins and stirred for 30 mins. After completion, the reaction mixture was poured into ice water (150 mL), extracted with EtOAc (2×100 mL). The combined extracts were washed with sat NaHCO₃ solution (100 mL), water (100 mL), brine (100 mL), dried over anhydrous Na₂SO₄, filtered and evaporated to afford crude (E)-ethyl 3-(thiazol-5-yl)acrylate (10 g, 82.3%) as a white solid. The crude was carried to next step without further purification.

Intermediate Z: (Trans)-ethyl 2-(thiazol-5-yl)cyclopropanecarboxylate

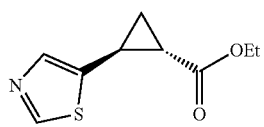 [SMILES: CCOC(=O)[C@H]1C[C@@H]1c1cncs1]

Trimethyl sulfoxonium iodide (14.40 g, 65.49 mmol) was added portionwise to a suspension of NaH (2.61 g, 108.75 mmol) in dry DMSO (200 mL) at RT over a period of 20 min and stirred for 1 h till the formation of clear solution. A solution of (E)-ethyl 3-(thiazol-5-yl)acrylate (Intermediate Y, 10 g, 54.57 mmol) in dry DMSO (50 mL) was then added dropwise and stirred at RT for 30 mins. After completion, the reaction mixture was poured into ice water (100 mL) and extracted with EtOAc (2×100 mL). Combined organic extracts were washed with water (2×50 mL), brine (50 mL), dried over anhydrous $Na_2SO_4$, filtered and evaporated to afford trans-ethyl 2-(thiazol-5-yl)cyclopropanecarboxylate (8 g, 61.9%) as a reddish brown liquid. The crude was carried to next step without further purification.

Intermediate AA:
(Trans)-2-(thiazol-5-yl)cyclopropanecarboxylic Acid

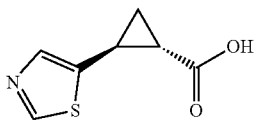 [SMILES: O=C(O)[C@H]1C[C@@H]1c1cncs1]

A 4N NaOH solution (40 mL) was added to a solution of trans-ethyl 2-(thiazol-5-yl)cyclopropanecarboxylate (Intermediate Z, 8 g, 40.55 mmol) in methanol (80 mL) and stirred at RT for 4 h. After completion, the solvent was evaporated, the residue was diluted with water (50 mL), acidified with Acetic acid and extracted with EtOAc (2×75 mL). The combined extracts were washed with water (50 mL), brine (50 mL), dried over anhydrous $Na_2SO_4$, filtered and evaporated to afford trans-2-(thiazol-5-yl)cyclopropanecarboxylic acid (4 g, 58.30%). The crude was carried to next step without further purification.

Intermediate AB:
(Trans)-2-(thiazol-5-yl)cyclopropanecarbonyl azide

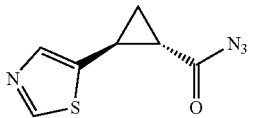 [SMILES: [N-]=[N+]=NC(=O)[C@H]1C[C@@H]1c1cncs1]

Ethyl chloroformate (3.34 g, 30.76 mmol) was added to a solution of trans-2-(thiazol-5-yl)cyclopropanecarboxylic acid (Intermediate AA, 4 g, 26.3 mmol) and triethylamine (3.62 g, 35.50 mmol) in acetone (40 mL) at −20° C., stirred at same temperature for 1 h. A solution of $NaN_3$ (2.84 g, 47.33 mmol) in water (10 mL) was then added and stirred at RT for 30 mins. After completion, the solvent was evaporated, the crude residue was dissolved in EtOAc (100 mL), washed with water (50 mL), brine (50 mL), dried over anhydrous $Na_2SO_4$, filtered and evaporated to afford trans-2-(thiazol-5-yl)cyclopropanecarbonyl azide (3 g, 58.7%) as brown liquid. The crude was carried to next step without further purification.

Intermediate AC: tert-butyl ((trans)-2-(thiazol-5-yl)cyclopropyl)carbamate

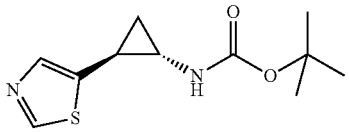 [SMILES: CC(C)(C)OC(=O)N[C@H]1C[C@@H]1c1cncs1]

A solution of trans-2-(thiazol-5-yl)cyclopropanecarbonyl azide (Intermediate AB, 3 g, 15.44 mmol) in tert-butanol (60 mL) was heated at 90° C. for 16 h. After completion, the solvent was evaporated and the residue was taken in water (50 mL), extracted with EtOAc (2×50 mL). The combined organic extracts were washed with water (50 mL), brine (50 mL), dried over anhydrous $Na_2SO_4$, filtered and evaporated. The crude residue was purified by column chromatography ($SiO_2$) by using EtOAc:Petroleum ether (20:80) to get tert-butyl trans-2-(thiazol-5-yl)cyclopropylcarbamate (1.1 g, 29.64%) as a pale yellow liquid.

Intermediate AD:
(Trans)-2-(thiazol-5-yl)cyclopropanamine hydrochloride

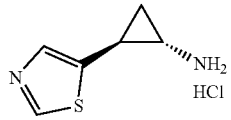

HCl in dioxane (10 mL) was added to a solution of tert-butyl trans-2-(thiazol-5-yl)cyclopropylcarbamate (Intermediate AC, 1.1 g, 45.83 mmol) in dioxane (10 mL) at 15° C. and stirred at RT for 3 h. After completion, the solvent was evaporated, the residue was triturated with EtOAc to afford trans-2-(thiazol-5-yl)cyclopropanamine hydrochloride (600 mg, 74.8%) as pale yellow solid.

Intermediate AE: tert-butyl ((trans)-2-(6-(3-(trifluoromethyl)phenyl)pyridin-3-yl)cyclopropyl)carbamate

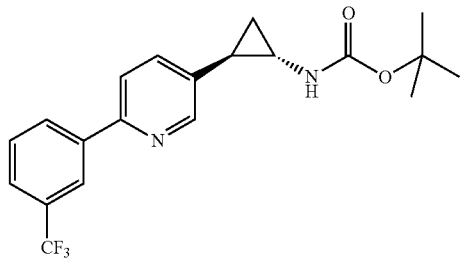 [SMILES: CC(C)(C)OC(=O)N[C@H]1C[C@@H]1c1ccc(-c2cccc(C(F)(F)F)c2)nc1]

A solution of tert-butyl (trans)-2-(6-bromopyridin-3-yl)cyclopropylcarbamate (Intermediate M, 100 mg, 0.32 mmol), potassium carbonate (132 mg, 0.96 mmol) and 3-trifluoromethylbenzeneboronic acid (72 mg, 0.38 mmol) in $CH_3CN:H_2O$ (4:1) (10 mL) was degassed for 30 mins. Tetrakis triphenylphosphine palladium (37 mg, 0.032 mmol) was added and degassed for 10 mins and the reaction mixture was heated at reflux temperature for 2 h. After completion, the reaction mixture was poured in ice water (100 mL), extracted with ethyl acetate (5×40 mL). The combined extract was washed with water (70 mL), brine (70 mL), dried over anhydrous $Na_2SO_4$, filtered and evaporated. The crude residue was purified by column chromatography ($SiO_2$), by using EtOAc:Petroleum ether (1:9) to get tert-butyl (trans)-2-(6-(3-(trifluoromethyl)phenyl)pyridin-3-yl)cyclopropylcarbamate (70 mg, 58.3%) as a white solid.

¹H-NMR (CDCl₃) δ (ppm): 1.26 (m, 2H), 1.46 (s, 9H), 2.10 (m, 1H), 2.78 (m, 1H), 4.86 (br, 1H), 7.55 (m, 2H), 7.65 (t, 2H), 8.14 (d, 1H), 8.24 (s, 1H), 8.54 (s, 1H). MS (M+H): 379.1.

Intermediate AF: (Trans)-2-(6-(3-(trifluoromethyl)phenyl)pyridin-3-yl)cyclopropanamine dihydrochloride

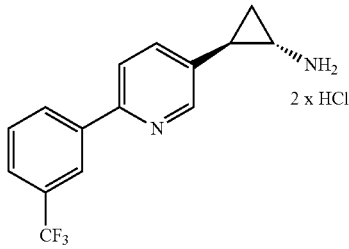 [SMILES: N[C@H]1C[C@@H]1c1ccc(-c2cccc(C(F)(F)F)c2)nc1]

HCl in diethyl ether (5 mL) was added to a solution of tert-butyl (trans)-2-(6-(3-(trifluoromethyl)phenyl)pyridin-3-yl)cyclopropylcarbamate (Intermediate AE, 70 mg, 0.185 mmol) in diethyl ether (10 mL) at 0° C. slowly dropwise over a period of 10 mins and then stirred for 2 h. After completion, the reaction mixture was filtered under inert atmosphere and washed with hexane (10 mL), EtOAC (5 mL), and dried under reduced pressure to get (trans)-2-(6-(3-(trifluoromethyl)phenyl)pyridin-3-yl)cyclopropanamine dihydrochloride (50 mg, 86.2%) as a pale yellow powder.

¹H-NMR (D₂O) δ (ppm): 1.52 (q, 1H), 1.63 (quin, 1H), 2.66 (m, 1H), 3.08 (m, 1H), 7.72 (t, 1H), 7.89 (d, 1H), 7.98 (d, 1H), 8.09 (s, 1H), 8.14 (d, 1H), 8.27 (d, 1H), 8.61 (s, 1H). MS (M+H): 279.1.

Intermediate AG: tert-butyl ((trans)-2-(3'-(trifluoromethyl)-[1,1'-biphenyl]-4-yl)cyclopropyl)carbamate

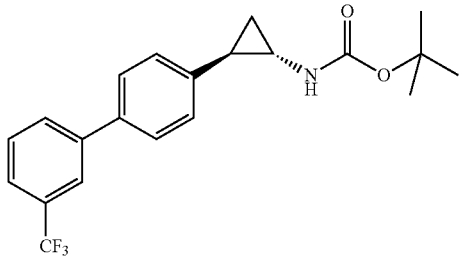

A solution of tert-butyl (trans)-2-(4-bromophenyl)cyclopropylcarbamate (Intermediate R, 1 g, 3.2 mmol), potassium carbonate (1.31 g, 9.6 mmol) and 3-(trifluoromethyl) phenylboronic acid (0.73 g, 3.8 mmol) in acetonitrile:water (4:1) was degassed for 30 mins. Tetrakis triphenylphosphine palladium (36 mg, 0.032 mmol) was then added, degassed again for 10 mins and the reaction mixture was heated at reflux temperature for 5 h. After completion, the reaction mixture was poured in ice water (50 mL) and extracted with ethyl acetate (2×50 mL). Combined extracts were washed with water (70 mL), brine (70 mL), dried over anhydrous Na₂SO₄ and then filtered and evaporated. The crude residue was purified by column chromatography (SiO₂), by using EtOAc:Petroleum ether (2:8) to get tert-butyl ((trans)-2-(3'-(trifluoromethyl)-[1,1'-biphenyl]-4-yl)cyclopropyl)carbamate (0.8 g, 66%) as a white solid.

Intermediate AH: (Trans)-2-(3'-(trifluoromethyl)-[1,1'-biphenyl]-4-yl)cyclopropanamine hydrochloride

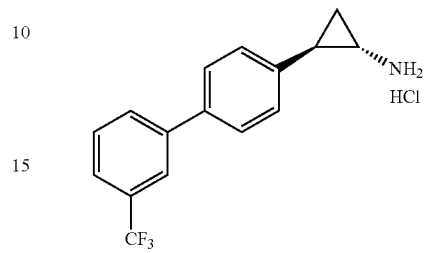

HCl in diethyl ether (3 mL) was added slowly dropwise to a solution of tert-butyl ((trans)-2-(3'-(trifluoromethyl)-[1,1'-biphenyl]-4-yl)cyclopropyl)carbamate (Intermediate AG, 200 mg, 0.53 mmol) in diethyl ether (5 mL) at 10° C. over a period of 10 min and then stirred for 4 h. After completion, the solvent was evaporated and the residue was triturated with hexane (5 mL), diethyl ether (5 mL) and dried under reduced pressure to get (trans)-2-(3'-(trifluoromethyl)-[1,1'-biphenyl]-4-yl)cyclopropanamine hydrochloride (140 mg, 77.8%) as a white solid.

¹H-NMR (DMSO-d6) δ (ppm): 1.27 (q, 1H), 1.46 (quin, 1H), 2.41 (m, 1H), 2.86 (m, 1H), 7.29 (d, 2H), 7.69 (m, 4H), 7.96 (m, 2H), 8.53 (s, 1H), 8.61 (br, 2H). MS (M+H): 278.3

Intermediate AI: 4,4-dimethoxycyclohexanecarboxamide

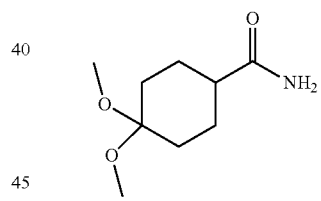

HCl in methanol (2 mL) was added to a solution of ethyl 4-oxocyclohexanecarboxylate (5 g, 29.41 mmol) in methanol (2 mL) at RT, stirred at RT for 3 h and then aq. ammonia (30 mL) was added and heated at 90° C. in a sealed tube for 48 h. After completion, solvent was evaporated. The crude was purified by column chromatography (SiO₂) to afford 4,4-dimethoxycyclohexanecarboxamide (1.2 g, 31.8%) as white solid.

Intermediate AJ: 4-oxocyclohexanecarboxamide

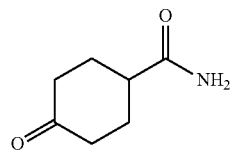

p-toluene sulphonic acid (500 mg, 2.90 mmol) was added to a solution of 4,4-dimethoxycyclohexanecarboxamide (Intermediate AI, 1.2 g, 7.36 mmol) in acetone-water (1:1) (20 mL) and heated to 60° C. for 3 h. After completion, the reaction mixture was poured into ice water (20 mL), extracted with 40% isopropanol in chloroform (3×30 mL). The combined extracts were washed with water, brine, dried over anhydrous Na$_2$SO$_4$, filtered and evaporated. The crude product was washed with 10% dichloromethane in petroleum ether to afford 4-oxocyclohexanecarboxamide (410 mg, 45.55%) as white solid.

Intermediate AK: 4-aminocyclohexanone hydrochloride

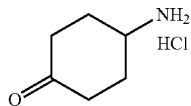

HCl in dioxane (1 mL) was added dropwise to a solution of tert-butyl 4-oxocyclohexylcarbamate (200 mg, 0.938 mmol) in dioxane (2 mL) at 5° C. and stirred at RT for 6 h. After completion, solvent was evaporated, the solid residue was triturated with Et$_2$O (10 mL) and dried to afford 4-aminocyclohexanone hydrochloride (150 mg, 100%) as off-white solid. The crude was carried to next step without further purification.

Intermediate AL: N-(4-oxocyclohexyl)methanesulfonamide

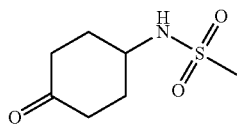

Methane sulphonyl chloride (1.83 g, 16.07 mmol) was added dropwise to a solution of 4-aminocyclohexanone hydrochloride (Intermediate AK, 1.5 g, 13.39 mmol) and K$_2$CO$_3$ (6.46 g, 46.87 mmol) in ACN-THF (1:1) (30 mL), and then stirred at RT for 16 h. After completion, solvent was evaporated, crude residue was diluted with water (50 mL), extracted with EtOAc (2×50 mL). The combined extracts were washed with water (50 mL), brine (50 mL), dried over anhydrous Na$_2$SO$_4$, filtered and evaporated to afford N-(4-oxocyclohexyl) methane sulfonamide (990 mg, 38.6%) as white solid.

Intermediate AM: (R)-tert-butyl (1-(1,4-dioxaspiro [4.5]decan-8-yl)pyrrolidin-3-yl)carbamate

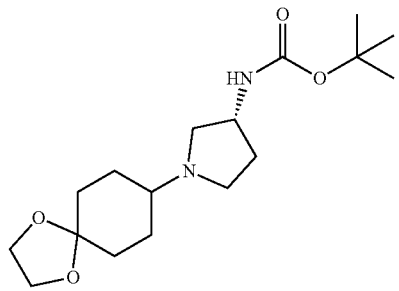 [SMILES: CC(C)(C)OC(=O)N[C@@H]1CCN(C2CCC3(CC2)OCCO3)C1]

1,4-dioxaspiro[4.5]decan-8-one (0.76 g, 4.88 mmol) was added to a solution of (R)-tert-butyl pyrrolidin-3-ylcarbamate (1.0 g, 5.36 mmol) in DCE (65 mL) and stirred for 15 mins. Sodium triacetoxy borohydride (1.55 g, 7.32 mmol) was then added at 0° C. and stirred at RT for 16 h. After completion, the reaction mixture was diluted with DCM (50 mL), washed with saturated NaHCO$_3$ solution (50 mL), water (50 mL), brine (50 mL) dried over anhydrous Na$_2$SO$_4$, filtered and evaporated. The crude residue was purified by column chromatography using SiO$_2$ by eluting Hexane: Methyl tert-butyl ether (80:20) to afford (R)-tert-butyl (1-(1,4-dioxaspiro[4.5]decan-8-yl)pyrrolidin-3-yl)carbamate (1.53 g, 96.8%).

Intermediate AN: (R)-4-(3-aminopyrrolidin-1-yl)cyclohexanone

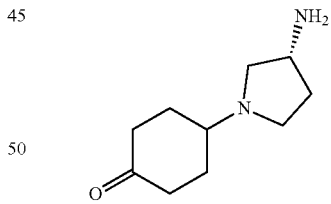

HCl in 1, 4 dioxane (5 mL) was added to a solution of (R)-tert-butyl (1-(1,4-dioxaspiro[4.5]decan-8-yl)pyrrolidin-3-yl)carbamate (Intermediate AM, 1.53 g, 8.39 mmol) in dioxane (25 mL) at 15° C. and stirred at RT for 16 h. After completion, saturated Na$_2$CO$_3$ solution (50 mL) was added, the solvent was evaporated and the residue was triturated with Et$_2$O and dried to afford (R)-4-(3-aminopyrrolidin-1-yl)cyclohexanone (0.61 g, 71.5%).

Intermediate AO: (R)-tert-butyl (1 (4-oxocyclo-hexyl)pyrrolidin-3-yl)carbamate

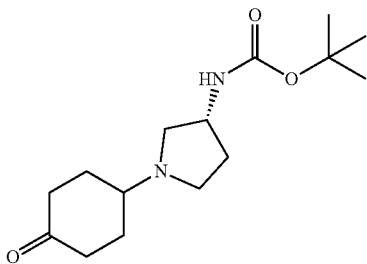 [SMILES: CC(C)(C)OC(=O)N[C@@H]1CCN(C2CCC(=O)CC2)C1]

Di-t-butyl dicarbonate (1.77 g, 9.98 mmol) was added to a solution of (R)-4-(3-aminopyrrolidin-1-yl)cyclohexanone (0.61 g, 3.34 mmol) in water (6 mL) and stirred at RT for 2 hours. After completion, the reaction mixture was washed with DCM (50 mL) and AcOEt (50 mL). The organic layer was then washed with H2O (50 mL) and brine (50 mL) dried over anhydrous Na$_2$SO$_4$, filtered and evaporated. The crude residue was purified by column chromatography using SiO$_2$ by eluting Hexane: Methyl tert-butyl ether (80:20) to afford (R)-tert-butyl (1-(4-oxocyclohexyl)pyrrolidin-3-yl)carbamate (0.23 g, 23.9%).

Intermediate AP: 1-ethyl-3-(4-oxocyclohexyl)urea

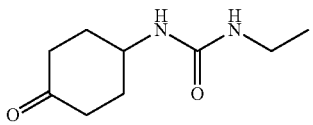

Isocyanatoethane (237 mg, 3.34 mmol) and triethylamine (0.85 mL, 6.68 mmol) was added to a solution of 4-amino-cyclohexanone hydrochloride (Intermediate AK, 500 mg, 3.34 mmol) in toluene (5 mL) and stirred at 110° C. for 16 h. After completion, the solvent was evaporated, the crude residue was purified by column chromatography (SiO$_2$) using EtOAc:petroleum ether (3:7) to afford 1-ethyl-3-(4-oxocyclohexyl) urea (600 mg, 98%) as a brown solid.

Intermediate AQ: 4-((2-methoxyethoxy)methoxy)benzaldehyde

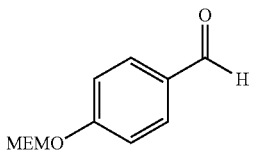

4-Hydroxybenzaldehyde (50 g, 409 mmol) in THF (50 mL) was added dropwise and slowly over a period of 30 min to a suspension of sodium hydride (19.6 g, 817 mmol) in THF (750 mL) at 0° C. and stirred for 15 min, followed by addition of 1-(chloromethoxy)-2-methoxyethane (MEM chloride, 61.10 g, 490 mmol) at 0° C. The reaction mixture was stirred at RT for 30 min and, after completion, poured into ice water (500 mL) and extracted with EtOAc (2×750 mL). The combined organic extracts were washed with ice water (500 mL), brine (500 mL), dried over anhydrous Na$_2$SO$_4$, filtered and concentrated affording 4-((2-methoxy-ethoxy)methoxy)benzaldehyde (52 g, 50%) as a pale yellow liquid. The crude was used in the next step without further purification.

Intermediate AR: (Trans)-2-(4-bromophenyl)cyclopropanamine

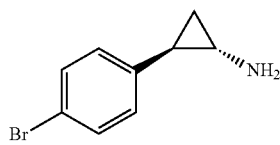 [SMILES: N[C@H]1C[C@@H]1c1ccc(Br)cc1]

To a solution of tert-butyl trans-2-(4-bromophenyl)cyclo-propylcarbamate (Intermediate R, 10 g, 32.05 mmol) in 1,4-dioxane (100 mL) at 10° C. was added HCl in dioxane (50 mL) and stirred at RT for 20 h. After completion, the solvent was evaporated and the residue was taken up in ice water, basified with saturated aq. NaHCO$_3$ and extracted with EtOAc (2×100 mL). The combined extracts were washed with water, brine, dried over anhydrous Na$_2$SO$_4$, filtered and concentrated to afford (trans)-2-(4-bromophe-nyl)cyclopropanamine (6.2 g, 91%). The crude product was used in the next step without further purification.

Intermediate AS: Tert-butyl (4-((trans)-2 (4-bro-mophenyl)cyclopropyl)amino)cyclohexyl)carbamate

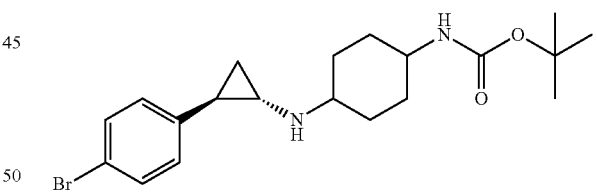

Tert-butyl 4-oxocyclohexylcarbamate (5 g, 23.58 mmol) was added to a solution of (trans)-2-(4-bromophenyl)cyclo-propanamine (Intermediate AR, 5 g, 23.58 mmol) in DCE (100 mL) followed by the addition of AcOH (1.41 g, 23.58 mmol). The mixture was stirred for 5 min and then cooled to 0° C. before sodium triacetoxy borohydride (8.9 g, 42.45 mmol) was added. The reaction mixture was stirred at RT for 16 h and, after completion, poured into sat. aq. NaHCO$_3$ and extracted with DCM (2×100 mL). The combined extracts were washed with water (100 mL), brine (100 mL), dried over anhydrous Na$_2$SO$_4$, filtered and concentrated. The crude residue was purified by column chromatography (SiO$_2$, petroleum ether/EtOAc 7:3) to afford tert-butyl (4-(((trans)-2-(4-bromophenyl)cyclopropyl)amino) cyclo-hexyl)carbamate (6.2 g, 64%).

Intermediate AT: Tert-butyl ((trans)-2-(4-bromophenyl)cyclopropyl)(4-((tert-butoxycarbonyl)amino)cyclohexyl)carbamate

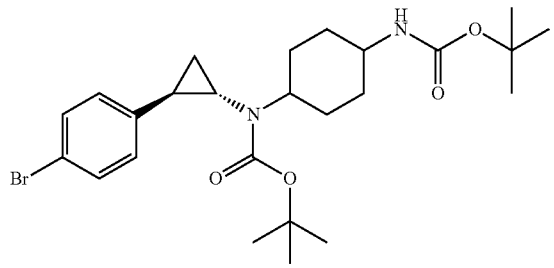 [SMILES: CC(C)(C)OC(=O)NC1CCC(N(C(=O)OC(C)(C)C)[C@H]2C[C@@H]2c2ccc(Br)cc2)CC1]

A NaOH solution (1.96 g, 49 mmol) was added to a solution of tert-butyl (4-(((trans)-2-(4-bromophenyl)cyclopropyl)amino)cyclohexyl)carbamate (Intermediate AS, 5 g, 12.25 mmol) in 1,4-dioxane/H₂O 9:1 (100 mL) followed by Boc anhydride (4 g, 18.37 mmol). The reaction mixture was stirred at RT for 16 h and, after completion, poured into water (50 mL) and extracted with EtOAc (2×50 mL). The combined extracts were washed with water (50 mL), brine (50 mL), dried over anhydrous Na₂SO₄, filtered and concentrated. The crude residue was purified by column chromatography (SiO₂, EtOAc/petroleum ether 2:8) affording tert-butyl ((trans)-2-(4-bromophenyl)cyclopropyl)(4-((tert-butoxycarbonyl) amino)cyclohexyl)carbamate (5.2 g, 83%) as a colorless liquid.

Intermediate AU: (Trans)-2-(6-bromopyridin-3-yl)cyclopropanamine

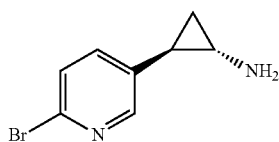 [SMILES: N[C@H]1C[C@@H]1c1ccc(Br)nc1]

This compound was synthesized by following the method described in Intermediate AR and utilizing the respective starting material (tert-butyl ((trans)-2-(6-bromopyridin-3-yl)cyclopropyl)carbamate) leading to 1.2 g of the title compound.

Intermediate AV: (2-bromo-1-fluoroethyl)benzene

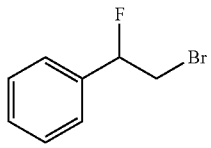

Triethylamine trihydrofluoride (36.3 mL, 216.01 mmol) and N-bromosuccinimide (30.75 g, 172.8 mmol) was added to a solution of styrene (15 g, 144.0 mmol) in DCM (150 mL) at 0° C. and stirred at RT for 16 h. After completion, the reaction mixture was neutralized with aq NH₄OH solution (150 mL) and extracted with DCM (2×200 mL). The combined extracts were washed with 0.1 N HCl solution (100 mL), 5% NaHCO₃ solution (100 mL), brine (100 mL) and dried over anhydrous Na₂SO₄, filtered and concentrated to afford (2-bromo-1-fluoroethyl) benzene (25 g, 85%) as a brown liquid.

Intermediate AW: (1-fluorovinyl)benzene

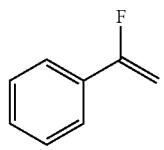

KOtBu (27.77 g, 247.54 mmol) was added portionwise to a solution of (2-bromo-1-fluoroethyl)benzene (Intermediate AV, 25 g, 123.7) in pentane (250 mL) at 0° C. The reaction mixture was stirred at reflux temperature for 1 h and, after completion, cooled to RT, then poured into ice water (150 mL) and extracted with hexane (2×200 mL). The combined extracts were washed with 5% NaHCO₃ solution (150 mL), 0.05 M HCl solution (150 mL), water (150 mL), brine (150 mL) and dried over anhydrous Na₂SO₄, filtered and concentrated to afford (1-fluorovinyl)benzene (13 g, 86%) as a pale yellow liquid.

Intermediate AX: Ethyl 2-fluoro-2-phenylcyclopropanecarboxylate (cis/trans)

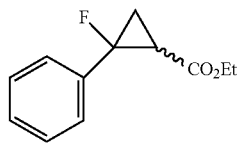 [SMILES: CCOC(=O)C1CC1(F)c1ccccc1]

Copper(II) acetylacetonate (321 mg, 1.23 mmol) was dissolved in dry DCM (10 mL) and stirred for few min, before a few drops of phenyl hydrazine were added. The solution was stirred at RT for 10 min, then a solution of (1-fluorovinyl)benzene (Intermediate AW, 5 g, 40.98 mmol) in dry DCM (50 mL) was added. The mixture was heated to reflux, before a solution of ethyl diazoacetate (6.46 ml, 61.47 mmol) in CH₂Cl₂ was added dropwise and slowly for 60 min. The reaction mixture was stirred at reflux temperature for 14 h and, after completion, cooled to room temperature, diluted with DCM (50 ml), washed with Na₂CO₃ solution (25 mL), water (25 mL), and brine (25 mL), dried over anhydrous Na₂SO₄, filtered and concentrated. The crude residue was purified by column chromatography (SiO₂) using DCM: Hexane (10:90) to afford ethyl 2-fluoro-2-phenylcyclopropanecarboxylate (cis) (540 mg, 6.3%) and ethyl 2-fluoro-2-phenylcyclopropanecarboxylate (trans) (480 mg, 5.6%).

Intermediate AY: (Cis)-ethyl 2-phenylcyclopropanecarboxylate

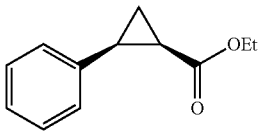 [SMILES: CCOC(=O)[C@@H]1C[C@@H]1c1ccccc1]

Ethyl diazo acetate (10.09 mL, 96.01 mmol) was added to a solution of styrene (10 g, 96.01 mmol) in dry chloroform (200 mL) followed by Cu(I)CI (catalytic) and stirred at 60° C. for 4 h. After completion, the solvent was evaporated and the crude residue was purified by column chromatography (SiO$_2$, EtOAc/petroleum ether 1:9) affording (cis)-ethyl 2-phenylcyclopropanecarboxylate (1.7 g, 9.3%) as a colorless liquid.

Intermediate AZ: N-(3-bromo-4-methoxyphenyl)methanesulfonamide

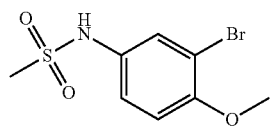

Methanesulphonyl chloride (55.82 mL, 0.494 mmol) was added to a solution of 3-bromo-4-methoxyaniline (100 mg, 0.494 mmol) in pyridine (1 mL) at 0° C. and stirred at RT for 2 h. After completion, reaction mixture was poured into ice water (10 mL) and extracted with EtOAc (2×15 mL). The combined extracts were washed with water (3×10 mL), brine (15 mL) and dried over anhydrous Na$_2$SO$_4$ filtered, and evaporated. The crude residue was purified by column chromatography (SiO$_2$) by using EtOAc:Hexane (3:7) to afford N-(3-bromo-4-methoxyphenyl)methanesulfonamide (137 mg, 99%) as a white solid.

Intermediate BA: N-(4-methoxy-3-(4,4,5,5-tetramethyl-1,3,2-dioxaborolan-2-yl)phenyl)methanesulfonamide

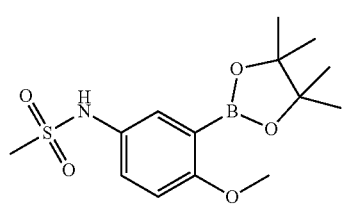

A solution of N-(3-bromo-4-methoxyphenyl)methanesulfonamide Intermediate AZ, 136 mg, 0.485 mmol), bis(pinacolato)diboron (147 mg, 0.58 mmol) and KOAc (87.3 mg, 0.888 mmol) in dioxane (5.5 mL) was degassed for 30 min, then PdCl$_2$(dppf)$_2$ (17.7 mg, 0.020 mmol) was added and the reaction mixture was heated at 100° C. for 3 h. After completion, the reaction mixture was poured into water (10 mL), extracted with EtOAc (2×15 mL). The combined extracts were washed with water (10 mL), brine (50 mL), dried over anhydrous Na$_2$SO$_4$, filtered and evaporated. The crude residue was purified by column chromatography (SiO$_2$, EtOAc:petroleum ether 1:9) to afford N-(4-methoxy-3-(4,4,5,5-tetramethyl-1,3,2-dioxaborolan-2-yl) phenyl) methanesulfonamide (100 mg, 63%) as a white solid.

Intermediate BB: 3-methoxy-5-(4,4,5,5-tetramethyl-1,3,2-dioxaborolan-2-yl)benzonitrile

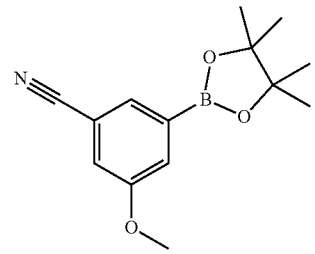 [SMILES: COc1cc(C#N)cc(B2OC(C)(C)C(C)(C)O2)c1]

This compound was synthesized by following the method described in Intermediate BA and utilizing the respective starting material (3-bromo-5-methoxybenzonitrile) leading to 1.4 g of the title compound as a white solid.

Intermediates BC ((Trans)-ethyl 2-(5-bromothiophen-2-yl)cyclopropanecarboxylate), BD ((Trans)-ethyl 2-(2-bromothiazol-5-yl)cyclopropanecarboxylate) and BE ((Trans)-ethyl 2-(4-((2-methoxyethoxy)methoxy)phenyl) cyclopropanecarboxylate)

These intermediates were synthesized by following the same method as described to obtain Intermediate T (Nicotinaldehyde was subjected to Horner-Wadsworth-Emmons reaction to get Intermediate S, which are then subjected to cyclopropanation reaction leading to Intermediate T) starting from the respective commercially available aldehyde listed below:

| Starting aldehyde | Intermediate |
|---|---|
| | BC |
| | BD |
| AQ (MEMO-phenyl-CHO) | BE |

Intermediates BF ((Trans)-2-(5-bromothiophen-2-yl)cyclopropanamine), BG ((Trans)-2-(2-bromothiazol-5-yl)cyclopropanamine), BH (4-((trans)-2-aminocyclopropyl)phenol), BI ((Cis)-2-fluoro-2-phenylcyclopropanamine), BJ ((Trans)-2-fluoro-2-phenylcyclopropanamine)) and BK ((Cis)-2-phenylcyclopropanamine)

These intermediates were synthesized by following the same method described to obtain Intermediate X from Intermediate T (Hydrolisis of (trans)-ethyl 2-(pyridin-3-yl) cyclopropanecarboxylate to get Intermediate U, which are then subjected to Curtius reaction leading, first to Intermediate V and later to intermediate W and final Boc-deprotection leads to Intermediate X) by using the respective intermediates.

Intermediates BF, BH and BK were obtained as hydrochloride salt.

Intermediates BG, BI and BJ were basified with saturated NaHCO$_3$ aq. solution after acidic treatment at Boc-deprotection step and were obtained as free base.

| Starting intermediate | Intermediate | $^1$H-NMR and MS data |
|---|---|---|
| BC | BF | $^1$HNMR (400 MHz, DMSO-d6 D$_2$O Exchange) δ (ppm): 7.05 (s, 1H), 6.75 (s, 1H), 2.82-2.78 (m, 1H), 2.48-2.42 (m, 1H), 1.42-1.38 (m, 1H), 1.28 (q, J = 6.4 Hz, 1H); Mass (M + H): 217.94 |
| BD | BG | 1HNMR (400 MHz, DMSO-d6 D2O Exchange) δ (ppm): 7.48 (s, 1H), 2.9-2.85 (m, 1H), 1.50-1.40 (m, 1H), 1.40-1.32 (m, 1H); Mass (M + H): 218.91/220.92 |
| BE | BH | 1HNMR (400 MHz, D2O) δ (ppm): 7.13 (d, J = 7.6 Hz, 2H), 6.88 (d, J = 7.6 Hz, 2H), 2.87-2.80 (m, 1H), 2.44-2.38 (m, 1H), 1.44-1.37 (m, 1H), 1.36-1.26 (m, 1H). |
| AX (cis) | BI | The crude was carried to next step without further purification |
| AX (trans) | BJ | The crude was carried to next step without further purification |
| AY | BK | 1HNMR (400 MHz, D2O) δ (ppm): 7.44-7.34 (m, 4H), 2.98-2.90 (m, 1H), 2.62-2.54 (m, 1H), 1.43-1.35 (m, 1H), 1.34-1.26 (m, 1H); Mass (M + H): 134.08 |

Intermediate BL: Tert-butyl ((trans)-2-(4-hydroxyphenyl)cyclopropyl)carbamate

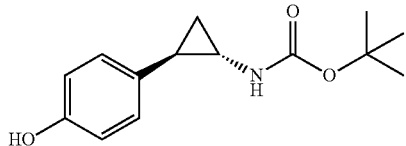 [SMILES: CC(C)(C)OC(=O)N[C@H]1C[C@@H]1c1ccc(O)cc1]

$K_2CO_3$ (20.36 g, 147.56 mmol) and $(Boc)_2O$ (16.8 mL, 70.27 mmol) was added to a solution of 4-((trans)-2-aminocyclopropyl)phenol hydrochloride (Intermediate BI, 13 g, 70.27 mmol) in 1,4-dioxane (78 mL) and water (195 mL) and stirred at RT for 16 h. After completion, the reaction mixture was poured into water (300 mL) and extracted with EtOAc (2×200 mL). The combined extracts were washed with water (75 mL), brine (75 mL), dried over anhydrous $Na_2SO_4$, filtered and concentrated. The crude residue was purified by column chromatography ($SiO_2$, EtOAc/petroleum ether 3:7) affording tert-butyl ((trans)-2-(4-hydroxyphenyl)cyclopropyl)carbamate (14 g, 80%) as a brown thick viscous liquid.

Intermediates BM (Tert-butyl (4-(((trans)-2-(6-bromopyridin-3-yl)cyclopropyl)amino)cyclohexyl)carbamate) BN (Tert-butyl (4-(((trans)-2-(5-bromothiophen-2-yl)cyclopropyl)amino)cyclohexyl)carbamate) and BO (Tert-butyl (4-(((trans)-2-(2-bromothiazol-5-yl)cyclopropyl)amino)cyclohexyl)carbamate)

These intermediates were synthesized by following the same method as described to obtain Intermediate AS from Intermediate AR (reductive alkylation) by using the respective starting intermediate.

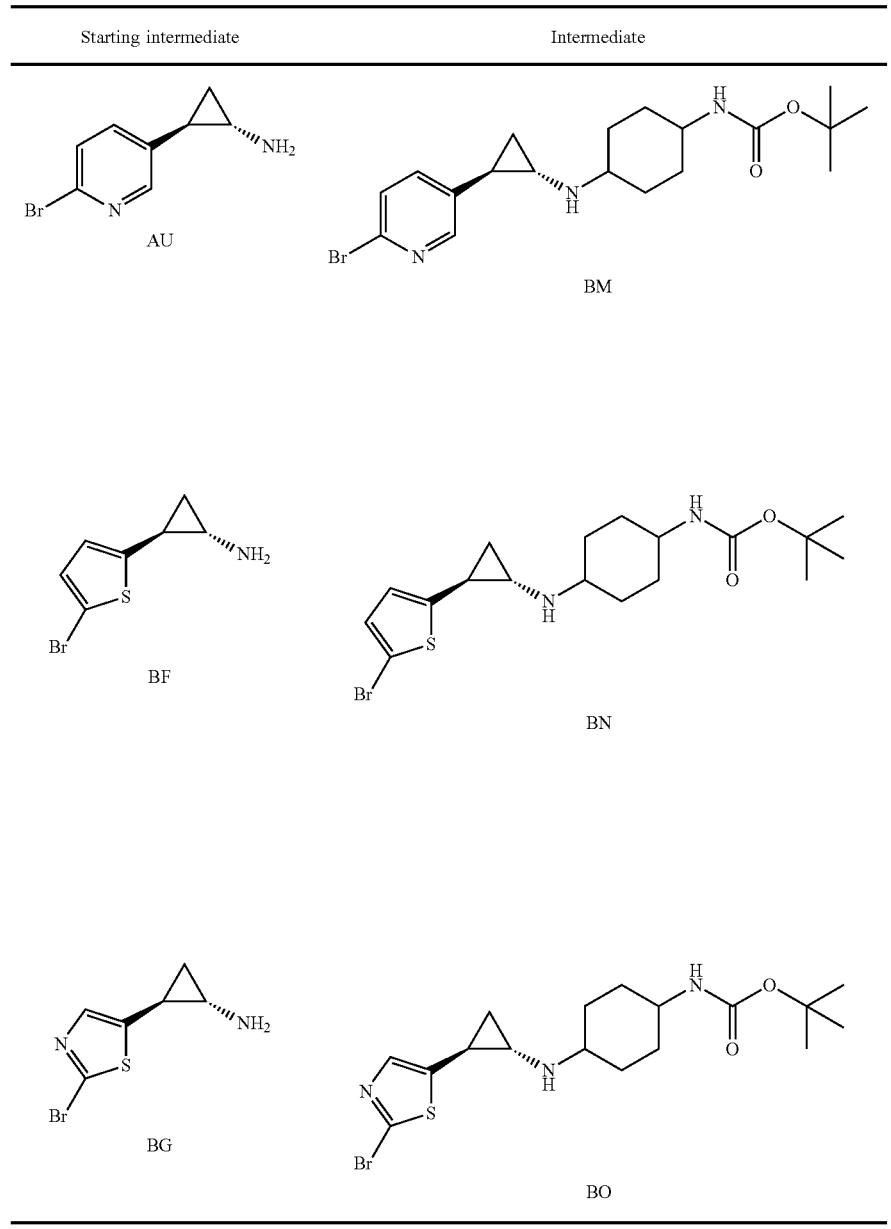

| Starting intermediate | Intermediate |
|---|---|
| AU | BM |
| BF | BN |
| BG | BO |

Intermediates BP (tert-butyl ((trans)-2-(6-bromopyridin-3-yl)cyclopropyl)(4-((tert-butoxycarbonyl)amino)cyclohexyl)carbamate) and BQ (tert-butyl ((trans)-2-(2-bromothiazol-5-yl)cyclopropyl) (4-((tert-butoxycarbonyl) amino)cyclohexyl) carbamate)

These intermediates were synthesized by following the same method described to obtain Intermediate AT from Intermediate AS (Boc-protection) by using the respective starting intermediate.

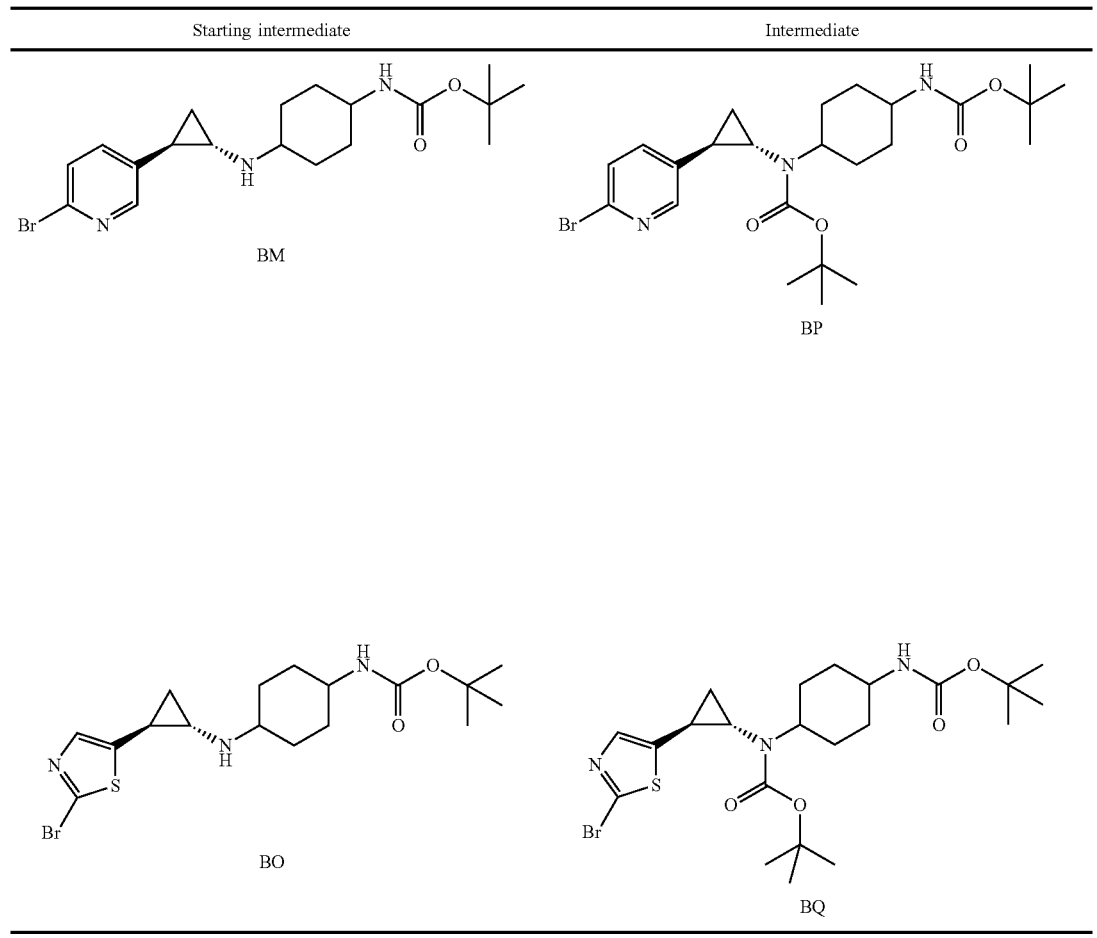

Intermediate BR: tert-butyl ((trans)-2-(3'-amino-[1,1'-biphenyl]-4-yl)cyclopropyl)(4-((tert-butoxycarbonyl)amino)cyclohexyl)carbamate

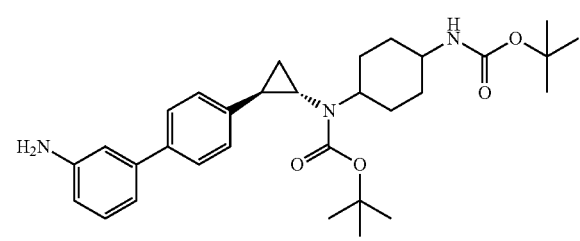 [SMILES: CC(C)(C)OC(=O)NC1CCC(N(C(=O)OC(C)(C)C)[C@H]2C[C@@H]2c2ccc(-c3cccc(N)c3)cc2)CC1]

A solution of ((trans)-2-(4-bromophenyl)cyclopropyl)(4-((tert-butoxycarbonyl)amino) cyclohexyl)carbamate (Intermediate AT, 1.5 g, 3.32 mmol), (3-aminophenyl)boronic acid (484 mg, 2.35 mmol) and $K_2CO_3$ (805 mg, 5.88 mmol) in ACN—$H_2O$ 8:2 (20 vol) was degassed for 15 min, before $Pd(PPh_3)_4$ (68 mg, 0.06 mmol) was added. The reaction mixture was stirred at 90° C. for 16 h and, after completion, poured into ice water and extracted with EtOAc (2×50 mL). The combined extracts were washed with water (50 mL), brine (50 mL), dried over anhydrous $Na_2SO_4$, filtered and concentrated. The crude residue was purified by column chromatography ($SiO_2$, EtOAc:petroleum ether 3:7) affording tert-butyl ((trans)-2-(3'-amino-[1,1'-biphenyl]-4-yl)cyclopropyl)(4-((tert-butoxycarbonyl)amino) cyclohexyl) carbamate (1.23 g, 71%) as a gummy solid.

Intermediates BS (N-(4'-((trans)-2-aminocyclopropyl)-6-methoxy-[1,1'-biphenyl]-3-yl)methanesulfonamide), BT (3-(5-((trans)-2-aminocyclopropyl) pyridin-2-yl)-5-methoxybenzonitrile) and BU (5-(5-((trans)-2-aminocyclopropyl)pyridin-2-yl)-2-methylphenol)

These intermediates were synthesized by following the same method described to obtain Intermediate R from intermediate AH (Suzuki coupling of Intermediate R with 3-(trifluoromethyl)phenylboronic acid to get Intermediate AG and later Boc-deprotection leads to Intermediate R) by using the respective starting intermediate and commercially available or boronic acid or ester derivatives listed below.

These intermediates were obtained as hydrochloride salt.

| Starting intermediate | Intermediate | ¹H-NMR and MS data |
|---|---|---|
| R (4-Br-phenyl cyclopropyl NHBoc) | BS (MsHN-phenyl-OMe-biaryl cyclopropyl NH₂) | 1HNMR (400 MHz, DMSO-d6) δ (ppm): 9.47 (s, 1H), 8.40-8.32 (brs, 3H), 7.38 (d, J = 8.4 Hz, 2H), 7.22-7.16 (m, 3H), 7.15-7.05 (m, 2H), 3.73 (s, 3H), 2.92 (s, 3H), 2.88-2.82 (brs, 1H), 2.38-2.30 (m, 1H), 1.44-1.36 (m, 1H), 1.30-1.22 (m, 1H); Mass (M + H): 331.3 |
| M (6-Br-pyridyl cyclopropyl NHBoc) | BT (NC-OMe-phenyl-pyridyl cyclopropyl NH₂) | 1HNMR (400 MHz, D2O) δ (ppm): 9.65 (s, 1H), 8.26 (brs, 1H), 8.13-8.08 (m, 1H), 7.78-7.70 (m, 1H), 7.65-7.59 (m, 1H), 7.57-7.50 (m, 1H), 3.89 (s, 3H), 3.20-3.10 (m, 1H), 2.75-2.65 (m, 1H), 1.74-1.65 (m, 1H), 1.64-1.55 (m, 1H); Mass (M + H): 266.2 |
|  | BU (methyl-OH-phenyl-pyridyl cyclopropyl NH₂) | 1HNMR (400 MHz, D2O) δ (ppm): 8.54 (s, 1H), 8.26 (d, J = 8.4 Hz, 1H), 8.10 (d, J = 8.4 Hz, 1H), 7.37 (d, J = 7.6 Hz, 1H), 7.28-7.20 (m, 1H), 3.12-3.08 (m, 1H), 2.68-2.62 (m, 1H), 2.24 (s, 3H), 1.70-1.60 (m, 1H), 1.59-1.48 (m, 1H); Mass (M + H): 241.0 |

Example 1: N1-((trans)-2-phenylcyclopropyl)cyclohexane-1,4-diamine dihydrochloride

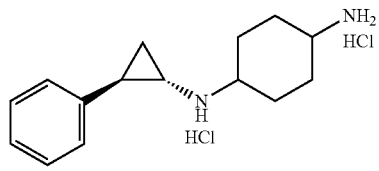 [SMILES: NC1CCC(N[C@H]2C[C@@H]2c2ccccc2)CC1 ; Cl ; Cl]

Step 1:

Acetic acid (586 mg, 9.77 mmol) was added to a solution of trans-2-phenylcyclopropanamine (1.3 g, 9.77 mmol) and tert-butyl 4-oxocyclohexylcarbamate (2.08 g, 9.77 mmol) in DCE (26 mL) and stirred for 5 mins. Sodium triacetoxy borohydride (3.72 g, 17.5 mmol) was then added at 0° C. and stirred at RT for 5 h. After completion, the reaction mixture was diluted with DCM (50 mL), water (50 mL), brine (50 mL) dried over anhydrous $Na_2SO_4$, filtered and evaporated. The crude residue was purified by column chromatography using $SiO_2$ by eluting EtOAc:Petroleum ether (1:9) to afford tert-butyl 4-(trans-2-phenylcyclopropylamino) cyclohexyl carbamate (2.5 g, 77.6%) as a pale yellow liquid.

Step 2:

HCl in 1, 4 dioxane (10 mL) was added to a solution of tert-butyl 4-(trans-2-phenylcyclopropylamino) cyclohexyl carbamate (2.45 g, 7.57 mmol) in dioxane (25 mL) at 15° C. and stirred at RT for 16 h. After completion, the solvent was evaporated and the residue was triturated with $Et_2O$ and dried to afford N1-((trans)-2-phenylcyclopropyl)cyclohexane-1,4-diamine dihydrochloride (1.5 g, 67.5%) as off white solid.

¹HNMR (400 MHz, DMSO-d6) δ (ppm): 9.66-9.56 (brd, 2H), 8.15-8.11 (d, 3H), 7.32-7.16 (m, 5H), 3.33 (brs, 1H), 3.24-3.16 (m, 1H), 2.99 (brs, 1H), 2.91 (brs, 1H), 2.55 (brs, 1H), 2.17 (brs, 1H), 2.0 (m, 1H), 1.96-1.75 (m, 4H), 1.63-1.43 (m, 2H), 1.4-1.3 (m, 1H), 1.29-1.26 (m, 1H); Mass (M+H): 231.34

N1-((trans)-2-phenylcyclopropyl)cyclohexane-1,4-diamine obtained above is a mixture of 4 isomers, which correspond to the combination of the two different (trans) conformations regarding the cyclopropyl ring (which are (1R,2S) and (1S,2R), respectively) with the CIS and TRANS conformations regarding the cyclohexane ring. The synthesis of each of these single isomers was performed as follows:

Example 2: (cis)-N1-((1S,2R)-2-phenylcyclopropyl) cyclohexane-1,4-diamine hydrochloride Step 1:

To a solution of trans-2-phenylcyclopropanamine (1.1 g, 8.2 mmol) in EtOH (6 mL) at 0° C., added D(−)Tartaric acid (1.24 g, 8.2 mmol), at 0° C. and stirred at RT for 1 h. After completion, solid was filtered and dried to afford trans-2-phenylcyclopropanamine as tartrate salt (2.15 g, 91.8%). The salt was taken in isopropanol (IPA):water (3:1) (20 mL) and stirred at 70° C. for 2 h. The clear solution was allowed to cool to RT. The solid separated was collected by filtration, taken in water (50 mL), basified with NaOH solution and extracted with EtOAc (2×50 mL). The combined extracts were washed with water (50 mL), brine (50 mL), dried over anhydrous $Na_2SO_4$, filtered and evaporated to afford (1S,2R)-2-phenylcyclopropanamine (510 mg, 46.3%).

Step 2:

To a solution of (1S,2R)-2-phenylcyclopropanamine (450 mg, 3.38 mmol), tert-butyl 4-oxocyclohexylcarbamate (792 mg, 3.72 mmol) and acetic acid (202 mg, 3.38 mmol) in DCE (10 mL) at 0° C. added sodium triacetoxy borohydride (1.29 g, 6.09 mmol) and stirred at RT for 3 h. After completion, solvent was evaporated, crude residue was taken in water (25 mL) basified with NaHCO$_3$, and extracted with EtOAc (2×25 mL). The combined extracts were washed with water (25 mL), brine (25 mL), dried over anhydrous Na$_2$SO$_4$, filtered and evaporated. The crude was purified by column chromatography using SiO$_2$ by eluting EtOAc:pet ether (3:7) to afford tert-butyl ((trans)-4-(((1S, 2R)-2-phenylcyclopropyl)amino)cyclohexyl)carbamate (210 mg, 18.8%) and tert-butyl ((cis)-4-(((1S,2R)-2-phenylcyclopropyl)amino)cyclohexyl)carbamate (280 mg, 25.1%).

Step 3:

To a solution of tert-butyl ((cis)-4-(((1S,2R)-2-phenylcyclopropyl)amino)cyclohexyl)carbamate (190 mg, 0.57 mmol) in 1, 4 dioxane (2 mL) at 10° C. added HCl in 1, 4 dioxane (2 mL) dropwise and stirred at RT for 16 h. After completion solvent was evaporated, the solid was stirred with Et$_2$O, filtered and dried to afford (cis)-N1-((1S,2R)-2-phenylcyclopropyl) cyclohexane-1, 4-diamine hydrochloride (110 mg, 71.89%) as off white solid.

$^1$HNMR (400 MHz, DMSO-d6) δ: 9.5 (brs, 2H), 8.12 (brs, 3H), 7.17-7.32 (m, 5H), 3.24 (brs, 2H), 2.98 (brs, 1H), 2.57 (brs, 1H), 1.98-1.74 (m, 8H), 1.61 (brs, 1H), 1.28 (m, 1H); Mass (M+H): 231.27; $[\alpha]_D^{28}$: +57.50 (C=0.54% in DMSO).

Example 3: (trans)-N1-((1S,2R)-2-phenylcyclopropyl)cyclohexane-1,4-diamine hydrochloride This compound was synthesized following the same procedure described in example 2 but performing the Boc-deprotection reaction to tert-butyl ((trans)-4-(((1S,2R)-2-phenylcyclopropyl)amino)cyclohexyl)carbamate as intermediate in Step 3, affording 120 mg (yield=59.4%) as off-white solid.

$^1$H-NMR (400 MHz, DMSO-d6) δ (ppm): 9.52 (brs, 2H), 8.03 (brs, 3H), 7.33-7.16 (m, 5H), 3.17 (brs, 1H), 2.9 (brm, 2H), 2.16 (brs, 2H), 2.03 (brd, 2H), 1.54-1.25 (m, 6H); Mass (M+H): 231.28; $[\alpha]^{28.1}_D$: +67.04° (C=0.53% in DMSO).

Example 4: (cis)-N1-((1R,2S)-2-phenylcyclopropyl)cyclohexane-1,4-diamine hydrochloride Step 1:

To a solution of trans-2-phenylcyclopropanamine (crude recovered from the mother liquors of the reaction described as Step 1 in Example 2) (0.8 g, 6.01 mmol) in EtOH (5.4 mL) at 0° C., added L (+) tartaric acid (0.90 g, 6.01 mmol), at 0° C. and stirred at RT for 1 h. After completion, solid was filtered and dried to afford trans-2-phenylcyclopropanamine as tartrate salt (1.5 g, 88.2%). Salt was taken in IPA:water (3:1) (15 mL) and stirred at 70° C. for 2 h. The clear solution was allowed to cool to RT. The solid separated was collected by filtration, taken in water (50 mL), basified with NaOH solution, and extracted with EtOAc (2×50 mL). The combined extracts were washed with water (50 mL), brine (50 mL), dried over anhydrous Na$_2$SO$_4$, filtered and evaporated to afford (1R,2S)-2-phenylcyclopropanamine (320 mg).

Step 2:

To a solution of (1R,2S)-2-phenylcyclopropanamine (280 mg, 1.21 mmol), tert-butyl 4-oxocyclohexylcarbamate (309 mg, 1.45 mmol) and acetic acid (72 mg, 1.21 mmol) in DCE (8 mL) at 0° C., added sodium triacetoxy borohydride (461 mg, 2.17 mmol) and stirred at RT for 3 h. After completion, solvent was evaporated, crude residue was taken in water (25 mL), treated with NaHCO$_3$, and extracted with EtOAc (2×25 mL). The combined extracts were washed with water (25 mL), brine (25 mL), dried over anhydrous Na$_2$SO$_4$, filtered and evaporated. The crude was purified by column chromatography using SiO$_2$ by eluting EtOAc:pet ether (3:7) to afford tert-butyl ((cis)-4-(((1R,2S)-2-phenylcyclopropyl)amino)cyclohexyl)carbamate (180 mg, 25.35%) and tert-butyl ((trans)-4-(((1R,2S)-2-phenylcyclopropyl)amino)cyclohexyl)carbamate (210 mg, 29.5%).

Step 3:

To a solution of tert-butyl ((cis)-4-(((1R,2S)-2-phenylcyclopropyl)amino)cyclohexyl)carbamate (160 mg, 0.48 mmol) in 1, 4 dioxane (2 mL) at 10° C. added HCl in 1, 4 dioxane (2 mL) dropwise and stirred at RT for 16 h. After completion solvent was evaporated, the solid was stirred with Et$_2$O, filtered and dried to afford (cis)-N1-((1R,2S)-2-phenylcyclopropyl)cyclohexane-1,4-diamine hydrochloride (80 mg, 58.3%) as off white solid.

$^1$HNMR (400 MHz, DMSO-d6) δ: 9.54 (brs, 2H), 8.14 (brs, 3H), 7.35-7.15 (m, 5H), 3.33 (brs, 1H), 3.25 (brs, 2H), 2.62-2.55 (m, 1H), 2.03-1.67 (m, 8H), 1.63-1.57 (m, 1H), 1.28 (q, 1H); Mass (M+H): 231.27; $[\alpha]_D^{28.5}$: −65.70° (C=0.5% in DMSO).

Example 5: (trans)-N1-((1R,2S)-2-phenylcyclopropyl)cyclohexane-1,4-diamine hydrochloride This compound was synthesized following the same procedure described in example 4 but performing the Boc-deprotection reaction to tert-butyl ((trans)-4-(((1R,2S)-2-phenylcyclopropyl)amino)cyclohexyl)carbamate in Step 3, affording 95 mg (yield=50.8%) as off-white solid.

$^1$HNMR (400 MHz, DMSO-d6, D2O Exchange) δ (ppm): 7.32 (t, J=7.2 Hz, 2H), 7.24 (t, J=7.2 Hz, 1H), 7.17 (d, J=8 Hz, 2H), 3.26-3.18 (m, 1H), 3.05-2.89 (m, 2H), 2.51-2.42 (m, 1H), 2.22-2.10 (m, 2H), 2.08-1.98 (m, 2H), 1.57-1.28 (m, 6H); Mass (M+H): 231.25; $[\alpha]_D^{28.5}$: −60.19° (C=0.54% in DMSO).

Using an alternative procedure, (trans)-N1-((1R,2S)-2-phenylcyclopropyl)cyclohexane-1,4-diamine was obtained as follows:

To a well stirred solution of (1R,2S)-2-phenylcyclopropanamine (0.752 g 5.64 mmol) in methanol (10 ml) at room temperature (22-25° C.), molecular sieves (1.0 g) was added followed by t-butyl-4-oxocyclohexylcarbamate (1.07 g, 5.0 mmol) at 100° C. and stirred for 5 min. Acetic acid (0.028 ml, 0.5 mmol) was added at 0-5° C. to the reaction mixture and stirred for 3 h at room temperature. The reaction mixture was cooled to −25 to −30° C., and sodium borohydride (0.229 g, 6.02 mmol) was added portionwise at the same temperature. The reaction mixture was stirred for 3 h allowing the reaction temperature to rise to room temperature.

The progress of the reaction was monitored by TLC (EtOAc/Hexane 8:2). After completion of reaction, the inorganics were filtered off over celite. The filtrate was evaporated, and the crude residue was taken up in water (20 ml) and DCM (20 ml) mixture and basified with 5% aq. NaOH solution (until pH 10). The DCM layer was separated and the aq. layer re-extracted with DCM (20 ml). The combined organic extracts were washed with water (20 ml) and 10% brine solution (20 ml), dried over anhydrous sodium sulfate, filtered and evaporated completely. The crude product was purified by stirring in 2% EtOAc in hexane for 2 h at room temperature to afford t-butyl-4-((1R,2S)-2-phenylcyclopropylamino)cyclohexylcarbamate as off-white solid (0.90 g, 54%).

To a well stirred solution of t-butyl-4-((1R,2S)-2-phenylcyclopropylamino) cyclohexylcarbamate (0.8 g, 2.42 mmol)

in 1, 4-dioxane (10 ml) at 10-15° C. was slowly added 15% HCl in dioxane (8 ml) and stirred at room temperature for 20 h. The progress of the reaction was monitored by HPLC. After completion of the reaction, the solvent was removed at reduced pressure. The residue was suspended in di-isopropyl ether (15 ml) and stirred for 1 h at room temperature, filtered and dried in vacuo. The crude product was further purified by stirring in di-isopropyl ether (15 ml) for 2 h at room temperature. The solid was filtered off affording (trans)-N1-((1R,2S)-2-phenylcyclopropyl)cyclohexane-1,4-diamine dihydrochloride (0.57 g, 77%) (the presence of the dihydrochloride salt form was determined by argentometric titration), as an off white solid.

$^1$HNMR (400 MHz, DMSO-d6) δ (ppm): 9.74 (bs, 2H), 8.18 (bs, 3H), 7.30 (m, 2H), 7.24 (m, 1H), 7.18 (m, 2H), 3.15 (bs, 1H), 2.94 (m, 2H), 2.56 (m, 1H), 2.18 (m, 2H), 2.04 (m, 2H), 1.58 (m, 3H), 1.44 (m, 2H), 1.26 (m, 1H); Mass (M+H): 231.5

The following compounds can be synthesized following the methodology described for example 1 by using the corresponding intermediates. The Step 2 was only performed in case the intermediate used in the reductive alkylation (Step 1) contained a Boc (tert-butyloxycarbonyl) protecting group.

Example 6: N1-((trans)-2-(thiazol-5-yl)cyclopropyl)cyclohexane-1,4-diamine hydrochloride

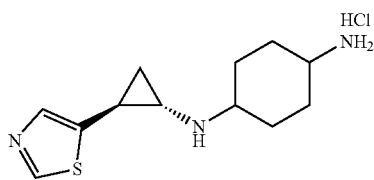 [SMILES: Cl ; NC1CCC(N[C@H]2C[C@@H]2c2cncs2)CC1]

$^1$HNMR (400 MHz, DMSO-d6-D$_2$O Exchange) δ (ppm): 8.95 (s, 1H), 7.75 (s, 1H), 3.3-3.18 (m, 1H), 3.1-2.9 (m, 2H), 2.85-2.72 (m, 1H), 2.25-1.98 (brm, 3H), 1.7-1.35 (brm, 5H); Mass (M+H): 238.19

Example 7: N1-((trans)-2-(pyridin-3-yl)cyclopropyl)cyclohexane-1,4-diamine hydrochloride

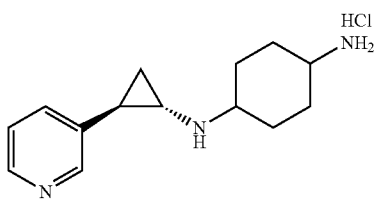 [SMILES: Cl ; NC1CCC(N[C@H]2C[C@@H]2c2cccnc2)CC1]

$^1$HNMR (400 MHz, D$_2$O) δ (ppm): 8.64 (2H, d), 8.32 (1H, d), 7.98 (1H, t), 3.37 (2H, m), 3.22 (2H, m), 2.77-2.72 (1H, m), 2.25-2.12 (3H, m), 1.92-1.46 (7H, m), Mass (M+H): 232.34

Example 8: N1-((trans)-2-(6-(3-(trifluoromethyl)phenyl)pyridin-3-yl)cyclopropyl)cyclohexane-1,4-diamine hydrochloride

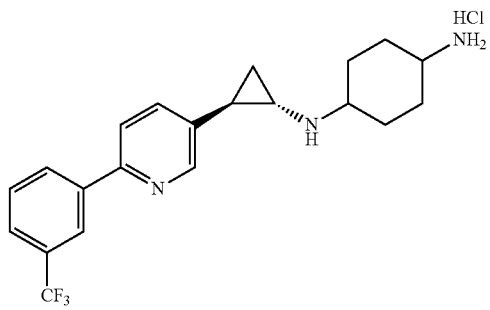 [SMILES: Cl ; NC1CCC(N[C@H]2C[C@@H]2c2ccc(-c3cccc(C(F)(F)F)c3)nc2)CC1]

$^1$HNMR (400 MHz, D$_2$O) δ (ppm): 8.60 (s, 1H), 8.20-8.00 (m, 3H), 7.90 (d, J=12 Hz, 1H), 7.76-7.72 (t, J=8 Hz, 1H), 7.60-7.40 (br, 1H), 3.60-3.40 (m, 2H), 3.20 (m, 1H), 2.70 (m, 1H), 2.30 (m, 1H), 2.20-2.00 (m, 2H), 1.97-1.67 (m, 5H), 1.65 (m, 1H), 1.60-1.40 (m, 1H); Mass (M+H): 376.3

Example 9: N1-((trans)-2 (3' (trifluoromethyl)-[1,1'-biphenyl]-4-yl)cyclopropyl)cyclohexane-1,4-diamine hydrochloride

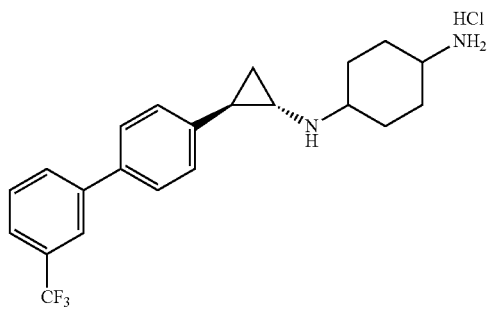 [SMILES: Cl ; NC1CCC(N[C@H]2C[C@@H]2c2ccc(-c3cccc(C(F)(F)F)c3)cc2)CC1]

$^1$HNMR (400 MHz, DMSO d6) δ: 9.65-9.48 (brd, 2H), 8.1 (s, 3H), 7.95 (m, 2H), 7.7 (m, 4H), 7.3 (d, 2H), 3.2 (brd, 1H), 2.9 (brd, 2H), 2.52 (m, 1H), 2.2 (brd, 2H), 2.05 (brd, 2H), 1.86-1.76 (m, 2H), 1.6-1.25 (m, 5H); Mass (M+H): 375.29

Example 10: N1-((trans)-2-(4-(benzyloxy)phenyl)cyclopropyl)cyclohexane-1,4-diamine hydrochloride

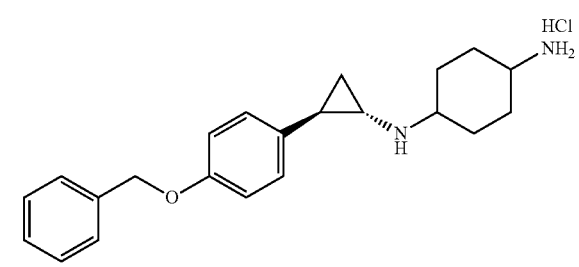 [SMILES: Cl ; NC1CCC(N[C@H]2C[C@@H]2c2ccc(OCc3ccccc3)cc2)CC1]

¹HNMR (400 MHz, DMSO d6) δ: 9.64-9.45 (brd, 2H), 8.2-8.05 (brd, 3H), 7.48-7.3 (m, 5H), 7.15 (d, 2H), 6.95 (d, 2H), 5.08 (s, 2H), 3.2-3.15 (brs, 1H), 2.9 (brs, 1H), 2.82 (brs, 1H), 2.45 (brs, 1H), 2.18 (brd, 2H), 2.05 (brd, 2H), 1.9 (brs, 1H), 1.58-1.27 (m, 4H), 1.22 (m, 1H); Mass (M+H): 337.31

Example 11: 4-(((trans)-2-(6-(3-(trifluoromethyl)phenyl)pyridin-3-yl)cyclopropyl)amino)cyclohexanol

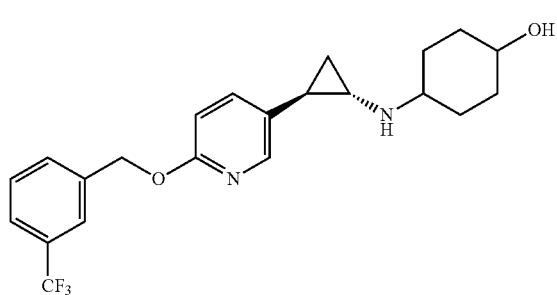 [SMILES: OC1CCC(N[C@H]2C[C@@H]2c2ccc(OCc3cccc(C(F)(F)F)c3)nc2)CC1]

¹HNMR (400 MHz, D₂O) δ (ppm): 8.76 (s, 1H), 8.37 (brs, 1H), 8.32-8.26 (m, 2H), 8.16 (m, 1H), 8.06 (m, 1H), 7.91 (t, J=8 Hz, 1H), 4.11 (brs, 1H), 3.84-3.65 (m, 1H), 3.60-3.40 (m, 1H), 3.33 (brs, 1H), 2.87 (brs, 1H), 2.28-2.03 (m, 3H), 1.90-1.70 (m, 4H), 1.68-1.57 (m, 1H), 1.55-1.40 (m, 1H); Mass (M+H): 377.2

Example 12: 4-(((trans)-2-(6-(3-(trifluoromethyl)phenyl)pyridin-3-yl)cyclopropyl)amino)cyclohexanecarboxamide hydrochloride

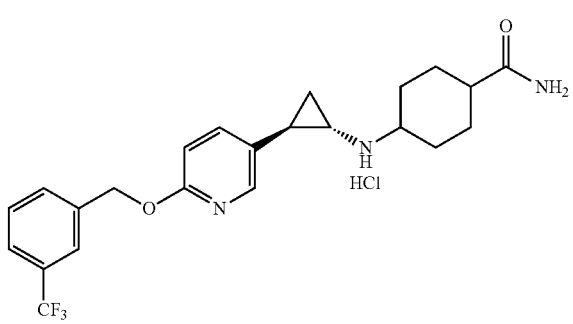 [SMILES: NC(=O)C1CCC(N[C@H]2C[C@@H]2c2ccc(OCc3cccc(C(F)(F)F)c3)nc2)CC1 ; Cl]

¹HNMR (400 MHz, D₂O) δ (ppm): 8.80 (brs, 1H), 8.50-8.40 (brs, 1H), 8.38-8.26 (m, 2H), 8.20-8.00 (m, 2H), 7.95-7.83 (m, 1H), 3.65-3.25 (m, 3H), 2.96-2.82 (m, 1H), 2.75-2.54 (m, 1H), 2.47-2.30 (m, 1H), 2.20-1.80 (m, 7H), 1.70-1.50 (m, 1H); Mass (M+H): 404.3

Example 13: N-(4-(((trans)-2-(6-(3-(trifluoromethyl)phenyl)pyridin-3-yl)cyclopropyl)amino)cyclohexyl)acetamide hydrochloride

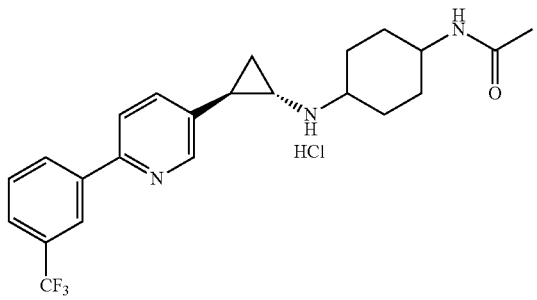 [SMILES: CC(=O)NC1CCC(N[C@H]2C[C@@H]2c2ccc(-c3cccc(C(F)(F)F)c3)nc2)CC1 ; Cl]

¹HNMR (400 MHz, D₂O) δ (ppm): 8.79 (s, 1H), 8.39 (m, 1H), 8.30 (m, 1H), 8.24 (s, 1H), 8.13 (m, 1H), 8.11 (m, 1H), 7.88 (t, J=8 Hz, 1H), 3.70-3.62 (m, 1H), 3.50-3.40 (m, 1H), 3.38-3.24 (m, 1H), 2.92-2.80 (m, 1H), 2.34-2.24 (m, 2H), 2.17-2.03 (m, 3H), 1.98 (s, 1H), 1.94-1.72 (m, 4H), 1.70-1.57 (m, 1H), 1.50-1.35 (m, 2H). Mass (M+H): 418.2

Example 14: N-(4-(((trans)-2-(6-(3-(trifluoromethyl)phenyl)pyridin-3-yl)cyclopropyl)amino)cyclohexyl)methanesulfonamide hydrochloride

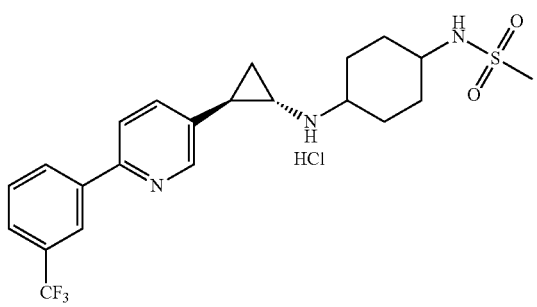 [SMILES: CS(=O)(=O)NC1CCC(N[C@H]2C[C@@H]2c2ccc(-c3cccc(C(F)(F)F)c3)nc2)CC1 ; Cl]

¹HNMR (400 MHz, D₂O) δ (ppm): 8.73 (s, 1H), 8.41-8.32 (m, 1H), 8.28-8.22 (m, 2H), 8.12 (d, J=8 Hz, 1H), 8.03 (d, J=8 Hz, 1H), 7.88 (t, J=8 Hz, 1H), 3.3.52-3.26 (m, 3H), 3.14 (s, 3H), 2.91-2.80 (m, 1H), 2.36-1.96 (m, 4H), 1.88-1.58 (m, 4H), 1.56-1.42 (m, 2H). Mass (M+H): 454.1

Example 15: (R)-1-(4-(((trans)-2-phenylcyclopropyl)amino)cyclohexyl)pyrrolidin-3-amine trihydrochloride

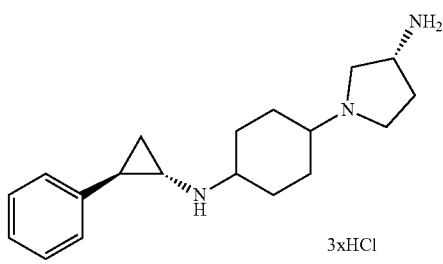 [SMILES: N[C@@H]1CCN(C2CCC(N[C@H]3C[C@@H]3c3ccccc3)CC2)C1]

$^1$HNMR (400 MHz, DMSO-d6) δ (ppm): 10.71-10.45 (m, 1H), 9.61-9.50 (brs, 1H), 9.49-9.34 (brs, 1H), 8.09 (t, J=6 Hz, 3H), 7.98 (quin, 2H), 4.85-4.20 (m, 7H), 4.08-3.92 (m, 1H), 3.82-3.65 (m, 1H), 3.47-3.38 (m, 1H), 3.10-2.32 (m, 11H), 2.07 (q, 1H). Mass (M+H): 300.1

The following compounds were synthesized following the methodology described for example 1 by using the corresponding intermediates and commercially available reagents. Step 2 was only applied to those intermediates used in the reductive alkylation (Step 1) that contained a Boc (tert-butyloxycarbonyl) protecting group.

Example 16: 1-methyl-N4-((trans)-2-phenylcyclopropyl)cyclohexane-1,4-diamine

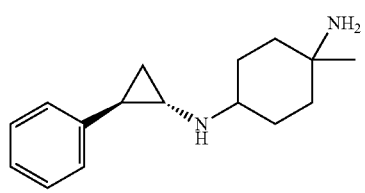 [SMILES: CC1(N)CCC(N[C@H]2C[C@@H]2c2ccccc2)CC1]

$^1$HNMR (400 MHz, D$_2$O) δ: 7.45-7.30 (m, 3H), 7.24 (d, J=8 Hz, 2H), 3.55-3.42 (m, 1H), 3.05-2.98 (m, 1H), 2.62-2.52 (m, 1H), 2.28-2.20 (m, 2H), 2.18-1.98 (m, 2H), 1.87-1.64 (m, 4H), 1.62-1.44 (m, 2H), 1.41 (s, 3H); Mass (M+H): 245.33. This compound was obtained as hydrochloride salt.

Example 17: 4-(aminomethyl)-N-trans)-2-phenylcyclopropyl)cyclohexanamine

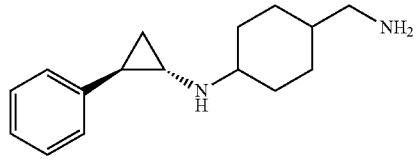 [SMILES: NCC1CCC(N[C@H]2C[C@@H]2c2ccccc2)CC1]

$^1$HNMR (400 MHz, CD$_3$OD) δ: 7.33-7.25 (m, 2H), 7.21-7.17 (m, 3H), 3.45 (brs, 1H), 2.98 (d, J=8 Hz, 1H), 2.95-2.92 (m, 1H), 2.82 (d, J=7 Hz, 1H), 2.57-2.55 (m, 1H), 2.28-2.26 (m, 1H), 1.95-1.90 (m, 4H), 1.73-1.70 (m, 3H), 1.62-1.58 (m, 2H), 1.45-1.39 (m, 1H); Mass (M+H): 245.29. This compound was obtained as hydrochloride salt.

Example 18: N-((trans)-2-phenylcyclopropyl)cyclohexane-1,3-diamine

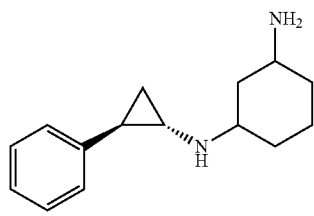 [SMILES: NC1CCCC(N[C@H]2C[C@@H]2c2ccccc2)C1]

$^1$HNMR (400 MHz, DMSO-d6-D$_2$O Exchange) δ (ppm): 7.33 (t, J=7.4 Hz, 2H), 7.26 (d, J=7.2 Hz, 1H), 7.23 (t, J=8 Hz, 2H), 4.1-4.0 (m, 1H), 4.0-3.9 (m, 1H), 2.96-2.86 (m, 1H), 2.5-2.43 (m, 1H), 2.10-1.90 (m, 2H), 1.88-1.76 (m, 2H), 1.75-1.63 (m, 3H), 1.62-1.48 (m, 2H), 1.40-1.30 (m, 1H); Mass (M+H): 231.29. This compound was obtained as hydrochloride salt.

Example 19: N1-((trans)-2-phenylcyclopropyl)cyclobutane-1,3-diamine

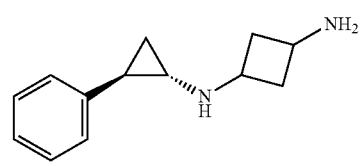 [SMILES: NC1CC(N[C@H]2C[C@@H]2c2ccccc2)C1]

$^1$HNMR (400 MHz, DMSO-d6-D$_2$O Exchange) δ (ppm): 7.33 (t, J=8 Hz, 2H), 7.25 (t, J=8 Hz, 1H), 7.17 (d, J=8 Hz, 2H), 4.1-4.0 (m, 1H), 2.95-2.85 (m, 1H), 2.74-2.60 (m, 2H), 2.5-2.42 (m, 3H), 1.48 (quin, 1H), 1.33 (q, 1H); Mass (M+H): 203.0. This compound was obtained as hydrochloride salt.

Example 20: N1-((trans)-2-phenylcyclopropyl)-2,3-dihydro-H-indene-1,3-diamine

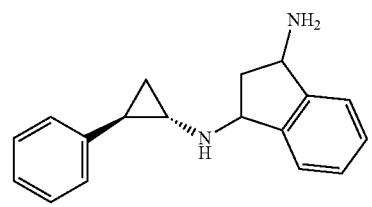 [SMILES: NC1CC(N[C@H]2C[C@@H]2c2ccccc2)c2ccccc21]

$^1$HNMR (400 MHz, D$_2$O) δ: 7.70-7.53 (m, 4H), 7.46-7.30 (m, 3H), 7.17 (d, J=8 Hz, 1H), 7.03 (d, J=8 Hz, 1H), 5.40-5.30 (m, 1H), 5.14-5.04 (m, 1H), 3.05-2.93 (m, 2H), 2.78-2.64 (m, 1H), 2.54-2.32 (m, 1H), 1.62-1.42 (m, 2H); Mass (M+H): 265.3. This compound was obtained as hydrochloride salt.

Example 21: N1-((cis)-2-phenylcyclopropyl)cyclohexane-1,4-diamine

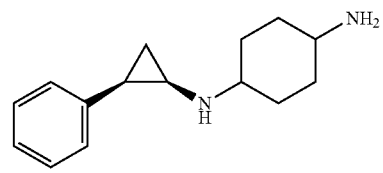 [SMILES: NC1CCC(N[C@@H]2C[C@@H]2c2ccccc2)CC1]

$^1$HNMR (400 MHz, DMSO-d6-D$_2$O Exchange) δ: 7.46-7.30 (m, 5H), 3.03-2.88 (m, 2H), 2.52-2.45 (m, 1H), 2.27-2.20 (m, 1H), 2.08-1.94 (m, 2H), 1.94-1.58 (m, 3H), 1.54-1.20 (m, 5H); Mass (M+H): 231.18. This compound was obtained as hydrochloride salt.

Example 22: N1-methyl-N4-((trans)-2-phenylcyclopropyl)cyclohexane-1,4-diamine

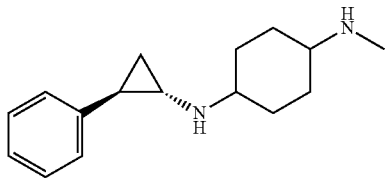 [SMILES: CNC1CCC(N[C@H]2C[C@@H]2c2ccccc2)CC1]

¹HNMR (400 MHz, D₂O) δ: 7.61-7.34 (m, 3H), 7.30-7.20 (m, 2H), 3.70-3.58 (brs, 1H), 3.53-3.33 (m, 1H), 3.22-2.95 (m, 1H), 2.82-2.70 (m, 3H), 2.63-2.47 (brs, 1H), 2.42-2.22 (m, 2H), 2.18-1.85 (m, 5H), 1.45-1.65 (m, 3H); Mass (M+H): 245.1. This compound was obtained as hydrochloride salt.

Example 23: Tert-butyl (4-(((trans)-2-phenylcyclopropyl)amino)cyclohexyl) carbamate

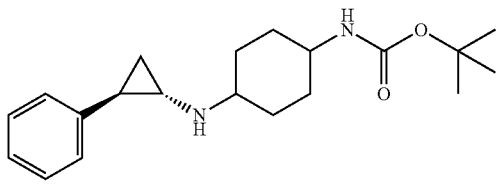 [SMILES: CC(C)(C)OC(=O)NC1CCC(N[C@H]2C[C@@H]2c2ccccc2)CC1]

¹HNMR (400 MHz, CDCl₃) δ (rotamers 1:1): 7.28-7.23 (m, 2H), 7.17-7.13 (m, 1H), 7.02 (d, J=8 Hz, 2H), 4.62 (brs, 0.5H), 4.35 (brs, 0.5H), 3.63 (brs, 0.5H), 3.39 (brs, 0.5H), 2.79 (brs, 0.5H), 2.69-2.57 (m, 0.5H), 2.38-2.22 (m, 1H), 1.98-1.94 (m, 3H), 1.87-1.82 (m, 1H), 1.75-1.60 (m, 2H), 1.43 (s, 9H), 1.33-1.00 (m, 5H); Mass (M+H): 331.27. This compound was obtained as the free amine.

Example 24: 1-ethyl-3-(4-(((trans)-2-phenylcyclopropyl)amino)cyclohexyl)urea

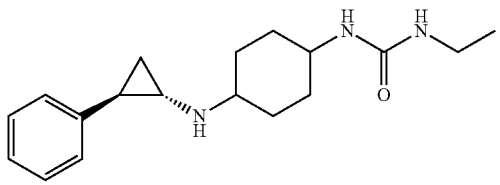 [SMILES: CCNC(=O)NC1CCC(N[C@H]2C[C@@H]2c2ccccc2)CC1]

¹HNMR (400 MHz, DMSO-d6-D₂O Exchange) δ: 7.33 (t, J=7.6 Hz, 2H), 7.24 (t, J=7.2 Hz, 1H), 7.18 (d, J=8 Hz, 2H), 3.36-3.14 (m, 1H), 3.04-2.92 (m, 3H), 2.50-2.40 (m, 2H), 2.12-2.04 (m, 1H), 1.93-1.81 (m, 2H), 1.75-1.61 (m, 2H), 1.60-1.40 (m, 3H), 1.39-1.30 (m, 1H), 1.20-1.13 (m, 1H), 1.03-0.94 (m, 3H); Mass (M+H): 302.26.

This compound was obtained as hydrochloride salt.

Example 25: 4-morpholino-N-((trans)-2-phenylcyclopropyl)cyclohexanamine

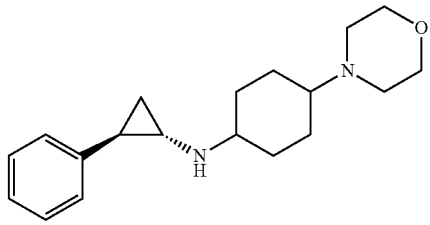 [SMILES: c1ccc([C@H]2C[C@@H]2NC2CCC(N3CCOCC3)CC2)cc1]

¹HNMR (400 MHz, CDCl₃) δ: 7.28-7.22 (m, 2H), 7.14 (t, J=8 Hz, 1H), 7.02 (d, J=8 Hz, 2H), 3.78-3.68 (m, 4H), 2.94-2.85 (m, 1H), 2.53 (brs, 4H), 2.30-2.23 (m, 1H), 2.22-2.16 (m, 1H), 1.92-1.84 (m, 1H), 1.70-1.62 (m, 2H), 1.61-1.47 (m, 5H), 1.10-1.02 (m, 1H), 1.01-0.96 (m, 1H); Mass (M+H): 301.2. This compound was obtained as the free amine.

Example 26: N1-((trans)-2-(4-bromophenyl)cyclopropyl)cyclohexane-1,4-diamine

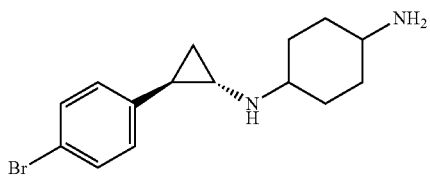 [SMILES: NC1CCC(N[C@H]2C[C@@H]2c2ccc(Br)cc2)CC1]

¹HNMR (400 MHz, D₂O) δ: 7.56 (d, J=8 Hz, 2H), 7.14 (d, J=8 Hz, 2H), 3.64-3.50 (m, 1H), 3.48-3.38 (m, 1H), 2.35-2.24 (m, 1H), 3.05-2.97 (m, 1H), 2.60-2.48 (m, 1H), 2.40-2.19 (m, 2H), 2.18-1.84 (m, 3H), 1.70-1.44 (m, 4H); Mass (M+H): 309.06. This compound was obtained as hydrochloride salt.

Example 27: N1-(2-(o-tolyl)cyclopropyl)cyclohexane-1,4-diamine

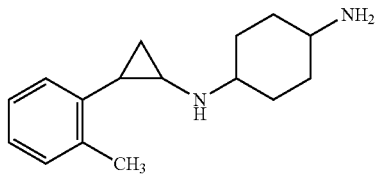 [SMILES: Cc1ccccc1C1CC1NC1CCC(N)CC1]

¹HNMR (400 MHz, CD₃OD) δ: 7.22-7.12 (m, 3H), 7.04-6.98 (m, 1H), 3.60-3.40 (m, 1H), 3.22-3.08 (m, 2H), 2.72-2.49 (m, 1H), 2.44 (s, 3H), 2.42-2.34 (m, 1H), 2.25-2.16 (m, 1H), 2.15-1.92 (m, 4H), 1.70-1.50 (m, 3H), 1.32-1.24 (m, 1H); Mass (M+H): 245.22. This compound was obtained as hydrochloride salt.

Example 28: N1-(2-(4-(trifluoromethyl)phenyl)cyclopropyl)cyclohexane-1,4-diamine

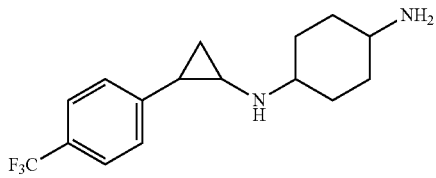 [SMILES: NC1CCC(NC2CC2c2ccc(C(F)(F)F)cc2)CC1]

¹HNMR (400 MHz, DMSO-d6-D₂O Exchange) δ: 7.73-7.63 (m, 2H), 7.50-7.36 (m, 2H), 3.26-3.10 (m, 1H), 3.07-2.92 (m, 1H), 2.48-2.41 (m, 1H), 2.20-2.09 (m, 2H), 2.08-1.98 (m, 1H), 1.90-1.67 (m, 5H), 1.60-1.32 (m, 4H); Mass (M+H): 299.24. This compound was obtained as hydrochloride salt.

Example 29: N1-(2-(4-methoxyphenyl)cyclopropyl)cyclohexane-1,4-diamine

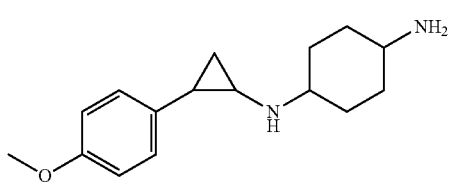 [SMILES: COc1ccc(C2CC2NC2CCC(N)CC2)cc1]

¹HNMR (400 MHz, CD₃OD) δ: 7.16-7.08 (m, 2H), 6.87 (d, J=8.8 Hz, 4H), 3.76 (s, 3H), 3.44-3.38 (m, 1H), 3.22-3.12 (m, 0.5H), 2.94-2.85 (m, 1H), 2.52-2.44 (m, 0.5H), 2.43-2.30 (m, 2H), 2.24-2.14 (m, 1H), 2.10-1.90 (m, 3H), 1.62-1.51 (m, 3H), 1.50-1.42 (m, 1H), 1.37 (q, 1H); Mass (M+H): 261.26. This compound was obtained as hydrochloride salt.

Example 30: 4-(2-((4-aminocyclohexyl)amino)cyclopropyl)phenol

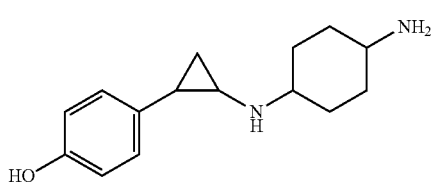 [SMILES: NC1CCC(NC2CC2c2ccc(O)cc2)CC1]

¹HNMR (400 MHz, DMSO-d6-D₂O Exchange) δ: 6.98 (d, J=8.4 Hz, 2H), 6.71 (d, J=8.4 Hz, 2H), 3.24-3.15 (m, 1H), 3.07-2.95 (m, 1H), 2.87-2.78 (m, 1H), 2.45-2.36 (m, 1H), 2.22-2.11 (m, 2H), 2.09-1.98 (m, 2H), 1.94-1.75 (m, 1H), 1.58-1.34 (m, 4H), 1.26-1.18 (m, 1H); Mass (M+H): 247.22. This compound was obtained as a hydrochloride salt.

Example 31: N1-(2-(2-fluorophenyl)cyclopropyl)cyclohexane-1,4-diamine

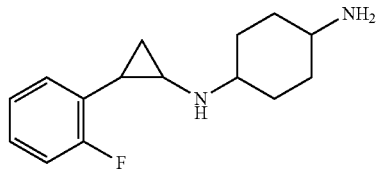 [SMILES: NC1CCC(NC2CC2c2ccccc2F)CC1]

¹HNMR (400 MHz, CD₃OD) δ: 7.33-7.31 (m, 1H), 7.29-7.26 (m, 3H), 3.52-3.30 (m, 2H), 3.17-3.06 (m, 2H), 2.73-2.61 (m, 1H), 2.36-2.33 (m, 1H), 2.17-2.20 (m, 1H), 2.05-1.95 (m, 4H), 1.58-1.45 (m, 4H); Mass (M+H): 249.23. This compound was obtained as a hydrochloride salt.

Example 32: N1-(2-(3,4-difluorophenyl)cyclopropyl)cyclohexane-1,4-diamine

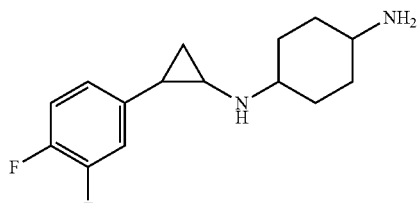

¹HNMR (400 MHz, CD₃OD) δ: 7.27-7.12 (m, 2H), 7.08-7.00 (m, 1H), 3.56-3.46 (m, 1H), 3.46-3.34 (m, 1H), 3.24-3.14 (m, 1H), 3.05-2.97 (m, 1H), 2.68-2.60 (m, 1H), 2.58-2.48 (m, 1H), 2.38-2.25 (m, 1H), 2.38-2.25 (m, 1H), 2.23-2.15 (m, 1H), 2.14-1.90 (m, 4H), 1.70-1.50 (m, 3H), 1.43 (q, 1H); Mass (M+H): 267.21. This compound was obtained as a hydrochloride salt.

Example 33: N1-(2-(naphthalen-2-yl)cyclopropyl)cyclohexane-1,4-diamine

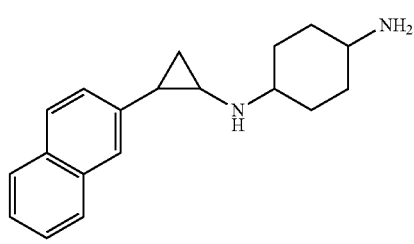 [SMILES: NC1CCC(NC2CC2c2ccc3ccccc3c2)CC1]

¹HNMR (400 MHz, DMSO-d6-D₂O Exchange) δ: 7.93-7.83 (m, 3H), 7.71 (s, 1H), 7.50 (quin, 2H), 7.34 (d, J=8.4 Hz, 2H), 3.28-3.19 (m, 1H), 3.10-2.97 (m, 1H), 2.68-2.60 (m, 1H), 2.24-2.15 (m, 2H), 2.08-1.98 (m, 2H), 1.62-1.35 (m, 6H); Mass (M+H): 281.14. This compound was obtained as a hydrochloride salt.

Example 34: N1-(2-methyl-2-phenylcyclopropyl)cyclohexane-1,4-diamine

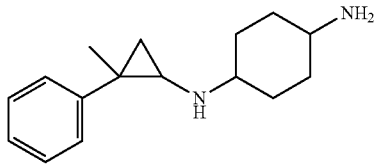 [SMILES: CC1(c2ccccc2)CC1NC1CCC(N)CC1]

¹HNMR (400 MHz, CD₃OD) δ: 7.40-7.30 (m, 4H), 7.27-7.21 (m, 1H), 3.58-3.46 (m, 1H), 2.95-2.85 (m, 1H), 2.54-2.28 (m, 1H), 2.25-2.18 (m, 1H), 2.16-1.92 (m, 5H), 1.67 (s, 3H), 1.62-1.52 (m, 2H), 1.35-1.25 (m, 1H); Mass (M+H): 245.22. This compound was obtained as a hydrochloride salt.

Example 35: (R)-1-(4-(((trans)-2-(3'-(trifluoromethyl)-[1,1'-biphenyl]-4-yl)cyclopropyl) amino)cyclohexyl)pyrrolidin-3-amine

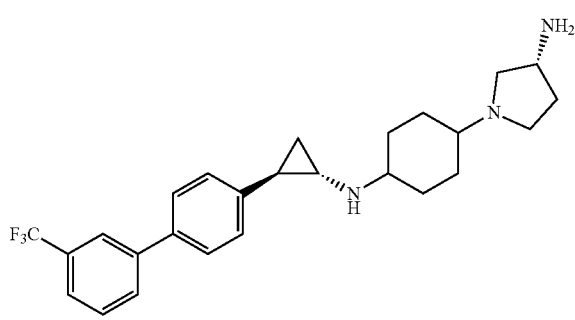 [SMILES: N[C@@H]1CCN(C2CCC(N[C@H]3C[C@@H]3c3ccc(-c4cccc(C(F)(F)F)c4)cc3)CC2)C1]

¹HNMR (400 MHz, D₂O) δ: 7.98 (s, 1H), 7.89 (d, J=8 Hz, 2H), 7.76-7.62 (m, 3H), 7.2 (d, J=8 Hz, 2H), 4.2 (brs, 2H), 4.06-3.96 (m, 2H), 3.72-3.62 (m, 2H), 3.10-3.01 (m, 1H), 2.70-2.56 (m, 2H), 2.34-2.20 (m, 2H), 2.18-2.02 (m, 3H), 2.00-1.86 (m, 2H), 1.65-1.55 (m, 2H); Mass (M+H): 444.3. This compound was obtained as hydrochloride salt.

Example 36: (Cis)-N1-((1S,2R)-2-(3'-(trifluoromethyl)-[1,1'-biphenyl]-4-yl)cyclopropyl)cyclohexane-1,4-diamine

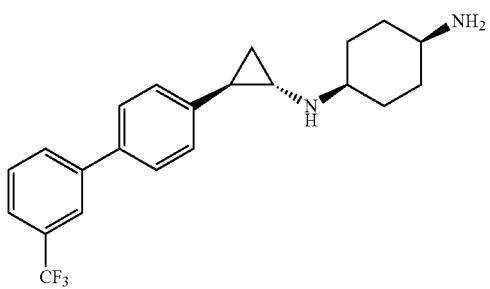 [SMILES: N[C@H]1CC[C@@H](N[C@H]2C[C@@H]2c2ccc(-c3cccc(C(F)(F)F)c3)cc2)CC1]

Step 1:
L (+) Mandelic acid (2.7 g, 18.05 mmol) was added to a solution of (trans)-2-(3'-(trifluoromethyl)-[1,1'-biphenyl]-4-yl)cyclopropanamine (free amine derived from Intermediate AH, 5 g, 18.05 mmol) in EtOH/H₂O 1:9 (25 vols) and refluxed for 2 h. After formation of a clear solution, the reaction mixture was allowed to cool to RT (16 h). The solid that had precipitated was filtered off, taken up in water (100 mL), basified with an aq. solution of NaHCO₃ and extracted with EtOAc (2×100 mL). The combined extracts were washed with water (100 mL), brine (100 mL), dried over anhydrous Na₂SO₄, filtered and evaporated to afford (1S, 2R)-2-(3'-(trifluoromethyl)-[1,1'-biphenyl]-4-yl)cyclopropanamine (1.3 g) as a light yellow solid.

Step 2:
Tert-butyl 4-oxocyclohexylcarbamate (999 mg, 4.69 mmol), acetic acid (280 mg, 4.69 mmol) and sodium triacetoxy borohydride (1.78 g, 8.44 mmol) were added to a solution of (1S,2R)-2-(3'-(trifluoromethyl)-[1,1'-biphenyl]-4-yl)cyclopropanamine (1.3 g, 4.69 mmol) in DCE (10 mL) at 0° C. and stirred at RT for 3 h. After completion of the reaction, the solvent was evaporated and the crude residue was taken up in water (25 mL), washed with NaHCO₃, and extracted with EtOAc (2×25 mL). The combined extracts were washed with water (25 mL), brine (25 mL), dried over anhydrous Na₂SO₄, filtered and evaporated.

The diasteriomers were separated by flash column chromatography using SiO₂ by eluting with EtOAc:petroleum ether (3:7). First, the less polar tert-butyl ((cis)-4-(((1S,2R)-2-(3'-(trifluoromethyl)-[1,1'-biphenyl]-4-yl)cyclopropyl)amino)cyclohexyl) carbamate (460 mg) was isolated followed by the more polar tert-butyl ((trans)-4-(((1S,2R)-2-(3'-(trifluoromethyl)-[1,1'-biphenyl]-4-yl)cyclopropyl)amino)cyclohexyl) carbamate (490 mg).

Step 3:
HCl in 1,4-dioxane (5 mL) was added to a solution of tert-butyl ((cis)-4-(((1S,2R)-2-(3'-(trifluoromethyl)-[1,1'-biphenyl]-4-yl)cyclopropyl)amino)cyclohexyl)carbamate (440 mg, 0.93 mmol) in 1,4-dioxane (9 mL) at 15° C. and stirred at RT for 16 h. After completion, the solvent was evaporated. The residue was triturated with Et₂O, filtered off and dried to afford (cis)-N1-((1S,2R)-2-(3'-(trifluoromethyl)-[1,1'-biphenyl]-4-yl)cyclopropyl)cyclohexane-1,4-diamine as hydrochloride salt (320 mg) an off white solid.

¹HNMR (400 MHz, DMSO-d6-D₂O Exchange) δ: 8.02-7.92 (m, 2H), 7.71 (d, J=8 Hz, 4H), 7.32 (d, J=8 Hz, 2H), 3.38 (brs, 1H), 3.27 (brs, 1H), 3.06 (brs, 1H), 2.60 (brs, 1H), 2.0-1.73 (m, 8H), 1.62 (brs, 1H), 1.44-1.35 (m, 1H); Mass (M+H): 375.23; $[\alpha]_D^{25.1}$: +53.93° (C=0.53% in DMSO).

Example 37: (Trans)-N1-((1S,2R)-2-(3'-(trifluoromethyl)-[1,1'-biphenyl]-4-yl)cyclo-propyl)cyclohexane-1,4-diamine

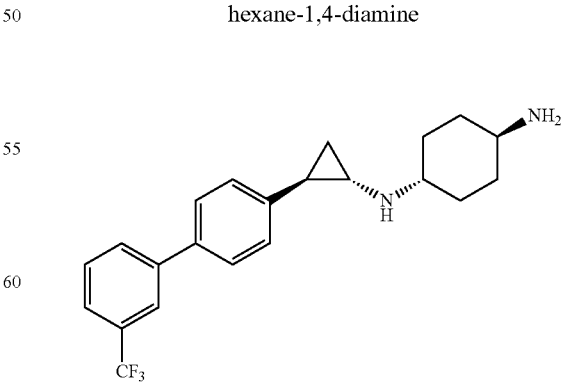

This compound was synthesized following the same procedure as described in example 36 leading to Boc-intermediate tert-butyl ((trans)-4-(((1S,2R)-2-(3'-(trifluoromethyl)-[1,1'-biphenyl]-4-yl)cyclopropyl)amino)cyclohexyl)carbamate as a second product in the reductive alkylation step and finally affording 328 mg of the title compound as a hydrochloride salt, a pale brown solid.

$^1$HNMR (400 MHz, DMSO-d6-D$_2$O Exchange) δ: 8.02-7.92 (m, 2H), 7.71 (d, J=8 Hz, 4H), 7.32 (d, J=8 Hz, 2H), 3.30-3.20 (m, 1H), 3.06-2.96 (m, 2H), 2.62-2.54 (m, 1H), 2.25-2.15 (m, 2H), 2.10-2.00 (m, 2H), 1.62-1.35 (m, 6H); Mass (M+H): 375.25; $[α]_D^{25.5}$: +52.83° (C=0.53% in DMSO).

Example 38: (Cis)-N1-((1R,2S)-2-(3'-(trifluoromethyl)-[1,1'-biphenyl]-4-yl)cyclo-propyl)cyclohexane-1,4-diamine

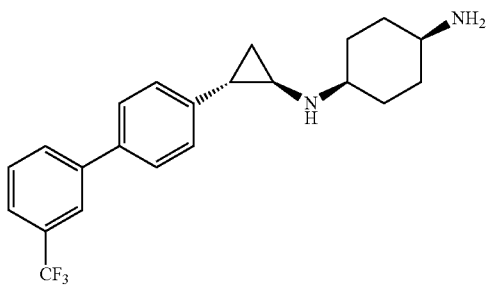 [SMILES: N[C@H]1CC[C@@H](N[C@@H]2C[C@H]2c2ccc(-c3cccc(C(F)(F)F)c3)cc2)CC1]

Step 1:
D (−) Mandelic acid (2.7 g, 18.05 mmol) was added to a solution of (trans)-2-(3'-(trifluoromethyl)-[1,1'-biphenyl]-4-yl)cyclopropanamine (free amine derived from Intermediate AH, 5 g, 18.05 mmol) in EtOH/H$_2$O 1: 9 (25 vols) and refluxed for 2 h. After formation of a clear solution, the reaction mixture was allowed to cool to RT (16 h). The precipitated solid was filtered off, taken up in water (100 mL), basified with an aq. solution of NaHCO$_3$ and extracted with EtOAc (2×100 mL). The combined extracts were washed with water (100 mL), brine (100 mL), dried over anhydrous Na$_2$SO$_4$, filtered and evaporated to afford (1R,2S)-2-(3'-(trifluoromethyl)-[1,1'-biphenyl]-4-yl)cyclopropanamine (900 mg) as a light yellow solid.
Step 2:
Tert-butyl 4-oxocyclohexylcarbamate (692 mg, 3.2 mmol), acetic acid (194 mg, 3.2 mmol) and sodium triacetoxy borohydride (1.2 g, 5.76 mmol) were added to a solution of (1R,2S)-2-(3'-(trifluoromethyl)-[1,1'-biphenyl]-4-yl)cyclopropanamine (900 mg, 3.2 mmol) in DCE (10 mL) at 0° C. and stirred at RT for 3 h. After completion, the solvent was evaporated. The residue was taken up in water (25 mL), washed with NaHCO$_3$, and extracted with EtOAc (2×25 mL). The combined extracts were washed with water (25 mL), brine (25 mL), dried over anhydrous Na$_2$SO$_4$, filtered and evaporated.
The diasteriomers were separated by flash column chromatography using SiO$_2$ by eluting with EtOAc:petroleum ether (3:7). First, the less polar isomer tert-butyl ((cis)-4-(((1R,2S)-2-(3'-(trifluoromethyl)-[1,1'-biphenyl]-4-yl)cyclopropyl)amino)cyclohexyl)carbamate (390 mg) was isolated followed by the more polar isomer tert-butyl ((trans)-4-(((1R,2S)-2-(3'-(trifluoromethyl)-[1,1'-biphenyl]-4-yl)cyclopropyl)amino)cyclohexyl)carbamate (480 mg).
Step 3:
HCl in dioxane (4 mL) was added to a solution of tert-butyl ((cis)-4-(((1R,2S)-2-(3'-(trifluoromethyl)-[1,1'-biphenyl]-4-yl)cyclopropyl)amino)cyclohexyl)carbamate (380 mg, 0.801 mmol) in 1, 4 dioxane (8 mL) at 15° C. and stirred at RT for 16 h. After completion, the solvent was evaporated. The residue was triturated with Et$_2$O, filtered off and dried to afford (cis)-N1-((1R,2S)-2-(3'-(trifluoromethyl)-[1,1'-biphenyl]-4-yl)cyclopropyl)cyclohexane-1,4-diamine as a hydrochloride salt (280 mg), a white solid.

$^1$HNMR (400 MHz, DMSO-d6-D$_2$O Exchange) δ: 8.02-7.92 (m, 2H), 7.71 (d, J=8 Hz, 4H), 7.33 (d, J=8 Hz, 2H), 3.39 (brs, 1H), 3.28 (brs, 1H), 3.05 (brs, 1H), 2.60 (brs, 1H), 2.0-1.75 (m, 8H), 1.68-1.60 (m, 1H), 1.46-1.38 (m, 1H); Mass (M+H): 375.28; $[α]_D^{28.1}$: −65.31° (C=0.53% in DMSO).

Example 39: (Trans)-N1-((1R,2S)-2-(3'-(trifluoromethyl)-[1,1'-biphenyl]-4-yl)cyclo-propyl)cyclohexane-1,4-diamine

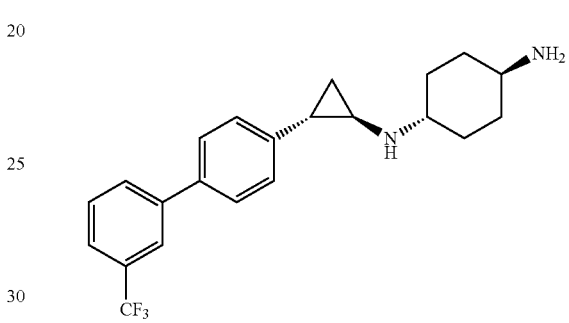

This compound was synthesized following the same procedure as described in example 38 leading to Boc-intermediate tert-butyl ((trans)-4-(((1R,2S)-2-(3'-(trifluoromethyl)-[1,1'-biphenyl]-4-yl)cyclopropyl)amino)cyclohexyl)carbamate as a second product in the reductive alkylation step and finally affording 350 mg of the title compound as a hydrochloride salt, a pale brown solid.

$^1$HNMR (400 MHz, DMSO-d6-D$_2$O Exchange) δ: 8.02-7.92 (m, 2H), 7.71 (d, J=8 Hz, 4H), 7.32 (d, J=8 Hz, 2H), 3.30-3.20 (m, 1H), 3.06-2.96 (m, 2H), 2.62-2.54 (m, 1H), 2.25-2.15 (m, 2H), 2.10-2.00 (m, 2H), 1.62-1.35 (m, 6H); Mass (M+H): 375.24; $[α]_D^{25.8}$: −48.30° (C=0.52% in DMSO).

Example 40: N1-((trans)-2-(4-cyclopropylphenyl)cyclopropyl)cyclohexane-1,4-diamine

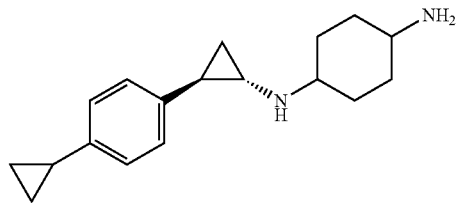 [SMILES: NC1CCC(N[C@H]2C[C@@H]2c2ccc(C3CC3)cc2)CC1]

Step 1:
A solution of tert-butyl ((trans)-2-(4-bromophenyl)cyclopropyl)(4-((tert-butoxycarbonyl)amino)cyclohexyl)carbamate (Intermediate AT, 400 mg, 0.78 mmol), cyclopropyl boronic acid (81 mg, 0.94 mmol) and K$_2$CO$_3$ (322 mg, 2.34 mmol) in ACN/H$_2$O 4:1 (8 mL) was degassed for 30 min. Pd(PPh$_3$)$_4$ (45 mg, 0.039 mmol) was added, and the mixture was stirred at reflux temperature for 16 h. After completion, the reaction mixture was poured into water and extracted with EtOAc (2×25 mL). The combined extracts were washed with water (25 mL), brine (25 mL), dried over anhydrous Na₂SO₄, filtered and evaporated. The crude material was purified by column chromatography (SiO₂) using EtOAc:petroleum ether (3:7) to afford tert-butyl (4-((tert-butoxycarbonyl) amino)cyclohexyl)((trans)-2-(4-cyclopropylphenyl)cyclopropyl)carbamate (160 mg) as a white solid.

Step 2:

HCl in dioxane (1 mL) was added to a solution of tert-butyl (4-((tert-butoxycarbonyl)amino)cyclohexyl)((trans)-2-(4-cyclopropylphenyl)cyclopropyl)carbamate (160 mg, 0.33 mmol) in dioxane (3 mL) at 10° C. and stirred at RT for 16 h. After completion, the solvent was evaporated. The solid was triturated with Et₂O, filtered off and dried to afford N1-((trans)-2-(4-cyclopropylphenyl)cyclopropyl)cyclohexane-1,4-diamine as a hydrochloride salt (60 mg), a white solid.

¹HNMR (400 MHz, DMSO d6) δ: 9.50-9.43 (m, 2H), 8.03 (brs, 3H), 7.02-6.98 (m, 4H), 3.28-3.18 (m, 1H), 2.97-2.80 (m, 1H), 2.43 (brs, 1H), 2.17 (brs, 1H), 2.02-1.75 (m, 6H), 1.58-1.20 (m, 5H), 0.92-0.87 (m, 2H), 0.61-0.57 (m, 2H); Mass (M+H): 271.24

The following compounds were synthesized according to the general methods disclosed under the General Synthetic Route Description Section and in particular by following the method described in example 40 and utilizing the respective intermediates or commercially available reagents.

Example 41: N1-((trans)-2-(4-(pyridin-3-yl)phenyl)cyclopropyl)cyclohexane-1,4-diamine

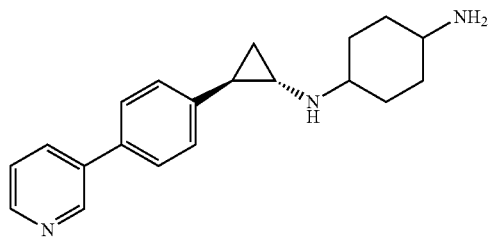 [SMILES: NC1CCC(N[C@H]2C[C@@H]2c2ccc(-c3cccnc3)cc2)CC1]

¹HNMR (400 MHz, DMSO d6) δ: 9.82-9.69 (m, 2H), 9.16 (m, J=12.8 Hz, 1H), 8.78 (brs, 1H), 8.68-8.63 (m, 1H), 8.19-8.15 (m, 3H), 7.95-7.92 (m, 1H), 7.81 (s, 2H), 7.38 (s, 2H), 3.28-3.08 (m, 2H), 2.99 (brs, 1H), 2.67 (brs, 1H), 2.20 (brs, 1H), 2.05-2.02 (m, 1H), 1.98-1.89 (m, 1H), 1.78-1.63 (m, 5H), 1.44-1.36 (m, 2H); Mass (M+H): 308.2. This compound was obtained as a hydrochloride salt.

Example 42: N1-((trans)-2-(4-(1H-indazol-6-yl)phenyl)cyclopropyl)cyclohexane-1,4-diamine

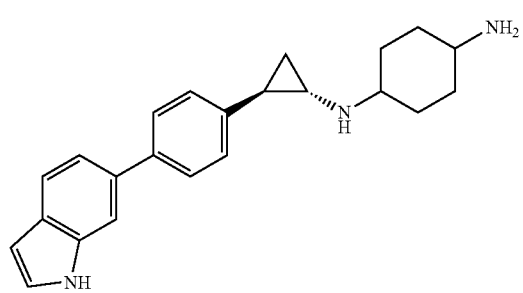 [SMILES: NC1CCC(N[C@H]2C[C@@H]2c2ccc(-c3ccc4cc[nH]c4c3)cc2)CC1]

¹HNMR (400 MHz, DMSO-d6-D₂O Exchange) δ: 8.11 (s, 1H), 7.86 (d, J=8 Hz, 1H), 7.75 (s, 1H), 7.69 (d, J=8 Hz, 2H), 7.42 (d, J=8 Hz, 1H), 7.31 (d, J=8 Hz, 2H), 3.42 (brs, 1H), 3.36-3.20 (m, 1H), 3.10-2.98 (m, 1H), 2.24-2.15 (m, 1H), 2.10-2.00 (m, 1H), 1.90 (brs, 2H), 1.81 (brs, 2H), 1.63-1.35 (m, 4H); Mass (M+H): 347.2.

This compound was obtained as a hydrochloride salt.

Example 43: N1-((trans)-2-(4-(1H-pyrazol-5-yl)phenyl)cyclopropyl)cyclohexane-1,4-diamine

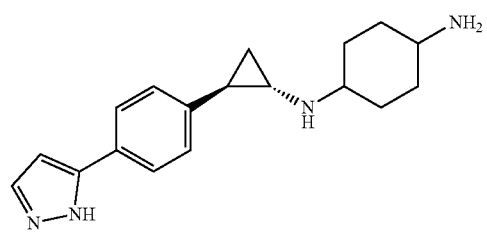 [SMILES: NC1CCC(N[C@H]2C[C@@H]2c2ccc(-c3ccn[nH]3)cc2)CC1]

¹HNMR (400 MHz, CD₃OD) δ: 8.24-8.15 (m, 1H), 7.80 (d, J=7.6 Hz, 2H), 7.43-7.37 (m, 2H), 7.09-7.02 (m, 1H), 3.58-3.50 (m, 1H), 3.46-3.40 (m, 1H), 3.22-3.08 (m, 1H), 2.77-2.59 (m, 1H), 2.40-2.29 (m, 1H), 2.24-2.15 (m, 1H), 2.13-1.93 (m, 4H), 1.80-1.48 (m, 4H); Mass (M+H): 297.32. This compound was obtained as a hydrochloride salt.

Example 44: 3-(5-((trans)-2-((4-aminocyclohexyl)amino)cyclopropyl)thiophen-2-yl)phenol

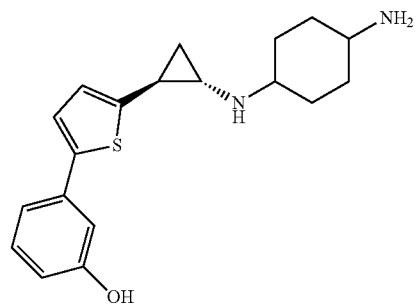 [SMILES: NC1CCC(N[C@H]2C[C@@H]2c2ccc(-c3cccc(O)c3)s2)CC1]

¹HNMR (400 MHz, D₂O) δ: 7.32-7.21 (m, 2H), 7.20 (d, J=8 Hz, 1H), 7.11 (s, 1H), 6.89-6.88 (m, 1H), 6.84 (d, J=7.6 Hz, 1H), 3.42-3.38 (m, 1H), 3.28-3.18 (m, 1H), 3.03-2.98 (m, 1H), 2.74-2.68 (m, 1H), 2.38-2.30 (m, 2H), 2.11-2.04 (m, 3H), 2.00-1.78 (m, 2H), 1.61-1.42 (m, 5H); Mass (M+H): 329.13. This compound was obtained as a hydrochloride salt.

Example 45: 3-(5-((trans)-2-((4-aminocyclohexyl)amino)cyclopropyl)thiazol-2-yl)phenol

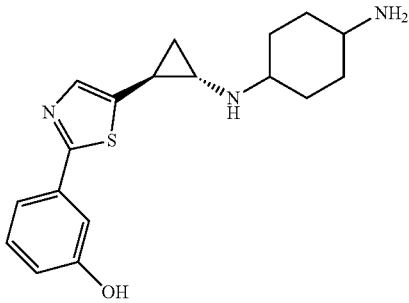 [SMILES: NC1CCC(N[C@H]2C[C@@H]2c2cnc(-c3cccc(O)c3)s2)CC1]

¹HNMR (400 MHz, DMSO d6) δ: 9.79 (brs, 1H), 9.70 (brs, 1H), 8.10 (brs, 2H), 7.72 (s, 1H), 7.30 (s, 2H), 6.86 (s, 1H), 3.40-3.19 (m, 2H), 3.18-2.95 (m, 2H), 2.85 (brs, 1H), 2.22-2.19 (m, 1H), 2.08-1.62 (m, 5H), 1.58-1.38 (m, 3H); Mass (M+H): 330.2. This compound was obtained as hydrochloride salt.

Example 46: 3-(5-((trans)-2-((4-aminocyclohexyl)amino)cyclopropyl)pyridin-2-yl)-5-methoxybenzonitrile

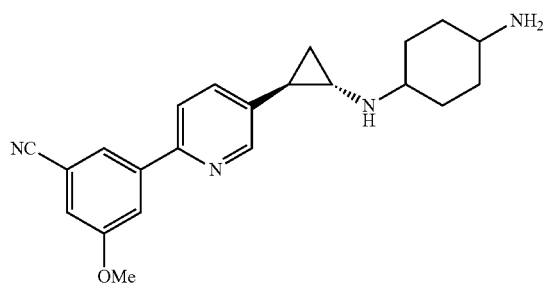 [SMILES: COc1cc(C#N)cc(-c2ccc([C@H]3C[C@@H]3NC3CCC(N)CC3)cn2)c1]

Step 1:
AcOH (12.9 mg, 0.215 mmol) was added to a solution of 3-(5-((trans)-2-aminocyclopropyl)pyridin-2-yl)-5-methoxybenzonitrile (Intermediate BT, 65 mg, 0.245 mmol) and tert-butyl 4-oxocyclohexylcarbamate (45.9 mg, 0.215 mmol) in DCE (2 mL) and stirred at RT for 15 min., then sodium triacetoxy borohydride (82 mg, 0.387 mmol) was added at 0° C. and stirred at RT for 5 h. After completion, the solvent was evaporated. The crude residue was taken up in water (10 mL), basified with NaHCO₃ (10 mL), and extracted with DCM (2×10 mL). The combined extracts were washed with water (10 mL), brine (10 mL), dried over anhydrous Na₂SO₄, filtered and evaporated to afford tert-butyl (4-(((trans)-2-(6-(3-cyano-5-methoxyphenyl)pyridin-3-yl)cyclopropyl)amino)cyclohexyl)carbamate (110 mg). The crude product was used in the next step without further purification.

Step 2:
HCl in dioxane (1 mL) was added to a solution of tert-butyl (4-(((trans)-2-(6-(3-cyano-5-methoxyphenyl)pyridin-3-yl)cyclopropyl)amino)cyclohexyl)carbamate (110 mg, 0.238 mmol) in dioxane (2 mL) at 10° C. and stirred at RT for 16 h. After completion, the solvent was evaporated. The residue was triturated with Et₂O, filtered off and dried to afford 3-(5-((trans)-2-((4-aminocyclohexyl)amino)cyclopropyl)pyridin-2-yl)-5-methoxybenzonitrile as a hydrochloride salt (20 mg), an orange solid.

¹HNMR (400 MHz, CD₃OD) δ: 8.70 (s, 1H), 8.07 (d, J=8.8 Hz, 1H), 7.96 (d, J=7.2 Hz, 1H), 7.93-7.88 (m, 1H), 7.85-7.80 (m, 1H), 7.46 (s, 1H), 3.94 (s, 3H), 3.26-3.16 (m, 1H), 2.77-2.68 (m, 1H), 2.42-2.25 (m, 1H), 2.24-2.10 (m, 1H), 2.08-1.90 (m, 3H), 1.89-1.80 (m, 1H), 1.78-1.27 (m, 6H); Mass (M+H): 363.30

The following compound was synthesized according to the general methods disclosed under the General Synthetic Route Description Section and in particular by following the method described in example 46 and utilizing the respective intermediates.

Example 47: 5-(5-((trans)-2-((4-aminocyclohexyl)amino)cyclopropyl)pyridin-2-yl)-2-methylphenol

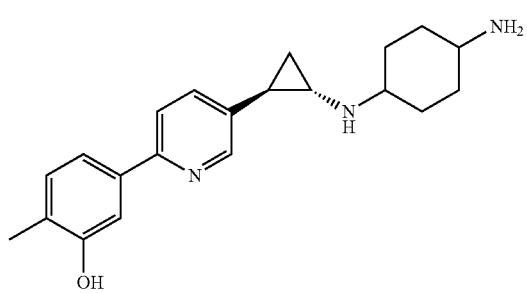 [SMILES: Cc1ccc(-c2ccc([C@H]3C[C@@H]3NC3CCC(N)CC3)cn2)cc1O]

¹HNMR (400 MHz, CD₃OD) δ: 8.74 (s, 1H), 8.33 (d, J=8.4 Hz, 1H), 8.17 (d, J=8.4 Hz, 1H), 7.35 (d, J=7.6 Hz, 1H), 7.34-7.25 (m, 2H), 3.50-3.42 (m, 1H), 3.38-3.32 (m, 1H), 3.24-3.10 (m, 1H), 2.90-2.82 (m, 1H), 2.43-2.31 (m, 2H), 2.28 (s, 3H), 2.23-2.12 (m, 2H), 1.84-1.78 (m, 1H), 1.76-1.50 (m, 5H); Mass (M+H): 338.32. This compound was obtained as hydrochloride salt.

Example 48: N-(4'-((trans)-2-((4-aminocyclohexyl)amino)cyclopropyl)-6-methoxy-[1,1'-biphenyl]-3-yl)methanesulfonamide

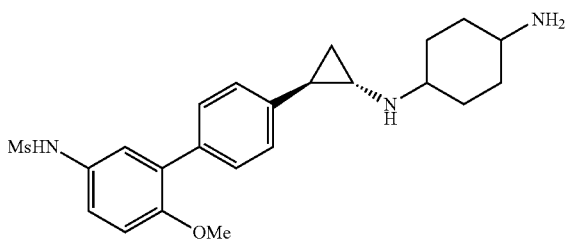

¹HNMR (400 MHz, CD₃OD) δ: 7.45 (d, J=8 Hz, 2H), 7.27-7.19 (m, 4H), 7.10-7.02 (m, 1H), 3.78 (s, 3H), 3.08-3.00 (m, 1H), 2.91 (s, 3H), 2.55-2.47 (m, 1H), 2.40-2.30 (m, 2H), 2.24-2.14 (m, 2H), 2.05-1.93 (m, 2H), 1.66-1.46 (m, 6H); Mass (M+H): 430.22. This compound was obtained as hydrochloride salt.

Example 49: N-(3-(5-((trans)-2-((4-aminocyclo-hexyl)amino)cyclopropyl)thiazol-2-yl)phenyl)-2-cyanobenzenesulfonamide

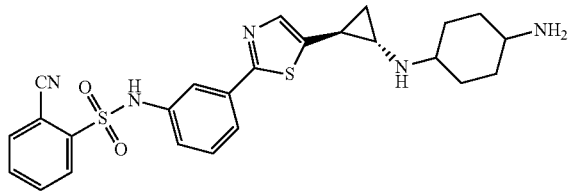 [SMILES: N#Cc1ccccc1S(=O)(=O)Nc1cccc(-c2ncc([C@H]3C[C@@H]3NC3CCC(N)CC3)s2)c1]

Step 1:

A solution of tert-butyl ((trans)-2-(2-bromothiazol-5-yl)cyclopropyl)(4-((tert-butoxycarbonyl)amino)cyclohexyl)carbamate (Intermediate BQ, 1.25 g, 2.42 mmol), 3-amino phenyl boronic acid (364 mg, 2.66 mmol) and $K_2CO_3$ (1 g, 7.26 mmol) in ACN—$H_2O$ (4:1) (12 mL) was degassed for 30 minutes. $Pd(PPh_3)_4$ (27.9 mg, 0.024 mmol) was added, and the mixture was stirred at reflux temperature for 16 h. After completion, the reaction mixture was poured into water and extracted with EtOAc (2×50 mL). The combined extracts were washed with water (50 mL), brine (50 mL), dried over anhydrous $Na_2SO_4$, filtered and evaporated. The crude was purified by column chromatography ($SiO_2$, EtOAc/petroleum ether 3:7) to afford tert-butyl ((trans)-2-(2-(3-aminophenyl)thiazol-5-yl)cyclopropyl)(4-((tert-butoxycarbonyl)amino)cyclohexyl)carbamate (950 mg) as yellow gummy liquid.

Step 2:

2-cyanobenzene-1-sulfonyl chloride (361 mg, 1.799 mmol) was added to a solution of tert-butyl ((trans)-2-(2-(3-aminophenyl)thiazol-5-yl)cyclopropyl)(4-((tert-butoxycarbonyl) amino)cyclohexyl)carbamate (950 mg, 1.799 mmol) in pyridine (5 mL) at 0° C. and stirred at RT for 5 h. After completion, the reaction mixture was poured into water and extracted with EtOAc (2×25 mL). The combined extracts were washed with water (2×25 mL), brine, dried over anhydrous $Na_2SO_4$, filtered and evaporated. The crude was purified by preparative HPLC to afford tert-butyl (4-((tert-butoxycarbonyl)amino)cyclohexyl)((trans)-2-(2-(3-(2-cyanophenylsulfonamido)phenyl)thiazol-5-yl)cyclopropyl)carbamate (240 mg) as a white solid.

Step 3:

HCl in dioxane (1.2 mL) was added to a solution of tert-butyl (4-((tert-butoxycarbonyl)amino)cyclohexyl)((trans)-2-(2-(3-(2-cyanophenylsulfonamido)phenyl) thiazol-5-yl)cyclopropyl)carbamate (240 mg, 0.34 mmol) in dioxane (2.4 mL) at 10° C. and stirred at RT for 16 h. After completion, the solvent was evaporated and the residue was triturated with $Et_2O$, filtered off and dried to afford N-(3-(5-((trans)-2-((4-aminocyclohexyl)amino)cyclopropyl)thiazol-2-yl)phenyl)-2-cyanobenzenesulfonamide as a hydrochloride salt (110 mg), a light brown solid.

$^1$HNMR (400 MHz, DMSO d6) δ: 11.11 (s, 1H), 9.81-9.71 (m, 2H), 8.24-8.08 (brs, 2H), 8.08 (dd, J=7.6 and 4.8 Hz, 2H), 7.93 (t, J=8 Hz, 1H), 7.83 (t, J=7.2 Hz, 1H), 7.73 (s, 1H), 7.66 (s, 1H). 7.56 (d, J=7.2 Hz, 1H), 7.38 (t, J=8 Hz, 1H), 7.18 (d, J=8 Hz, 1H), 3.4-3.18 (m, 2H), 3.05-2.85 (m, 2H), 2.2 (m, 1H), 2.1-1.8 (m, 4H), 1.75 (brd, 2H), 1.42 (m, 3H); Mass (M+H): 494.1

The following compound was synthesized according to the general methods disclosed under the General Synthetic Route Description Section and in particular by following the method described in example 49 and utilizing the respective intermediates or commercially available reagents.

Example 50: N-(4'-((trans)-2-((4-aminocyclohexyl)amino)cyclopropyl)-[1,1'-biphenyl]-3-yl)-2-cyanobenzenesulfonamide

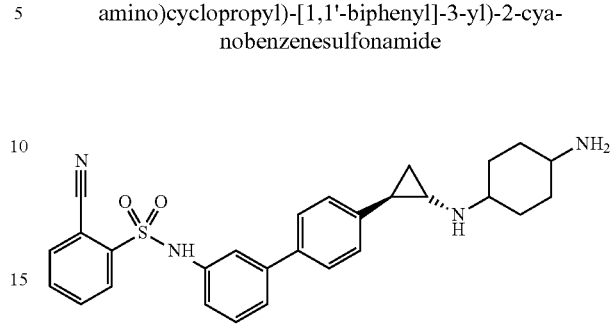

$^1$HNMR (400 MHz, DMSO-d6-$D_2O$ Exchange) δ: 8.11 (d, J=8 Hz, 1H), 8.06 (d, J=8 Hz, 1H), 7.93 (t, J=8 Hz, 1H), 7.83 (t, J=8 Hz, 1H), 7.72-7.60 (m, 1H), 7.48 (d, J=8 Hz, 2H), 7.40-7.31 (m, 2H), 7.30-7.24 (m, 2H), 7.07-7.01 (m, 1H), 3.39 (brs, 1H), 3.35-3.18 (m, 1H), 3.08-2.94 (m, 2H), 2.15 (brs, 1H), 2.10-2.00 (m, 1H), 1.88 (brs, 2H), 1.80 (brs, 2H), 1.62-1.35 (m, 4H); Mass (M+H): 487.27. This compound was obtained as hydrochloride salt.

Example 51: 6-amino N-(4' ((trans)-2-((4-aminocyclohexyl)amino)cyclopropyl)-[1,1'-biphenyl]-3-yl)pyridine-3-sulfonamide

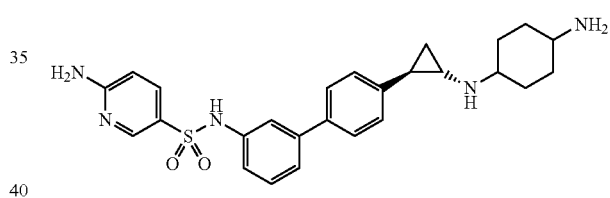

Step 1:

6-nitropyridine-3-sulfonyl chloride (223 mg, 1 mmol) was added to a solution of tert-butyl ((trans)-2-(3'-amino-[1,1'-biphenyl]-4-yl)cyclopropyl)(4-((tert-butoxycarbonyl) amino) cyclohexyl)carbamate (Intermediate BR, 500 mg, 0.95 mmol) in pyridine (10 mL) at 0° C. and stirred at RT for 16 h. After completion, the reaction mixture was poured into water (25 mL) and extracted with EtOAc (2×25 mL). The combined extracts were washed with water (3×25 mL), brine (25 mL), dried over anhydrous $Na_2SO_4$, filtered and evaporated to afford tert-butyl (4-((tert-butoxycarbonyl)amino)cyclohexyl)((trans)-2-(3'-(6-nitropyridine-3-sulfonamido)-[1,1'-biphenyl]-4-yl)cyclopropyl)carbamate (580 mg). The crude product was used in the next step without further purification.

Step 2:

Ammonium chloride (217 mg, 4.1 mmol) was added to a solution of tert-butyl (4-((tert-butoxycarbonyl)amino)cyclohexyl)((trans)-2-(3'-(6-nitropyridine-3-sulfonamido)-[1,1'-biphenyl]-4-yl)cyclopropyl)carbamate (580 mg, 0.82 mmol) in EtOH (12 mL) followed by iron powder (229 mg, 4.1 mmol) and the reaction mixture was stirred at reflux temperature for 4 h. After completion, the reaction mixture was filtered through a pad of celite, the filtrate was concentrated and the residue taken up in water (25 mL) and extracted with EtOAc (2×25 mL). The combined extracts were washed with water (25 mL), brine (25 mL), dried over anhydrous Na$_2$SO$_4$, filtered and evaporated. The crude was purified by preparative HPLC to afford tert-butyl ((trans)-2-(3'-(6-aminopyridine-3-sulfonamido)-[1,1'-biphenyl]-4-yl)cyclopropyl)(4-((tert-butoxycarbonyl)amino)cyclohexyl)carbamate (190 mg) as an off white solid.

Step 3:

HCl in dioxane (1 mL) was added dropwise to a solution of tert-butyl ((trans)-2-(3'-(6-aminopyridine-3-sulfonamido)-[1,1'-biphenyl]-4-yl)cyclopropyl)(4-((tert-butoxycarbonyl) amino)cyclohexyl)carbamate (90 mg, 0.13 mmol) in dioxane (2 mL) at 10° C. and stirred at RT for 16 h. After completion, the solvent was evaporated. The residue was triturated with Et$_2$O, filtered off and dried to render 6-amino-N-(4'-((trans)-2-((4-aminocyclohexyl)amino)cyclopropyl)-[1,1'-biphenyl]-3-yl)pyridine-3-sulfonamide as a hydrochloride salt (60 mg) an off white solid.

$^1$HNMR (400 MHz, DMSO-d6-D$_2$O Exchange) δ: 8.24 (s, 1H), 7.72 (dd, J=8 Hz, 2.5 Hz, 1H), 7.50 (d, J=8 Hz, 2H), 7.38-7.32 (m, 3H), 7.28 (d, J=8 Hz, 1H), 7.10-7.05 (m, 1H), 6.57 (d, J=8 Hz, 2H), 3.30-3.19 (m, 1H), 3.05-2.98 (m, 2H), 2.54-2.46 (m, 1H), 2.23-2.13 (m, 2H), 2.10-2.00 (m, 2H), 1.59-1.36 (m, 6H); Mass (M+H): 478.06

Example 52: N-(4'-((trans)-2-((4-aminocyclohexyl) amino)cyclopropyl)-[1,1'-biphenyl]-3-yl)piperazine-1-sulfonamide

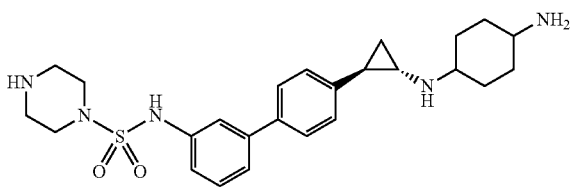

This compound was synthesized following the same procedure as described in example 51 using tert-butyl 4-(chlorosulfonyl)piperazine-1-carboxylate in Step 1 and omitting Step 2. Final deprotection (Boc removal, Step 3) afforded 80 mg of the title compound as a hydrochloride salt, a white solid.

$^1$HNMR (400 MHz, DMSO-d6-D$_2$O Exchange) δ: 7.57 (d, J=8 Hz, 2H), 7.50-7.38 (m, 3H), 7.35-7.25 (m, 2H), 7.24 (d, J=8 Hz, 1H), 3.37 (brs, 4H), 3.36-3.20 (m, 2H), 3.37 (brs, 4H), 3.11 (brs, 3H), 3.05-2.96 (m, 2H), 2.23-2.15 (m, 1H), 2.10-2.0 (m, 1H), 1.90 (brs, 2H), 1.81 (brs, 2H), 1.63-1.35 (m, 4H); Mass (M+H): 470.33

Example 53: N1-((trans)-2-fluoro-2-phenylcyclopropyl)cyclohexane-1,4-diamine

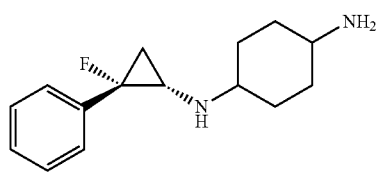 [SMILES: NC1CCC(N[C@H]2C[C@]2(F)c2ccccc2)CC1]

Step 1:

Tert-butyl 4-oxocyclohexylcarbamate (493 mg, 2.31 mmol) was added to a solution of (trans)-2-fluoro-2-phenylcyclopropanamine (Intermediate BJ, 350 mg, 2.31 mmol) in DCE (7 mL). The mixture was stirred at RT for 10 min and then cooled to 0° C. Sodium triacetoxy borohydride (978 mg, 4.62 mmol) was added and stirring was continued at RT for 15 min. After completion the reaction mixture was poured into ice water and extracted with DCM (2×25 mL). The combined extracts were washed with water (10 mL), brine (10 mL) and dried over anhydrous Na$_2$SO$_4$. The filtrate was used in the next step without evaporation.

HCl in Dioxane (1.6 mL) was added the solution of tert-butyl (4-(((trans)-2-fluoro-2-phenylcyclopropyl)amino) cyclohexyl)carbamate in DCM (3.2 mL) and stirred at RT for 16 h. After completion, the solvent was evaporated, and the crude residue was triturated with diethyl ether (10 mL) and hexane (10 mL) to afford N1-((trans)-2-fluoro-2-phenylcyclopropyl)cyclohexane-1,4-diamine as hydrochloride salt (300 mg) as a yellow solid.

Step 2:

2N NaOH solution (5.8 mL) and (Boc)$_2$O (0.54 mL, 2.26 mmol) was added to a solution of N1-((trans)-2-fluoro-2-phenylcyclopropyl)cyclohexane-1,4-diamine (290 mg, 0.906 mmol) in 1,4 dioxane (10 vols) at 10° C. and stirred at room temp for 4 h. After completion, the reaction mixture was diluted with water (10 mL) and extracted with EtOAc (2×15 mL). The combined extracts were washed with water (10 mL), brine (10 mL), dried over anhydrous Na$_2$SO$_4$, filtered and evaporated. The crude was purified by preparative HPLC to afford tert-butyl (4-((tert-butoxycarbonyl) amino)cyclohexyl)((trans)-2-fluoro-2-phenylcyclopropyl) carbamate (140 mg) as a white solid.

Step 3:

HCl in dioxane (0.7 ml) was added to a solution of tert-butyl (4-((tert-butoxycarbonyl)amino)cyclohexyl) ((trans)-2-fluoro-2-phenylcyclopropyl)carbamate (140 mg, 0.312 mmol) in dioxane (1.4 mL) at 0° C. and stirred at RT for 6 h. After completion, the solvent was evaporated and the residue was triturated with diethyl ether (5 mL) followed by n-pentane (5 mL) to get N1-((trans)-2-fluoro-2-phenylcyclopropyl)cyclohexane-1,4-diamine as a hydrochloride salt (80 mg), an off white solid.

$^1$HNMR (400 MHz, D$_2$O) δ: 7.49 (s, 2H), 7.42 (s, 3H), 3.60-3.43 (m, 2H), 3.22-3.12 (m, 2H), 2.33-2.18 (m, 3H), 1.98-1.91 (m, 3H), 1.68-1.45 (m, 3H), Mass (M+H): 249.17

Example 54: N1-((cis)-2-fluoro-2-phenylcyclopropyl)cyclohexane-1,4-diamine

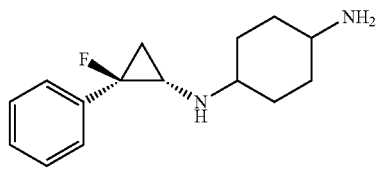 [SMILES: NC1CCC(N[C@H]2C[C@@]2(F)c2ccccc2)CC1]

This compound was synthesized following the same procedure as described in example 53 starting from (cis)-2-fluoro-2-phenylcyclopropanamine (Intermediate BI), affording 80 mg as a hydrochloride salt, an off white solid.

$^1$HNMR (400 MHz, D$_2$O) δ: 7.79 (s, 2H), 7.62 (s, 3H), 3.69-3.53 (m, 2H), 3.4-3.18 (m, 2H), 2.39 (s, 1H), 2.28-2.08 (m, 3H), 2.02-1.81 (m, 4H), 1.68-1.45 (m, 3H), Mass (M+H): 249.17

Example 55: N1-((trans)-2-(4-((3-(piperazin-1-yl)benzyl)oxy)phenyl)cyclopropyl) cyclohexane-1,4-diamine

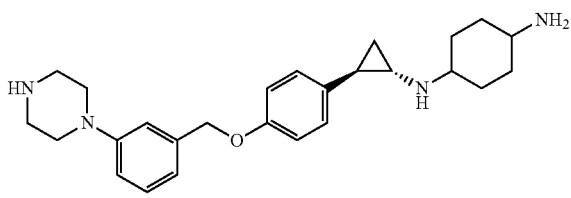 [SMILES: NC1CCC(N[C@H]2C[C@@H]2c2ccc(OCc3cccc(N4CCNCC4)c3)cc2)CC1]

Step 1:

$K_2CO_3$ (1.1 g, 8.0 mmol) was added to a solution of tert-butyl ((trans)-2-(4-hydroxyphenyl)cyclopropyl)carbamate (Intermediate BL, 1 g, 4.0 mmol) and 1-bromo-3-(bromomethyl)benzene (997 mg, 4.0 mmol) in DMF (10 mL) at 0° C. and stirred at RT for 18 h. After completion, the reaction mixture was poured into ice water (20 mL) and extracted with ethyl acetate (2×20 mL). The combined extracts were washed with water (20 mL), brine (20 mL), dried over anhydrous $Na_2SO_4$, filtered and evaporated. The crude product was purified by column chromatography ($SiO_2$, EtOAc/petroleum ether 2:8) to afford tert-butyl ((trans)-2-(4-((3-bromobenzyl)oxy)phenyl)cyclopropyl) carbamate (1.2 g) as an off white solid.

Step 2:

HCl in dioxane (10 mL) was added dropwise to a solution of tert-butyl ((trans)-2-(4-((3-bromobenzyl)oxy)phenyl)cyclopropyl)carbamate (1.2 g, 2.8 mmol) in dioxane (5 mL) at 15° C. and stirred at RT for 2 h. After completion, the solvent was evaporated. The residue was taken up in water (15 mL), basified with $NaHCO_3$ solution (5 mL) and extracted with EtOAc (2×20 mL). The combined extracts were washed with water (20 mL), brine (20 mL), dried over anhydrous $Na_2SO_4$, filtered and evaporated to afford (trans)-2-(4-((3-bromobenzyl)oxy)phenyl)cyclopropanamine (800 mg). The crude was used in the next step without further purification.

Step 3:

Acetic acid (0.17 mL, 2.515 mmol) was added to a solution of (trans)-2-(4-((3-bromobenzyl)oxy)phenyl)cyclopropanamine (800 mg, 2.51 mmol) and tert-butyl 4-oxocyclohexylcarbamate (537 mg, 2.515 mmol) in DCE (20 mL). At 0° C., sodium triacetoxy borohydride (960 mg, 4.52 mmol) was added, and the mixture was stirred at RT for 4 h. After completion, the reaction mixture was diluted with DCM (20 mL), washed with aq. $NaHCO_3$ solution, followed by water (10 mL), brine (10 mL). The organic phase was dried over anhydrous $Na_2SO_4$, filtered and evaporated. The crude product was purified by column chromatography ($SiO_2$, EtOAc/petroleum ether 6:4) to afford tert-butyl (4-(((trans)-2-(4-((3-bromobenzyl)oxy)phenyl)cyclopropyl) amino) cyclohexyl)carbamate (900 mg).

Step 4:

NaOH (310 mg, 7.76 mmol) was added to a solution of tert-butyl (4-(((trans)-2-(4-((3-bromobenzyl)oxy)phenyl)cyclopropyl)amino)cyclohexyl)carbamate (1.0 g, 1.94 mmol) in 1,4-dioxane/water (4:1) at 10° C. Subsequently, $Boc_2O$ (830 mg, 3.88 mmol) was added, and the mixture was stirred at RT for 18 h. After completion, the reaction mixture was poured into ice water (20 mL) and extracted with ethyl acetate (2×20 mL). The combined extracts were washed with water (20 mL), brine (20 mL), dried over anhydrous $Na_2SO_4$, filtered and evaporated. The crude product was purified by column chromatography ($SiO_2$, EtOAc/petroleum ether 3:7) to afford tert-butyl ((trans)-2-(4-((3-bromobenzyl)oxy)phenyl)cyclopropyl)(4-((tert-butoxycarbonyl)amino)cyclohexyl) carbamate (600 mg).

Step 5:

$NaO^tBu$ (141 mg, 1.46 mmol) was added to a solution of tert-butyl ((trans)-2-(4-((3-bromobenzyl)oxy)phenyl)cyclopropyl)(4-((tert-butoxycarbonyl)amino)cyclohexyl)carbamate (600 mg, 0.975 mmol) and tert-butyl piperazine-1-carboxylate (363 mg, 1.95 mmol) in dioxane (15 mL) at RT which was then degassed with argon for 15 min. $Pd_2(dba)_3$ (44.6 mg, 0.0487 mmol) was added followed by xantphos (169 mg, 0.292 mmol), and degassing was repeated for 15 min. The reaction mixture was stirred at reflux temperature for 18 h. After completion, the mixture was filtered through a pad of celite, and the filtrate was concentrated. The residue was taken up in water (20 mL) and extracted with ethyl acetate (2×20 mL). The combined extracts were washed with water (20 mL), brine (20 mL), dried over anhydrous $Na_2SO_4$, filtered and evaporated. The crude product was purified by column chromatography (neutral alumina, EtOAc/petroleum ether 2:8) to afford tert-butyl 4-(3-((4-(((trans)-2-((tert-butoxycarbonyl)(4-((tert-butoxycarbonyl)amino)cyclohexyl)amino)cyclopropyl)phenoxy)methyl) phenyl) piperazine-1-carboxylate (260 mg) as a white solid.

Step 6:

HCl in dioxane (3 mL) was added to a solution of tert-butyl 4-(3-((4-(((trans)-2-((tert-butoxycarbonyl)(4-((tert-butoxycarbonyl)amino)cyclohexyl)amino)cyclopropyl)phenoxy) methyl)phenyl)piperazine-1-carboxylate (150 mg, 0.208 mmol) in 1, 4-dioxane (2 mL) at 10° C. and stirred at RT for 6 h. After completion, the solvent was evaporated and the residue was triturated with EtOAc (4 mL), followed by n-hexane (2 mL) to afford N1-((trans)-2-(4-((3-(piperazin-1-yl)benzyl)oxy)phenyl)cyclopropyl)cyclohexane-1,4-diamine as hydrochloride salt (80 mg), a pale yellow solid.

$^1$HNMR (400 MHz, $D_2O$) δ: 7.40 (t, J=8 Hz, 1H), 7.19 (s, 1H), 7.18-7.07 (m, 4H), 7.01 (d, J=8 Hz, 2H), 5.11 (s, 2H), 3.6-3.3 (m, 9H), 3.28-3.18 (m, 1H), 3.95-3.84 (m, 1H), 2.50-2.39 (m, 1H), 2.32-2.24 (m, 1H), 2.19-2.11 (m, 1H), 2.09-1.99 (m, 1H), 1.98-1.77 (m, 3H), 1.62-1.33 (m, 4H); Mass (M+H): 421.28

The following compounds were synthesized according to the general methods disclosed under the General Synthetic Route Description Section and in particular by following the method described in example 55, omitting Steps 4 and 5, and utilizing the respective intermediates or commercially available reagents.

Example 56: N1-((trans)-2-(4-(pyridin-3-ylmethoxy)phenyl)cyclopropyl)cyclohexane-1,4-diamine

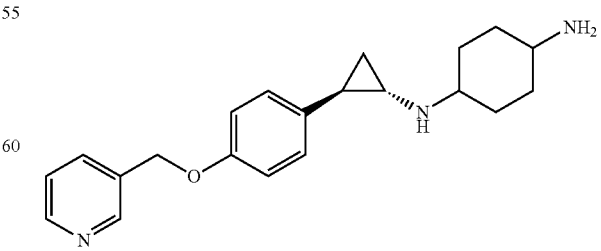

$^1$HNMR (400 MHz, DMSO-d6-$D_2O$ Exchange) δ: 8.79 (s, 1H), 8.68 (s, 1H), 8.31-8.24 (m, 1H), 7.83-75 (m, 1H), 7.20-7.10 (m, 2H), 7.01 (d, J=8.4 Hz, 2H), 5.23 (s, 2H), 3.42-3.17 (m, 2H), 3.08-2.95 (m, 1H), 2.94-2.83 (m, 1H), 2.48-2.35 (m, 1H), 2.22-2.10 (m, 1H), 2.09-1.98 (m, 1H), 1.97-1.72 (m, 3H), 1.55-1.38 (m, 3H), 1.37-1.25 (m, 1H); Mass (M+H): 338.19. This compound was obtained as hydrochloride salt.

Example 57: N1-((trans)-2-(4-((2-fluorobenzyl)oxy)phenyl)cyclopropyl)cyclohexane-1,4-diamine

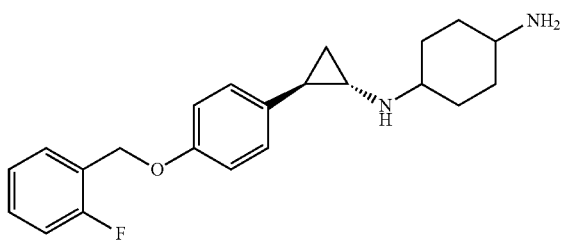 [SMILES: NC1CCC(N[C@H]2C[C@@H]2c2ccc(OCc3ccccc3F)cc2)CC1]

$^1$HNMR (400 MHz, DMSO d6) δ: 9.55 (brd, 2H), 8.1 (brs, 3H), 7.58 (t, 1H), 7.62 (d, 1H), 7.28 (m, 2H), 7.18 (d, 2H), 6.98 (d, 2H), 5.1 (s, 2H), 3.25-3.15 (m, 2H), 2.88-2.81 (m, 2H), 2.45 (brs, 1H), 2.15 (brs, 1H), 2.05-1.7 (m, 5H), 1.6-1.3 (m, 3H), 1.25 (d, 1H); Mass (M+H): 355.25. This compound was obtained as hydrochloride salt.

Example 58: N1-((trans)-2-(6-((3-methylbenzyl)amino)pyridin-3-yl)cyclopropyl) cyclohexane-1,4-diamine

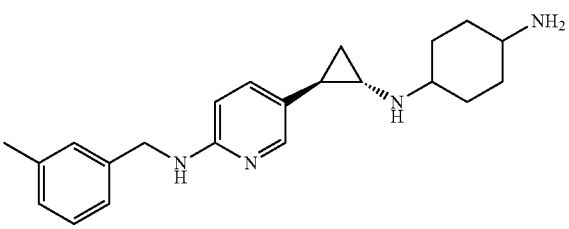 [SMILES: Cc1cccc(CNc2ccc([C@H]3C[C@@H]3NC3CCC(N)CC3)cn2)c1]

Step 1:
A solution of tert-butyl ((trans)-2-(6-bromopyridin-3-yl)cyclopropyl)(4-((tert-butoxycarbonyl)amino)cyclohexyl)carbamate (Intermediate BP, 300 mg, 0.58 mmol), m-tolylmethanamine (78 mg, 0.64 mmol), sodium tert-butoxide (83 mg, 0.87 mmol) and BINAP (108 mg, 0.17 mmol) in 1,4-dioxane (6 mL) was degassed for 10 min. Tris(dibenzylideneacetone) dipalladium(0) (26 mg, 0.029 mmol) was added, and the reaction mixture was stirred at 100° C. for 16 h. After completion, the reaction mixture was poured in ice cold water (15 mL) and extracted with EtOAc (2×10 mL). The combined extracts were washed with water (10 mL), brine (10 mL), dried over anhydrous Na$_2$SO$_4$, filtered and evaporated. The crude residue was purified by column chromatography (SiO$_2$) using EtOAc:petroleum ether (3:7) to afford tert-butyl (4-((tert-butoxycarbonyl)amino)cyclohexyl)((trans)-2-(6-((3-methylbenzyl)amino)pyridin-3-yl)cyclopropyl)carbamate (100 mg) as a white solid.
Step 2:
HCl in 1,4-dioxane (1 mL) was added to a solution of tert-butyl (4-((tert-butoxycarbonyl)amino)cyclohexyl)((trans)-2-(6-((3-methylbenzyl)amino)pyridin-3-yl) cyclopropyl)carbamate (100 mg, 0.181 mmol) in dioxane (2 mL) at 10° C., and the reaction mixture was stirred at RT for 16 h. After completion, the solvent was evaporated. The solid residue was triturated with Et$_2$O and hexane to afford N1-((trans)-2-(6-((3-methylbenzyl)amino)pyridin-3-yl)cyclopropyl)cyclohexane-1,4-diamine as hydrochloride salt (60 mg), a brown solid.
$^1$HNMR (400 MHz, D$_2$O) δ: 7.68 (d, J=9.6 Hz, 1H), 7.63 (s, 1H), 7.30 (t, J=8 Hz, 1H), 7.24-7.16 (m, 3H), 6.99 (d, J=9.4 Hz, 2H), 4.56 (s, 2H), 3.58-3.47 (m, 1H), 3.42-3.31 (m, 1H), 3.27-3.17 (m, 1H), 3.05-2.95 (m, 1H), 2.52-2.41 (m, 1H), 2.30 (s, 3H), 2.27-2.23 (m, 1H), 2.20-2.12 (m, 2H), 2.00-1.80 (m, 2H), 1.64-1.39 (m, 4H); Mass (M+H): 351.41

Example 59: 3-((5-((trans)-2-((4-aminocyclohexyl)amino)cyclopropyl)pyridin-2-yl) amino)benzonitrile

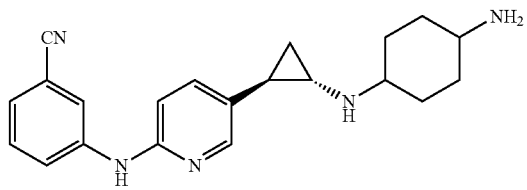 [SMILES: N#Cc1cccc(Nc2ccc([C@H]3C[C@@H]3NC3CCC(N)CC3)cn2)c1]

Step 1:
A solution of tert-butyl (trans)-2-(6-bromopyridin-3-yl) cyclopropylcarbamate (Intermediate M, 250 mg, 0.798 mmol), 3-aminobenzonitrile (113 mg, 0.957 mmol) and sodium tert-butoxide (115 mg, 1.197 mmol) in 1,4-dioxane (5 mL) was degassed for 30 min., then tris(dibenzylideneacetone)dipalladium(0) (36 mg, 0.039 mmol) and 4,5-bis(diphenylphosphino)-9,9-dimethylxanthene (Xantphos) (138 mg, 0.238 mmol) was added and the reaction was heated for 1 h at 80° C. After completion, the solvent was evaporated, the residue was taken in ice water (10 mL) and extracted with EtOAc (2×20 mL). The combined extracts were washed with water (10 mL), brine (10 mL), dried over anhydrous Na$_2$SO$_4$, filtered and evaporated. The crude residue was purified by column chromatography (SiO$_2$) using EtOAc:petroleum ether (2:8) to give tert-butyl ((trans)-2-(6-((3-cyanophenyl)amino)pyridin-3-yl)cyclopropyl)carbamate (100 mg) as a yellow solid.
Step 2:
HCl in 1, 4 dioxane (1 ml) was added to a solution of tert-butyl ((trans)-2-(6-((3-cyanophenyl)amino)pyridin-3-yl)cyclopropyl)carbamate (100 mg, 0.285 mmol) in 1, 4-dioxane (1 mL) at 0° C. and stirred at RT for 4 h. After completion, the solvent was evaporated and the residue was triturated with diethyl ether (5 mL) followed by n-pentane (5 mL) to give 3-((5-((trans)-2-aminocyclopropyl)pyridin-2-yl)amino)benzonitrile as hydrochloride salt (80 mg), a pale yellow solid.
Step 3:
AcOH (11.46 mg, 0.191 mmol) was added to a solution of 3-((5-((trans)-2-aminocyclopropyl)pyridin-2-yl)amino)benzonitrile (55 mg, 0.191 mmol) and tert-butyl 4-oxocyclohexylcarbamate (40.68 mg, 0.191 mmol) in DCE (1 mL) and stirred at RT for 15 min., then sodium triacetoxy borohydride (72.8 mg, 0.343 mmol) was added at 0° C. and stirred at RT for 5 h. After completion, solvent was evaporated. The crude residue was taken up in water (10 mL), basified with NaHCO$_3$ (10 mL), and extracted with DCM (2×10 mL). The combined extracts were washed with water (10 mL), brine (10 mL), dried over anhydrous Na$_2$SO$_4$, filtered and evaporated to afford tert-butyl (4-(((trans)-2-(6-((3-cyanophenyl)amino)pyridin-3-yl)cyclopropyl)amino)carbamate (75 mg) as light yellow oil. The crude product was used in the next step without further purification.

Step 4:

HCl in 1,4-dioxane (1 mL) was added to a solution of tert-butyl (4-(((trans)-2-(6-((3-cyanophenyl)amino)pyridin-3-yl)cyclopropyl)amino)cyclohexyl)carbamate (75 mg, 0.167 mmol) in 1,4-dioxane (2 mL) at 10° C. and stirred at RT for 16 h. After completion, the solvent was evaporated. The solid was triturated with Et$_2$O and dried to afford crude product. The crude was purified by Preparative HPLC to afford 3-((5-(((trans)-2-((4-aminocyclohexyl)amino)cyclopropyl)pyridin-2-yl)amino)benzonitrile as a hydrochloride salt (28 mg), an off white sticky solid.

$^1$HNMR (400 MHz, DMSO-d6-D$_2$O Exchange) δ: 8.35 (s, 1H), 8.15 (s, 1H), 7.78 (d, J=8 Hz, 1H), 7.54-7.42 (m, 2H), 7.31 (d, J=8 Hz, 1H), 6.85 (d, J=8.8 Hz, 1H), 3.45-3.17 (m, 2H), 3.08-2.93 (m, 2H), 2.44-2.34 (m, 1H), 2.22-2.10 (m, 1H), 2.09-1.98 (m, 1H), 1.97-1.70 (m, 3H), 1.55-1.32 (m, 4H); Mass (M+H): 348.20

The following compounds can be synthesized following the general methods disclosed under the General Synthetic Route Description Section, including the methodologies described in Schemes 1, 2, 3, 4, 5, 6, 7 or 8 and the examples above.

Example 60: N1-((trans)-2-(4'-chloro-[1,1'-biphenyl]-4-yl)cyclopropyl)cyclohexane-1,4-diamine NH$_2$

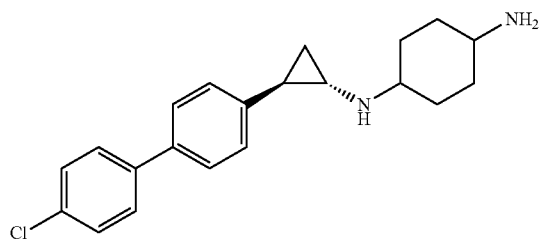 [SMILES: NC1CCC(N[C@H]2C[C@@H]2c2ccc(-c3ccc(Cl)cc3)cc2)CC1]

Example 61: N1-((trans)-2-(3'-chloro-[1,1'-biphenyl]-4-yl)cyclopropyl)cyclohexane-1,4-diamine

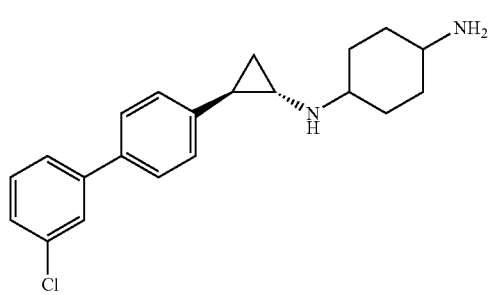 [SMILES: NC1CCC(N[C@H]2C[C@@H]2c2ccc(-c3cccc(Cl)c3)cc2)CC1]

Example 62: 4'-((trans)-2-((4-aminocyclohexyl)amino)cyclopropyl)-[1,1'-biphenyl]-3-ol

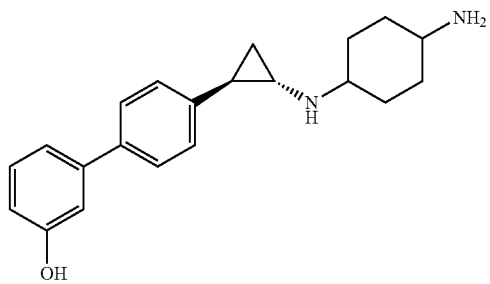 [SMILES: NC1CCC(N[C@H]2C[C@@H]2c2ccc(-c3cccc(O)c3)cc2)CC1]

Example 63: N-(4'-((trans)-2-((4-aminocyclohexyl)amino)cyclopropyl)[1,1'-biphenyl]-3-yl)methanesulfonamide

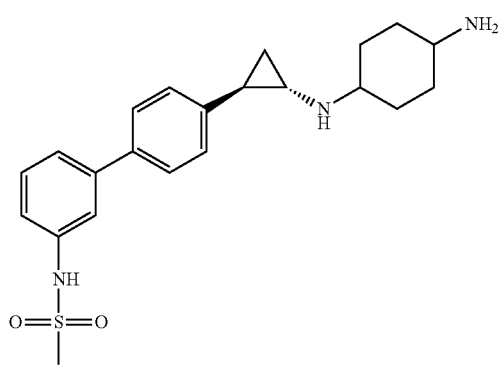 [SMILES: CS(=O)(=O)Nc1cccc(-c2ccc([C@H]3C[C@@H]3NC3CCC(N)CC3)cc2)c1]

Example 64: N1-((trans)-2-(4-((3-fluorobenzyl)oxy)phenyl)cyclopropyl)cyclohexane-1,4-diamine

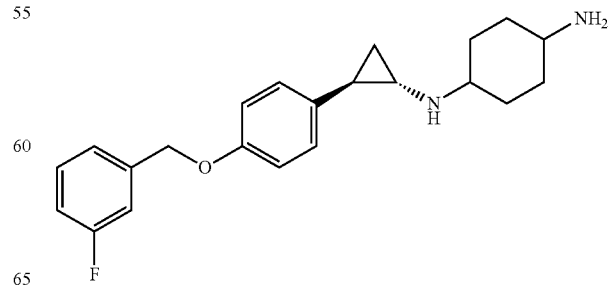

Example 65: N1-((trans)-2-(4-((4-fluorobenzyl)oxy)phenyl)cyclopropyl)cyclohexane-1,4-diamine

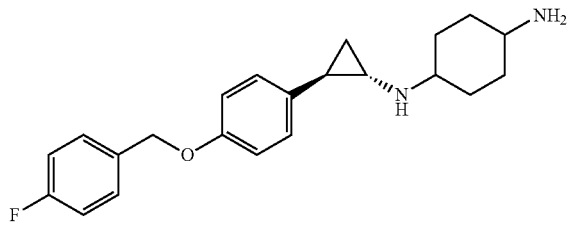 [SMILES: NC1CCC(N[C@H]2C[C@@H]2c2ccc(OCc3ccc(F)cc3)cc2)CC1]

Example 66: N1-methyl-N4-((trans)-2-(3'-(trifluoromethyl)-[1,1'-biphenyl]-4-yl)cyclopropyl)cyclohexane-1,4-diamine

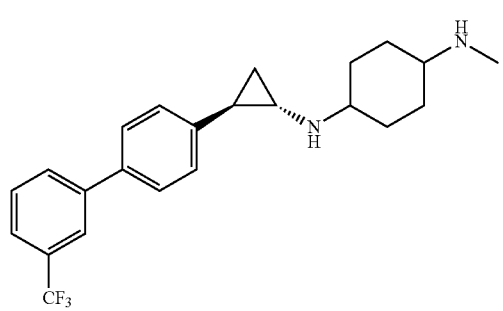 [SMILES: CNC1CCC(N[C@H]2C[C@@H]2c2ccc(-c3cccc(C(F)(F)F)c3)cc2)CC1]

Example 67: N1-((trans)-2-(4-(benzyloxy)phenyl)cyclopropyl)-N4-methylcyclohexane-1,4-diamine

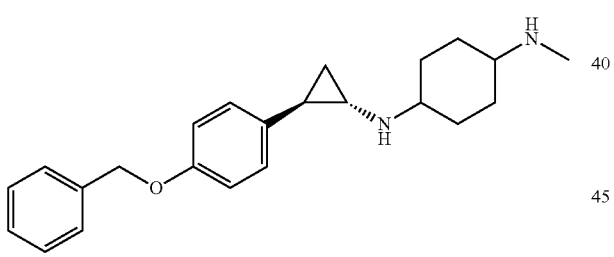

Example 68: N1-((trans)-2-(3'-(trifluoromethyl)-[1,1'-biphenyl]-4-yl)cyclopropyl)cyclobutane-1,3-diamine

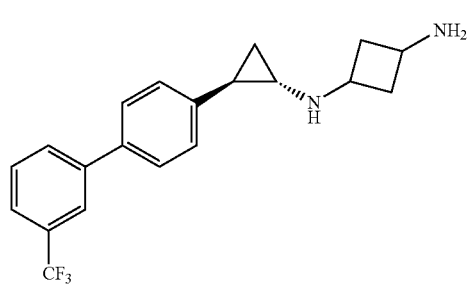 [SMILES: NC1CC(N[C@H]2C[C@@H]2c2ccc(-c3cccc(C(F)(F)F)c3)cc2)C1]

Example 69: N1-((trans)-2-(4-(benzyloxy)phenyl)cyclopropyl)cyclobutane-1,3-diamine

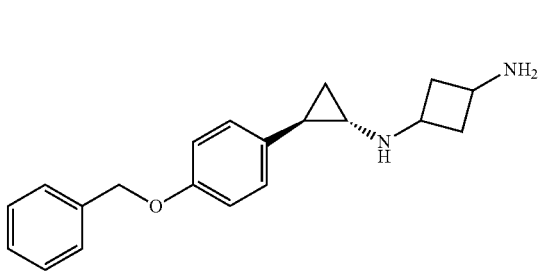 [SMILES: NC1CC(N[C@H]2C[C@@H]2c2ccc(OCc3ccccc3)cc2)C1]

Example 70: N1-((trans)-2 (3'-(trifluoromethyl)-[1,1'-biphenyl]-4-yl)cyclopropyl)-2,3-dihydro-1H-indene-1,3-diamine

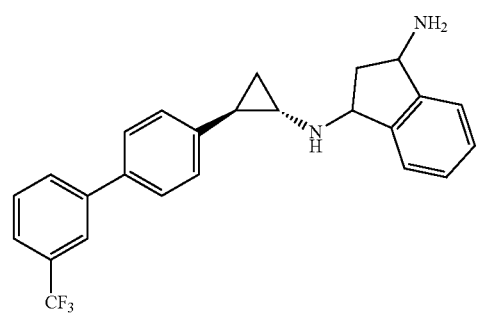 [SMILES: NC1CC(N[C@H]2C[C@@H]2c2ccc(-c3cccc(C(F)(F)F)c3)cc2)c2ccccc21]

Example 71: N1-((trans)-2-(4-(benzyloxy)phenyl)cyclopropyl)-2,3-dihydro-1H-indene-1,3-diamine

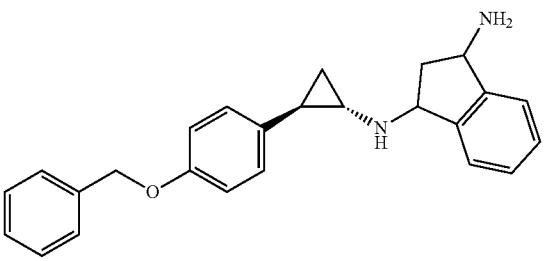 [SMILES: NC1CC(N[C@H]2C[C@@H]2c2ccc(OCc3ccccc3)cc2)c2ccccc21]

Example 72: N1-((1S,2S)-2-fluoro-2-phenylcyclopropyl)cyclohexane-1,4-diamine

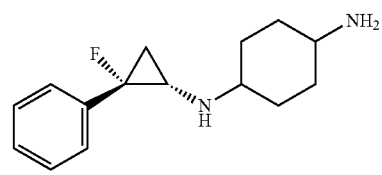 [SMILES: NC1CCC(N[C@H]2C[C@]2(F)c2ccccc2)CC1]

Example 73: N1-((1R,2R)-2-fluoro-2-phenylcyclo-
propyl)cyclohexane-1,4-diamine

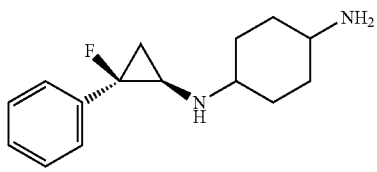 [SMILES: NC1CCC(N[C@@H]2C[C@@]2(F)c2ccccc2)CC1]

Example 74: N1-((trans)-2-(naphthalen-2-yl)cyclo-
propyl)cyclohexane-1,4-diamine

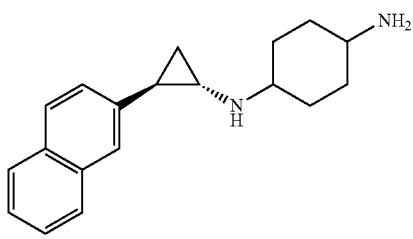 [SMILES: NC1CCC(N[C@H]2C[C@@H]2c2ccc3ccccc3c2)CC1]

Example 75: N1-((trans)-2-(o-tolyl)cyclopropyl)
cyclohexane-1,4-diamine

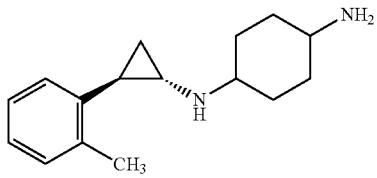 [SMILES: Cc1ccccc1[C@H]1C[C@@H]1NC1CCC(N)CC1]

Example 76: N1-((trans)-2-(4-(trifluoromethyl)phe-
nyl)cyclopropyl)cyclohexane-1,4-diamine

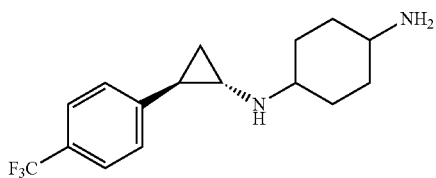 [SMILES: NC1CCC(N[C@H]2C[C@@H]2c2ccc(C(F)(F)F)cc2)CC1]

Example 77: N1-((trans)-2-(4-methoxyphenyl)cy-
clopropyl)cyclohexane-1,4-diamine

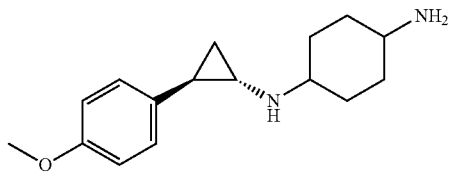 [SMILES: COc1ccc([C@H]2C[C@@H]2NC2CCC(N)CC2)cc1]

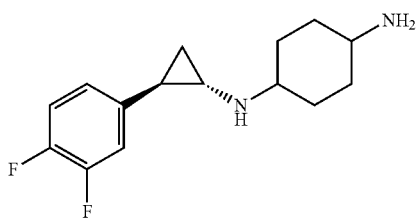 [SMILES: NC1CCC(N[C@H]2C[C@@H]2c2ccc(F)c(F)c2)CC1]

Example 79: N1-((trans)-2-(3,4-difluorophenyl)
cyclopropyl)cyclohexane-1,4-diamine

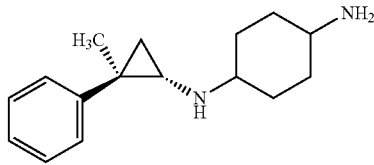 [SMILES: C[C@]1(c2ccccc2)C[C@@H]1NC1CCC(N)CC1]

Example 80: N1-((trans)-2-methyl-2-phenylcyclo-
propyl)cyclohexane-1,4-diamine

Example 81: (cis)-N1-((1S,2R)-2-(pyridin-3-yl)cy-
clopropyl)cyclohexane-1,4-diamine

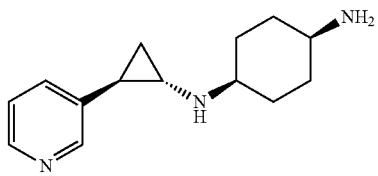 [SMILES: N[C@H]1CC[C@@H](N[C@H]2C[C@@H]2c2cccnc2)CC1]

Example 82: (trans)-N1-((R,2S)-2-(pyridin-3-yl)cyclopropyl)cyclohexane-1,4-diamine

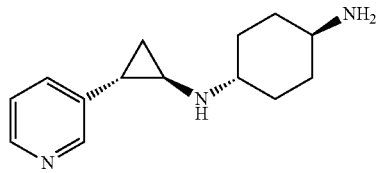 [SMILES: N[C@H]1CC[C@H](N[C@@H]2C[C@H]2c2cccnc2)CC1]

Example 83: (cis)-N1-((1R,2S)-2-(pyridin-3-yl)cyclopropyl)cyclohexane-1,4-diamine

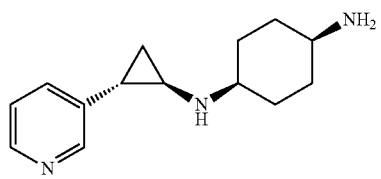 [SMILES: N[C@H]1CC[C@@H](N[C@@H]2C[C@H]2c2cccnc2)CC1]

Example 84: (trans)-N1-((1S,2R)-2-(pyridin-3-yl)cyclopropyl)cyclohexane-1,4-diamine

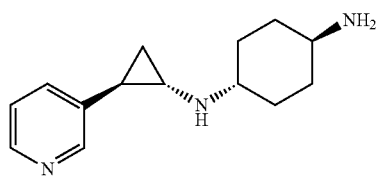 [SMILES: N[C@H]1CC[C@H](N[C@H]2C[C@@H]2c2cccnc2)CC1]

Example 85: (cis)-N1-((1S,2R)-2-phenylcyclopropyl)cyclobutane-1,3-diamine

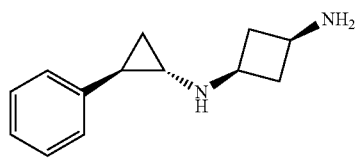 [SMILES: N[C@H]1C[C@@H](N[C@H]2C[C@@H]2c2ccccc2)C1]

Example 86: (trans)-N1-((1R,2S)-2-phenylcyclopropyl)cyclobutane-1,3-diamine

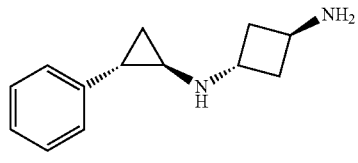 [SMILES: N[C@H]1C[C@H](N[C@@H]2C[C@H]2c2ccccc2)C1]

Example 87: (cis)-N1-((1R,2S)-2-phenylcyclopropyl)cyclobutane-1,3-diamine

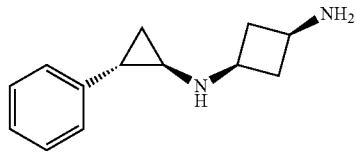 [SMILES: N[C@H]1C[C@@H](N[C@@H]2C[C@H]2c2ccccc2)C1]

Example 88: (trans)-N1-((1S,2R)-2-phenylcyclopropyl)cyclobutane-1,3-diamine

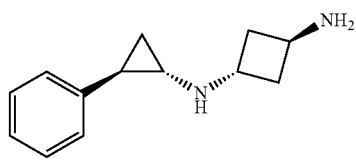 [SMILES: N[C@H]1C[C@H](N[C@H]2C[C@@H]2c2ccccc2)C1]

Example 89: (cis)-N1-((1S,2R)-2-(3,4-difluorophenyl)cyclopropyl)cyclohexane-1,4-diamine

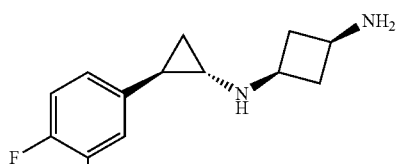

Example 90: (trans)-N1-((1R,2S)-2-(3,4-difluorophenyl)cyclopropyl)cyclohexane-1,4-diamine

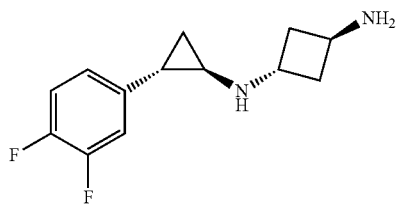 [SMILES: N[C@H]1C[C@H](N[C@@H]2C[C@H]2c2ccc(F)c(F)c2)C1]

Example 91: (cis)-N1-((1R,2S)-2-(3,4-difluorophenyl)cyclopropyl)cyclohexane-1,4-diamine

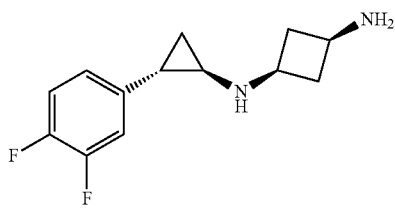 [SMILES: N[C@H]1C[C@@H](N[C@@H]2C[C@H]2c2ccc(F)c(F)c2)C1]

Example 92: (trans)-N1-((1S,2R)-2-(3,4-difluorophenyl)cyclopropyl)cyclohexane-1,4-diamine

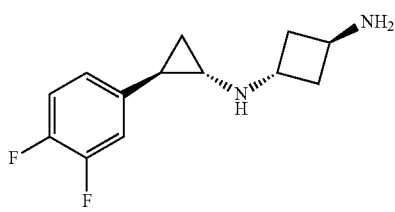 [SMILES: N[C@H]1C[C@H](N[C@H]2C[C@@H]2c2ccc(F)c(F)c2)C1]

Example 93: (cis)-N1-((1S,2R)-2-(naphthalen-2-yl)cyclopropyl)cyclohexane-1,4-diamine

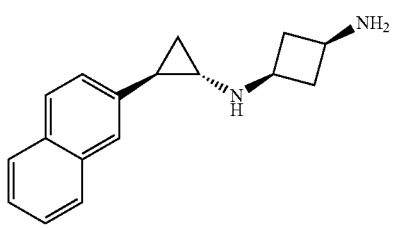 [SMILES: N[C@H]1C[C@@H](N[C@H]2C[C@@H]2c2ccc3ccccc3c2)C1]

Example 94: (trans)-N1-((1R,2S)-2-(naphthalen-2-yl)cyclopropyl)cyclohexane-1,4-diamine

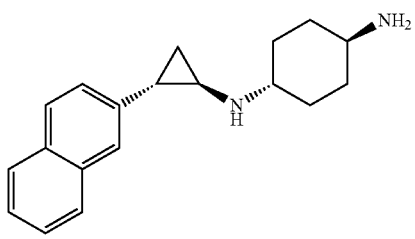 [SMILES: N[C@H]1CC[C@H](N[C@@H]2C[C@H]2c2ccc3ccccc3c2)CC1]

Example 95: (cis)-N1-((1R,2S)-2-(naphthalen-2-yl)cyclopropyl)cyclohexane-1,4-diamine

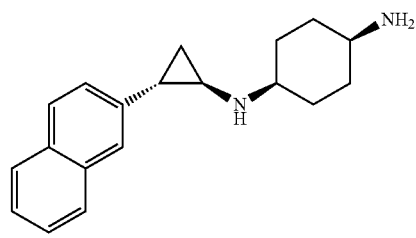 [SMILES: N[C@H]1CC[C@@H](N[C@@H]2C[C@H]2c2ccc3ccccc3c2)CC1]

Example 96: (trans)-N1-((1S,2R)-2-(naphthalen-2-yl)cyclopropyl)cyclohexane-1,4-diamine

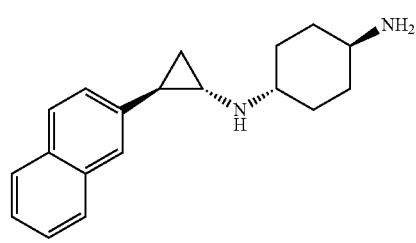 [SMILES: N[C@H]1CC[C@H](N[C@H]2C[C@@H]2c2ccc3ccccc3c2)CC1]

Example 97: (cis)-N1-((1S,2R)-2-(4-(1H-pyrazol-5-yl)phenyl)cyclopropyl)cyclohexane-1,4-diamine

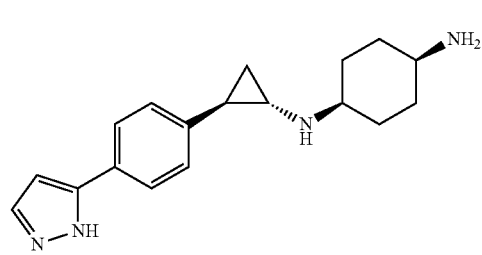 [SMILES: N[C@H]1CC[C@@H](N[C@H]2C[C@@H]2c2ccc(-c3ccn[nH]3)cc2)CC1]

Example 98: (trans)-N1-((1R,2S)-2-(4-(1H-pyrazol-5-yl)phenyl)cyclopropyl)cyclohexane-1,4-diamine

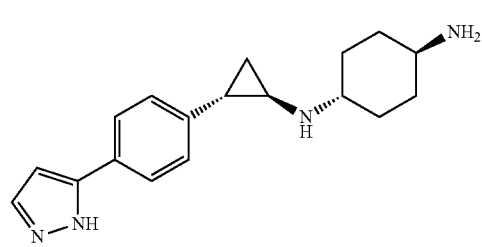 [SMILES: N[C@H]1CC[C@H](N[C@@H]2C[C@H]2c2ccc(-c3ccn[nH]3)cc2)CC1]

Example 99: (cis)-N1-((1R,2S)-2-(4-(1H-pyrazol-5-yl)phenyl)cyclopropyl)cyclohexane-1,4-diamine

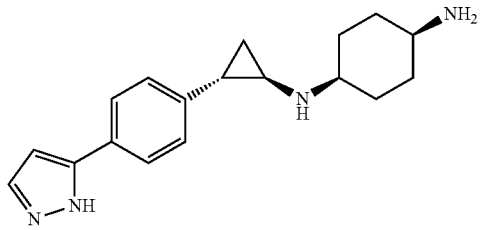 [SMILES: N[C@H]1CC[C@@H](N[C@@H]2C[C@H]2c2ccc(-c3ccn[nH]3)cc2)CC1]

Example 100: (trans)-N1-((1S,2R)-2-(4-(1H-pyrazol-5-yl)phenyl)cyclopropyl)cyclohexane-1,4-diamine

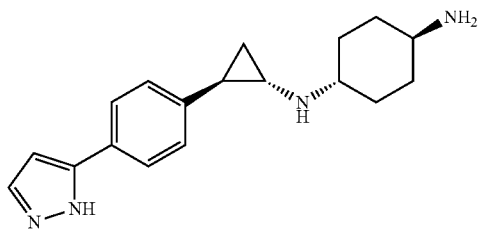 [SMILES: N[C@H]1CC[C@H](N[C@H]2C[C@@H]2c2ccc(-c3ccn[nH]3)cc2)CC1]

Example 101: N-(4'-((1R,2S)-2-(((cis)-4-aminocyclohexyl)amino)cyclopropyl-[1,1'-biphenyl]-3-yl)piperazine-1-sulfonamide

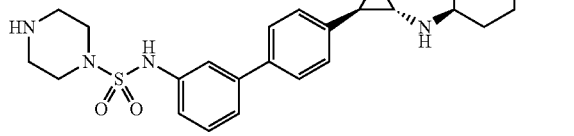

Example 102: N-(4'-((1S,2R)-2-(((trans)-4-aminocyclohexyl)amino)cyclopropyl)-[1,1'-biphenyl]-3-yl)piperazine-1-sulfonamide

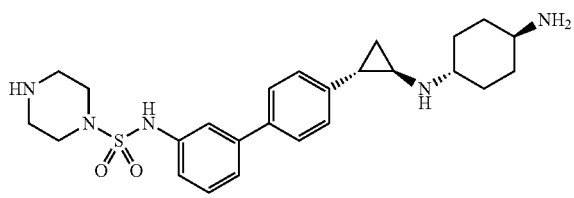 [SMILES: N[C@H]1CC[C@H](N[C@@H]2C[C@H]2c2ccc(-c3cccc(NS(=O)(=O)N4CCNCC4)c3)cc2)CC1]

Example 103: N-(4'-((1S,2R)-2-(((cis)-4-aminocyclohexyl)amino)cyclopropyl)-[1,1'-biphenyl]-3-yl)piperazine-1-sulfonamide

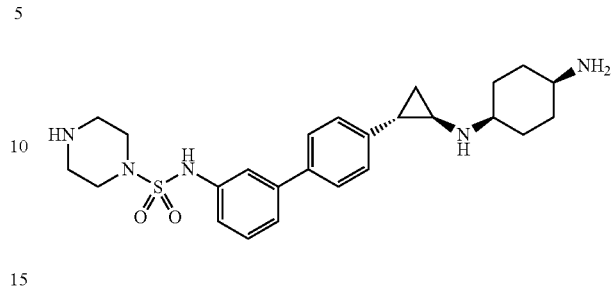

Example 104: N-(4'-((1R,2S)-2-(((trans)-4-aminocyclohexyl)amino)cyclopropyl)-[1,1'-biphenyl]-3-yl)piperazine-1-sulfonamide

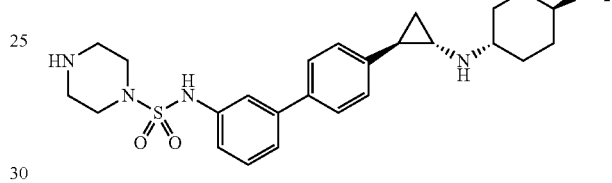

Example 105: (cis)-N1-((1S,2R)-2-(4-((2-fluorobenzyl)oxy)phenyl)cyclopropyl)cyclohexane-1,4-diamine

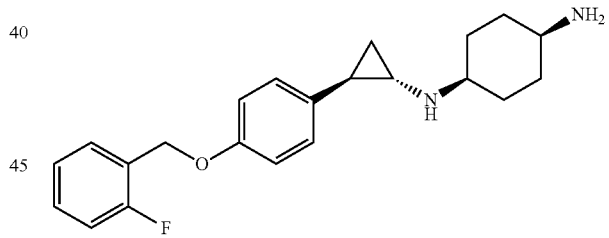

Example 106: (trans)-N1-((1R,2S)-2-(4-((2-fluorobenzyl)oxy)phenyl)cyclopropyl)cyclohexane-1,4-diamine

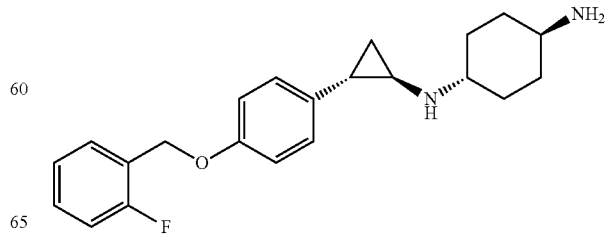

Example 107: (cis)-N1-((1R,2S)-2-(4-((2-fluorobenzyl)oxy)phenyl)cyclopropyl)cyclohexane-1,4-diamine

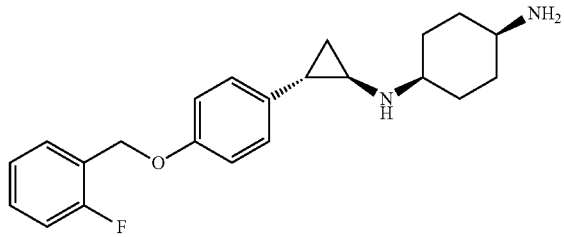 [SMILES: N[C@H]1CC[C@@H](N[C@@H]2C[C@H]2c2ccc(OCc3ccccc3F)cc2)CC1]

Example 108: (trans)-N1-((1S,2R)-2-(4-((2-fluorobenzyl)oxy)phenyl)cyclopropyl)cyclohexane-1,4-diamine

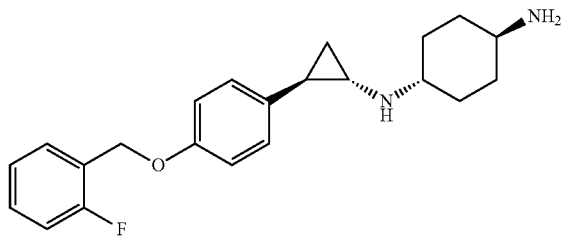 [SMILES: N[C@H]1CC[C@H](N[C@H]2C[C@@H]2c2ccc(OCc3ccccc3F)cc2)CC1]

Biological Assays

Example 109: Biological Assays—Inhibition of LSD1

The compounds of the invention can be tested for their ability to inhibit LSD1. The ability of the compounds of the invention to inhibit LSD1 can be tested as follows. Human recombinant LSD1 protein was purchased from BPS Bioscience Inc (catalog reference number 50100: human recombinant LSD1, GenBank accession no. NM_015013, amino acids 158-end with N-terminal GST tag, MW: 103 kDa). In order to monitor LSD1 enzymatic activity and/or its inhibition rate by our inhibitor(s) of interest, di-methylated H3-K4 peptide (Anaspec) was chosen as a substrate. The demethylase activity was estimated, under aerobic conditions, by measuring the release of $H_2O_2$ produced during the catalytic process, using the Amplex® Red hydrogen peroxide/peroxidase assay kit (Invitrogen).

Briefly, a fixed amount of LSD1 was incubated on ice for 15 minutes, in the absence and/or in the presence of at least eight 3-fold serial dilutions of the respective inhibitor (e.g., from 0 to 75 µM, depending on the inhibitor strength). Tranylcypromine (Biomol International) was used as a control for inhibition. Within the experiment, each concentration of inhibitor was tested in duplicate. After leaving the enzyme interacting with the inhibitor, $K_M$ of di-methylated H3-K4 peptide was added to each reaction and the experiment was left for 30 minutes at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 5 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The IC50 value of each inhibitor was calculated with GraphPad Prism Software.

The results presented in Table 1 below show the results of the LSD1 inhibition studies for a number of the Example compounds. In Table 2 the IC50 values for all examples tested in this assay are shown. Parnate (tranylcypromine; i.e., 2-trans phenylcyclopropylamine) was found to have a IC50 value of 35±10 micromolar. The studies show that the compounds of the invention have unexpectedly potent LSD1 inhibition.

Example 110: Biological Assays—Monoamine Oxidase Assays for Determining the Selectivity of the Compounds of the Invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescence-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAO-A and MAO-B activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 µL. The assay buffer was 100 mM HEPES, pH 7.5. Each experiment was performed in duplicate within the same experiment.

Briefly, a fixed amount of MAO (0.25 µg for MAO-A and 0.5 µg for MAO-B) was incubated on ice for 15 minutes in the reaction buffer, in the absence and/or in the presence of at least eight 3-fold serial dilutions each. Clorgyline and Deprenyl (Sigma Aldrich) was used as a control for specific inhibition of MAO-A and MAO-B respectively.

After leaving the enzyme(s) interacting with the inhibitor, $K_M$ of kynuramine was added to each reaction for MAO-B and MAO-A assay respectively, and the reaction was left for 1 hour at 37° C. in the dark. The oxidative deamination of the substrate was stopped by adding 50 µL of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The IC50 values of each inhibitor were calculated with GraphPad Prism Software.

The results obtained with compounds of the invention in the biological assays of examples 109 and 110 are shown below.

TABLE 1

Summary of Data from MAO-A, MAO-B, and LSD1 Inhibition Studies

| Example No. | MAO-A (Ki) | MAO-B (Ki) | LSD1 (Ki) |
|---|---|---|---|
| 1 | I | I | IV |
| 2 | I | I | III |
| 3 | I | I | III |
| 4 | I | I | IV |
| 5 | I | I | IV |
| 8 | I | II | III |
| 11 | II | II | III |
| 12 | II | II | IV |
| 13 | II | II | III |
| 14 | II | II | III |
| 15 | II | II | IV |

The ranges for the Ki value reported in Table 1 are for MAO-A, MAO-B and LSD1: I=higher than 40 µM; II=between 1 µM and 40 µM; III=between 0.1 µM and 1 µM; IV=between 0.001 µM and 0.1 µM. The term Ki value is used herein as a designation for the IC50 value, i.e. the concentration required for a half-maximal (50%) inhibition of the corresponding target (MAO-A, MAO-B, or LSD1).

Generally compounds of the invention were found to have particularly low IC50 values for LSD1, as compared to MAO-A and MAO-B. For some of the compounds of the Examples, IC50 values for LSD1 were lower than 0.1 µM.

The specific IC50 values obtained for the compounds disclosed in the Examples when tested in the assays of Examples 109 (LSD1 inhibition) and 110 (MAO-A and B inhibition) are provided in Table 2 below:

| Example no. | MAO-A (IC50 - µM) | MAO-B (IC50 - µM) | LSD1 (IC50 - µM) |
|---|---|---|---|
| 1 | >100 | 44.17 | 0.017 |
| 2 | >100 | >100 | 0.135 |
| 3 | >100 | >100 | 0.292 |
| 4 | >100 | >100 | 0.033 |
| 5 | >100 | >100 | 0.015 |
| 6 | >100 | >100 | 0.034 |
| 7 | >100 | >100 | 0.069 |
| 8 | >100 | 10.07 | 0.118 |
| 9 | ≈50 | 1.84 | 0.048 |
| 10 | 1.64 | 0.98 | 0.040 |
| 11 | 32.02 | 6.80 | 0.131 |
| 12 | 25.20 | 2.50 | 0.091 |
| 13 | ≈100 | 2.45 | 0.402 |
| 14 | ≈50 | 2.23 | 0.146 |
| 15 | >100 | >100 | 0.081 |
| 16 | >100 | ≈100 | 0.148 |
| 17 | >100 | ≈100 uM | 0.062 |
| 18 | >100 | >100 | 0.045 |
| 19 | >100 | >100 | 0.068 |
| 20 | >100 | 59.09 | 0.034 |
| 21 | 5.23 | 1.36 | 0.053 |
| 22 | >100 | ≈100 | 0.066 |
| 23 | >100 | 46.36 | 31.070 |
| 24 | >100 | ≈100 | 5.705 |
| 25 | >100 | ≈100 | 1.330 |
| 26 | ≈100 | ≈100 | 0.051 |
| 27 | >100 | >100 | 0.027 |
| 28 | >100 | 7.56 | 0.037 |
| 29 | >100 | >100 | 0.036 |
| 30 | >100 | >100 | 6.772 |
| 31 | >100 | >100 | 0.035 |
| 32 | >100 | >100 | 0.037 |
| 33 | >50 | ≈50 | 0.021 |
| 34 | >50 | ≈50 | 0.047 |
| 35 | 5.58 | 6.50 | 0.128 |
| 36 | 10.70 | 2.27 | 0.086 |
| 37 | 14.64 | 6.65 | 0.094 |
| 38 | 26.78 | 2.41 | 0.053 |
| 39 | 26.29 | 10.56 | 0.089 |
| 40 | >100 | 18.35 | 0.034 |
| 41 | ≈100 | ≈100 | 0.047 |
| 42 | 8.93 | 8.48 | 0.027 |
| 43 | >100 | >100 | 0.022 |
| 44 | 18.18 | 2.04 | 0.041 |
| 45 | 29.46 | 3.23 | 0.032 |
| 46 | >100 | >100 | 0.138 |
| 47 | ≈100 | ≈50 | 0.083 |
| 48 | 17.48 | >100 | 0.027 |
| 49 | ≈100 | ≈100 | 0.079 |
| 50 | >100 | ≈100 | 0.062 |
| 51 | ≈100 | ≈100 | 0.030 |
| 52 | ≈100 | 65.01 | 0.019 |
| 53 | ≈100 | 15.36 | 0.045 |
| 54 | >100 | >100 | 22.080 |
| 55 | >100 | 17.13 | 0.033 |
| 56 | ≈100 | >50 | 0.094 |
| 57 | 13.56 | 3.24 | 0.012 |
| 58 | 51.70 | 3.62 | 0.042 |
| 59 | >100 | ≈50 | 0.054 |

As the data in the above table show, the compounds of the invention are very potent LSD1 inhibitors, with IC50 values in many cases below 100 nM or even below 50 nM. In addition, the compounds exhibit high selectivity versus MAO-A and MAO-B, with IC50 values for LSD1 in general ≥100-fold more potent than the corresponding IC50 values for MAO-A and MAO-B.

Example 111: Cellular Assay—Induction of Differentiation of THP-1 Leukemia Cells Acute Myeloid Leukemia (AML) is characterized by the presence of leukemic cells with a maturation arrest that divide rapidly. With the induction of terminal differentiation, AML cells lose the ability to proliferate and end up dying without the need of a direct cytotoxic effect.

By analyzing the induction of CD11b membrane expression on THP-1 cells we are assessing the ability of LSD1 inhibitors to induce terminal monocytic differentiation of a MLL-AF9 AML cell line.

The assay was performed as follows:

THP-1 cells were established from the peripheral blood of a 1-year-old boy with acute monocytic leukemia at relapse in 1978. They carry t(9;11)(p21;q23) leading to MLL-MLLT3 (MLL-AF9) fusion gene. This cell line can undergo monocytic differentiation upon treatment with the appropriate stimulus. THP-1 were purchased from DSMZ GmbH (Deutsche Sammlung von Mikroorganismen und Zellkulturen) and cultured in RPMI 1640 medium containing 10% of fetal bovine serum.

In this assay, 150,000 THP-1 cells were seeded in 1 ml of complete culture medium in 6-well tissue culture plates. Serial dilutions of the compounds were prepared in DMSO and then further diluted in complete medium to generate solutions of concentrations that are double of the final concentration at which the cells will be exposed. 1 ml of these 2× concentrated solutions was added to the cells. DMSO final content must be the same in all the wells and must be kept below 0.1% v/v (usually 0.01-0.02% v/v), since higher DMSO content can induce differentiation of THP-1 cells.

Cells were kept in the presence of test compound for 96 h at a 5% $CO_2$ atmosphere at 37° C. After this treatment period, cells were harvested, washed twice with PBS buffer and placed in a V-bottom 96-well plate. Each treated sample was split in two. One was stained with a phycoerythrin-labeled anti-CD11b antibody (clone ICRF44, purchased from eBiosciences) and the other with the relevant phycoerythrin-labeled isotype control antibody (mouse $IgG_1$, purchased from eBiosciences). Samples were incubated in the dark at 4° C. for 30-60 minutes and washed three times in PBS buffer containing 1% fetal bovine serum.

Samples were analyzed in a flow cytometer equipped with a blue laser (488 nm). Emitted fluorescence was detected and quantified with a 575/30 nm filter. Percentage of CD11b positive cells, as an indicator of monocytic differentiation, was determined compared to isotype control antibody stained cells. EC50 values were calculated by non-linear regression analysis.

The results obtained with compounds of the invention in this test are shown in Table 3 below.

| Example No | EC50 (nM) |
| --- | --- |
| 3 | 13% CD11b+ cells at 100 nM |
| 4 | 5.3 |
| 5 | 0.8 |
| 6 | >200 |
| 17 | 6.3 |
| 19 | 2.2 |
| 22 | 3.6 |
| 26 | 9.7 |
| 33 | 13.9 |
| 38 | 20.0 |
| 39 | 6.6 |
| 40 | 2.5 |
| 42 | 82.4 |
| 57 | 2.0 |

These results show that compounds of the invention exhibit very potent activity in inducing differentiation of leukemia THP-1 cells, which indicates that these compounds are particularly useful for the treatment or prevention of leukemias.

Previous reports of LSD1 have found that it is involved in cell proliferation and growth. Some studies have implicated LSD1 as a therapeutic target for cancer. Huang et al. (2007) PNAS 104:8023-8028 found that polyamine inhibitors of LSD1 modestly cause the reexpression of genes aberrantly silenced in cancer cells and particularly colorectal cancer (Huang et al. Clin Cancer Res. (2009) December 1; 15 (23):7217-28. Epub 2009 Nov. 24. PMID: 19934284). Scoumanne et al. ((2007) J. Biol. Chem. May 25; 282 (21):15471-5) found that deficiency in LSD1 leads to a partial cell cycle arrest in G2/M and sensitizes cells to growth suppression induced by DNA damage. Kahl et al. ((2006) Cancer Res. 66 (23):11341-7) found that LSD1 expression is correlated with prostate cancer aggressiveness. Metzger et al. ((2005) Nature, 437 (7057), 436-439) reported that LSD1 modulation by siRNA and pargyline regulates androgen receptor (AR) and may have therapeutic potential in cancers where AR plays a role, like prostate, testis, and brain cancers. Lee et al. ((2006) Chem. Biol. 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) Cancer Cell International 4:1 exogenous expression of EGR-1 resulted in growth arrest and eventual cell death in primary cancer cell lines; Lucerna et al. (2006) Cancer Research 66 (13), 6708-6713 show that sustained expression of Egr-1 causes antiangiogeneic effects and inhibits tumor growth in some models; Ferraro et al. ((2005) J. Clin. Oncol. March 20; 23 (9):1921-6) reported that Egr-1 is downregulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) Cancer Res. March 1; 69 (5):2065-71). Other studies have implicated LSD1 in breast cancer (Lim et al. Carcinogenesis, (2010), 31 (3): 512-20, Epub 2009 Dec. 30. [Epub ahead of print] PMID: 20042638), lung, bladder and colorectal cancers (Hayami et al (2011), Int J Cancer, 128 (3): 574-86, PMID: 20333681) and leukemia (Binda et al (2010), J Am Chem Soc, 132 (19): 6827-33, PMID: 20415477).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the (hetero)aryl cyclopropylamine compounds of the invention can be used to treat such diseases.

Recent studies have also implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) Nat. Med. 15 (11):1312-1317). Therefore it is believed that the compounds of the invention can be used for treating or preventing viral infection. Furthermore, it is believed that the compounds of the invention can treat or prevent viral reactivation after latency.

Thus, without being bound by theory, the inventors have identified a new class of cyclopropanamine-based LSD1 inhibitors with unexpected potency and selectivity for LSD1, a biologically relevant target in oncology and other diseases.

All publications and patent applications mentioned in the specification are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:

1. A compound chosen from N-(4'-((trans)-2-((4-aminocyclohexyl)amino) cyclopropyl)-[1,1'-biphenyl]-3-yl)-2-cyanobenzenesulfonamide, an optically active stereoisomer thereof, and a salt or solvate thereof.

2. The compound of claim 1, wherein the compound is an optically active stereoisomer.

3. The compound of claim 1, wherein the compound is N-(4'-((trans)-2-((4-aminocyclohexyl)amino) cyclopropyl)-[1,1'-biphenyl]-3-yl)-2-cyanobenzenesulfonamide or a pharmaceutically acceptable salt or solvate thereof.

4. The compound of claim 1, wherein the compound is a hydrochloride salt of N-(4'-((trans)-2-((4-aminocyclohexyl)amino) cyclopropyl)-[1,1'-biphenyl]-3-yl)-2-cyanobenzenesulfonamide.

5. A pharmaceutical composition comprising a compound chosen from N-(4'-((trans)-2-((4-aminocyclohexyl)amino) cyclopropyl)-[1,1'-biphenyl]-3-yl)-2-cyanobenzenesulfonamide, an optically active stereoisomer thereof, and a pharmaceutically acceptable salt or solvate thereof, and a pharmaceutically acceptable carrier.

6. The pharmaceutical composition of claim 5, wherein the compound is an optically active stereoisomer.

7. The pharmaceutical composition of claim 5, wherein the compound is N-(4'-((trans)-2-((4-aminocyclohexyl)amino)cyclopropyl)-[1,1'-biphenyl]-3-yl)-2-cyanobenzenesulfonamide or a pharmaceutically acceptable salt or solvate thereof.

8. The pharmaceutical composition of claim 5, wherein the compound is a hydrochloride salt of N-(4'-((trans)-2-((4-aminocyclohexyl)amino)cyclopropyl)-[1,1'-biphenyl]-3-yl)-2-cyanobenzenesulfonamide.

\* \* \* \* \*